(12) United States Patent
Meerpoel et al.

(10) Patent No.: US 8,114,880 B2
(45) Date of Patent: Feb. 14, 2012

(54) PIPERIDINE OR PIPERAZINE SUBSTITUTED TETRAHYDRO-NAPHTHALENE-1-CARBOXYLIC ACID MTP INHIBITING COMPOUNDS

(75) Inventors: Lieven Meerpoel, Beerse (BE); Joannes Theodorus Maria Linders, Eindhoven (NL); Libuse Jaroskova, Vosselaar (BE); Marcel Viellevoye, Breda (NL); Leo Jacobus Jozef Backx, Arendonk (BE); Didier Jean-Claude Berthelot, Antwerpen (BE); Guuske Frederike Busscher, Turnhout (BE)

(73) Assignee: Janssen Pharmaceutica N.V., Beerse (BE)

( * ) Notice: Subject to any disclaimer, the term of this patent is extended or adjusted under 35 U.S.C. 154(b) by 281 days.

(21) Appl. No.: 12/446,580

(22) PCT Filed: Oct. 22, 2007

(86) PCT No.: PCT/EP2007/061286
§ 371 (c)(1),
(2), (4) Date: Apr. 22, 2009

(87) PCT Pub. No.: WO2008/049806
PCT Pub. Date: May 2, 2008

(65) Prior Publication Data
US 2009/0325980 A1    Dec. 31, 2009

(30) Foreign Application Priority Data
Oct. 24, 2006   (EP) .................................... 06122817

(51) Int. Cl.
*A61K 31/4468* (2006.01)
*A61K 31/4965* (2006.01)
*A61K 31/4545* (2006.01)
*C07D 295/10* (2006.01)
*C07D 401/14* (2006.01)
*C07D 401/12* (2006.01)
*C07D 211/58* (2006.01)
*A61P 3/00* (2006.01)

(52) U.S. Cl. .................. 514/255; 514/255.01; 514/316; 514/318; 514/319; 514/387; 544/387; 546/187; 546/194; 546/205

(58) Field of Classification Search ........................ None
See application file for complete search history.

(56) References Cited

U.S. PATENT DOCUMENTS
5,712,279 A    1/1998   Biller et al.
2003/0114442 A1  6/2003   Heckel et al.
2010/0016291 A1  1/2010   Meerpoel et al.

FOREIGN PATENT DOCUMENTS
EP          0643057 A    3/1995
WO       WO 96/40640 A1  12/1996
WO       WO 98/23593 A1  6/1998
WO       WO 00/32582 A1  6/2000
WO       WO 01/47899 A1  7/2001
WO       WO 01/92241 A1  12/2001
WO       WO 02/42291 A1  5/2002
WO       WO 2008/049808 A1  5/2008

OTHER PUBLICATIONS

Gentles et al. In J. Chem. Soc. Perkin Trans. I, 1423-1431 (1991).*
International Search Report, International Application No. PCT/EP2007/061286, Date of Mailing of International Search Report, Dec. 28, 2007.
Dyatkin et al., "Determination of the Absolute Configuration of a Key Tricyclic Component of a Novel Vasopressin Receptor Antagonist by Use of Vibrational Circular Dichroism.", *Chirality*, 2002, vol. 14, pp. 215-219.
Wetterau et al, "Purification and characterization of microsomal triglyceride and cholesteryl ester transfer protein from bovine liver microsomes.", Chemistry and Physics of Lipids, 1985, vol. 38, pp. 205-222.
Hudson D., "Methodological Implications of Simultaneous Solid-Phase Peptide Synthesis. 1. Comparison of Different Coupling Procedures.", Journal of Organic Chemistry, 1988, vol. 53, pp. 617-624.
Wilson and Gisvold, "Metabolic Changes of Drugs and Related Organic Compounds.", *Textbook of Medicinal and Pharmaceutical Chemistry*, 1977, pp. 70-75.
Albericio et al., "Coupling Methods: Solid Phase Formation of Amide and Ester Bonds.", Solid Phase Synthesis: A Practical Guide, Marcel Dekker, Inc., 2000 (ISBN: 0-8247-0359-6) pp. 275-330.

* cited by examiner

*Primary Examiner* — Timothy Thomas
*Assistant Examiner* — Dennis Heyer

(57) ABSTRACT

The present invention is concerned with novel piperidine or piperazine substituted tetrahydro-naphthalene-1-carboxylic acid derivatives having apoB secretion/MTP inhibiting activity and concomitant lipid lowering activity. The invention further relates to methods for preparing such compounds, pharmaceutical compositions comprising said compounds as well as the use of said compounds as a medicine for the treatment of atherosclerosis, pancreatitis, obesity, hypertriglyceridemia, hypercholesterolemia, hyperlipidemia, diabetes and type II diabetes.

(I)

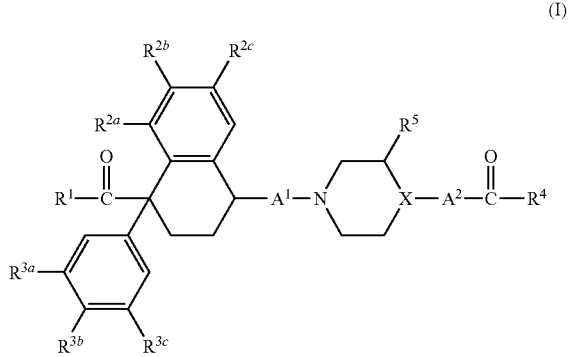

10 Claims, No Drawings

PIPERIDINE OR PIPERAZINE SUBSTITUTED TETRAHYDRO-NAPHTHALENE-1-CARBOXYLIC ACID MTP INHIBITING COMPOUNDS

CROSS REFERENCE TO RELATED APPLICATIONS

This application is the US national stage of Application No. PCT/EP2007/061286, filed Oct. 22, 2007, which application claims priority from EP 06122817.7 filed Oct. 24, 2006.

The present invention is concerned with novel piperidine or piperazine substituted tetrahydro-naphthalene-1-carboxylic acid derivatives having apoB secretion/MTP inhibiting activity and concomitant lipid lowering activity. The invention further relates to methods for preparing such compounds, pharmaceutical compositions comprising said compounds as well as the use of said compounds as a medicine for the treatment of atherosclerosis, pancreatitis, obesity, hypertriglyceridemia, hypercholesterolemia, hyperlipidemia, diabetes and type II diabetes.

Obesity is the cause of a myriad of serious health problems like the adult onset of diabetes and heart disease. In addition, losing weight is getting an obsession among an increasing proportion of the human population.

The causal relationship between hypercholesterolemia, particularly that associated with increased plasma concentrations of low density lipoproteins (hereinafter referred as LDL) and very low density lipoproteins (hereinafter referred as VLDL), and premature atherosclerosis and/or cardiovascular disease is now widely recognized. However, a limited number of drugs are presently available for the treatment of hyperlipidemia.

Drugs primarily used for the management of hyperlipidemia include bile acid sequestrant resins such as cholestyramine and colestipol, fibric acid derivatives such as bezafibrate, clofibrate, fenofibrate, ciprofibrate and gemfibrozil, nicotinic acid and cholesterol synthesis inhibitors such as HMG Co-enzyme-A reductase inhibitors. There still remains a need for new lipid lowering agents with improved efficiency and/or acting via other mechanisms than the above mentioned drugs.

Plasma lipoproteins are water-soluble complexes of high molecular weight formed from lipids (cholesterol, triglyceride, phospholipids) and apolipoproteins. Five major classes of lipoproteins that differ in the proportion of lipids and the type of apolipoprotein, all having their origin in the liver and/or the intestine, have been defined according to their density (as measured by ultracentrifugation). They include LDL, VLDL, intermediate density lipoproteins (hereinafter referred as IDL), high density lipoproteins (hereinafter referred as HDL) and chylomicrons. Ten major human plasma apolipoproteins have been identified. VLDL, which is secreted by the liver and contains apolipoprotein B (hereinafter referred as Apo-B), undergoes degradation to LDL which transports 60 to 70% of the total serum cholesterol. Apo-B is also the main protein component of LDL. Increased LDL-cholesterol in serum, due to oversynthesis or decreased metabolism, is causally related to atherosclerosis. In contrast high density lipoproteins (hereinafter referred as HDL), which contain apolipoprotein A1, have a protective effect and are inversely correlated with the risk of coronary heart disease. The HDL/LDL ratio is thus a convenient method of assessing the atherogenic potential of an individual's plasma lipid profile.

The two isoforms of apolipoprotein (apo) B, apo B-48 and apo B-100, are important proteins in human lipoprotein metabolism. Apo B-48, is about 48% the size of apo B-100 on sodium dodecyl sulfate-polyacrylamide gels, is synthesized by the intestine in humans. Apo B-48 is necessary for the assembly of chylomicrons and therefore has an obligatory role in the intestinal absorption of dietary fats. Apo B-100, which is produced in the liver in humans, is required for the synthesis and secretion of VLDL. LDL, which contain about ⅔ of the cholesterol in human plasma, are metabolic products of VLDL. Apo B-100 is virtually the only protein component of LDL. Elevated concentrations of apo B-100 and LDL cholesterol in plasma are recognized risk factors for developing atherosclerotic coronary artery disease.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias have also been classified into common hypercholesterolaemia, familial combined hyperlipidaemia, familial hypercholesterolaemia, remnant hyperlipidaemia, chylomicronaemia syndrome and familial hypertriglyceridaemia.

Microsomal triglyceride transfer protein (hereinafter referred as MTP) is known to catalyze the transport of triglyceride, cholesteryl ester and phospholipids such as phosphatidylcholine. This indicates that MTP is required for the synthesis of Apo B-containing lipoproteins such as chylomicrons and VLDL, the precursor to LDL. It therefore follows that an MTP inhibitor would inhibit the synthesis of VLDL and LDL, thereby lowering levels of VLDL, LDL, cholesterol and triglyceride in humans. Compounds capable of inhibiting MTP are believed to be useful in the treatment of disorders such as obesity, hyperlipidemia, hypercholesterolemia, hypertriglyceridemia, class II diabetes, atherosclerosis and for the reduction of postprandial serum triglyceride plasma levels.

The present invention is based on the unexpected finding that a group of tetrahydro-naphthalene-1-carboxylic acid derivatives have apoB secretion/MTP inhibiting activity. These compounds of formula (I) can act systemically and/or as selective MTP inhibitors, i.e. is able to selectively block MTP at the level of the gut wall in mammals.

The present invention relates to a family of novel compounds of formula (I)

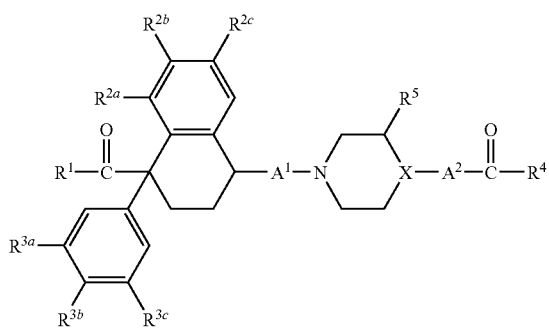

(I)

the pharmaceutically acceptable acid addition salts thereof, the N-oxides thereof, and the stereochemically isomeric forms thereof, wherein X is N, or CH;

$A^1$ is —$CH_2$—, or —(C=O)—;

$A^2$ is absent or represents —$CH_2$—, when X represents N, or $A^2$ is —$NR^6$—, when X represents CH, wherein $R^6$ is hydrogen or $C_{1-4}$alkyl;

$R^1$ is —$NR^7R^8$ or —$OR^9$;
wherein each $R^7$ and $R^8$ are independently selected from
hydrogen,
$C_{1-8}$alkyl,
$C_{1-8}$alkyl substituted with one, two or three substituents each independently from one another selected from halo, cyano, $C_{3-8}$cycloalkyl, $C_{1-4}$alkylcarbonyl, $C_{1-4}$alkyloxycarbonyl, polyhalo$C_{1-4}$alkyl, hydroxycarbonyl, —$OR^{10}$, —$NR^{10}R^{11}$, —$CONR^{12}R^{13}$, aryl, polycyclic aryl, or heteroaryl;
$C_{3-8}$cycloalkyl;
$C_{3-8}$cycloalkenyl;
$C_{3-8}$alkenyl;
$C_{3-8}$alkynyl;
aryl;
polycyclic aryl;
heteroaryl;
or $R^7$ and $R^8$ combined with the nitrogen atom bearing $R^7$ and $R^8$ may form an azetidinyl, pyrrolidinyl, piperidinyl, morpholinyl, azepanyl, or azocanyl ring wherein each of these rings may optionally be substituted by one or two substituents each independently selected from $C_{1-4}$alkyl, $C_{1-4}$alkyloxy, hydroxy, hydroxycarbonyl, $C_{1-4}$alkyloxycarbonyl or $C_{1-4}$alkyloxycarbonyl$C_{1-4}$alkyl;
wherein $R^{10}$ is hydrogen, $C_{1-4}$alkyl, $C_{1-4}$alkylcarbonyl, $C_{1-4}$alkyloxycarbonyl, $R^{12}$—NH-carbonyl, aryl, aryl$C_{1-4}$alkyl, polycyclic aryl, heteroaryl;
$R^{11}$ is hydrogen or $C_{1-4}$alkyl;
$R^{12}$ is hydrogen, $C_{1-4}$alkyl, phenyl or phenyl$C_{1-4}$alkyl;
$R^{13}$ is hydrogen, $C_{1-4}$alkyl, phenyl or phenyl$C_{1-4}$alkyl;
$R^9$ is $C_{1-8}$alkyl,
$C_{1-8}$alkyl substituted with one, two or three substituents each independently from one another selected from halo, cyano, $C_{3-8}$cycloalkyl, $C_{1-4}$alkylcarbonyl, $C_{1-4}$alkyloxycarbonyl, polyhalo$C_{1-4}$alkyl, hydroxycarbonyl, —$OR^{10}$, —$NR^{10}R^{11}$, —$CONR^{12}R^{13}$, aryl, polycyclic aryl, or heteroaryl;
$C_{3-8}$cycloalkyl;
$C_{3-8}$cycloalkenyl;
$C_{3-8}$alkenyl;
$C_{3-8}$alkynyl;
aryl;
polycyclic aryl;
heteroaryl;
wherein
aryl is phenyl; phenyl substituted with one to five substituents each independently selected from $C_{1-4}$alkyl, $C_{1-4}$alkyloxy, halo, hydroxy, trifluoromethyl, cyano, $C_{1-4}$alkyloxycarbonyl, $C_{1-4}$alkyloxycarbonyl-$C_{1-4}$alkyl, methylsulfonylamino, methylsulfonyl, $NR^{10}R^{11}$, $C_{1-4}$alkyl$NR^{10}R^{11}$, $CONR^{12}R^{13}$ or $C_{1-4}$alkyl$CONR^{12}R^{13}$;
polycyclic aryl is naphthalenyl, indanyl, fluorenyl, or 1,2,3,4-tetrahydronaphtalenyl, and said polycyclic aryl is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^{10}R^{11}$, $C_{1-4}$alkyl$NR^{10}R^{11}$, $CONR^{12}R^{13}$, $C_{1-4}$alkyl$CONR^{12}R^{13}$ or $C_{1-4}$alkyloxycarbonylamino and
heteroaryl is pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, thienyl; quinolinyl; isoquinolinyl; 1,2,3,4-tetrahydro-isoquinolinyl; benzothiazolyl; benzo[1,3]dioxolyl; 2,3-dihydro-benzo[1,4]dioxinyl; indolyl; 2,3-dihydro-1H-indolyl; 1H-benzoimidazolyl; and said heteroaryl is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^{10}R^{11}$, $C_{1-4}$alkyl$NR^{10}R^{11}$, $CONR^{12}R^{13}$ or $C_{1-4}$alkyl$CONR^{12}R^{13}$;

$R^{2a}$, $R^{2b}$, and $R^{2c}$ are independently from one another selected from hydrogen, $C_{1-4}$alkyl, $C_{1-4}$alkyloxy, halo, hydroxy, cyano, nitro, polyhalo$C_{1-4}$alkyl, polyhalo$C_{1-4}$alkyloxy or $C_{1-4}$alkyloxycarbonyl;

$R^{3a}$, $R^{3b}$, and $R^{3c}$ are independently from one another selected from hydrogen, $C_{1-4}$alkyl, $C_{1-4}$alkyloxy, halo, hydroxy, cyano, nitro, polyhalo$C_{1-4}$alkyl, polyhalo$C_{1-4}$alkyloxy or $C_{1-4}$alkyloxycarbonyl;

$R^4$ is phenyl; phenyl substituted with one to five substituents each independently selected from $C_{1-4}$alkyl, halo, hydroxy, $C_{1-4}$alkyloxy, amino, cyano, nitro, polyhalo$C_{1-4}$ alkyl, polyhalo$C_{1-4}$alkyloxy, $C_{1-4}$alkylcarbonyl, $C_{1-4}$alkyloxycarbonyl, sulfamoyl, a heterocyclic group, or phenyl optionally substituted with 1, 2 or 3 substituents each independently selected from $C_{1-4}$alkyl, halo, $C_{1-4}$alkyloxy, or trifluoromethyl; or heteroaryl selected from the group consisting of pyridinyl, pyrazinyl, pyrimidinyl, pyridazinyl, triazinyl, furanyl, and thienyl, wherein each of these heteroaryls may optionally be substituted with one or two substituents each independently selected from $C_{1-4}$alkyl, halo, hydroxy, $C_{1-4}$alkyloxy, oxo, cyano, polyhalo$C_{1-4}$alkyl, $C_{1-4}$alkylcarbonyl, $C_{1-4}$alkyloxycarbonyl or a heterocyclic group;

wherein heterocyclic group is selected from azetidinyl, pyrrolidinyl, piperidinyl, piperazinyl, morpholinyl, azepanyl, and azocanyl which may optionally be substituted by one or two substituents each independently selected from $C_{1-4}$alkyl or halo; and $R^5$ is hydrogen, $C_{1-4}$alkyl, $C_{1-4}$alkyloxy, hydroxy or halo.

As used in the foregoing definitions:

halo is generic to fluoro, chloro, bromo and iodo;

$C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;

$C_{1-6}$alkyl is meant to include $C_{1-4}$alkyl and the higher homologues thereof having 5 or 6 carbon atoms, such as, for example, 2-methylbutyl, pentyl, hexyl and the like;

$C_{1-8}$alkyl is meant to include $C_{1-6}$alkyl and the higher homologues thereof having 7 to 8 carbon atoms, such as for instance heptyl, ethylhexyl, octyl, and the like;

polyhalo$C_{1-4}$alkyl is defined as polyhalosubstituted $C_{1-4}$alkyl, in particular $C_{1-4}$alkyl (as hereinabove defined) substituted with 1 to 4 halogen atoms such as fluoromethyl, difluoromethyl, trifluoromethyl, trifluoroethyl, and the like;

$C_{3-8}$cycloalkyl is generic to cyclopropyl, cyclobutyl, cyclopentyl, cyclohexyl, cycloheptyl and cyclooctyl;

C₃₋₈cycloalkenyl is generic to cyclopropenyl, cyclobutenyl, cyclopentenyl, cyclohexenyl, cycloheptenyl and cyclooctenyl;

C₃₋₈alkenyl defines straight and branched chain hydrocarbon radicals containing one double bond and having from 3 to 8 carbon atoms such as, for example, 2-propenyl, 3-butenyl, 2-butenyl, 2-pentenyl, 3-pentenyl, 3-methyl-2-butenyl, 3-hexenyl, 2-hexenyl, 2-pentenyl, 2-octenyl and the like;

C₃₋₈alkynyl defines straight and branched chain hydrocarbon radicals containing one triple bond and having from 3 to 8 carbon atoms such as, for example, 2-propynyl, 3-butynyl, 2-butynyl, 2-pentynyl, 3-pentynyl, 3-methyl-2-butynyl, 3-hexynyl, 2-hexynyl, 2-pentynyl, 2-octynyl and the like.

The pharmaceutically acceptable acid addition salts as mentioned hereinabove are meant to comprise the therapeutically active non-toxic acid addition salt forms which the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular complex comprising a compound of the invention and one or more pharmaceutically acceptable solvent molecules, e.g. ethanol. The term 'hydrate' is used when said solvent is water.

The N-oxide form of the compound according to formula (I) is meant to comprise a compound of formula (I) wherein one or several nitrogen atoms are oxidized to so-called N-oxides, particularly those N-oxides wherein one or more tertiary nitrogens (e.g. of the piperazinyl or piperidinyl radical) are N-oxidized. Such N-oxides can easily be obtained by a skilled person without any inventive skills and they are obvious alternatives for a compound according to formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

A compound of formula (I) may be converted to the corresponding N-oxide form following art-known procedures for converting a trivalent nitrogen into its N-oxide form. Said N-oxidation reaction may generally be carried out by reacting the compound of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art using well-known methods such as, for example, X-ray diffraction.

The compounds of formula (I) have at least two asymmetric carbon atoms as illustrated below wherein the asymmetric carbon atoms are identified by a *.

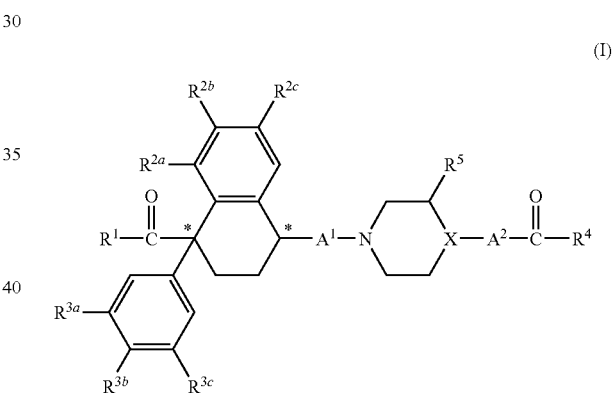

Due to the the presence of at least two asymmetric carbon atoms, generally the term "a compound of formula (I)" encompasses a mixture of four stereoisomers. Most compounds of the present invention have been prepared either with the trans-configuration or the cis-configuration:

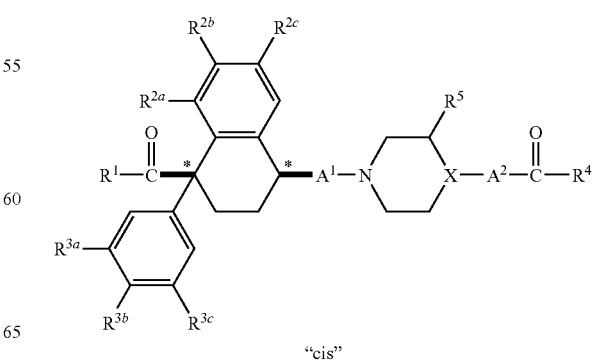

"cis"

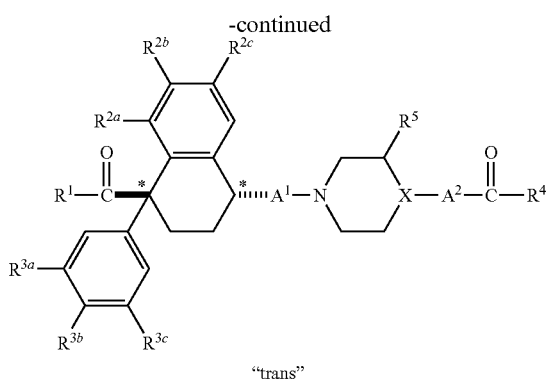

"trans"

Each of the above depicted "cis"- or "trans" compounds consists of a racemic mixture of two enantiomers and bold bonds or hashed bonds have been used to indicate this relative stereochemical configuration.

In case a "cis"- or "trans"-compound was separated into its two individual enantiomers, the bold and hashed bonds were replaced by wedged bonds to indicate the compound is a single enantiomer. If the absolute stereochemistry of a specific chiral carbon atom in a single enantiomer was not determined, its stereochemical configuration was than designated as R*, or S* indicating a relative stereochemistry.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy the keto-form may be the mainly populated tautomer.

In the framework of this application, with the expression "a compound according to the invention" it is also meant to include a compound according to the general formula (I) and a pro-drug thereof, or a isotopically labelled compound thereof.

Also within the scope of the invention are so-called "pro-drugs" of the compounds of formula (I). Pro-drugs are certain derivatives of pharmaceutically active compounds which may have little or no pharmacological activity themselves which can, when administered into or onto the body, be converted into compounds of formula (I) having the desired pharmaceutical activity, e.g. by hydrolytic cleavage. Such derivatives are referred to as "pro-drugs".

In the framework of this application, a compound according to the invention is inherently intended to comprise all isotopic combinations of its chemical elements. In the framework of this application, a chemical element, in particular when mentioned in relation to a compound according to formula (I), comprises all isotopes and isotopic mixtures of this element, either naturally occurring or synthetically produced,

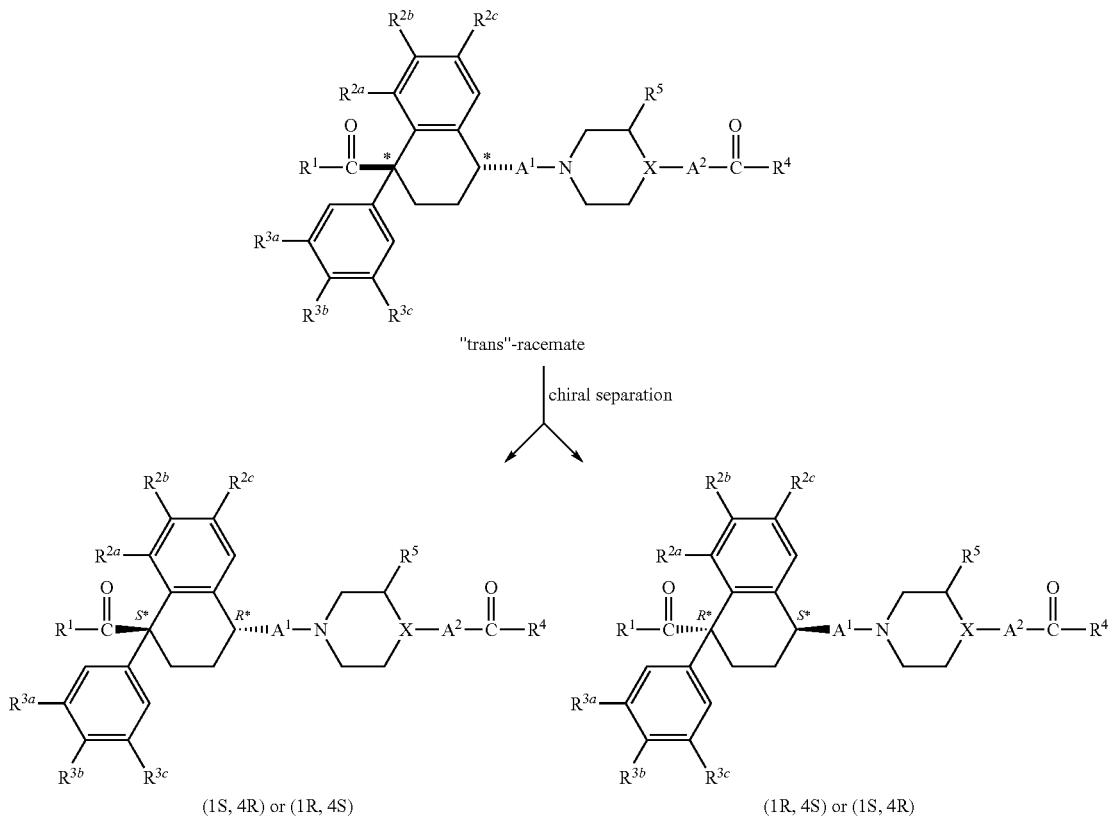

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

either with natural abundance or in an isotopically enriched form. In particular, when hydrogen is mentioned, it is understood to refer to $^1H$, $^2H$, $^3H$ and mixtures thereof; when carbon is mentioned, it is understood to refer to $^{11}C$, $^{12}C$, $^{13}C$, $^{14}C$ and mixtures thereof, when nitrogen is mentioned, it is understood to refer to $^{13}$N, $^{14}$N, $^{15}$N and mixtures thereof; when oxygen is mentioned, it is understood to refer to $^{14}$O, $^{15}$O, $^{16}$O, $^{17}$O, $^{18}$O and mixtures thereof; and when fluor is mentioned, it is understood to refer to $^{18}$F, $^{19}$F and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (I), a pharmaceutically acceptable acid or base addition salt thereof, an N-oxide form thereof, or a quaternary ammonium salt thereof, which contains at least one radioactive atom. For example, a compound can be labelled with positron or with gamma emitting radioactive isotopes. For radioligand-binding techniques (membrane receptor assay), the $^3$H-atom or the $^{125}$I-atom is the atom of choice to be replaced. For imaging, the most commonly used positron emitting (PET) radioactive isotopes are $^{11}$C, $^{18}$F, $^{15}$O and $^{13}$N, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}$F, $^{99m}$Tc, $^{201}$Tl and $^{123}$I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Interesting compounds of formula (I) are those compounds of formula (I) wherein one or more of the following restrictions apply:
a) X is CH; or
b) X is N; or
c) $R^{2a}=R^{3a}$, $R^{2b}=R^{3b}$ and $R^{2c}=R^{3c}$; in particular $R^{2a}=R^{3a}=H$, $R^{2b}=R^{3b}=H$, and $R^{2c}=R^{3c}=H$, or
d) $A^1$ is —(C=O)—; or
e) $A^1$ is —CH$_2$—; or
f) $R^1$ is $NR^7R^8$ wherein each $R^7$ and $R^8$ are independently selected from hydrogen; $C_{1-8}$alkyl; $C_{1-8}$alkyl substituted with one, or two substituents each independently from one another selected from hydroxy, $C_{1-4}$alkyloxy, $C_{1-4}$alkyloxycarbonyl, hydroxycarbonyl, $NR^{10}R^{11}$, $CONR^{12}R^{13}$, aryl, or heteroaryl; or aryl; or
g) $R^1$ is $NR^7R^8$ wherein $R^7$ and $R^8$ are combined with the nitrogen atom bearing $R^7$ and $R^8$ to form a pyrrolidinyl or piperidinyl ring wherein each of these rings may optionally be substituted by one or two substituents each independently selected from $C_{1-4}$alkyl, $C_{1-4}$alkyloxy, hydroxy, hydroxycarbonyl, or $C_{1-4}$alkyloxycarbonyl; or
h) $R^1$ is $OR^9$ wherein $R^9$ is $C_{1-6}$alkyl or $C_{3-8}$alkenyl; or
i) $R^4$ is phenyl; phenyl substituted with 1, 2 or 3 substituents each independently selected from $C_{1-4}$alkyl, halo, hydroxy, $C_{1-4}$alkyloxy, polyhalo$C_{1-4}$alkyloxy, sulfamoyl, phenyl substituted with trifluoromethyl, or a heterocyclic group wherein said heterocyclic group is mopholinyl or piperazinyl substituted with $C_{1-4}$alkyl; or
j) $R^4$ is a heteroaryl wherein said heteroaryl is pyridinyl or pyridazinyl optionally substituted with one or two substituents each independently selected from $C_{1-4}$alkyl, hydroxy, $C_{1-4}$alkyloxy, or oxo; or
k) aryl is phenyl; or phenyl substituted with one to two substituents each independently selected from $C_{1-4}$alkyl, $C_{1-4}$alkyloxy, halo, or hydroxy; or
l) $R^9$ is heteroaryl wherein heteroaryl is indolyl; or
m) $R^5$ is hydrogen or $C_{1-4}$alkyloxy.

In an embodiment, the present invention relates to those compounds of formula (I) wherein X is CH or N; when X represents CH than $A^2$ is —NR$^6$— wherein R$^6$ is hydrogen or $C_{1-4}$alkyl, or when X represents N than $A^2$ is absent; $A^1$ is —(C=O)— or —CH$_2$—; $R^{2a}=R^{3a}=H$, $R^{2b}=R^{3b}=H$, and $R^{2c}=R^{3c}=H$; $R^1$ is $NR^7R^8$ wherein each $R^7$ and $R^8$ are independently selected from hydrogen; $C_{1-8}$alkyl; $C_{1-8}$alkyl substituted with one, or two substituents each independently from one another selected from hydroxy, $C_{1-4}$alkyloxy, $C_{1-4}$alkyloxycarbonyl, hydroxycarbonyl, $NR^{10}R^{11}$, $CONR^{12}R^{13}$, aryl, or heteroaryl; or aryl; or $R^1$ is $NR^7R^8$ wherein $R^7$ and $R^8$ are combined with the nitrogen atom bearing $R^7$ and $R^8$ to form a pyrrolidinyl or piperidinyl ring wherein each of these rings may optionally be substituted by one or two substituents each independently selected from $C_{1-4}$alkyl, $C_{1-4}$alkyloxy, hydroxy, hydroxycarbonyl, or $C_{1-4}$alkyloxycarbonyl; or $R^1$ is $OR^9$ wherein $R^9$ is hydrogen, $C_{1-6}$alkyl, or $C_{3-8}$alkenyl; $R^4$ is phenyl; or phenyl substituted with 1, 2 or 3 substituents each independently selected from $C_{1-4}$alkyl, halo, hydroxy, $C_{1-4}$alkyloxy, polyhalo$C_{1-4}$alkyloxy, sulfamoyl, phenyl substituted with trifluoromethyl, or a heterocyclic group wherein said heterocyclic group is mopholinyl or piperazinyl substituted with $C_{1-4}$alkyl; or $R^4$ is a heteroaryl wherein said heteroaryl is pyridinyl or pyridazinyl optionally substituted with one or two substituents each independently selected from $C_{1-4}$alkyl, hydroxy, $C_{1-4}$alkyloxy, or oxo; $R^5$ is hydrogen or $C_{1-4}$alkyloxy; aryl is phenyl; or phenyl substituted with one to two substituents each independently selected from $C_{1-4}$alkyl, $C_{1-4}$alkyloxy, halo, or hydroxy; and heteroaryl is indolyl.

In another embodiment, the present invention relates to
a) compounds of formula (I) wherein $R^{2a}=R^{3a}=H$, $R^{2b}=R^{3b}=H$, and $R^{2c}=R^{3c}=H$;
b) compounds of formula (I) wherein $R^4$ is phenyl substituted with a heterocyclic group wherein said heterocyclic group is piperazinyl substituted with $C_{1-4}$alkyl, in particular methyl or isopropyl;
c) compounds of formula (I) wherein the substituents on the 1,2,3,4-tetrahydro-naphthalenyl moiety have the trans-configuration;
d) compounds of formula (I) wherein the substituents on the 1,2,3,4-tetrahydro-naphthalenyl moiety have the (1R, 4S) configuration.

Particular compounds of formula (I) are compounds (34), (39), (47), (129), (199), (208), (246), (247), (248), (249), (252), and (276).

In general compounds of formula (I-a), defined a compounds of formula (I) wherein $A^1$ represents —CH$_2$—, can be prepared by N-alkylating an intermediate of formula (III) with an intermediate of formula (II) wherein W is an appropriate leaving group such as, for example, halo, e.g. chloro, bromo, iodo, or in some instances W may also be a sulfonyloxy group, e.g. methanesulfonyloxy, arylsulfonyloxy such as benzenesulfonyloxy or p-methylbenzenesulfonyloxy, trifluoromethanesulfonyloxy and the like reactive leaving groups. The reaction can be performed in a reaction-inert solvent such as, for example, acetonitrile, 2-pentanol, isobutanol, dimethyl acetamide, dichloromethane, chloroform, 1,2-dichloroethane or DMF, and optionally in the presence of a suitable base such as, for example, sodium carbonate, potassium carbonate, or triethylamine. Stirring may enhance the rate of the reaction. The reaction may conveniently be carried out at a temperature ranging between room temperature and the reflux temperature of the reaction mixture. Reaction rate and yield may be enhanced by microwave assisted heating.

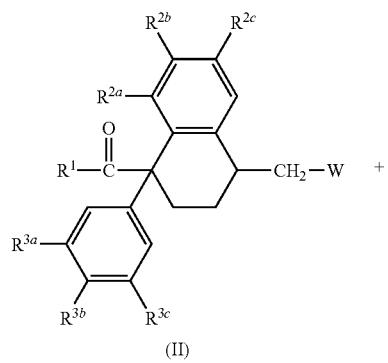

(II)

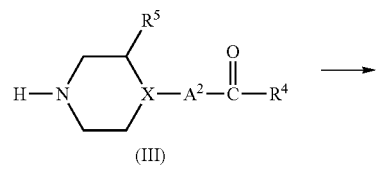

(III)

(I-a)

Compounds of formula (I-b), defined as compounds of formula (I) wherein radical $A^1$ represents —(C═O)—, can be prepared by reacting an intermediate of formula (V) with an intermediate of formula (IV), in at least one reaction-inert solvent and optionally in the presence of at least one suitable coupling reagent such as those described on pages 275-330 of "Solid-Phase Synthesis: A Practical Guide" by S. Kates and F. Albericio, Marcel Dekker, Inc., 2000, (ISBN 0-8247-0359-6) and/or a suitable base such as sodium carbonate, potassium carbonate, cesium carbonate, triethylamine, N,N-diisopropylethylamine or N-methylmorpholine, the said process further optionally comprising converting a compound of formula (I-b) into an addition salt thereof, and/or preparing stereochemically isomeric forms thereof. Reaction rate and yield may be enhanced by microwave assisted heating.

(IV)

(V)

(I-b)

The intermediate of formula (IV) may conveniently be converted into an acyl halide derivative by reacting it with e.g. thionyl chloride, oxalyl bromide, oxalyl chloride, phosgene, phosphorus trichloride or phosphorus tribromide, before addition of the intermediate of formula (V) and the suitable base.

It may also be convenient to activate the carboxylic acid of formula (IV) by adding an effective amount of a reaction promoter. Non-limiting examples of such reaction promoters include carbonyldiimidazole, diimides such as N,N'-dicyclohexyl-carbodiimide or 1-(3-dimethylaminopropyl)-3-ethyl-carbodiimide, and functional derivatives thereof. In case a chirally pure reactant of formula (IV) is used, a fast and enantiomerization-free reaction of the intermediate of formula (IV) with the said intermediate (V) may be performed in the further presence of an effective amount of a compound such as hydroxybenzotriazole (HOBT), benzotriazolyloxy-tris (dimethylamino)-phosphonium hexafluorophosphate, tetrapyrrolidinophosphonium hexafluorophosphate, bromot-ripyrrolidinophosphonium hexafluorophosphate, or a functional derivative thereof, such as disclosed by D. Hudson, *J. Org. Chem.* (1988), 53:617. Or the intermediate of formula (IV) may conveniently be converted into an acyl halide derivative by reacting it with e.g. thionyl chloride, oxalyl bromide, oxalyl chloride, phosgene, phosphorus trichloride or phosphorus tribromide, before addition of the intermediate of formula (V) and the suitable base.

Intermediates of formula (XVII), wherein the substituents $R^{2a}$, $R^{2b}$, $R^{2c}$, $R^{3a}$, $R^{3b}$, $R^{3c}$, $R^4$, $R^5$, $A^1$, $A^2$, and X are as defined for compounds of formula (I), can be converted into compounds of formula (I-c), defined as compounds of formula (I) wherein $R^1$ represents $NR^7R^8$, by art-known N-acylation methods using H—$NR^7R^8$ as the reagent.

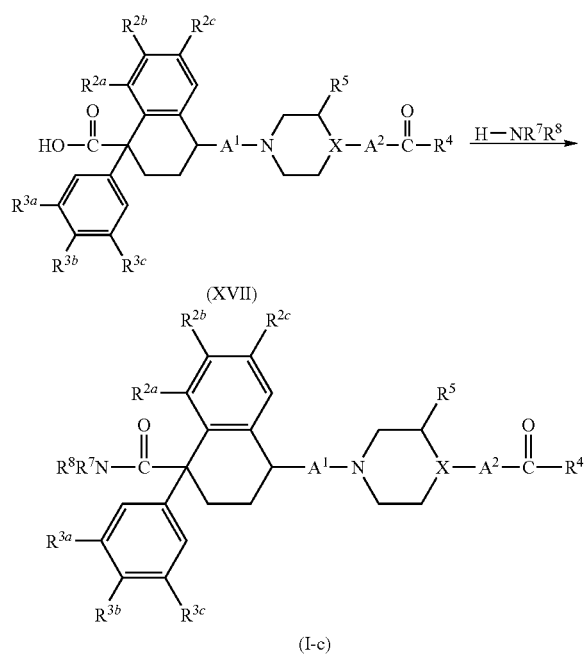

Also compounds of formula (I) wherein $R^1$ is $OR^9$ and $R^9$ is $C_{1-6}$alkyl can be converted into compounds of formula (I) wherein $R^1$ is $OR^9$ and $R^9$ is hydrogen by hydrolysis under acidic conditions. Compounds of formula (I) wherein $R^1$ is $OR^9$ and $R^9$ is $C_{3-8}$alkenyl can be converted into compounds of formula (I) wherein $R^1$ is $OR^9$ and $R^9$ is hydrogen by art-known reduction procedures such as, e.g. treatment with sodiumborohydride in the presence of tetrakis(triphenylphosphine)palladium in a suitable solvent such as e.g. THF. Compounds of formula (I) wherein $R^1$ is $OR^9$ and $R^9$ is protective group such as allyl; benzyl or tert-butyl, can be converted into compounds of formula (I) wherein $R^1$ is $OR^9$ and $R^9$ is hydrogen by art-known deprotection methods such as palladium mediated hydrogenolysis, acid and base catalysed deprotection, or any method described in "Protective Groups in Organic Synthesis" by T. W. Greene and P. G. M. Wuts, Wiley-Interscience; 3 edition (May 15, 1999) (ISBN 0471160199).

Intermediates of formula (XIII), defined as intermediates of formula (IV) wherein $R^1$ represents $OR^9$, $R^{2a}=R^{3a}$, $R^{2b}=R^{3b}$ and $R^{2c}=R^{3c}$, can be prepared as outlined below.

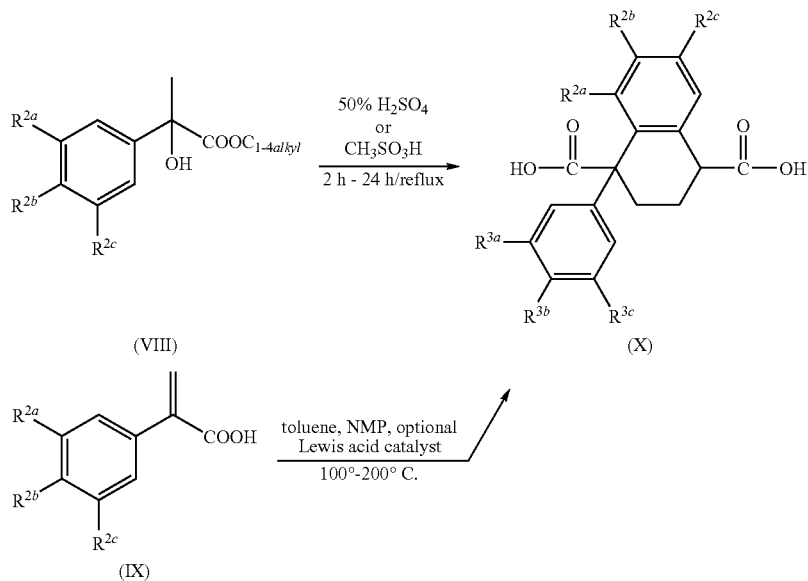

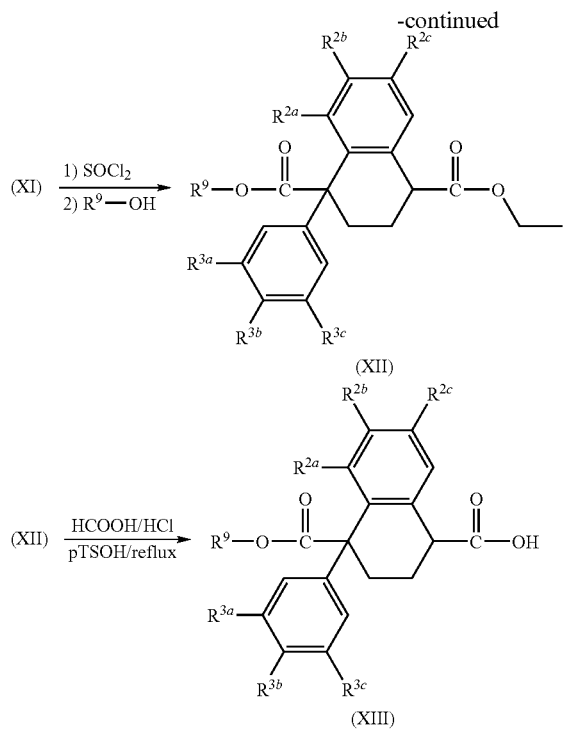

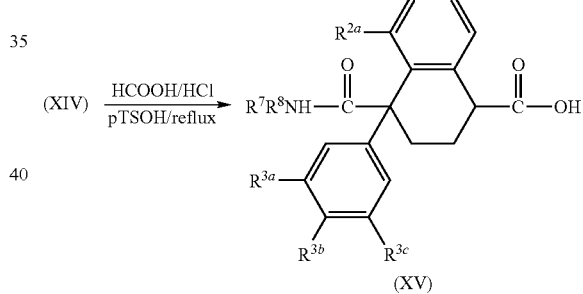

Intermediates of formula (XV) can be prepared as outlined below. The intermediates of formula (XV) are intermediates of formula (IV) wherein $R^1$ represents $NR^7R^8$.

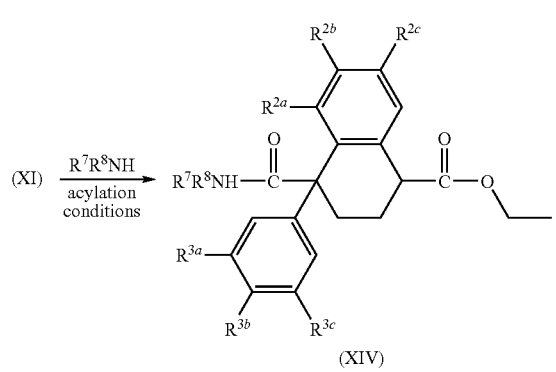

Intermediates of formula (II) can be prepared as outlined below. Intermediates of formula (II-a) are defined as intermediates of formula (II) wherein $R^1$ represents $NR^7R^8$ and intermediates of formula (II-b) are defined as intermediates of formula (II) wherein $R^1$ represents $OR^9$.

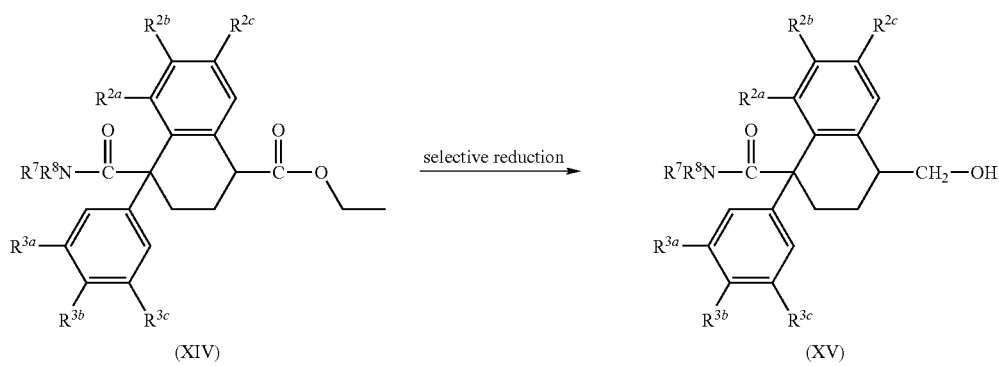

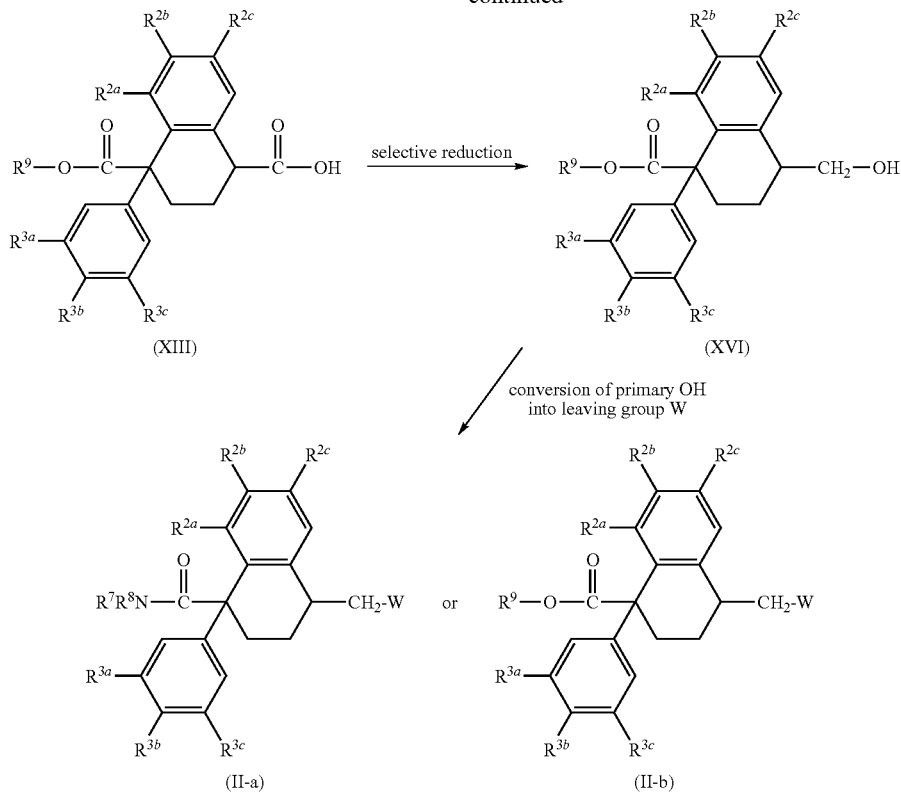

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable salts and stereoisomeric forms thereof possess favourable apoB secretion and MTP inhibiting activity and concomitant lipid lowering activity. Therefore the present compounds of formula (I) are useful as a medicine especially in a method of treating patients suffering from hyperlipidemia, obesity, atherosclerosis or type II diabetes. Subsequently the present compounds may be used for the manufacture of a medicine for treating disorders caused by an excess of very low density lipoproteins (VLDL) or low density lipoproteins (LDL), and especially disorders caused by the cholesterol associated with said VLDL and LDL. In particular the present compounds may be used for the manufacture of a medicament for the treatment of hyperlipidemia, obesity, atherosclerosis or type II diabetes.

The principal mechanism of action of the compounds of formula (I) appears to involve inhibition of MTP (microsomial triglyceride transfer protein) activity in hepatocytes and intestinal epithelial cells, resulting in decreased VLDL and chylomicron production, respectively. This is a novel and innovative approach to hyperlipidemia, and is expected to lower LDL-cholesterol and triglycerides through reduced hepatic production of VLDL and intestinal production of chylomicrons.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylomicronaemia syndrome, familial hypertriglyceridaemia. The present compounds may also be used to prevent or treat patients suffering from obesitas or from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of the utility of the compounds of formula (I), it follows that the present invention also provides a method of treating warm-blooded animals, including humans, (generally called herein patients) suffering from disorders caused by an excess of very low density lipoproteins (VLDL) or low density lipoproteins (LDL), and especially disorders caused by the cholesterol associated with said VLDL and LDL. Consequently a method of treatment is provided for relieving patients suffering from conditions, such as, for example, hyperlipidemia, obesity, atherosclerosis or type II diabetes.

Apo B-48, synthetized by the intestine, is necessary for the assembly of chylomicrons and therefore has an obligatory role in the intestinal absorption of dietary fats. The present invention provides compounds which are acting as selective MTP inhibitors at the level of the gut wall.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

The compounds of formula (I) may be used in conjunction with other pharmaceutical agents, in particular the pharmaceutical compositions of the present invention may further comprise at least one additional lipid-lowering agent, thus leading to a so-called combination lipid-lowering therapy. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors, CB-1 antagonists, cholesterol absorption inhibitors such as ezetimibe, and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the biotransformation of hydroxymethylglutaryl-coenzyme A to mevalonic acid as catalyzed by the enzyme HMG-CoA reductase. Such "HMG-CoA reductase inhibitors" are, for example, lovastatin, simvastatin, fluvastatin, pravastatin, rivastatin, and atorvastatin.

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetyl-coenzyme A, catalyzed by the enzyme HMG-CoA synthase Any HMG-CoA reductase gene expression inhibitor may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly or may be biotransformed into compounds having the above-mentioned attributes by one or more enzymes in the cholesterol biosynthetic cascade or may lead to accumulation of a metabolite having the above-mentioned activities.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL.

Any ACAT inhibitor may be used as the second compound in the combination therapy aspect of this invention. The term "ACAT inhibitor" as used herein, unless otherwise stated, refers to a compound which inhibits the intracellular esterification of dietary cholesterol by the enzyme acyl CoA:cholesterol acyltransferase.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase.

Those of skill in the treatment of hyperlipidemia will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 5 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 350 mg, more particularly from about 1 to about 200 mg, of the active ingredient per unit dosage form.

The exact dosage and frequency of administration depends on the particular compound of formula (I) used, the particular condition being treated, the severity of the condition being treated, the age, weight and general physical condition of the particular patient as well as the other medication (including the above-mentioned additional lipid-lowering agents), the patient may be taking, as is well known to those skilled in the art. Furthermore, said effective daily amount may be lowered or increased depending on the response of the treated patient and/or depending on the evaluation of the physician prescribing the compounds of the instant invention. The effective daily amount ranges mentioned hereinabove are therefore only guidelines.

EXPERIMENTAL PART

In the procedures described hereinafter the following abbreviations were used: "DCM" stands for dichloromethane; "DMA" means N,N-dimethyl-acetamide, "DMF" means N,N-dimethyl-formamide; "TFA" stands trifluoroacetic acid, "THF" stands for tetrahydrofuran; "EtOH" stands for ethanol; "MeOH" stands for methanol and "DIPE" stands for diisopropylether.

N-cyclohexylcarbodiimide N-methyl polystyrene HL resin (1.90 mmol/g) is a Novabiochem 01-64-021 resin; polymer-supported carbonate base [polystyrylmethyl]-trimethyl ammonium bicarbonate resin (5.8 mmol/g) is a Novabiochem 01-64-041 resin; polystyrene-carbodiimide resin (1.90 mmol/g) is a Novabiochem 01-64-024 resin; polystyrene-N-methyl morpholine HL (3.80 mmol/g) resin is a Novabiochem 01-64-0211 resin; polystyrene-bicarbonate (5.8 mmol/g) resin is a Novabiochem-01-064-0419 resin. The Novabiochem resins can be obtained from Calbiochem-Novabiochem AG, Weidenmattweg 4, CH-4448 Läufelfingen, Switzerland. PS-carbodiimide resin (polystyrene resin-bound N-cyclohexylcarbodiimide) and PS-isocyanate resin (1% crosslinked polystyrene-co-divinylbenzene resin with benzylisocyanate functionality) were obtained from Argonaut (Biotage), New Road, Hengoed, Mid Glamorgan, UK.

Extrelut™ is a product of Merck KgaA, Darmstadt, Germany, and is a short column comprising diatomaceous earth. Chiralcel OD, OJ and AD are chiral stationary phase column materials purchased from Daicel Chemical Industries, Ltd., in Japan. Prochrom® Dynamic Axial Compression column are available from Novasep S.A.S., Boulevard de la Moselle, B.P. 50 F-54340 Pompey, France.

The absolute stereochemical configuration for some of the compounds was determined using vibrational circular dichroism (VCD). A description on the use of VCD for the determination of absolute configuration can be found in Dyatkin A. B. et. al, *Chirality*, 14:215-219 (2002).

A. Synthesis of the Intermediates

Example A.1

Preparation of

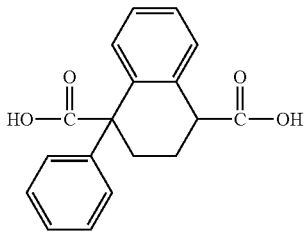

intermediate (1)

2-Hydroxy-2-phenyl-propionic acid methyl ester (0.1 mol) was added to a solution of sulfuric acid (300 ml) in water (250 ml) and the reaction mixture was stirred at 100° C. for 20 hours. The precipitate was filtered off and dissolved in DCM (600 ml) and washed with water and brine. The organic layer was separated, dried, filtered and the solvent was evaporated until a volume of 100 ml. The precipitate was filtered off and dried, yielding 9 g of intermediate (1).

Example A.2

Preparation of

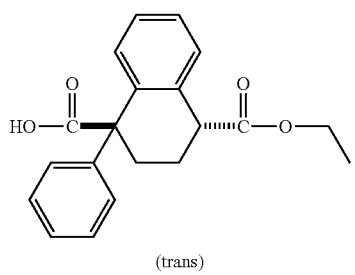

intermediate (2)

(trans)

A mixture of intermediate (1) (1.327 mol) in dry ethanol (2360 ml) was stirred and concentrated sulfuric acid (4 ml) was added. The reaction mixture was refluxed for 22 hours under nitrogen and then the reaction mixture was allowed to cool overnight to room temperature. The resulting precipitate was filtered off, washed with dry ethanol and dried, yielding 120 g of intermediate (2) (mp. 186-187° C.).

The ethanol-layers were combined and evaporated, and the resulting residue was dissolved in DCM (1450 ml), washed with an aqueous NaHCO₃ solution (twice with 500 ml), dried and the solvent was evaporated. The residue was stirred in DIPE (680 ml) at a temperature of 50-55° C. and the residual DCM was distilled off and the concentrate was left to stand for more than 2 hours at room temperature. The resulting solids were filtered off, washed with DIPE (120 ml) and with pentane and then dried at 40° C., yielding another 103.2 g of intermediate (2) (mp. 187-188° C.).

Preparation of

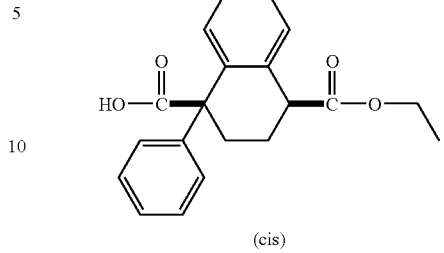

intermediate (3)

(cis)

The previous DIPE/pentane layers were evaporated and the residue was dissolved in dry acetonitrile (200 ml), then the solvent was evaporated again, yielding 166.3 g of intermediate (3) (mp. 75° C.).

Example A.3

Preparation of

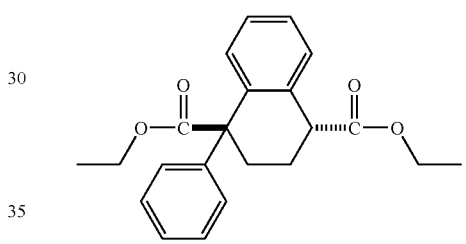

intermediate (4)

Intermediate (2) (0.03 mol) was stirred in chloroform (50 ml). Thionyl chloride (0.06 mol) was added and the reaction mixture was stirred and refluxed for 4 hours until gas evolution ceased. The reaction mixture was concentrated by evaporation of the solvent. Chloroform (200 ml) was added and the solvent was evaporated again, yielding a residue that was slowly added to dry ethanol (100 ml) which was cooled on an ice-water bath at ±5° C. The ice-bath was removed and reaction mixture was allowed to warm to room temperature. The reaction mixture was stirred for 4 hours at room temperature. The solvent was evaporated, yielding intermediate (4) (mp. 78-80° C.).

Intermediate (5) was prepared analogously but starting from intermediate (3).

Preparation of

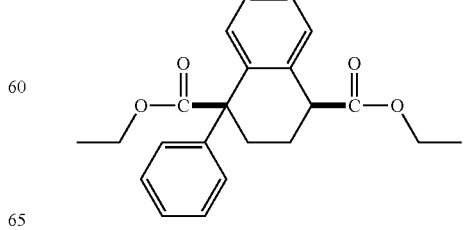

intermediate (5)

Example A.4

Preparation of

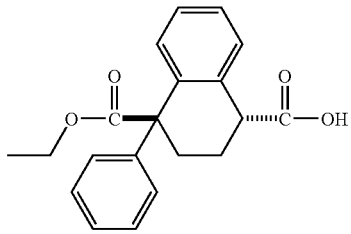

intermediate (6)

A mixture of intermediate (4) (0.0567 mol) and p-toluene sulfonic acid (1 g) was stirred and refluxed in a mixture of formic acid (500 ml) and concentrated HCl (125 ml) for 3 hours. The reaction mixture was concentrated by evaporation of the solvent, the residue was dissolved in DCM, washed with an aqueous NaHCO$_3$ solution and dried. The solvent was evaporated and the residue was purified by column chromatography on silica (eluent: ethyl acetate/hexane 1/9), yielding intermediate (6) (mp. 115-118° C.).

Intermediate (7) (mp. 133-135° C.) was prepared analogously but starting from intermediate (5).

Preparation of

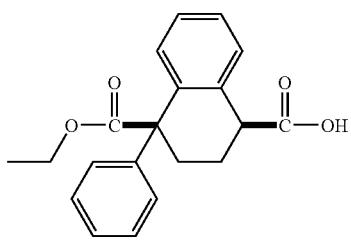

intermediate (7)

Example A.5 a) Preparation of

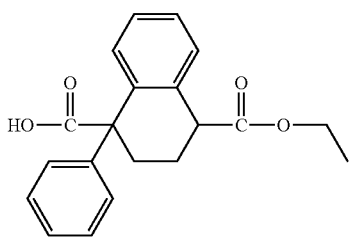

intermediate (8)

Intermediate (1) (0.1 mol) was dissolved in ethanol (500 ml), H$_2$SO$_4$ was added (5 ml) and the reaction mixture was stirred and refluxed overnight, then cooled and the ethanol was evaporated. The residue was dissolved in DCM, washed with water (2×200 ml) and brine (100 ml). The organic layer was dried, the solvent was concentrated and the residue was triturated with DIPE, filtered and dried, yielding 18 g of intermediate (8).

b) Preparation of

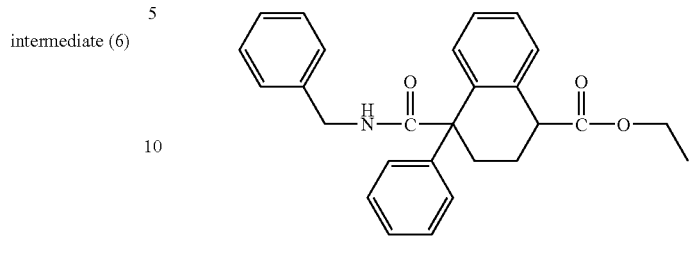

intermediate (9)

Thionyl chloride (0.255 mol) was added to a solution of intermediate (8) (0.03409 mol) in trichloromethane (200 ml). The mixture was stirred and refluxed for 4 hours. The solvent was evaporated. The residue was dissolved in DCM (125 ml) under nitrogen flow. The mixture was cooled to −10° C. A solution of benzenamine (0.230 mol) in DCM (75 ml) was added dropwise at −10° C. under nitrogen flow. The mixture was stirred at room temperature overnight. The precipitate was filtered off, washed with 1M HCl (until pH<7), washed with water (until pH=7), washed with a saturated NaCl solution, dried, filtered and the solvent was evaporated. The obtained residue was purified by column chromatography over silica gel (eluent: (hexane/ethyl acetate 2/1)/CH$_2$Cl$_2$). The pure fractions were collected and the solvent was evaporated, yielding 10.244 g of intermediate (9).

c) Preparation of

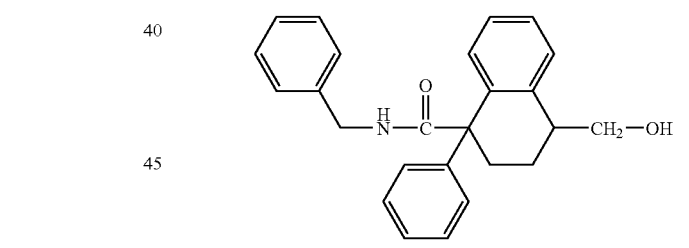

intermediate (10)

A solution of intermediate (9) (0.01985 mol) in dry THF (400 ml) was cooled to 0° C. under nitrogen flow. LiBH$_4$ (2M in THF) (0.1 mol) was added dropwise at 0° C. under nitrogen flow. The mixture was stirred for 15 minutes. Ethanol (100 ml) was added. The mixture was stirred at room temperature overnight. A HCl 1M (200 ml) solution was added. The mixture was extracted with ethyl acetate (500 ml). The organic layer was separated, washed with water (till pH=7), washed with a saturated NaCl solution, dried, filtered and the solvent was evaporated. The obtained residue was purified by column chromatography over silica gel (eluent: hexane/ethyl acetate 1/2). The pure fractions were collected and the solvent was evaporated. The residual fraction (6.62 g, 90%) was dried in vacuo at 60° C. over the weekend, yielding intermediate (10).

d) Preparation of

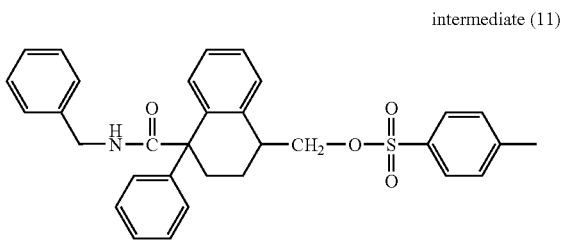

intermediate (11)

4-Methylbenzenesulfonyl chloride (0.024 mol) was added portionwise to a solution of intermediate (10) (0.00782 mol) in pyridine (75 ml) under nitrogen flow. The mixture was stirred at room temperature for 16 hours. The solvent was evaporated. The residue was dissolved in DCM (300 ml) and washed with water and brine. The organic layer was separated, washed with HCl (0.1M), washed with water (till pH=7), washed with a saturated NaCl solution, dried and the solvent was evaporated. The residue was dissolved in toluene. The solvent was evaporated twice and the obtained residue was purified by column chromatography over silica gel (eluent: hexane/ethyl acetate 2/1). The pure fractions were collected and the solvent was evaporated, yielding 3.57 g of intermediate (11).

Example A.6 a) Preparation of

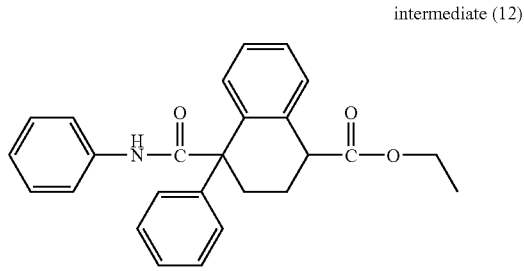

intermediate (12)

Thionyl chloride (0.01551 mol) was added to a solution of intermediate (8) (0.0031 mol) in trichloromethane (20 ml). The mixture was stirred at 80° C. for 4 hours. The solvent was evaporated. The residue was dissolved in DCM (20 ml). The mixture was cooled to −10° C. A solution of benzenamine (0.05487 mol) in DCM (20 ml) was added dropwise at −10° C. under nitrogen flow. The mixture was stirred at room temperature for 15 hours. The precipitate was filtered off. The filtrate was washed three times with water (20 ml), washed with a saturated NaCl solution, dried, filtered and the solvent was evaporated. The residue was dissolved in 1M HCl (100 ml). The mixture was extracted with DCM, washed several times with water and washed with a saturated NaCl solution. The organic layer was dried, filtered and the solvent was evaporated. The obtained fraction was treated with DIPE. The precipitate was filtered off and dried, yielding 0.6355 g of intermediate (12).

b) Preparation of

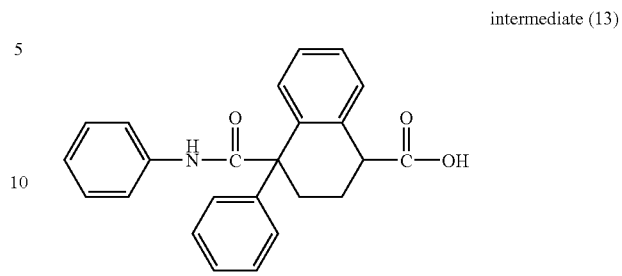

intermediate (13)

A mixture of intermediate (12) (0.00439 mol) in a 36% HCl solution (50 ml) was stirred and refluxed overnight. The precipitate was filtered off. The residue was stirred in DCM (a few ml) for 1 hour. Hexane was added and the mixture was stirred. The precipitate was filtered off and dried, yielding 1.2 g of intermediate (13).

Example A.7

Preparation of

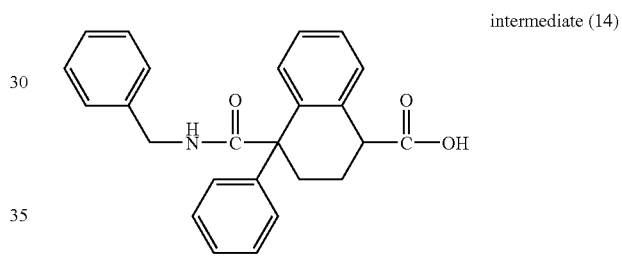

intermediate (14)

A mixture of intermediate (9) (0.00469 mol) in a 36% HCl solution (40 ml) was stirred and refluxed overnight. The solvent was evaporated. The residue was dried and was then stirred in NaOH 1M. The mixture was extracted twice with DCM (2×20 ml) and separated into its layers. The aqueous layer was acidified with a HCl solution and extracted with DCM. The combined organic layer was washed with a saturated NaCl solution, dried, filtered and the solvent was evaporated. The residue was dried in vacuo, yielding 1.07 g of intermediate (14).

Example A.8 a) Preparation of

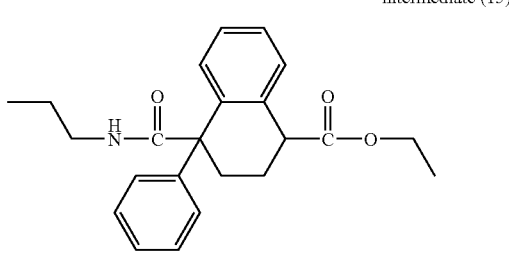

intermediate (15)

Thionyl chloride (0.0426 mol) was added to a solution of intermediate (8) (0.00852 mol) in trichloromethane (50 ml).

The mixture was stirred at 80° C. for 4 hours. The solvent was evaporated. The residue was dissolved in dry DCM (60 ml). The mixture was cooled to −10° C. A mixture of 1-propanamine (0.1338 mol) in dry DCM (50 ml) was added dropwise at −10° C. under nitrogen flow. The mixture was stirred overnight while the temperature was brought to room temperature and then washed with water, 0.5M HCl (20 ml) and water. The organic layer was separated, washed with a saturated NaCl solution, dried, filtered and the solvent was evaporated. This obtained fraction was purified by column chromatography over silica gel (eluent: DCM 100%). The pure fractions were collected and the solvent was evaporated. The residue was suspended in DIPE. The precipitate was filtered off and dried, yielding 2.694 g of intermediate (15).

b) Preparation of

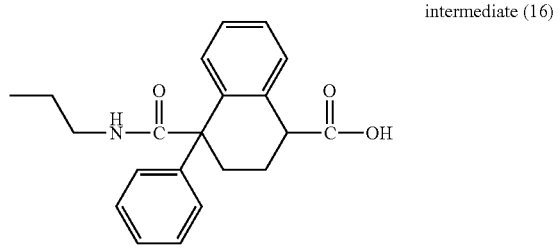

intermediate (16)

A mixture of intermediate (15) (0.00548 mol) in a HCl solution (36%, 50 ml) was stirred and refluxed for 3 hours. More HCl solution (36%, 20 ml) was added. The mixture was stirred and refluxed overnight. The precipitate was filtered off and dried, yielding 0.516 g of intermediate (16).

Example A.9 a) Preparation of

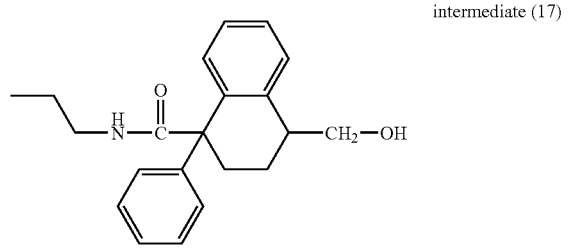

intermediate (17)

Reaction under nitrogen atmosphere. Intermediate (15) (0.00478 mol) was dissolved in dry THF (150 ml) and cooled to 0° C. LiBH$_4$ (2M in THF) (0.028 mol) was added at 0° C. The mixture was stirred for 15 minutes. Ethanol (20 ml) was added and the reaction mixture was stirred overnight at room temperature. 1 M HCl (100 ml) was added. Ethyl acetate (125 ml) was added and the layers were separated. The organic layer was washed with water, once with brine, dried, filtered and the solvent was evaporated, yielding 1.5 g of intermediate (17).

b) Preparation of

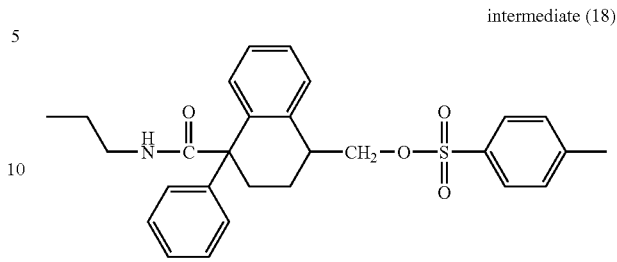

intermediate (18)

4-Methylbenzenesulfonyl chloride (0.0418 mol) was added portionwise to a solution of intermediate (17) (0.00836 mol) in pyridine (75 ml). The mixture was stirred at room temperature for 20 hours. The solvent was evaporated. The residue was dissolved in DCM (250 ml). The organic layer was separated, washed with HCl (0.1M), washed with water (till pH=7), washed with a saturated NaCl solution, dried and the solvent was evaporated. The residue was dissolved in toluene (2×20 ml). The solvent was evaporated and the residual fraction was purified by column chromatography over silica gel (eluent: hexane/ethyl acetate 2:1). The pure fractions were collected and the solvent was evaporated. The obtained fraction was suspended in DIPE. The precipitate was filtered off and dried, yielding 3.305 g of intermediate (18).

Example A.10 a) Preparation of

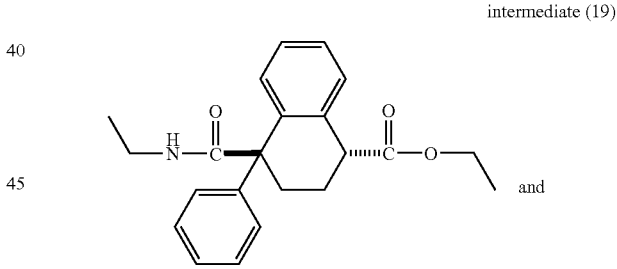

intermediate (19)

trans and

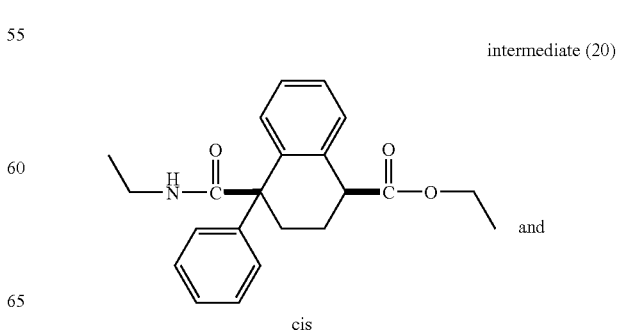

intermediate (20)

and cis

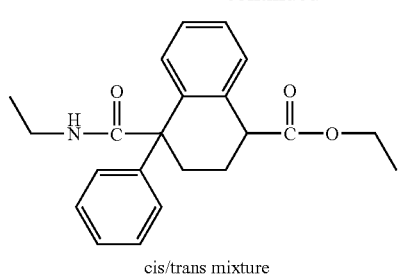

intermediate (21)

cis/trans mixture

A solution of intermediate (8) (0.14 mol) in DCM (600 ml) and chloroform (600 ml) was stirred at 20° C. under nitrogen, then thionyl chloride (79 ml) was added over 5 minutes and the reaction mixture was stirred and refluxed for 4 min. The mixture was cooled to 20° C. and the solvent was evaporated. The residue was dissolved in THF (1000 ml) and the solution was cooled to −5° C. under nitrogen, then a solution of ethanamine (1.4 mol, 70% aqueous solution) in THF (100 ml) was added dropwise while keeping the temperature below 0° C. The mixture was then warmed to 20° C. and stirred for 2 hours. Ether (1000 ml) was added and the organic layer was separated, then washed with water (3 times 400 ml) and with brine (400 ml). The mixture was dried and the solvent was evaporated, yielding intermediate (21) which can be separated by chromatography in the trans-isomer intermediate (19) and the cis-isomer intermediate (20).

b) Preparation of

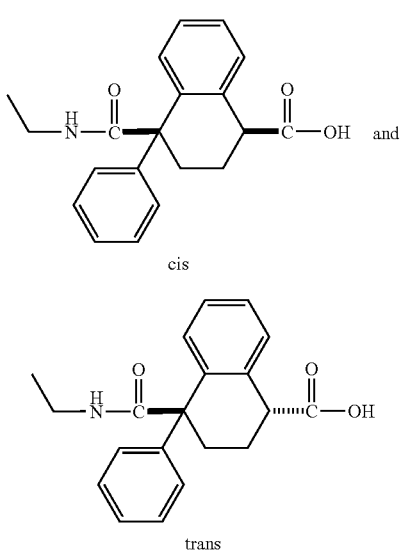

intermediate (22)

cis and intermediate (23)

trans

A suspension of intermediate (21) (0.043 mol) in a 37% concentrated HCl solution (200 ml) was stirred and refluxed overnight, then the HCl solution (±100 ml) was distilled off and the residue was diluted with water (400 ml). The resulting mixture was extracted with DCM (2 times 200 ml) and the combined extracts were dried. The solvent was evaporated and the solid residue was purified by flash column chromatography (eluent: first ether/hexane 1/1, then ether/hexane 1/0). The product fractions were collected to give a mixture of cis/trans-isomers which was purified by flash column chromatography (eluent 1: ether; eluent 2: ethyl acetate/petroleum ether 80/20; eluent 3: ethyl acetate). The desired product fractions were collected and the solvent was evaporated. The residue was washed with ether (2 times 100 ml), to give solid residue (I) and ether-washes (II).

Residue (I) (9.8 g) was crystallised from ethyl acetate and the resulting crystals were collected, to give Residue (Ia) (4.6 g 'TRANS'-isomer, mp.: 182-187° C.).

The ether-washes (II) were purified by flash column chromatography (eluent: DCM/ethyl acetate 70/30) and then further purified by flash column chromatography (eluent: DCM/ethyl acetate 80/20). Two product fractions were collected and the solvent was evaporated. Both residual fractions were crystallised from ethyl acetate and collected. One obtained fraction, 4.9 g of Residue (IIa), was combined with Residue (Ia), yielding 9.5 g of intermediate (23) (mp.: 182-187° C.). The other obtained fraction, 2: 7 g of Residue (IIb) was collected, yielding intermediate (22) (mp.: 179-182° C.).

Example A.11 a) Preparation of

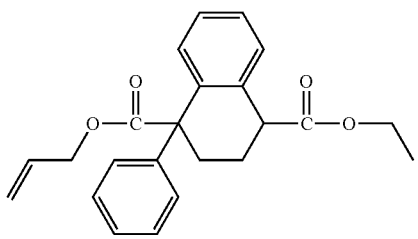

intermediate (24)

A solution of intermediate (8) (0.15 mol) in NaHCO$_3$ 0.15M in water (200 ml) was stirred and tricaprylylmethylammonium chloride (Aliquat 336®) (0.15 mol) and 3-bromo-1-propene (0.75 mol) in DCM (200 ml) was added, then the reaction mixture was stirred for 4 days at 20° C. and the organic layer was separated. The aqueous layer was extracted with DCM (300 ml) and the combined organic layers were dried. The solvent was evaporated and the residue was stirred in hexane (500 ml), then cooled to 0° C. The resulting precipitate was filtered off, washed with hexane and dried overnight at 60° C., yielding 46 g of intermediate (24).

b) Preparation of intermediate (25)

and trans intermediate (26)

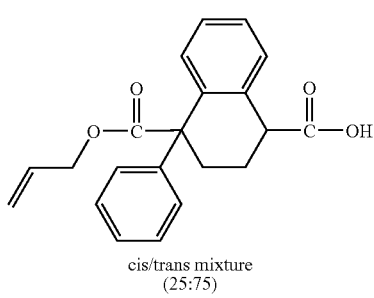

cis/trans mixture
(25:75)

A 28% concentrated HCl solution (100 ml) and 4-methylbenzenesulfonic acid (0.7 g) were added to a solution of intermediate (24) (0.13 mol) in formic acid (400 ml), then the reaction mixture was stirred and refluxed for 6 hours. The solvent was evaporated and the residue was partitioned between DCM (300 ml) and a saturated aqueous $NaHCO_3$ solution (200 ml). The DCM-layer was separated, dried and the solvent was evaporated. The residue was triturated under ether to give Solid (I) and the mother layers were concentrated, then crystallised from ethyl acetate/hexane to give Solid (II). Solids (I) and (II) were combined and purified by flash column chromatography (eluent: $DCM/CH_3OH$ 95/5). The product fractions were collected, the solvent was evaporated and the residue was triturated under hexane. The recovered residue (9.5 g) was then triturated under ether and filtered off. One solid fraction was collected, yielding 7 g of intermediate (25) ('TRANS'-isomer, mp.: 138-139° C.) and the collected mother layers were concentrated, yielding 2 g of intermediate (26) ('CIS/TRANS'-mixture 25/75).

Example A.12 a) Preparation of intermediate (27)

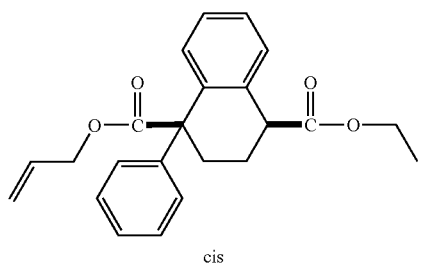

cis

A solution of intermediate (3) (0.0031 mol) and $NaHCO_3$ (0.0031 mol) in water (10 ml) and a mixture of tricaprylylmethylammonium chloride (Aliquat 336®) (0.0031 mol) and 3-bromo-1-propene (0.0031 mol) in DCM (10 ml) were stirred vigorously for 3 days. The reaction mixture was extracted with DCM, dried, concentrated and purified by flash column chromatography (eluent: $CH_3OH/CHCl_3$ 10/90). The pure product fractions were collected and the solvent was evaporated, yielding intermediate (27).

b) Preparation of intermediate (28)

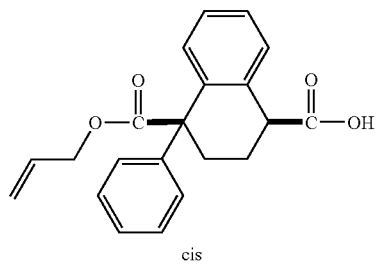

cis

A mixture of intermediate (27) (0.0165 mol) in formic acid (100 ml) and a concentrated HCl solution (50 ml) with methanesulfonic acid (catalytic quantity) was stirred and refluxed overnight, then the reaction mixture was cooled and the solvent was evaporated. The residue was dissolved in DCM, washed with a saturated $NaHCO_3$ solution, dried and the solvent was evaporated, yielding 1.81 g of intermediate (28).

Example A.13 a) Preparation of intermediate (29)

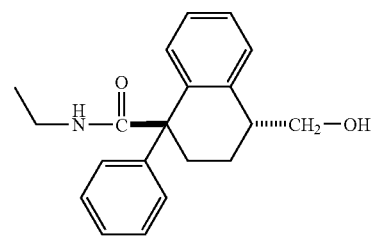

trans

A solution of intermediate (19) (0.0568 mol) in THF (800 ml) was cooled to 0° C. under nitrogen, then lithium bromide (0.17 mol) and sodium borohydride (0.17 mol) were added in one portion and the reaction mixture was stirred for 1 hour at 0° C. Ethanol (300 ml) was added and the mixture was stirred overnight at 20° C. HCl (1N, 100 ml) was added and the organic layer was separated, washed with brine and dried. The solvent was evaporated and the resulting residue was triturated under ether. A solid residue was then filtered off and crystallized from ether, yielding 16.3 g of intermediate (29) (mp. 122-129° C.).

b) Preparation of intermediate (30)

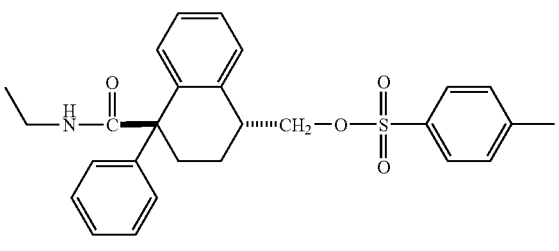

trans

A solution of intermediate (29) (0.0038 mol) and tosyl chloride (0.019 mol) in pyridine (35 ml) was stirred at room temperature (16° C.) for 20 hours, then the reaction mixture was poured out into ice-water (100 ml) and the mixture was stirred for 1 hour. The aqueous solution was extracted with DCM (3 times 50 ml), then the organic layers were combined, washed with brine, dried and the solvent was evaporated, yielding 0.9 g of intermediate (30) (mp. 130-132° C.).

Example A.14 a) Preparation of

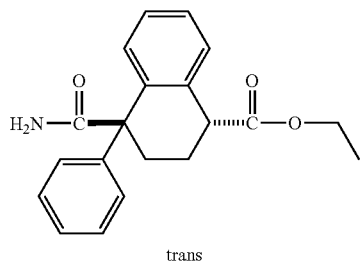

intermediate (31)

trans

Thionyl chloride (15 ml) was added to a suspension of intermediate (2) (0.05 mol) in DCM. The reaction mixture was stirred and refluxed for one hour. The solvent was evaporated. DCM (100 ml) was added. The solvent was evaporated. The residue was dissolved in DCM. Concentrated $NH_4OH$/$H_2O$ (100 ml) was added and the reaction mixture was stirred overnight. The organic layer was separated, dried, filtered and the solvent evaporated, yielding intermediate (31).

b) Preparation of

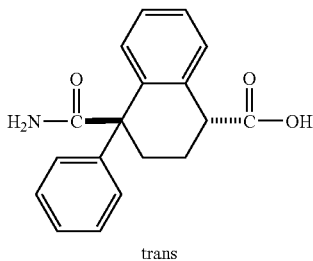

intermediate (32)

trans

A mixture of intermediate (31) (0.05 mol) in HCl concentrated (60 ml) and dioxane (60 ml) was stirred and refluxed for 2 hours. The mixture was cooled to room temperature. Water (200 ml) was added and stirring was continued for one hour. The precipitate was filtered off, washed with water and 2-propanol, then dried, yielding 13.1 g of intermediate (32).

Example A.15 a) Preparation of

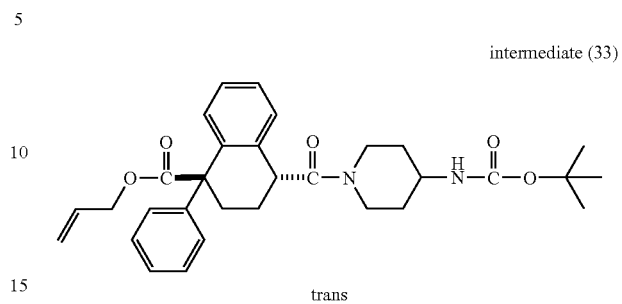

intermediate (33)

trans

Reaction under nitrogen atmosphere. A mixture of 4-(tert-butyloxycarbonylamino)-piperidine (0.0345 mol), intermediate (25) (0.0345 mol), 1-hydroxy-1H-benzotriazole (HOBT) (0.0517 mol) and N'-(ethylcarbonimidoyl)-N,N-dimethyl-1,3-propanediamine (0.0517 mol) in DCM (1000 ml) was stirred for 4 hours at room temperature. The solvent was evaporated and ethyl acetate (400 ml) was added to the residue. The organic solution was washed with water, 1N HCl (300 ml), an aqueous $NaHCO_3$ solution (300 ml), brine (300 ml), then dried, filtered and the solvent was evaporated. The residue was purified by column chromatography over silica gel (eluent: hexane/ethyl acetate 2/1). The product fractions were collected and the solvent was evaporated, yielding 5.16 g of intermediate (33).

b) Preparation of

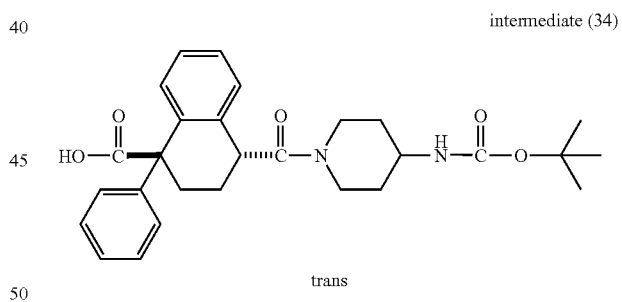

intermediate (34)

trans

A solution of intermediate (33) (4.5 g, 0.0087 mol) and triphenyl phosphine (2.28 g, 0.0087 mol) in dry acetonitrile (60 ml) was stirred at room temperature under nitrogen atmosphere. Pyrrolidine (0.75 ml) and tetrakis(triphenylphosphine)palladium (0.5 g, 5 mol %) were added and the reaction mixture was stirred for 18 hours at room temperature. Ethyl acetate (80 ml) was added and the mixture was extracted with a saturated aqueous $NaHCO_3$ solution (4×100 ml). The combined base extracts were acidified with 1 N HCl, then extracted with DCM (3×150 ml). The combined organic layers were dried, filtered and the solvent was evaporated, yielding 2.82 g of intermediate (34).

c) Preparation of

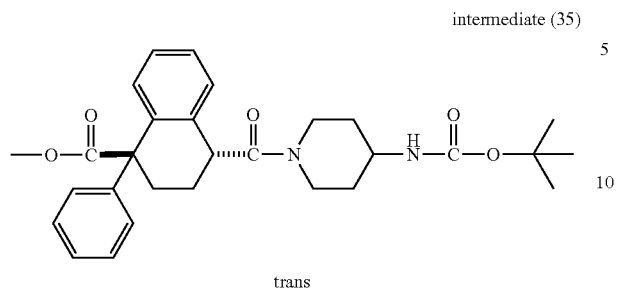

intermediate (35)

trans

A mixture of intermediate (34) (0.001 mol), potassium carbonate (0.003 mol) and iodomethane (0.065 ml) in DMF (6 ml) was stirred for 92 hours at room temperature. Then the reaction mixture was poured out into water (15 ml) and the resulting solids were filtered off, which were purified by Biotage flash chromatography (eluent 1: DCM; eluent 2: hexane/ethyl acetate 4/1→3/1→2/1→1/1→1/2). The pure fractions were collected and the solvent was evaporated. The residue was stirred overnight in hexane, yielding intermediate (35) (mp. 190-191° C.; trans).

Example A.16 a) Preparation of

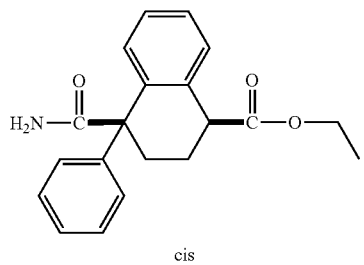

intermediate (36)

cis

Intermediate (3) (0.05 mol) was dissolved in DCM (100 ml). Thionyl chloride (0.2 mol) was added and the mixture was stirred. A few drops of DMF were added and the reaction mixture was stirred and refluxed for one hour. The solvent was evaporated. DCM was added, then evaporated again. The residue was dissolved in DCM, stirred and concentrated NH$_4$OH/water 1/1 (50 ml; 1/1) was added. The reaction mixture was stirred for 2 hours. The layers were separated. The organic layer dried, filtered and the solvent evaporated, yielding 16 g of intermediate (36).

b) Preparation of

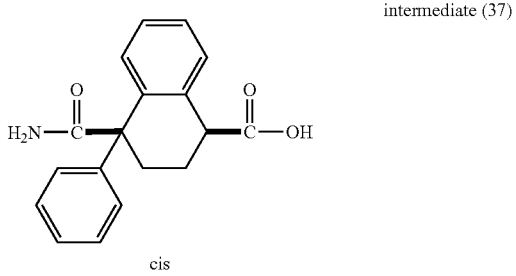

intermediate (37)

cis

A mixture of intermediate (36) (0.05 mol) in HCl concentrated (60 ml) and dioxane (60 ml) was stirred and refluxed for 2 hours. Water (200 ml) was added. The mixture was cooled. The precipitate was filtered off, washed with water and 2-propanol, then dried, yielding 13.2 g of intermediate (37).

Example A.17

Preparation of

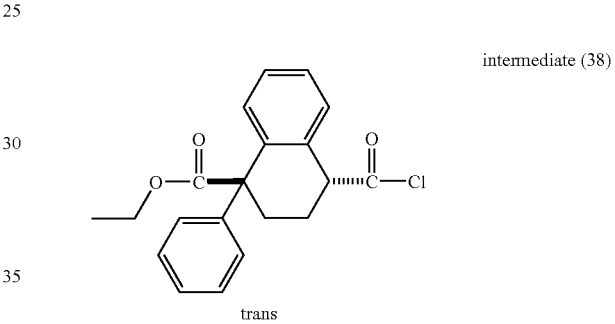

intermediate (38)

trans

Intermediate (6) (0.154 mol) was stirred in DCM (200 ml) and DMF (5 drops) were added, followed by thionyl chloride (37 ml). The mixture was stirred and refluxed for 1 hour and then the solvent was evaporated. Fresh DCM (100 ml) was added and the solvent was evaporated two times, yielding intermediate (38).

Example A.18 a) Preparation of

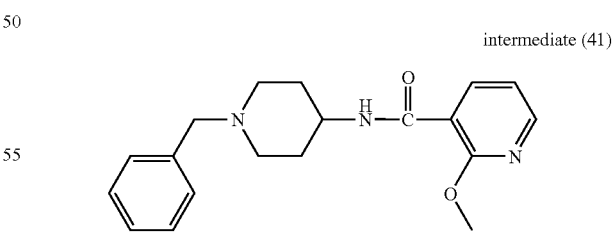

intermediate (41)

First 2-methoxy-3-pyridinecarboxylic acid was turned into its acid chloride by refluxing the carboxylic acid in DCM (100 ml, p.a.) and thionyl chloride (7 ml). The solvent was evaporated. To a mixture of this residue (0.024 mol) in an aqueous saturated NaHCO$_3$ solution (75 ml), a mixture of 1-(phenylmethyl)-4-piperidinamine (0.024 mol) in DCM (150 ml) was added. The reaction mixture was stirred for 2 hours. The layers were separated. The separated organic layer was dried (MgSO$_4$), filtered and the solvent was evaporated. The residue was purified by column chromatography (CH$_3$OH/CH$_2$Cl$_2$ 1/99). The desired fractions were collected and the solvent was evaporated. The residue was triturated from diisopropyl ether, yielding 7.38 g of intermediate (41).

b) Preparation of intermediate (42)

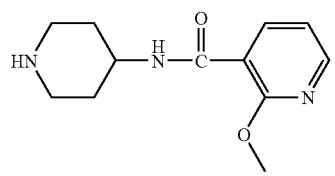

A mixture of intermediate (41) (7 g, 0.021 mol) in methanol (50 ml) was hydrogenated at room temperature with palladium-on-carbon 10% (1 g) as a catalyst. After uptake of hydrogen (1 equivalent), the catalyst was filtered off and the filtrate was evaporated. A small amount of HCl in 2-propanol was added resulting in a white solid, yielding 4.08 g of intermediate (42).

Example A.19 a) Preparation of intermediate (43)

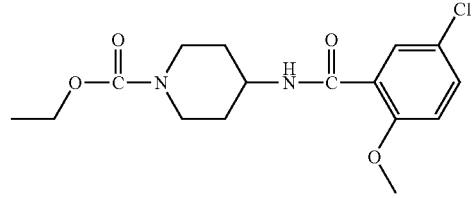

A mixture of 1-(ethoxycarbonyl)-4-aminopiperidine (0.065 mol), triethylamine (0.09 mol) in toluene (160 ml) was stirred on an ice-bath. A solution of 2-methoxy-5-chlorobenzoyl chloride (0.072 mol) dissolved in toluene (40 ml) was added dropwise. The reaction mixture was stirred overnight and water was added. The organic layer was separated, washed twice with water, dried and evaporated. The solid residue was crystallised from DIPE, yielding 16.2 g of intermediate (43) (mp. 113.2° C.).

b) Preparation of intermediate (44)

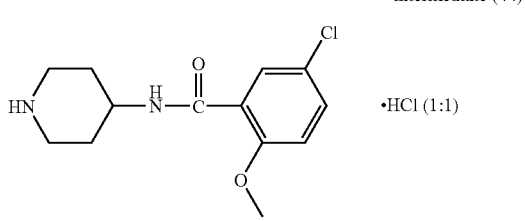

·HCl (1:1)

A mixture of intermediate (43) (0.044 mol), potassium hydroxide (12 g), isopropanol (150 ml) and water (1 ml) was stirred and heated under reflux for 3 hours. The reaction mixture was evaporated and the residue was dissolved in a mixture of water and chloroform. The organic layer was separated, washed twice with water, dried and evaporated. The residue was dissolved in methyl isobutyl ketone and and acidified by adding isopropanol saturated with HCl. The resulting precipitate was filtered off and dried, yielding 9.1 g of intermediate (44).

Intermediate (45) was prepared analogously but starting from cis-4-amino-3-methoxy-piperidine-1-carboxylic acid ethyl ester and 2-methoxy-benzoic acid.

intermediate (45)

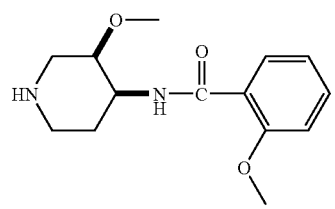

·HCl (1:1)

Example A.20

Preparation of intermediate (46)

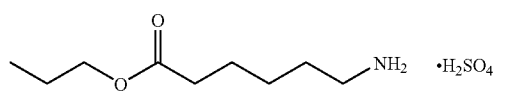

6-Amino-n-hexanoic acid (0.01 mol) was dissolved in propanol (30 ml) and sulfuric acid (1 ml) was added and the reaction mixture was refluxed for 48 hours. The solvent was evaporated, yielding 2.1 g of intermediate (46).

Example A.21

Preparation of intermediate (47)

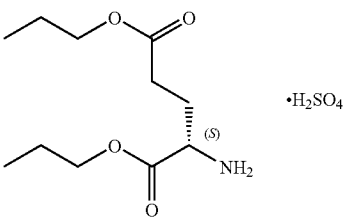

·H$_2$SO$_4$

A mixture of (S)-2-aminopentanedioic acid (0.0068 mol) and sulfuric acid (0.00816 mol) in propanol (40 ml) was refluxed for 48 hours. The solvent was evaporated and the residue was dried, yielding intermediate (47).

Example A.22

Preparation of

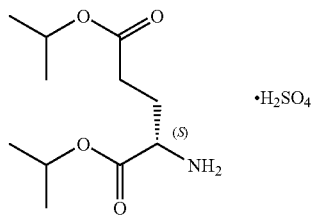

intermediate (48)

Sulfuric acid (0.00816 mol) was added to a solution of (S)-2-aminopentanedioic acid (0.0136 mol) in isopropanol (40 ml) and refluxed for 48 hours. The solvent was evaporated, yielding intermediate (48).

Example A.23

Preparation of

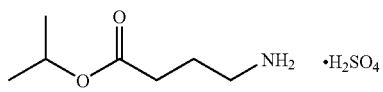

intermediate (49)

Sulfuric acid (0.012 mol) was added to a solution of 4-aminobutanoic acid (0.01 mol) in isopropanol (30 ml) and refluxed for 48 hours. The solvent was evaporated, yielding intermediate (49).

Example A.24 a) Preparation of

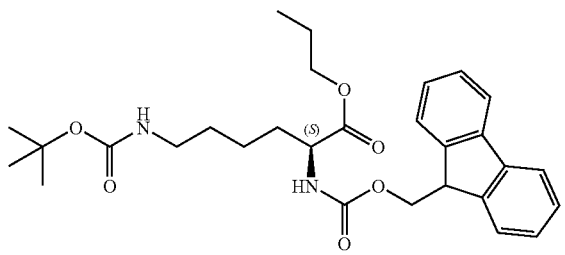

intermediate (50)

$N^6$-[(1,1-dimethylethoxy)carbonyl]-$N^2$-[(9H-fluoren-9-ylmethoxy)carbonyl]-L-lysine (5 g) was dissolved in methanol (100 ml, dry) and then cesium carbonate (17 g, 0.5 equivalent) was added. The solution was stirred for 10 minutes. The solvent was evaporated and the residue was co-evaporated with toluene. The residue was dissolved in acetonitrile (30 ml, dry) and 1-iodopropane (18 g, 10 equivalents) was added portionwise. The reaction mixture was stirred. The solvent was evaporated under reduced pressure keeping the temperature as low as possible. The residue was taken up in water and extracted with ether. The organic layers was separated and the solvent was evaporated. The residue was purified by column chromatography (eluent: ethyl acetate/hexane 1/4). The desired fractions were collected and the solvent was evaporated. The residue was stirred in water and filtered off, yielding 2 g of intermediate (50).

b) Preparation of

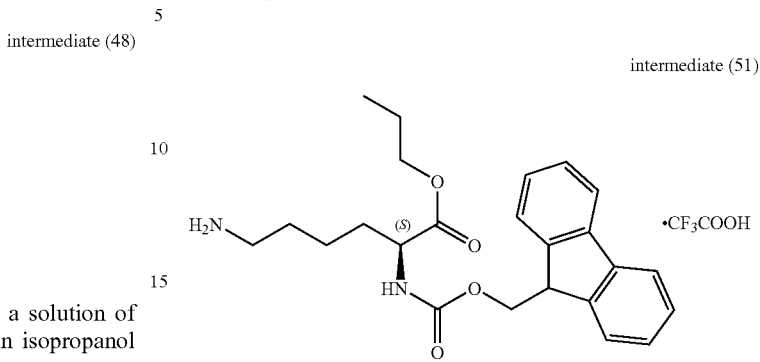

intermediate (51)

Intermediate (50) (4 g, 0.0078 mol) was dissolved in DCM (30 ml) and TFA (10 ml) was added. The reaction mixture was stirred at room temperature until TLC showed that the reaction was finished. The solvent was evaporated under reduced pressure keeping the temperature as low as possible, yielding intermediate (51).

c) Preparation of

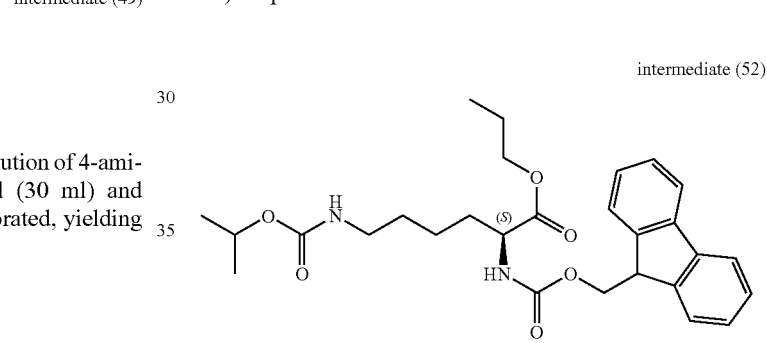

intermediate (52)

Intermediate (51) (0.0078 mol) was dissolved in DCM (200 ml). A saturated aqueous NaHCO₃ solution (200 ml) was added and the reaction mixture was stirred for 20 minutes under nitrogen. Then 1-methylethyl-carbonochloridic acid, ester (11.4 ml) was added portionwise. The reaction was stirred and the layers were separated. The separated organic layer was washed with water, dried and the solvent was evaporated, yielding 3.5 g intermediate (52).

d) Preparation of

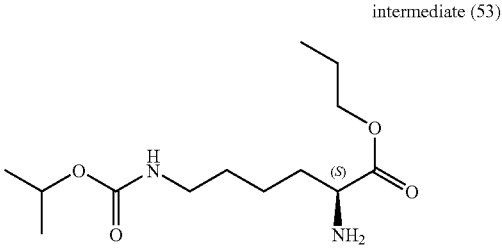

intermediate (53)

Intermediate (52) (3.5 g, 0.007 mol) was dissolved in acetonitrile (40 ml) and then piperidine (10 ml) was added. The reaction mixture was stirred for 10 minutes. The solvent was evaporated to dryness. The crude residue was used as such in the next reaction, yielding intermediate (53).

Example A.25 a) Preparation of

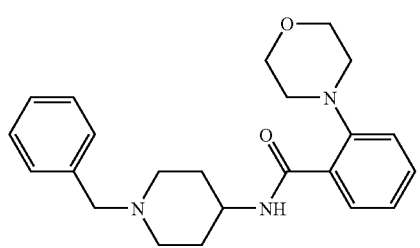

intermediate (54)

Thionyl chloride (0.0965 mol) was added dropwise to a solution of 2-(4-morpholinyl)-benzoic acid (0.029 mol) dissolved in DCM (150 ml). Then a few drops of DMF were added and the reaction mixture was refluxed for 2 hours. The solvent was evaporated, some DCM was added and the solvent was evaporated again. Again some DCM was added. 1-(Phenylmethyl)-4-piperidinamine (0.029 mol) was added to the reaction mixture. Then a saturated aqueous $NaHCO_3$ solution (75 ml) was added to the reaction mixture and stirred for 2 hours. The separated organic layer was dried, filtered and the solvent was evaporated. The residue was triturated under DIPE. The precipitate was filtered off and dried, yielding 10.06 g intermediate (54).

b) Preparation of

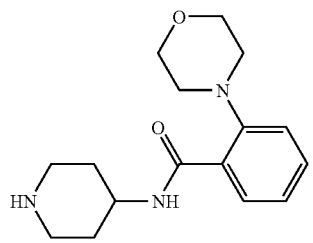

intermediate (55)

A mixture of intermediate (54) (0.026 mol) in DCM (150 ml) and THF (10 ml) was hydrogenated with palladium-on-carbon 10% (2 g) as a catalyst. The catalyst was filtered off. Then some extra palladium-on-carbon 10% (2 g) was added to the filtrate. This mixture was hydrogenated again with hydrogen (1 equivalent for the complete process). The catalyst was filtered off and the solvent was evaporated, yielding 5.3 g intermediate (55).

Example A.26 a) Preparation of

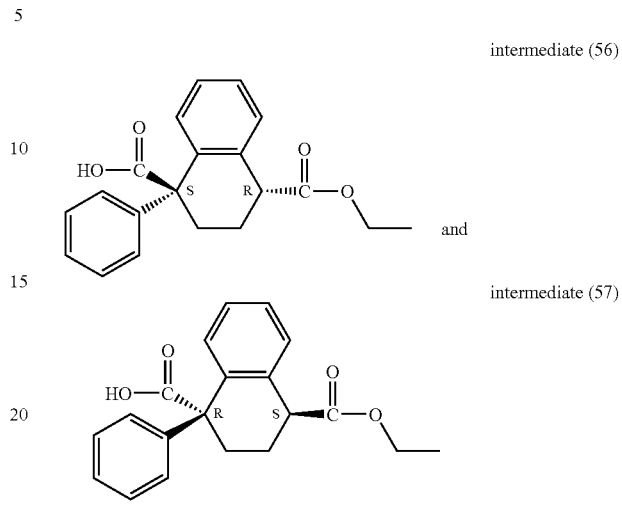

intermediate (56)

and intermediate (57)

Intermediate (2) was purified by Supercritical Fluid Chromatography over a AD-H column (20×250 mm) with a flow rate of 50 ml/min (eluent: $CO_2$/(methanol with 0.1% 2-propanol) 85/15). Column oven was set at 40° C. and nozzle pressure was 100 bar. Two different product fractions were collected and the solvent was evaporated, yielding intermediate (56) and intermediate (57) OR: −7.46° (c=0.7502 w/v %, MeOH, 20° C., 365 nm).

b) Preparation of

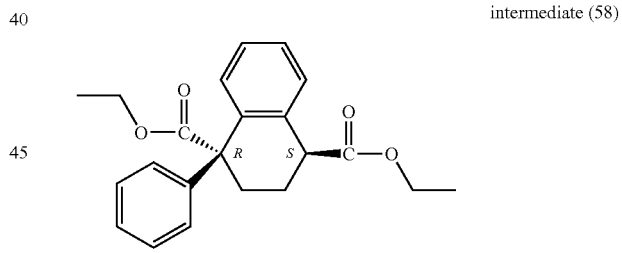

intermediate (58)

Intermediate (57) (0.000308 mol, 0.1 g) was dissolved in DCM (3 ml). Thionyl chloride (0.045 ml) and DMF (one drop) were added and the mixture was refluxed. The reaction mixture was concentrated and DCM (3 ml) was added again. The solvent was evaporated. The residue was added slowly to ethanol (6 ml) and was cooled to 0° C. in an ice bath. The ice bath was removed and the reaction mixture was allowed to reach room temperature. The reaction mixture was stirred at room temperature for 4 hours. The solvent was evaporated. The residue was dissolved in DCM and washed with a saturated aqueous $NaHCO_3$ solution. It was then purified by column chromatography (from 100% $CH_2Cl_2$ till 2% MeOH/$CH_2Cl_2$). One product fraction was collected and the solvent was evaporated, yielding intermediate (58).

c) Preparation of

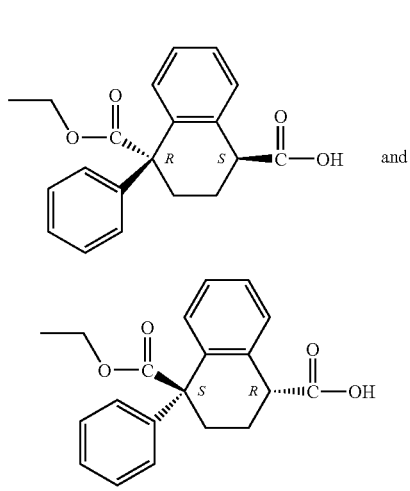

intermediate (59)

and intermediate (60)

Intermediate (58) (0.00284 mol, 1 g) was dissolved in p-toluenesulfonic acid (0.050 g), formic acid (25 ml) and concentrated hydrochloric acid (6 ml). The reaction mixture was refluxed. The reaction mixture was concentrated in vacuo. The residue was then dissolved in DCM, washed with a saturated aqueous NaHCO$_3$ solution, dried and the solvent was evaporated. The residue was purified by column chromatography (ethyl acetate/hexane 1/9). The product fractions were collected and the solvent was evaporated, yielding 0.74 g intermediate (59) and 0.75 g intermediate (60).

Example A.27 a) Preparation of

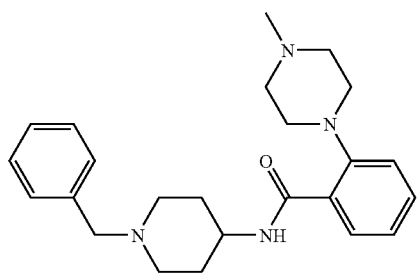

intermediate (61)

2-(4-Methyl-1-piperazinyl)benzoic acid (6.33 g, 0.0287 mol) was dissolved in DCM (150 ml) and DMF (1 drop) was added. Then thionyl chloride (8.34 ml, 0.1148 mol, 4 equivalents) was added and the mixture was refluxed for 2 hours and 30 minutes. The solvent was evaporated and DCM (150 ml) was added again. The solvent was evaporated and DCM (150 ml) was added a third time. Then 1-(phenylmethyl)-4-piperidinamine (5.46 g, 0.0287 mol) and a saturated aqueous NaHCO$_3$ solution (75 ml) were added and the two layer system was stirred at room temperature. The layers were separated. The separated organic layer was dried (MgSO$_4$), filtered and the solvent was evaporated. The residue was purified by column chromatography (eluent: CH$_3$OH/CH$_2$Cl$_2$ 1/9). The desired fractions were collected and the solvent was evaporated. The residue was crystallized from DCM and isopropylether, yielding 10.03 g of intermediate (61).

b) Preparation of

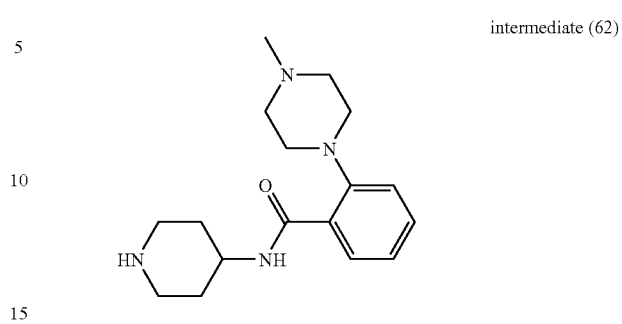

intermediate (62)

A mixture of intermediate (61) (7 g, 0.017 mol) in methanol (100 ml) was hydrogenated with palladium-on-carbon 10% (2 g) as a catalyst. After uptake of hydrogen (1 equivalent), the catalyst was filtered off and the filtrate was evaporated, yielding intermediate (62).

Example A.28

Preparation of

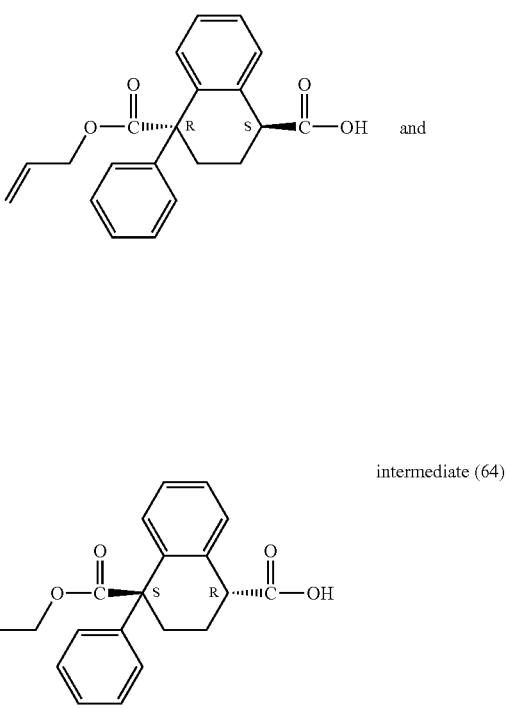

intermediate (63)

and intermediate (64)

Intermediate (25) was purified by Supercritical Fluid Chromatography over a AD-H column (20×250 mm) with a flow rate of 50 ml/min (eluent: CO$_2$/CH$_3$OH with 0.1% 2-propanol) 85/15). Column oven was set at 40° C. and nozzle pressure was 100 bar. Two different product fractions were collected and the solvent was evaporated, yielding 7.23 g of intermediate (63) (1R, 4S) and 7.55 g of intermediate (64) (1S, 4R).

Example A.29 a) Preparation of

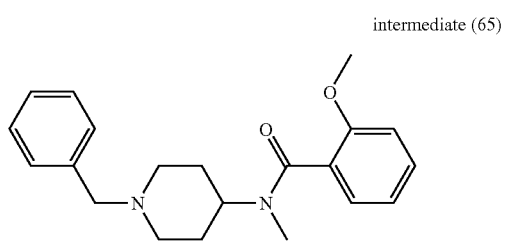
intermediate (65)

2-Methoxybenzoic acid (10.655 g, 0.0699 mol) was dissolved in DCM (100 ml). Thionyl chloride (10.09 ml, 0.1398 mol, 2 equivalents) and DMF (1 drop) were added and the mixture was refluxed for 2 hours. The solvent was evaporated and DCM (100 ml) was added again. The solvent was evaporated and again DCM (100 ml) was added. Then 1-benzyl-4-(methylamino)piperidine (14.2 g, 0.0699 mol) and a saturated aqueous $NaHCO_3$ solution (50 ml) were added. The two layer system was stirred and the layers were separated. The separated organic layer was dried ($MgSO_4$), filtered and the solvent was evaporated, yielding 22.83 g of intermediate (65).

b) Preparation of

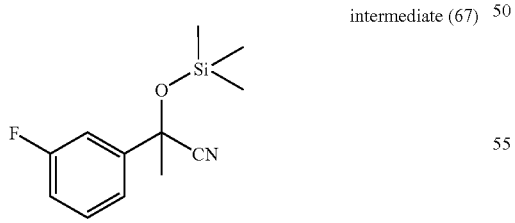
intermediate (66)

A mixture of intermediate (65) (0.067 mol) in methanol (250 ml) was hydrogenated at 50° C. with palladium-on-carbon 10% (2 g) as a catalyst. After uptake of hydrogen (1686 ml), the catalyst was filtered off and the filtrate was evaporated, yielding 16 g of intermediate (66).

Example A.30 a) Preparation of

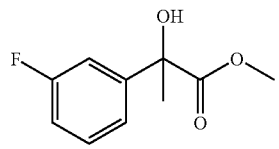
intermediate (67)

Trimethylsilyl cyanide (48 ml, 0.36 mol) and zinc iodide (0.114 g, 0.00036 mol) were added to 3-acetyl-1-fluorobenzene (44.6 ml, 0.36 mol). The reaction mixture was heated slowly to 50° C. (temperature was raised with 10° C. every 15 minutes). The mixture was stirred for 3 hours at 50° C. and then for 20 hours at room temperature. The solvent was evaporated and co-evaporated with toluene, yielding intermediate (67).

b) Preparation of intermediate (68)

Methanol (400 ml) was cooled to 0° C. and the solvent was saturated with HCl-gas. Cooled intermediate (67) (85.4 g, 0.36 mol) was added and the reaction mixture was stirred at room temperature for 30 minutes. Then the mixture was heated overnight at 60° C. A $NaHCO_3$ solution was added until pH 7 and the mixture was extracted twice with DCM. The separated organic layer was dried ($MgSO_4$), filtered and the solvent was evaporated. The residue was purified by column chromatography ($CH_2Cl_2$). The desired fractions were collected and the solvent was evaporated, yielding 55.3 g of intermediate (68).

c) Preparation of intermediate (69)

Intermediate (68) (5.8 g, 0.02 g) was dissolved in methanesulfonic acid (36 ml) and the solution was heated to 80° C. and stirred overnight. Then the mixture was quenched with water, and ethyl acetate was added. The separated organic layer was dried ($MgSO_4$), filtered and the solvent was evaporated. The residue was purified by column chromatography ($CH_2Cl_2$). Two different product fractions were collected and the solvent was evaporated. The first fraction was identified as 3-fluoro-α-methylene-benzeneacetic acid methyl ester. The second fraction was dissolved in ethyl acetate and the solution was washed with a NaOH solution and then with a sulfuric acid solution. The organic layer was dried ($MgSO_4$), filtered and the solvent was evaporated, yielding 1.2 g of intermediate (69).

d) Preparation of

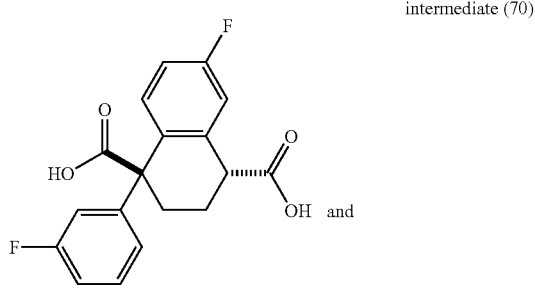
intermediate (70)

and

-continued

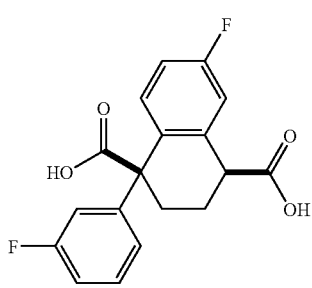

intermediate (71)

Intermediate (69) (10 g, 0.06 mol) was dissolved in B (80 ml) and the solution was heated overnight to 100° C. The precipitate was filtered off and washed with DCM. The mixture was reacted again overnight and again the precipitate was filtered off, washed with DCM and purified by reversed-phase high-performance liquid chromatography (Shandon Hyperprep® C18 BDS (Base Deactivated Silica) 8 m, 250 g, I.D. 5 cm). A gradient with a buffer solution and organic solvents was applied. Two different product fractions were collected and the solvent was evaporated. Each residue was dissolved in a small amount of methanol. Then DCM was added and the solution was washed with HCl (1 N). The solvent of both fractions was evaporated, yielding 1.8 g of intermediate (70) and 2.67 g of intermediate (71).

e) Preparation of

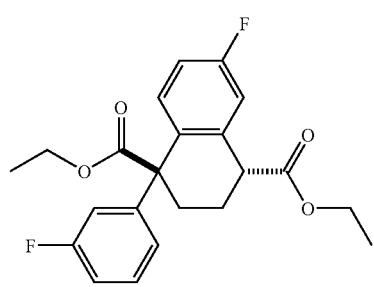

intermediate (72)

Intermediate (70) (0.2 g, 0.000602 mol) was dissolved in DCM (6 ml) and then thionyl chloride (10 g, 0.0015 mol, 2.5 equivalents) was added. The reaction mixture was refluxed for 2 hours. The mixture was cooled to room temperature and dry ethanol (2 ml) was added. The mixture was stirred for 2 hours. The solvent was evaporated. The residue was purified by column chromatography. The desired fractions were collected and the solvent was evaporated, yielding intermediate (72).

f) Preparation of

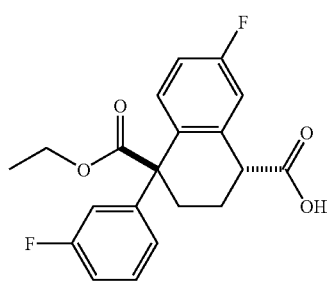

intermediate (73)

Intermediate (72) was dissolved in a mixture of formic acid (2 ml) and concentrated HCl (2 ml). The mixture was heated for 3 hours. The mixture was purified by column chromatography ($CH_3OH/CH_2Cl_2$ 1/9). The desired fractions were collected and the solvent was evaporated, yielding intermediate (73).

Example A.31 a) Preparation of

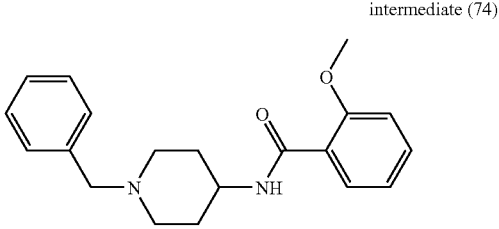

intermediate (74)

A mixture of 1-(phenylmethyl)-4-piperidinamine (7 g, 0.037 mol) in DCM (100 ml) was added to a mixture of 2-methoxybenzoyl chloride (6.4 g, 0.037 mol) in DCM (100 ml). Then a solution of sodium hydrogen carbonate (100 ml) was added and the mixture was stirred for 2 hours at room temperature. The layers were separated. The separated organic layer was dried and the solvent was evaporated. The residue was triturated in DIPE, filtered off and dried, yielding 10.6 g of intermediate (74).

b) Preparation of

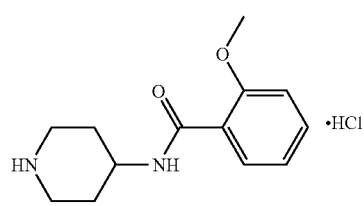

intermediate (75)

A mixture of intermediate (74) (10.7 g, 0.033 mol) in methanol (150 ml) was hydrogenated with palladium-on-carbon 10% (1 g) as a catalyst. After uptake of hydrogen (1 equivalent), the catalyst was filtered off and the filtrate was evaporated. The residue was dissolved in 2-propanol and the solution was acidified with a solution of hydrochloric acid in 2-propanol. The product was crystallized from this solution. The precipitate was filtered off and dried, yielding 8.3 g intermediate (75).

Example A.32 a) Preparation of

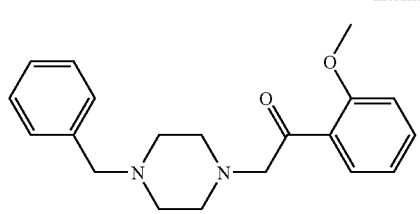

intermediate (76)

2-Bromo-1-(2-methoxyphenyl)ethanone (0.1 g, 0.000436 mol) was dissolved in dry DCM (4 ml) and 1-(phenylmethyl)piperazine (0.077 g) and triethylamine (0.061 ml, 1.2 equivalents) were added. The mixture was stirred for 2 hours at room temperature. Then the mixture was washed with water and the water-layer was extracted with DCM, yielding intermediate (76).

b) Preparation of

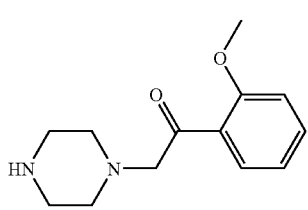

intermediate (77)

A mixture of intermediate (76) (0.00308 mol) in methanol (100 ml) was hydrogenated with palladium-on-carbon 10% (0.050 g) as a catalyst in the presence of 2-propanol saturated with HCl (5 ml). After reaction, the catalyst was filtered off and the filtrate was evaporated, yielding 0.46 g of intermediate (77).

Example A.33 a) Preparation of

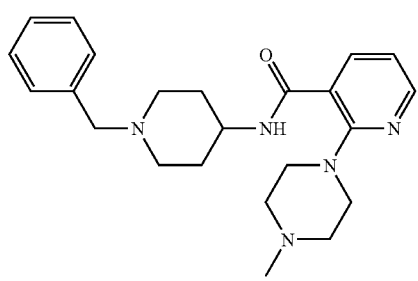

intermediate (84)

2-(4-Methyl-1-piperazinyl)-3-pyridinecarboxylic acid (11.9 g, 0.0538 mol) was dissolved in DCM (10 ml) and thionyl chloride (12.7 g) was added and a drop of DMF. The reaction mixture was stirred and refluxed for 90 minutes. The solvent was evaporated. Extra DCM (10 ml) was added and evaporated. More DCM (10 ml) was added, then evaporated. 1-(Phenylmethyl)-4-piperidinamine (10.20 g) and a saturated aqueous NaHCO$_3$ solution (5 ml) were added and the reaction mixture was stirred at room temperature until reaction was complete. Extra DCM and saturated aqueous NaHCO$_3$ solution were added a few times and the organic layer was separated, dried (MgSO$_4$), filtered and the solvent was evaporated, yielding 4.24 g of intermediate (84).

b) Preparation of

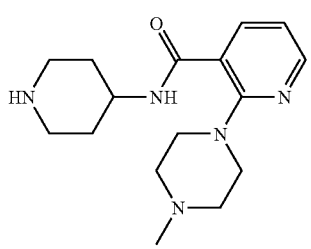

intermediate (85)

A mixture of intermediate (84) (4.24 g, 0.0107 mol) in methanol was hydrogenated with palladium on activated carbon (2 g) as a catalyst. After uptake of hydrogen (1 equivalent), the catalyst was filtered off over Celite and the filtrate was evaporated, yielding intermediate (85).

Example A.34 a) Preparation of

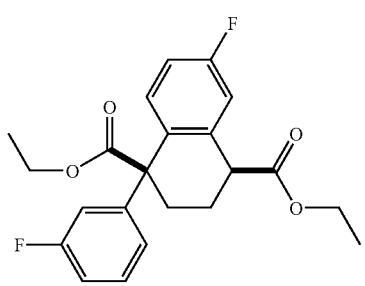

intermediate (87)

Intermediate (71) (0.2 g, 0.00052 mol) was dissolved in ethanol (5 ml) and sulfuric acid (0.5 ml) was added. The reaction mixture was pre-stirred for 10 seconds in the microwave and was then heated for 2 hours at 100° C. and then for 2 hours at 140° C. The solvent was evaporated, yielding intermediate (87).

b) Preparation of

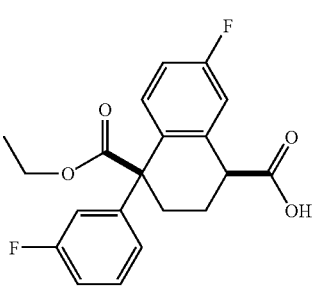

intermediate (88)

Intermediate (87) (0.00052 mol) was dissolved in formic acid (2 ml), concentrated hydrochloric acid (1 ml) and p-toluene sulfonic acid (catalytic amount) were added. The solution was heated for 3 hours. Then the solvent was evaporated and the residue was purified by reversed-phase high-performance liquid chromatography (Shandon Hyperprep® C18 BDS (Base Deactivated Silica) 8 μm, 250 g, I.D. 5 cm). A gradient with a buffer solution and organic solvents was applied. The desired fractions were collected and worked-up, yielding intermediate (88).

Example A.35 a) Preparation of intermediate (89)

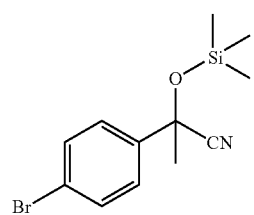

Trimethylsilyl cyanide (0.05 mol) and zinc iodide (50 mg) were added to 1-acetyl-4-bromobenzene (5 g, 0.05 mol). This mixture was stirred for 5.5 hours at 50° C. and then for 12 hours at room temperature. The precipitate was filtered off, washed with toluene and the filtrate was evaporated, yielding 15 g of intermediate (89).

b) Preparation of intermediate (90)

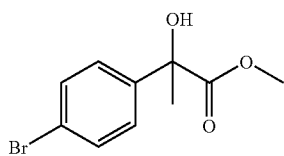

Intermediate (89) (0.05 mol) was added to a cooled solution of methanol saturated with hydrochloric acid (150 ml). The mixture was stirred and refluxed for 20 hours, neutralized with a saturated solution of NaHCO$_3$ (220 ml) and extracted three times with DCM (100 ml). The combined organic layer was washed with a saturated solution of NaCl, dried (MgSO$_4$), filtered and the solvent was evaporated, yielding 15 g of intermediate (90).

c) Preparation of intermediate (91)

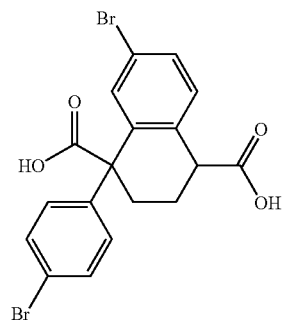

A solution of intermediate (90) (0.05 mol) in sulfuric acid (50%) (300 ml) was stirred at 100° C. for 20 hours. The precipitate was filtered off and dissolved in DCM and 2-propanone. The mixture was separated into its layers. The aqueous layer was extracted with DCM (200 ml). The combined organic layer was dried (MgSO$_4$), filtered and the solvent was evaporated. The residue was dissolved in DCM. Hexane was added. The precipitate was filtered off and dried, yielding 4 g of residue. The residue was triturated with 2-propanone. The precipitate was filtered off and dried. The residue was triturated with diethyl ether. The precipitate was filtered off and dried, yielding 1 g of intermediate (91).

d) Preparation of intermediate (92)

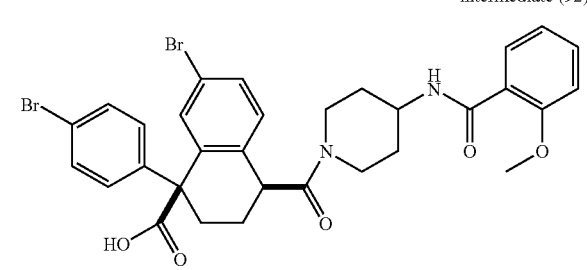

Intermediate (94) (0.1 g, 0.0002 mol) was dissolved in acetonitrile (2 ml) and intermediate (91) (0.09 g, 0.0002 mol) and triethylamine (0.033 ml) were added. The mixture was stirred for 6 days. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% NH$_4$HCO$_3$ solution in water; phase B: CH$_3$OH (optional); phase C: CH$_3$CN). The desired fractions were collected and the solvent was evaporated, yielding 0.031 g of intermediate (92).

Example A.36

Preparation of intermediate (93)

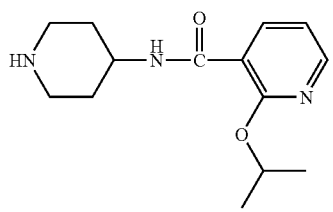

Intermediate (42) (0.0043 mol) was dissolved in 2-propanol (10 ml). Potassium hydroxide (2.38 g) was added and the reaction mixture was refluxed for 24 hours. Reaction mixture was cooled to room temperature. The excess of solvent was removed under vacuum. The reaction mixture was extracted with water and ethyl acetate. The organic layer was dried and the solvent was evaporated, yielding intermediate (93).

Example A.37

Preparation of

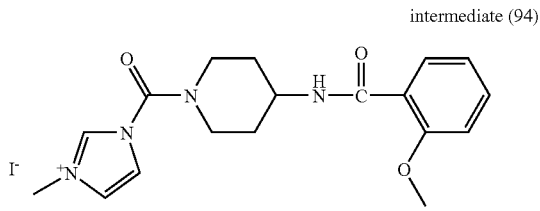

intermediate (94)

2-Methoxy-N-4-piperidinylbenzamide monohydrochloride (0.1 g, 0.000426 mol;) was dissolved in DCM. First 1,1'-carbonylbisimidazole (0.083 g, 1.2 equivalents) and then triethylamine (0.120 ml) were added and the reaction mixture was stirred overnight. Then the mixture was washed with water, filtered over Isolute and the solvent was evaporated. The residue was dissolved in acetonitrile. Iodomethane was added and the mixture was shaken. Then the solvent and the excess of iodomethane was evaporated in vacuo, yielding 0.127 g of intermediate (94).

Other intermediate compounds that were used in the preparation of the final compounds are art known compounds such as, 4-(phenylcarboxamido)piperidine, 4-(2-methoxybenzamido)piperidine, 2-methyl-N-4-piperidinyl-benzamide, 4-amino-5-chloro-2-methoxy-N-4-piperidinyl-benzamide, 4-amino-5-chloro-2-methoxy-N-(3-methoxy-4-piperidinyl)-benzamide, N-4-piperidinyl-4'-(trifluoromethyl)-[1,1'-biphenyl]-2-carboxamide, 3-hydroxy-6-methoxybenzoic acid, 1-benzoyl-piperazine, 1-(2-methoxybenzoyl)-piperazine, piperazin-1-yl-(4'-trifluoromethyl-biphenyl-2-yl)-methanone, methyl glycinate, ethyl glycinate hydrochloride, tert-butyl glycinate, N6-acetyl-L-lysine methyl ester, N6-acetyl-L-lysine ethyl ester, ethyl glycinate, ethyl (R)-alaninate hydrochloride, ethyl (S)-alaninate hydrochloride, ethyl N-methylglycinate hydrochloride, β-alanine methyl ester hydrochloride, (R)-valine ethyl ester, ethyl D-valinate hydrochloride, ethyl L-valinate hydrochloride, ethyl L-leucinate hydrochloride, L-serine ethyl ester hydrochloride, (S)-aspartic acid diethyl ester hydrochloride, 2-ethoxycarbonyl-piperidine, 3-ethoxycarbonyl-piperidine, L-glutamine methyl ester hydrochloride, diethyl L-glutamate hydrochloride, (R)-proline ethyl ester hydrochloride, (S)-proline ethyl ester hydrochloride, (2S,4R)-4-hydroxy-pyrrolidine-2-carboxylic acid methyl ester hydrochloride, (R)-phenylglycine ethyl ester hydrochloride, (S)-phenylglycine ethyl ester hydrochloride, (R)-phenylalanine ethyl ester, (S)-phenylalanine ethyl ester, tyrosine ethyl ester hydrochlorid, tryptophan ethyl ester hydrochloride, tert-butyl glycinate, tert-butyl L-alaninate hydrochloride, tert-butyl D-alaninate hydrochloride, N-methylglycine tert-butyl ester hydrochloride, tert-butyl β-alaninate hydrochloride, L-valine tert-butyl ester, tert-butyl L-leucinate hydrochloride, O-tert-butyl-L-serine tert-butyl ester hydrochloride, L-aspartic acid di-tert-butyl ester hydrochloride, L-glutamine tert-butyl ester hydrochloride, L-glutamic acid di-tert-butyl ester hydrochloride, lysine, N6-carboxy-, di-tert-butyl ester, hydrochloride; L-proline tert-butyl ester, D-proline tert-butyl ester, (4R)-4-(1,1-dimethylethoxy)-L-proline 1,1-dimethylethyl ester, R-aminophenyl-acetic acid tert-butyl ester hydrochloride, S-aminophenyl-acetic acid tert-butyl ester hydrochloride, L-phenylalanine tert-butyl ester hydrochloride, D-phenylalanine tert-butyl ester hydrochloride, L-tyrosine tert-butyl ester, L-tryptophan tert-butyl ester, L-asparagine tert-butyl ester, 4-amino-butyric acid propyl ester, 4-aminobutyric acid isopropyl ester.

B. Preparation of the Final Compounds

Example B.1

A mixture of intermediate (30) (0.0017 mol), 4-(phenylcarboxamido)piperidine (0.0034 mol) and diisopropylethylamine (0.0051 mol) in acetonitrile (30 ml) was stirred and refluxed for 8 days and then the solvent was evaporated. The residue was taken up in DCM (10 ml) and purified by column chromatography (eluent:ethyl acetate), yielding compound (17).

Example B.2

PS-carbodiimide resin (0.170 g) was added to DCM (2 ml) and a solution of intermediate (13) (0.000135 mol) in DCM (0.5 ml) was added. This reaction mixture was shaken for 30 minutes at room temperature. A solution of 4-(phenylcarboxamido)-piperidine (0.00095 mol) in DCM (0.5 ml) was added and the reaction mixture was shaken overnight. The reaction mixture was filtered and the resin was washed with DCM (3×3 ml). The filtrate was evaporated and the residue was dissolved in DCM (1 ml) and the solution was added to a PS-isocyanate resin (100 mg), then shaken overnight. The mixture was filtered and the resin was washed with DCM (3×3 ml) and the filtrate was evaporated, yielding compound (2).

Example B.3

A mixture of intermediate (25) (0.004 mol), N-4-piperidinyl-benzamide (0.004 mol), N'-(ethylcarbonimidoyl)-N,N-dimethyl-1,3-propanediamine (0.006 mol), 1-hydroxy-1H-benzotriazole (HOBT) (0.006 mol) and 4-methylmorpholine (0.016 mol) in DCM (100 ml) was stirred for 24 hours at 20° C. under nitrogen. The mixture was diluted with ethyl acetate (300 ml), then washed with HCl (0.5N, 100 ml), with a saturated aqueous $NaHCO_3$ solution (100 ml) and with brine (100 ml). The resulting mixture was dried and the solvent was evaporated. The residue was purified by flash column chromatography (eluent: ethyl acetate/hexane 75/25). The product fractions were collected and the solvent was evaporated, yielding 1.2 g of compound (13) (mp. 103-107° C.).

Example B.4

Intermediate (6) (0.0001 mol) was dissolved in DCM (3 ml). Thionyl chloride (0.001 mol) was added. The tube was capped, then shaken for 2 hours. The solvent was evaporated under a gentle stream of nitrogen. DCM (3 ml) was added, then evaporated again. 4-Amino-5-chloro-2-methoxy-N-4-piperidinyl-benzamide (0.0002 mol) and polystyrene-N-methyl morpholine HL resin (0.0002 mol) were added. DCM (4 ml) was added. The reaction mixture was shaken overnight (16 hours) at room temperature. The resin was removed by filtration. The resin was rinsed once with DCM (3 ml). Then PS-isocyanate resin (0.0004 mol) was added and the reaction mixture was shaken for 3 hours at room temperature. The resin was filtered off, washed with DCM and the filtrate's solvent was evaporated. The residue was purified by reversed-phase high-performance liquid chromatography. A gradient with a buffer solution and organic solvents was applied. The desired fractions were collected and worked-up, yielding 0.027 g of compound (24).

Example B.5

A mixture of 1-(2-methoxybenzoyl)-piperazine monohydrochloride (0.0001 mol), a polystyrene-carbodiimide (1.90 mmol/g) resin (0.0002 mol, 0.105 g), a polystyrene-N-methyl morpholine HL (3.80 mmol/g) resin (0.0005 mol, 0.132 g), a solution of intermediate (6) (0.00015 mol) in DCM (1 ml) and 1-hydroxybenzotriazole (HOBT) (0.0015 mol, 0.020 g) in THF (1 ml) was shaken overnight at room temperature. A polystyrene-bicarbonate (5.8 mmol/g) resin (0.0005 mol, 0.086 g) was added as a scavenger to remove excess of HOBT. The reaction mixture was shaken for two hours, filtered, and the filtrate was evaporated. The residue was purified by reversed-phase high-performance liquid chromatography. A gradient with a buffer solution and organic solvents was applied. The desired fractions were collected and worked-up, yielding compound (27).

Example B.6

A mixture of intermediate (38) (0.0175 mol) in DCM was added to a stirring mixture of N-4-piperidinyl-benzamide (0.0175 mol) and 4-methylmorpholine (0.0175 mol) in DCM (50 ml) and then the reaction mixture was stirred for 2 hours. The mixture was washed with water, with a 10% NaHCO$_3$ solution, with HCl (1N) and with brine, then the mixture was dried and filtered. The crude product was purified by column chromatography (eluent 1: diethyl ether; eluent 2: ethyl acetate/hexane 1/1). The product fractions were collected and the solvent was evaporated, yielding 5.1 g of compound (25) (mp. 112-115° C.).

Example B.7

Compound (25) (0.0137 mol) was separated into its enantiomers by high-performance liquid chromatography (stationary phase: OD Chiralcel) (eluent: hexane/ethanol 50/50). Two product fractions were collected and the solvent was evaporated. The residues were each triturated under 2-propanol/DIPE and then the desired products were collected, yielding 2.66 g of compound (32) and 2.71 g of compound (33).

Example B.8

Compound (26) (0.0159 mol) was separated into its enantiomers by high-performance liquid chromatography (stationary phase: OJ Chiralcel) (eluent: hexane/ethanol 50/50). Two product fractions were collected and the solvent was evaporated. The residues were each triturated under DIPE with a small amount of 2-propanol and then the desired products were collected, yielding 3.23 g of compound (34) and 3.18 g of compound (35).

Example B.9

A mixture of intermediate (32) (0.029 mol), 2-methoxy-N-4-piperidinyl-benzamide (0.029 mol) and 1-hydroxy-1H-benzotriazole (HOBT) (0.035 mol) was stirred in DCM (300 ml) and N'-(ethylcarbonimidoyl)-N,N-dimethyl-1,3-propanediamine (0.035 mol) was added. The reaction mixture was stirred for 20 hours at room temperature and diisopropylethylamine (10 ml) was added. The resulting mixture was stirred for 24 hours and then stirred with a diluted HCl solution for 1 hour. The layers were separated and the organic layer was washed 3 times with a NaHCO$_3$ solution. The solvent was evaporated and the residue was crystallised from 2-propanol. The precipitate was filtered off, dried and purified by column chromatography over silica gel (eluent: DCM/methanol 99/1, 95/5). The pure product fractions were collected and the solvent was evaporated. The residue was triturated under DIPE and then the desired product was filtered off and dried (1.51 g). A part (0.150 g) of this residue was separated into its enantiomers by chiral chromatography (Prochrom® Dynamic Axial Compression column of 5 cm internal diameter loaded with 500 g of AD Chiral phase) (isocratic elution with a mixture of hexane/ethanol 50/50 with a flow rate of 110 ml/min). Two product fractions were collected and the solvent was evaporated, yielding 67 mg compound (43) and 69 mg of compound (44).

Example B.10

Intermediate (37) (0.027 mol) was stirred in dioxane (100 ml) at room temperature. Thionyl chloride (0.2 mol) was added and the reaction mixture was stirred and refluxed for one hour. The solvent was evaporated. DCM (100 ml) was added to the residue, then evaporated again. The residue was dissolved in DCM (100 ml). A solution of 2-methoxy-N-4-piperidinyl-benzamide (0.027 mol) in DCM (50 ml) was added. A NaHCO$_3$ solution (50 ml) was added and the resultant reaction mixture was stirred for another 4 hours. The organic layer was separated, dried, filtered and the solvent evaporated. The residue was purified by column chromatography over silica gel (eluent: DCM/methanol 99/1 up to 97/3). The product fractions were collected and the solvent was evaporated. The residue was crystallized from 2-propanol (over 4 days, while stirring). The precipitate was filtered off and dried, yielding 6.9 g of compound (37).

Compound (37) was purified and separated into its enantiomers by high-performance liquid chromatography over Chiralcel OD (250 g, 20 μm, column diameter 50 mm, column length 21 cm) with methanol as eluent (flow rate: 80 ml/min). Two product fraction groups were collected and their solvent was evaporated. Each residue was stirred in DIPE for 20 hours, then filtered off and dried, yielding 3.02 g of compound (40) and 2.72 g of compound (41).

Example B.11 a) A mixture of compound (35) (0.00092 mol) in HCl 12N (3 ml) and dioxane (3 ml) was shaken for 16 hours at 100° C. The solvent was evaporated. The residue was purified by reversed-phase high-performance liquid chromatography. A gradient with a buffer solution and organic solvents was applied. The product fractions were collected and the solvent was evaporated. The residue was dissolved in DCM, then washed with dilute hydrochloric acid. The organic layer was separated, dried, filtered and the solvent evaporated. The residue was triturated under DIPE, filtered off and dried, yielding 0.024 g of 4-[4-(2-methoxy-benzoylamino)-piperidine-1-carbonyl]-1-phenyl-1,2,3,4-tetrahydro-naphthalene-1-carboxylic acid (intermediate (78)) (1S, 4R); OR=+23° (c=0.4000 w/v %, EtOH, 20° C., 589 nm)).

b) Thionyl chloride (0.02 mol) and DMF (3 drops) were added to a solution of intermediate (78) (0.0058 mol) in DCM (100 ml), then the reaction mixture was stirred and refluxed for 1 hour. The solvent was evaporated and the residue was dissolved in DCM. The resulting solution was stirred at room temperature and then ethyl glycinate (0.01 mol) was added, followed by an aqueous NaHCO$_3$ solution (50 ml). The reaction mixture was further stirred for 1 hour and the layers were separated. The organic layer was washed with 1N hydrochloric acid, dried, filtered off and the solvent was evaporated. The residue was purified by column chromatography over silica gel (eluent: DCM/methanol 99/1 up to 90/10). The product fractions were collected and the solvent was evaporated. The residue was crystallised from 2-propanol/DIPE and then the desired product was collected, yielding 2.78 g of compound (48) (1S, 4R).

Example B.12

Intermediate (35) (0.000061 mol) was dissolved in DCM (19 ml) and DCM/TFA (9/1) (1 ml) was added, then the reaction mixture was stirred for 16 hours at room temperature and the solvent was evaporated. The residue was dissolved in DCM (9 ml) and the solution was washed with an aqueous 10% Na$_2$CO$_3$ solution, then filtered through Extrelut® and the filter was washed with DCM (2×3 ml). The filtrate was collected and the solvent was evaporated. The resulting residue was dissolved in DCM (14 ml), to give Solution (I).

Solution (I) (1 ml) was added to a stirring solution of 2,3-dimethoxy-benzoic acid (0.000091 mol) and N'-(ethylcarbonimidoyl)-N,N-dimethyl-1,3-propanediamine (0.000122 mol) in DMF (1 ml) and diisopropylethylamine (0.000134 mol) at room temperature and then the reaction mixture was stirred for 70 hours at room temperature. N,N-dimethyl-4-pyridinamine was added and the resulting mixture was shaken for 80 hours at room temperature, then the solvent was evaporated and the residue was dissolved in methanol (2 ml) and water (0.5 ml). The obtained solution was purified by reversed-phase high-performance liquid chromatography. A gradient with a buffer solution and organic solvents was applied. The desired fractions were collected and worked-up, yielding compound (49).

Example B.13

Compound (62) was dissolved in DCM (1 ml). TFA (0.4 ml) was added. The mixture was shaken for one hour at room temperature (500 rpm), then over the weekend at room temperature (400 rpm). The reaction mixture was evaporated and the residue was purified by reversed-phase high-performance liquid chromatography (Column: Xterra Prep MS C18, particle size: 5 μm; length: 10 cm, internal diameter: 19 mm, eluent: (0.2% NH$_4$HCO$_3$ in H$_2$O)/CH$_3$OH/acetonitrile gradient). The product fractions were combined and the solvent was evaporated. DCM (3 ml) was added to the residue, then evaporated again, yielding 0.031 g of compound (63).

Example B.14

Compound (243) (0.0215 mol) was separated into its enantiomers by reversed-phase HPLC over Daicel Chiralpak AD (2 kg, 1000 Å, diameter: 20 μm; eluent: ethanol 100%, flow rate: 750 ml/min). Two product fraction groups were collected and their solvent was evaporated. Each residue was stirred in DIPE, filtered off and dried, yielding compound (245) (OR: +32.8° (at 589 nm, CH$_3$OH, 20° C.)) and compound (244), (OR: −37.55° (at 589 nm, 26.1 mg/5 ml, CH$_3$OH, 20° C.)).

Example B.15 a) A solution of compound (45) (0.0186 mol) and tetrakis(triphenylphosphine)-palladium (0.00037 mol) in THF (100 ml) was stirred and cooled on an ice-bath. Sodium borohydride (0.0186 mol) was added and the reaction mixture was stirred for 4 hours while cooling on the ice-bath. Extra sodium borohydride (0.22 g) was added and the reaction mixture was stirred over the weekend at room temperature. The reaction was quenched with 1 N HCl solution. This mixture was extracted with DCM The separated organic layer was dried (MgSO$_4$), filtered and the solvent evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: (0.5% NH$_4$OAc in H$_2$O)/CH$_3$CN 90/10); phase B: CH$_3$OH (optional); phase C: CH$_3$CN). The desired fractions were collected and the solvent was evaporated The residue was dissolved in DCM, washed with water, separated, dried (MgSO$_4$), filtered and the solvent was evaporated. The residue was triturated under DIPE, filtered off and dried, yielding 5.65 g of (1R, 4S)-4-[4-(2-methoxy-benzoylamino)-piperidine-1-carbonyl]-1-phenyl-1,2,3,4-tetrahydro-naphthalene-1-carboxylic acid [intermediate (79)] (OR: −25.38° (at 589 nm, 0.532 w/v %, 20° C., ethanol)).

b) Intermediate (79) (0.0078 mol) and 4-methyl-morpholine (3 ml) were dissolved in DCM (40 ml). 1-Hydroxy-1H-benzotriazole (HOBT) (0.0075 mol), 1-(3-dimethyl-amino-propyl)-3-ethylcarbodiimide hydrochloride (0.010 mol) and then intermediate (46) (0.0078 mol) were added to the reaction mixture and was stirred overnight. The reaction mixture was washed with water. The separated organic layer's solvent was evaporated. The residue was purified by column chromatography over silica gel (eluent: hexane/ethyl acetate from 1/1 to 1/2). The product fractions were collected and the solvent was evaporated, yielding 3.1 g of compound (246) (1R, 4S).

Example B.16

Intermediate (25) (10 g; 0.0297 mol) was dissolved in DCM (150 ml, p.a.). Then a small amount of DMF was added together with thionyl chloride (20 ml). The mixture was refluxed for 1 hour and then the solvent was evaporated. Intermediate (42) (6.99 g; 1 equivalent), an aqueous saturated NaHCO$_3$ solution (150 ml) and DCM (150 ml) were added and the reaction mixture was stirred at room temperature for 2 hours. Then the organic layer was separated. The separated organic layer was dried and the solvent was evaporated. The residue was crystallized from isopropanol and isopropylether. The precipitate was purified by column chromatography (reversed phase; a NH$_4$HCO$_3$ solution was used as the buffer solution in combination with organic solvents). The desired fractions were collected and the solvent was evaporated. The residue was separated into its enantiomers by supercritical fluid chromatography over an AD-H column (60% methanol and 0.1% isopropyl alcohol; flow: 50 ml/min) The product fractions were collected and the solvent was evaporated, yielding 2.0 g of compound (265), and 2.3 g of compound (266).

Example B.17 a) Compound (265) (2 g, 0.0036 mol) was dissolved in THF (18 ml, dry). The reaction was bubbled with nitrogen and then tetrakis(triphenylphosphine)palladium (0.083 g, 2 mol %) was added. The mixture was cooled to 0° C. with an ice-bath and then sodium borohydride (0.0036 mol) was added. Cooling was continued for 4 hours and the mixture was reacted overnight at temperature. Then acetone was added (0.5 ml) and the solvent was evaporated. The residue was dissolved in DCM and HCl (1 N) was added. The separated organic layer was dried (MgSO$_4$), filtered and the solvent was evaporated. The residue was purified by column chromatography (eluent: CH$_2$Cl$_2$/CH$_3$OH from 1/99 till 10/90. The desired fractions were collected and the solvent was evaporated. The residue was dissolved in CH$_3$OH/CH$_2$Cl$_2$ and the solution was treated with activated charcoal Norit. The mixture was filtered over decalite and the solvent was evaporated, yielding intermediate (80).

b) Intermediate (80) (0.00194 mol, 1 g) was dissolved in DCM (10 ml). Thionyl chloride (0.00388 mol, 0.282 ml) and a few drops of DMF were added. The reaction mixture was refluxed for 90 minutes. The solvents were evaporated and DCM (10 ml) was added. The solvent was evaporated again. The crude was dissolved in DCM (10 ml) and 3-aminopropionic acid methyl ester hydrochloride (0.00194 mol, 0.272 g) was added. To this mixture, a saturated aqueous NaHCO$_3$ solution (10 ml) was added and the reaction mixture was stirred overnight at room temperature. The layers were separated and the water layer was extracted with DCM. The combined organic layers were dried (MgSO$_4$), filtered and the solvents were evaporated. The residue was purified by high-performance liquid chromatography (Shandon Hyperprep® C18 BDS (Base Deactivated Silica) 8 µm, 250 g, I.D. 5 cm). A gradient with two or three mobile phases was applied (phase A: a 0.25% NH$_4$HCO$_3$ solution in water; phase B: CH$_3$OH (optional); phase C: CH$_3$CN). Two different product fractions were collected and the solvent was evaporated, yielding as a first fraction 0.160 g of compound (254) and as a second fraction 0.244 g of compound (255).

Example B.18 a) A solution of compound (46) (0.0139 mol) and tetrakis (triphenylphosphine)-palladium (0.00083 mol) in THF (80 ml) was stirred and cooled on an ice-bath. Sodium borohydride (0.0139 mol) was added and the reaction mixture was stirred for 4 hours while cooling on the ice-bath, then stirred for 20 hours at room temperature. The reaction was quenched with a aqueous 1 N HCl solution. This mixture was extracted twice with DCM. The separated organic layer was dried (MgSO$_4$), filtered and the solvent evaporated. The residue was purified over silica gel on a glass filter (eluent: CH$_2$Cl$_2$/CH$_3$OH 97/3, then 95/5). The product fractions were collected and the solvent was evaporated. The residue was purified by reversed-phase HPLC (Shandon Hyperprep® C18 BDS (Base Deactivated Silica) 8 µm, 250 g, I.D. 5 cm). A gradient with two or three mobile phases was applied (phase A: (0.5% NH$_4$OAc in H$_2$O)/CH$_3$CN 90/10); phase B: CH$_3$OH (optional); phase C: CH$_3$CN). The product fractions were collected and the solvent was evaporated. The residue was triturated under DIPE, filtered off and dried, yielding 4.50 g of intermediate (81) (63%; (1S, 4R); OR: +21.03° (c=0.504 w/v %, MeOH, 20° C., 589 nm)).

b) Intermediate (81) (0.000194 mol, 0.1 g) was dissolved in dry DCM (10 ml). Then 1-hydroxy-1H-benzotriazole (HOBT) (1.2 equivalents, 0.031 g), 1-ethyl-3-(3'-dimethyl-aminopropyl)carbodiimide hydrochloride (EDCI) (1.2 equivalents, 0.045 g) and 3-amino-propionic acid methyl ester hydrochloride (3 equivalents, 0.081 g) and diisopropylethylamine (10 equivalents, 0.320 ml) were added to the mixture. The reaction mixture was stirred at room temperature overnight. Extra 3-amino-propionic acid methyl ester hydrochloride (3 equivalents, 0.081 g) was added and the mixture was washed 3 times with a saturated aqueous NaHCO$_3$solution. The separated organic layer was dried (MgSO$_4$), filtered and the solvent was evaporated. The residue was then purified by column chromatography (from 100% CH$_2$Cl$_2$ till 2% CH$_3$OH/CH$_2$Cl$_2$), yielding 0.060 g of compound (256).

Example B.19

Intermediate (25) (0.00297 mol, 1 g) was dissolved in DCM (5 ml). Thionyl chloride (0.00742 mol, 0.539 ml) and a few drops of DMF were added. The reaction mixture was refluxed for 90 minutes. The solvents were evaporated and DCM (5 ml) was added. The solvent was evaporated again. The crude was dissolved in DCM (5 ml) and intermediate (55) (0.00297 mol, 0.859 g) was added. To this mixture, a saturated aqueous NaHCO$_3$ solution (5 ml) was added and the reaction mixture was stirred overnight at room temperature. The layers were separated and the water layer was extracted with DCM. The combined organic layers were dried (MgSO$_4$), filtered and the solvents were evaporated, yielding 1.80 g of compound (264).

Example B.20 a) Compound (264) (0.00297 mol) was dissolved in THF (20 ml). The reaction was bubbled with nitrogen and then tetrakis(triphenylphosphine)palladium (0.070 g) was added. The mixture was cooled to 0° C. with an ice-bath and then sodium borohydride (0.00297 mol) was added. Cooling was continued for 4 hours and the mixture was reacted overnight at room temperature. Then the reaction was quenched with HCl (1 N) and extracted with DCM. The separated organic layer was dried (MgSO$_4$), filtered and the solvent was evaporated. The product was purified by column chromatography (eluent: (CH$_2$Cl$_2$/CH$_3$OH) from 99/1 till 90/10). The product fractions were collected and the solvents were evaporated in vacuo. The residue was redissolved in CH$_2$Cl$_2$/CH$_3$OH and treated with activated charcoal. The mixture was filtered over decalite and the solvent was evaporated. The residue was purified by reversed-phase high-performance liquid chromatography (Shandon Hyperprep® C18 BDS (Base Deactivated Silica) 8 µm, 250 g, I.D. 5 cm). A gradient with two or three mobile phases was applied (phase A: a 0.25% NH$_4$HCO$_3$ solution in water; phase B: CH$_3$OH (optional); phase C: CH$_3$CN). Two different product fractions were collected and the solvent was evaporated. The residues were redissolved in DCM and both solutions were added to diisopropyl ether. In both cases, the precipitate was filtered off and the solid was dried, yielding intermediate (82) (31%; m.p.: 257° C.), and compound (260) (36%).

b) Intermediate (82) (0.000176 mol, 0.100 g) was dissolved in dry DCM. Then (HOBT (1-hydroxy-1H-benzotriazole) (1.2 equivalent, 0.028 g), 1-ethyl-3-(3'-dimethyl-aminopropyl)carbodiimide hydrochloride (EDCI) (1.2 equivalents 0.04052 g) and 3-amino-propionic acid methyl ester hydrochloride (3 equivalents, 0.073 g) and diisopropylethylamine (10 equivalents, 0.290 ml) were added to the mixture. The reaction mixture was stirred at room temperature overnight. Extra diisopropylethylamine (3 equivalents, 0.073 g) was added and the mixture was washed 3 times with a saturated aqueous NaHCO$_3$ solution. The separated organic layer was dried (MgSO$_4$), filtered and the solvent was evaporated. The residue was then purified by column chromatography (from 100% CH$_2$Cl$_2$ till 20% CH$_3$OH/CH$_2$Cl$_2$). The desired fractions were collected and the solvent was evaporated, yielding compound (263).

Example B.21 a) Compound (269) (0.00359 mol) was dissolved in THF (18 ml) and this solution was cooled to 0° C. Then tetrakis (triphenylphosphine)palladium (0.083 g, 2 mol %) and sodium borohydride (0.136 g, 1 equivalent) was added and the mixture was stirred at 0° C. for 4 hours. Then the mixture was quenched with HCl (1 N). DCM was added and the organic layer was dried ($MgSO_4$), filtered and the solvent was evaporated. HCl (1 N) was added to the residue and the mixture was stirred for 2 hours. The water layer was evaporated and co-evaporated with toluene, yielding intermediate (83) as a hydrochloric acid addition salt.

b) Intermediate (83) (1 g, 0.0017 mol) was dissolved in DCM (15 ml) and 1-ethyl-3-(3'-dimethyl-aminopropyl)carbodiimide hydrochloride (EDCI) (0.397 g, 0.002 mol) was added to the solution. Then DIPEA (2.8 ml, 0.017 mol), 1-hydroxy-1H-benzotriazole (HOBT) (0.276 g, 0.002 mol) and isopropyl 3-aminopropionate hydrochloride (0.851 g;) in a small amount of DCM were added to the reaction mixture. The reaction mixture was stirred at room temperature. The mixture was washed four times with water. The separated organic layer was dried ($MgSO_4$), filtered and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% $NH_4HCO_3$ solution in water; phase B: $CH_3OH$ (optional); phase C: $CH_3CN$). The product fractions were collected and the solvent was evaporated. The product was dissolved in ethyl acetate and the solution was washed with a saturated aqueous $NaHCO_3$ solution. The organic layer was dried and the solvent was evaporated, yielding 0.324 g of compound (276).

Compound (272) was prepared analogously by reacting intermediate (83) in the presence of methyl 3-aminopropionate hydrochloride instead of isopropyl 3-aminopropionate hydrochloride.

Example B.22

Intermediate (63) (2.49 g, 0.00739 mol) was dissolved in DCM (6 ml). Thionyl chloride (1.07 ml) and a drop of DMF were added to the solution. The mixture was refluxed for 1 hour and the solvent was evaporated. DCM (6 ml) was added, evaporated again and added (6 ml) again. Then intermediate (85) (2.24 g, 0.00739 mol) and saturated aqueous $NaHCO_3$ solution (3 ml) were added and the two layer system was stirred at room temperature. The layers were separated and the organic layer was dried ($MgSO_4$). The crude compound was purified by flash column chromatography (eluent: DCM/MeOH from 100/0 to 20/1). The compound was purified again by flash column chromatography (eluent: DCM/MeOH from 100/0 to 99/1). The desired fractions were collected and the solvent was evaporated, yielding compound (278).

Example B.23

Compound (278) (1.52 g, 0.00244 mol) was dissolved in THF (12 ml) and nitrogen gas was bubbled through for 10 minutes at 0° C. Tetrakis(triphenylphosphine)palladium (0.056 g, 2 mol %) and sodium borohydride (0.092 g) were added and the reaction mixture was stirred for one hour at 0° C. The reaction mixture was treated with 1N HCl and stirred overnight. After extraction with ethyl acetate, the product was in the water layer. The pure product was extracted out of the water layer by addition of ammonia until the pH was 7. The separated organic layer was dried, filtered and the solvent evaporated, yielding intermediate (86).

b) Intermediate (86) (0.3 g, 0.000515 mol) was dissolved in DCM and EDCI (0.395 g) was added to the solution. To this mixture was added diisopropylethylamine (0.850 ml) and isopropyl 3-aminopropionate hydrochloride (0.259 g, 3 equivalents) in a small amount of DCM. The reaction mixture was stirred at room temperature until completion. The mixture was washed four times with water, dried ($MgSO_4$), filtered and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% $NH_4HCO_3$ solution in water; phase B: $CH_3OH$ (optional); phase C: $CH_3CN$). The product fractions were collected and the solvent was evaporated, yielding 0.324 g compound (277).

Example B.24

Intermediate (88) (0.000602 mol) was dissolved in DCM (6 ml). Then thionyl chloride (87 ml, 0.001204) was added and the reaction mixture was refluxed for 2 hours. The solvent was evaporated and DCM (6 ml) was added again. The solvent was evaporated once more and again DCM (6 ml) was added. Then intermediate (75) (0.000602 mol) and saturated aqueous $NaHCO_3$ solution (3 ml) were added. The mixture was stirred. Subsequently, the mixture was washed with water and the separated organic layer was dried ($MgSO_4$), filtered and the solvent was evaporated, yielding compound (273).

Example B.25

Intermediate (92) was dissolved in DCM (4 ml) and EDCI (0.011 g) was added. To this mixture was added DIPEA (0.076 ml), 1-hydroxy-1H-benzotriazole (0.008 g) and isopropyl 3-aminopropionate hydrochloride (0.023 g) in a little bit DCM, and DMF. The reaction mixture was stirred overnight at room temperature. The reaction mixture was washed with water (three times), dried ($MgSO_4$) and purified by column chromatography (Isolute) DCM to DCM/MeOH (1/9), yielding 14 mg of compound (275).

Example B.26

Intermediate (80) (0.0040 mol) was dissolved in DCM (20 ml) and 1-ethyl-3-(N,N-dimethylamino)propylcarbodiimide (0.920 g) was added. To this mixture was added DIPEA (0.659 ml), 1-hydroxy-1H-benzotriazole (0.648 g) and isopropyl 3-aminopropionate hydrochloride (2.00 g) in a little bit DCM (20 ml), and DMF. The reaction mixture was stirred at room temperature. The reaction mixture was worked up. Extra DCM was added and the reaction mixture was washed with water (three times), dried ($MgSO_4$) and the organic layer was evaporated. The residue was purified by column chromatography (heptane/ethyl acetate; 1/1 —MeOH/DCM; 1/10). The product was further purified by reversed-phase high-performance liquid chromatography (Shandon Hyperprep® C18 BDS (Base Deactivated Silica) 8 μm, 250 g, I.D. 5 cm). A gradient with a buffer solution and organic solvents was applied, yielding 850 mg of compound (280).

Tables F-1 and F-1a lists the compounds that were prepared according to one of the above Examples. The stereochemical configuration for some compounds has been designated as R*, or S* indicating a relative stereochemistry when the absolute stereochemistry is undetermined although the compound itself been isolated as a single stereoisomer and is enantiomerically pure. For some compounds the melting point (m.p.) has been included.

TABLE F-1
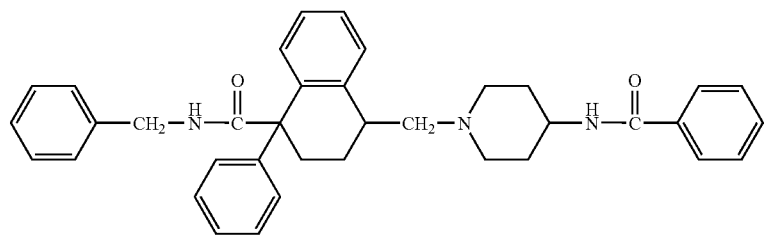
Co. No. 1; B.1
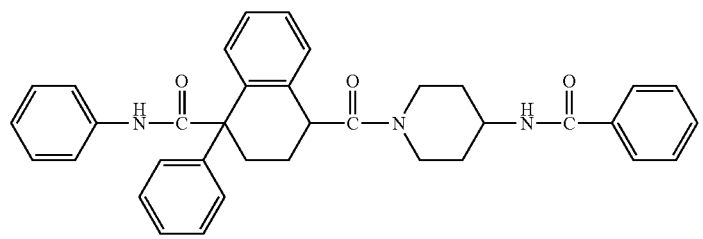
Co. No. 2; B.2
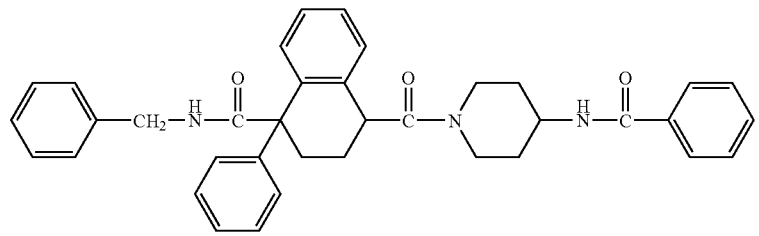
Co. No. 3; B.2
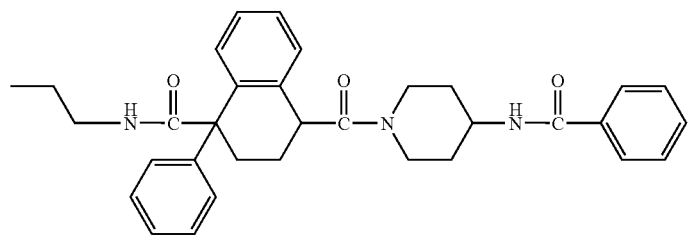
Co. No. 4; B.2
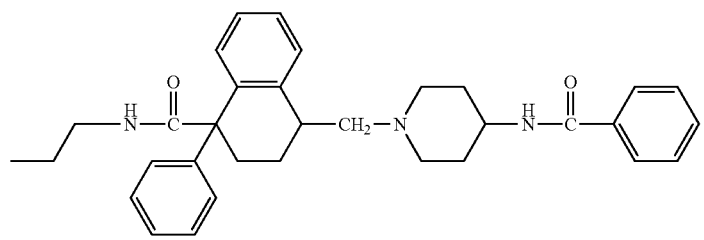
Co. No. 5; B.1
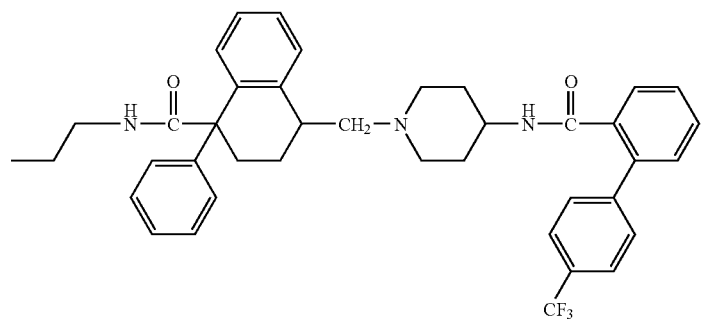
Co. No. 6; B.1

TABLE F-1-continued
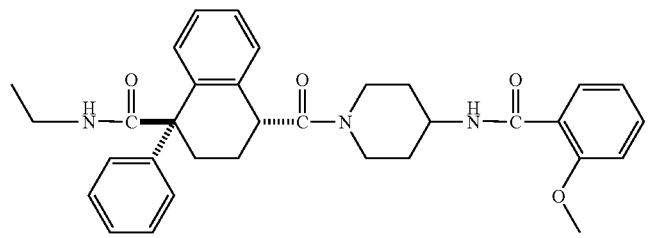
Co. No. 7; B.3; trans
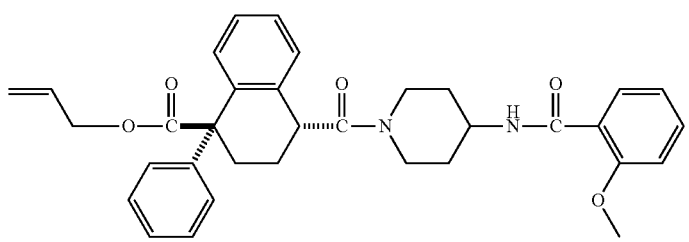
Co. No. 8; Ex. B.3; trans
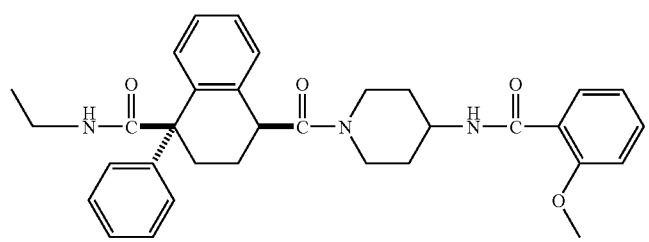
Co. No. 9; Ex. B.3; cis
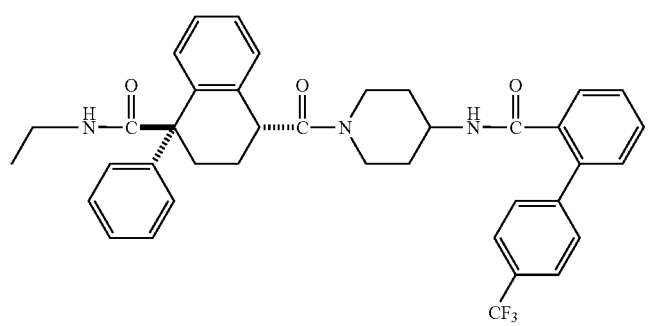
Co. No. 10; Ex. B.3; trans
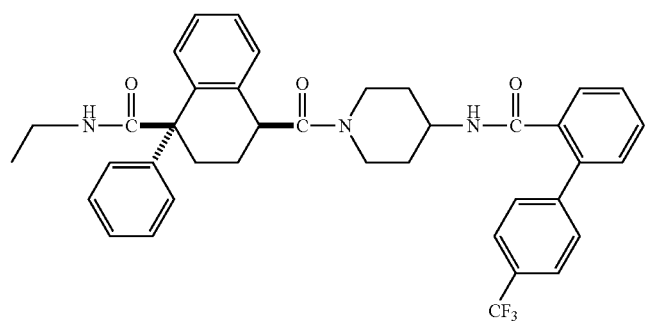
Co. No. 11; Ex. B.3; cis TABLE F-1-continued
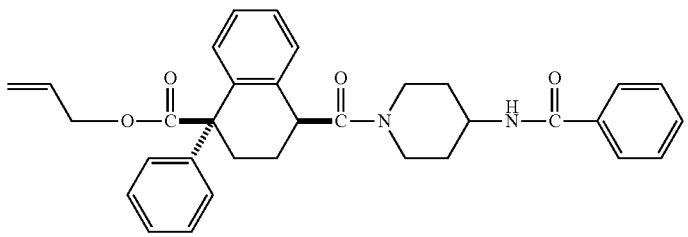
Co. No. 12; Ex. B.3; cis
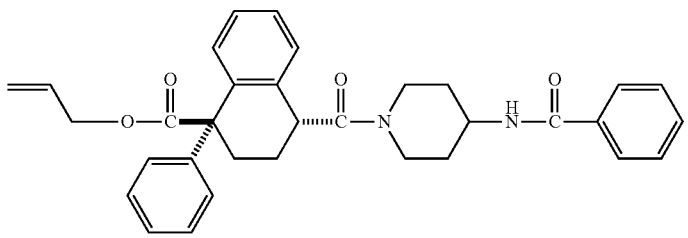
Co. No. 13; Ex. B.3; trans; m.p. 103-107° C.
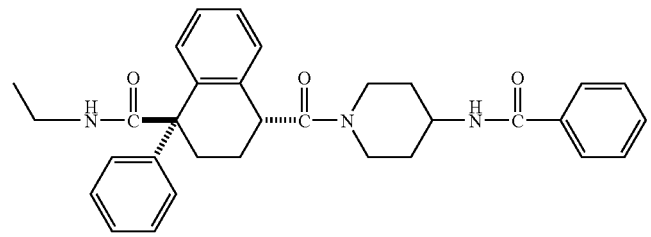
Co. No. 14; Ex. B.3; trans
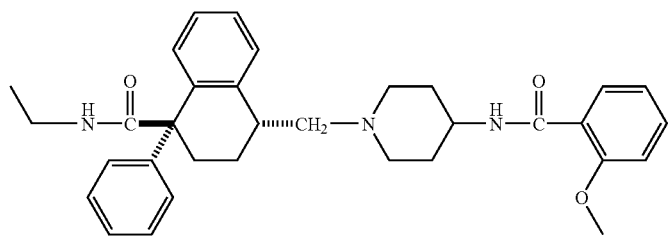
Co. No. 15; Ex. B.1; trans
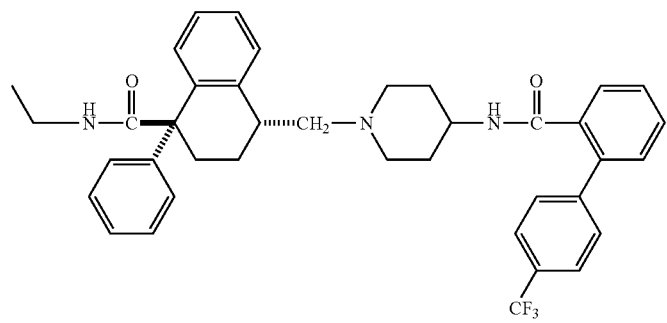
Co. No. 16; Ex. B.1; trans
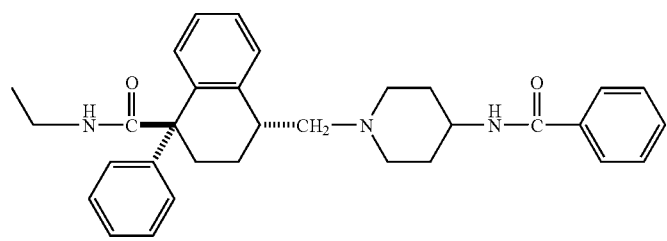
Co. No. 17; Ex. B.1; trans TABLE F-1-continued
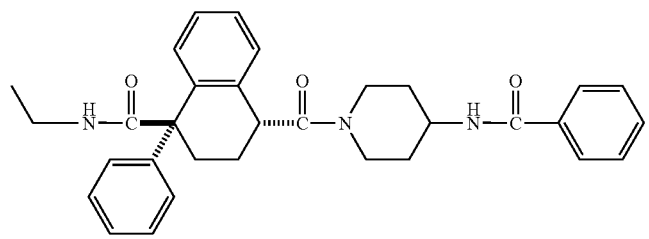
Co. No. 18; Ex. B.3; trans
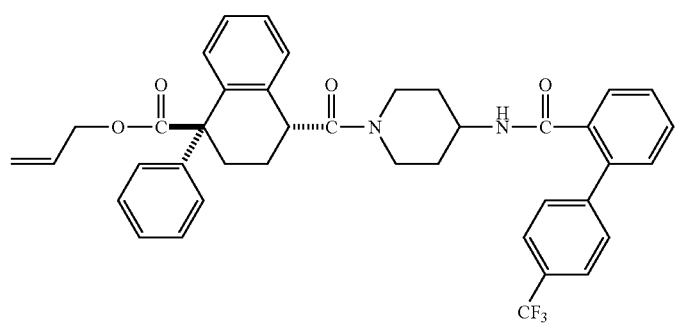
Co. No. 19; Ex. B.3; trans
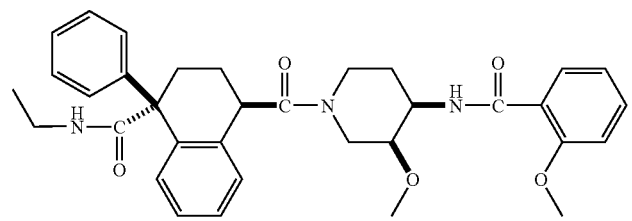
Co. No. 20; Ex. B.4
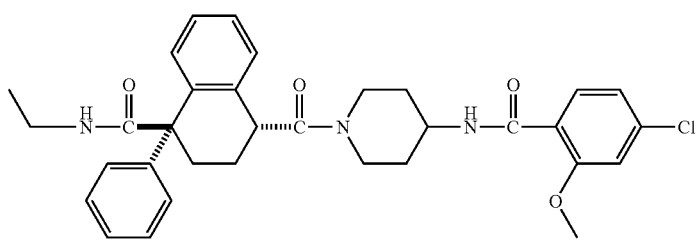
Co. No. 21; Ex. B.4; trans
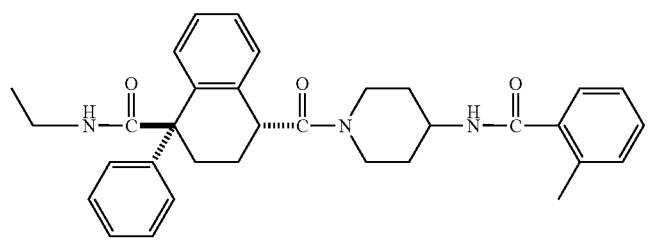
Co. No. 22; Ex. B.5; trans TABLE F-1-continued
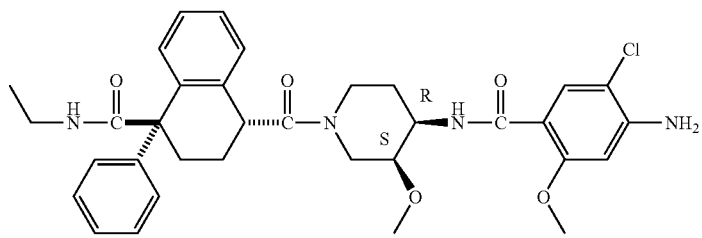
Co. No. 23; Ex. B.4
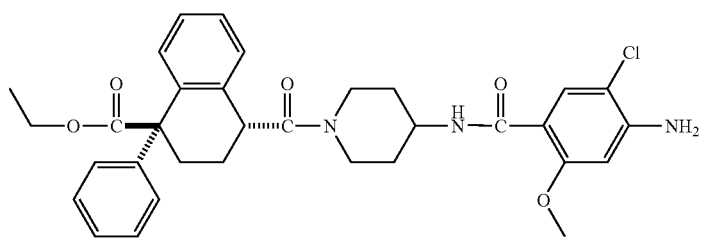
Co. No. 24; Ex. B.4; trans
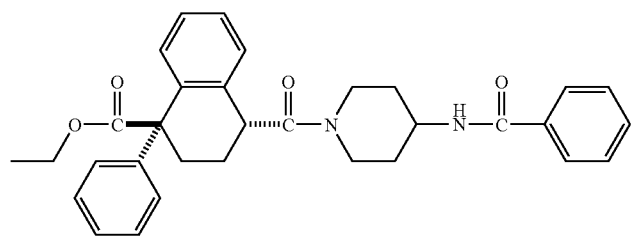
Co. No. 25; Ex. B.6; trans; 112-115° C.
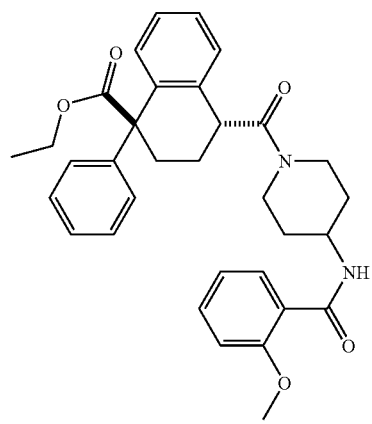
Co. No. 26; Ex. B.6; trans
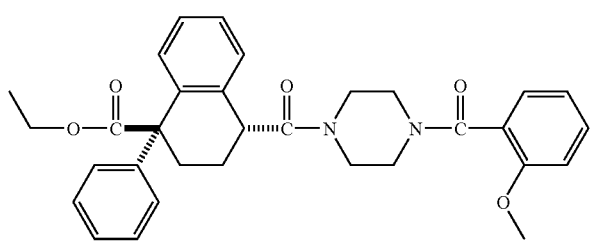
Co. No. 27; Ex. B.5; trans TABLE F-1-continued
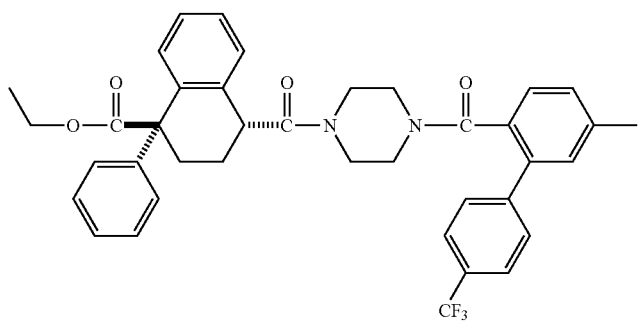
Co. No. 28; Ex. B.5; trans
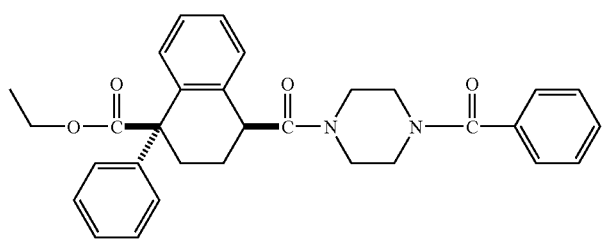
Co. No. 29; Ex. B.5; cis
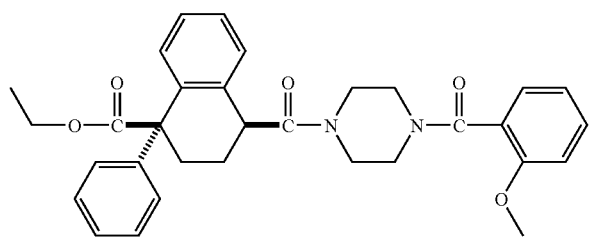
Co. No. 30; Ex. B.5; cis
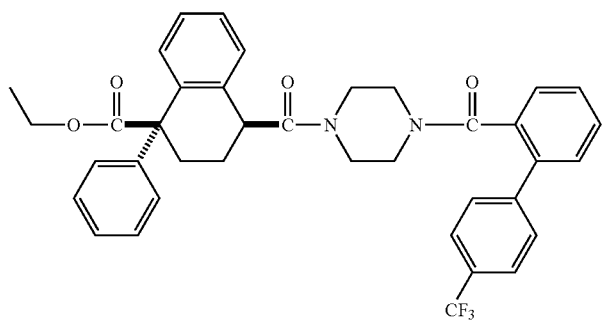
Co. No. 31; Ex. B.5; cis
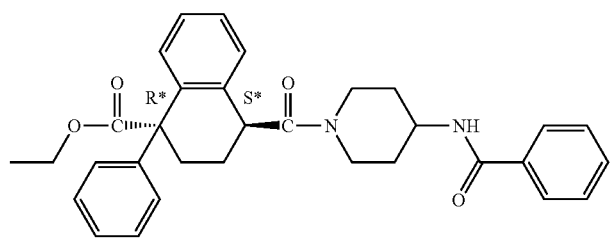
Co. No. 32; Ex. B.7; m.p. 164° C.
(Büchi visual)

TABLE F-1-continued
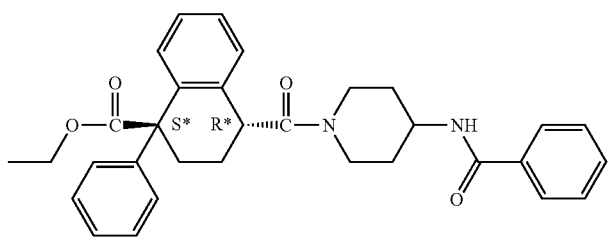
Co. No. 33; Ex. B.7; m.p. 165.4° C.
(Büchi visual)
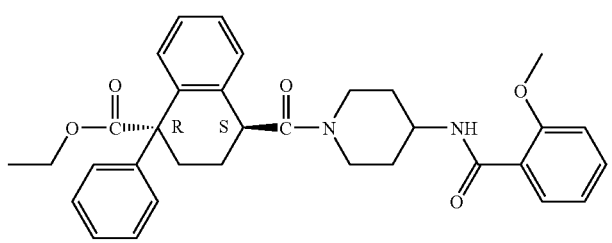
Co. No. 34; Ex. B.8; (1R, 4S);
m.p. 111.47° C. (DSC)
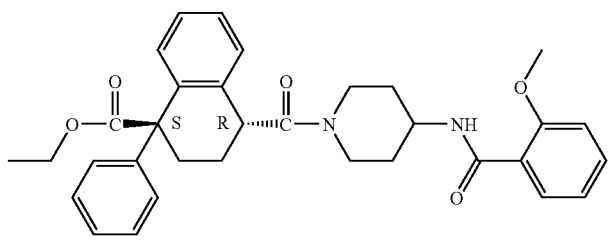
Co. No. 35; Ex. B.8; (1S, 4R); m.p.
101.6° C. (Büchi automatics)
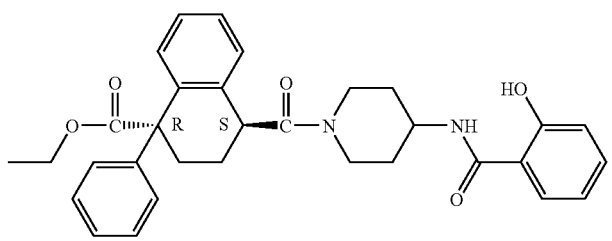
Co. No. 36; Ex. B.10; (1R, 4S); m.p.:
206.0-207.3° C. (Büchi visual)
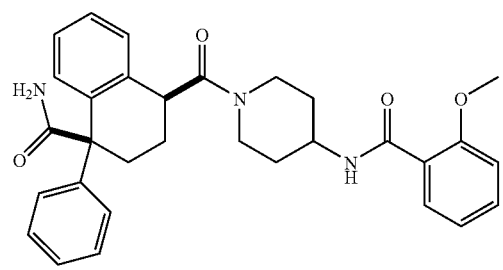
Co. No. 37; Ex. B.10; cis

TABLE F-1-continued
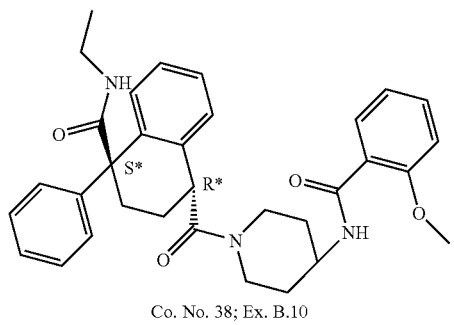
Co. No. 38; Ex. B.10
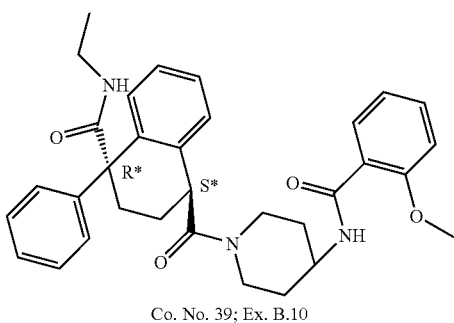
Co. No. 39; Ex. B.10
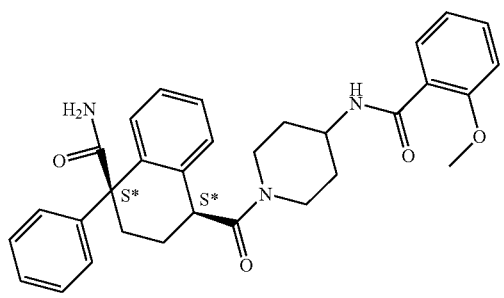
Co. No. 40; Ex. B.10
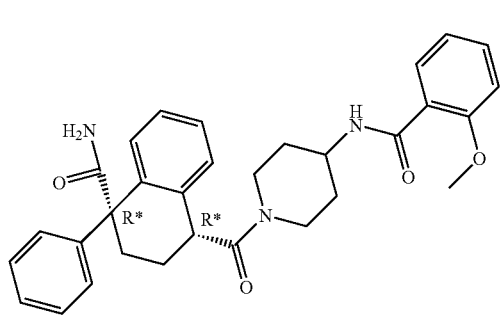
Co. No. 41; Ex. B.10
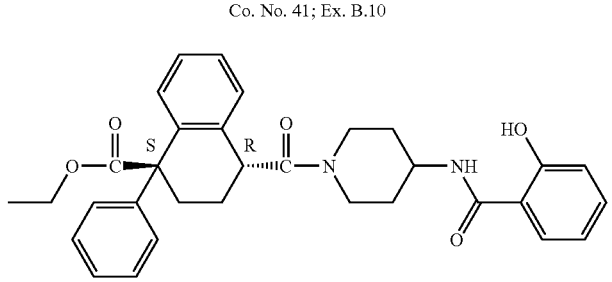
Co. No. 42; Ex. B.10; (1S, 4R); m.p. 206.6-207.4° C. (Büchi visual)

TABLE F-1-continued
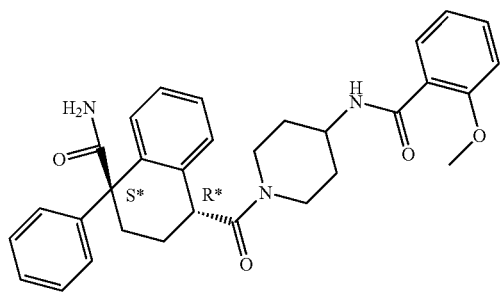
Co. No. 43; Ex. B.9
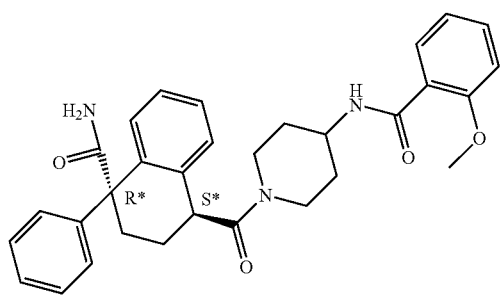
Co. No. 44; Ex. B.9
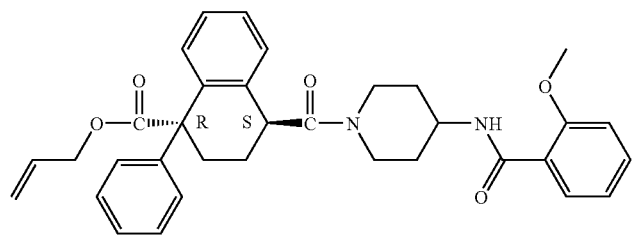
Co. No. 45; Ex. B.10; (1R, 4S); m.p.
114.0-126.0° C. (Büchi visual)
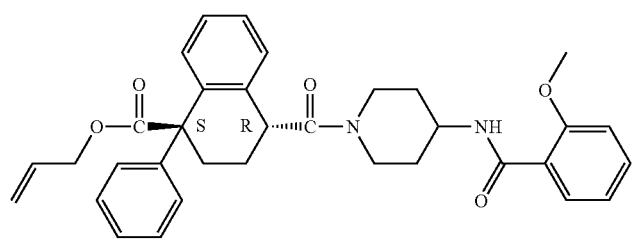
Co. No. 46; Ex. B.10; (1S, 4R); m.p.
112.7-118.6° C. (Büchi visual)
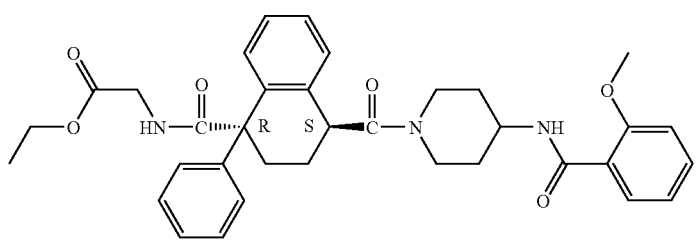
Co. No. 47; Ex. B.17; (1R, 4S); m.p.
223.7-233.8° C. (Büchi visual)

TABLE F-1-continued
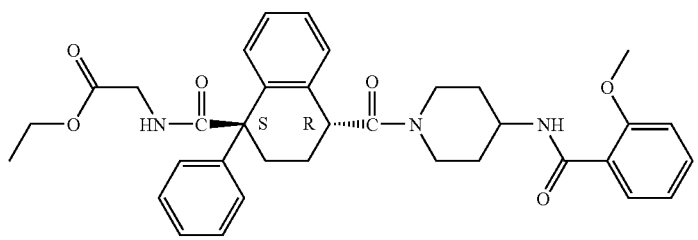
Co. No. 48; Ex. B.11; (1S, 4R); m.p.
226.1-233.0° C. (Büchi visual)
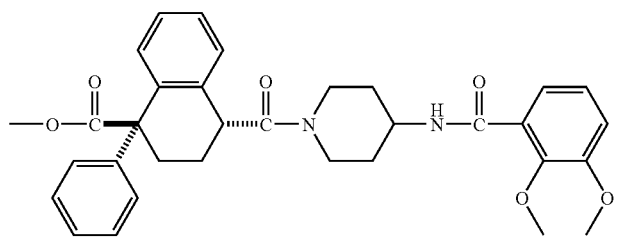
Co. No. 49; Ex. B.12
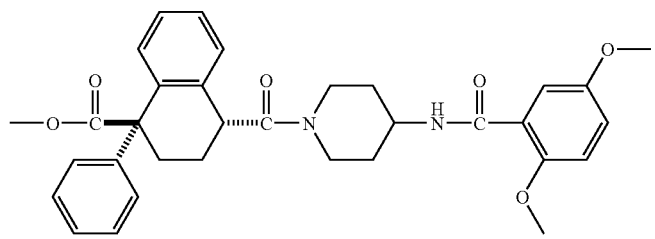
Co. No. 50; Ex. B.12
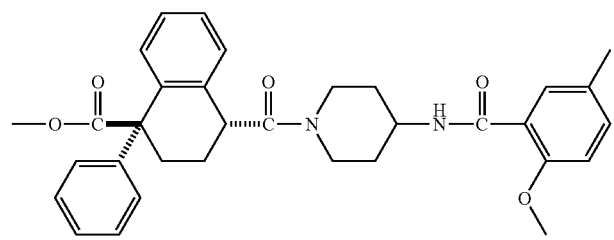
Co. No. 51; Ex. B.12
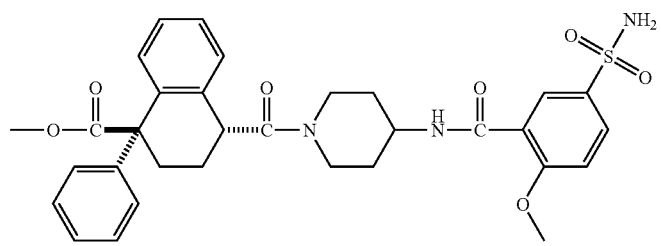
Co. No. 52; Ex. B.12
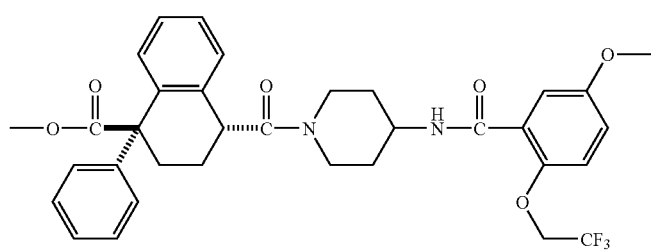
Co. No. 53; Ex. B.12

TABLE F-1-continued
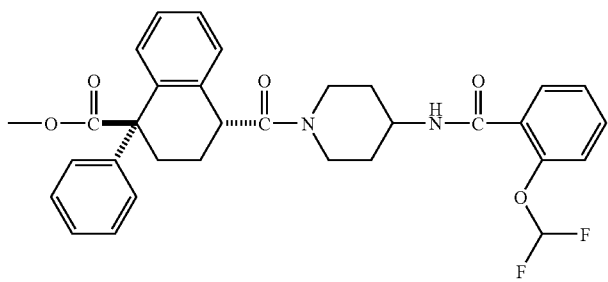
Co. No. 54; Ex. B.12
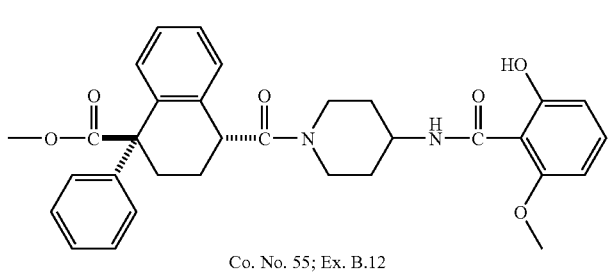
Co. No. 55; Ex. B.12
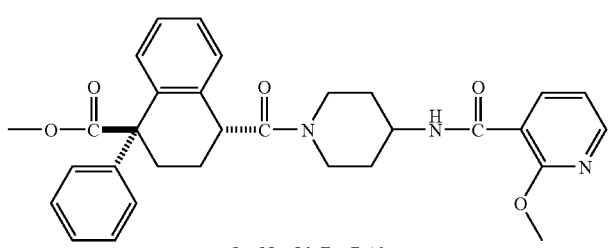
Co. No. 56; Ex. B.12
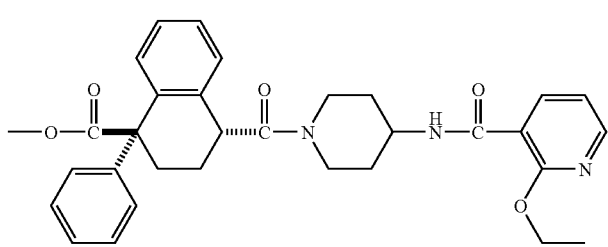
Co. No. 57; Ex. B.12
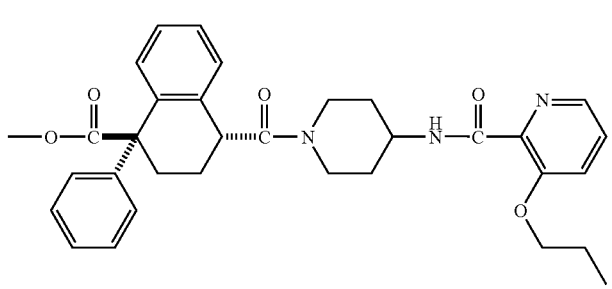
Co. No. 58; Ex. B.12
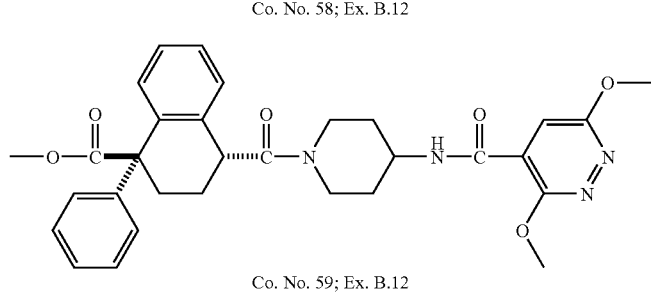
Co. No. 59; Ex. B.12

TABLE F-1-continued
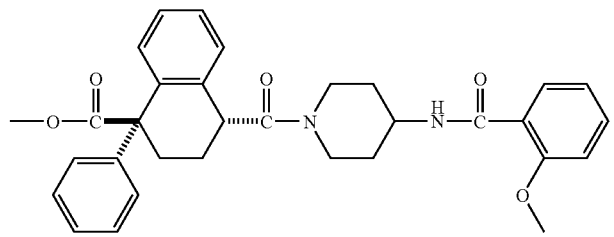
Co. No. 60; Ex. B.12
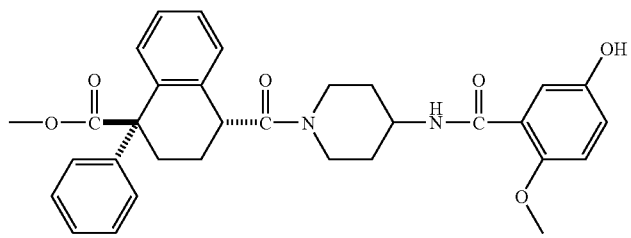
Co. No. 61; Ex. B.12
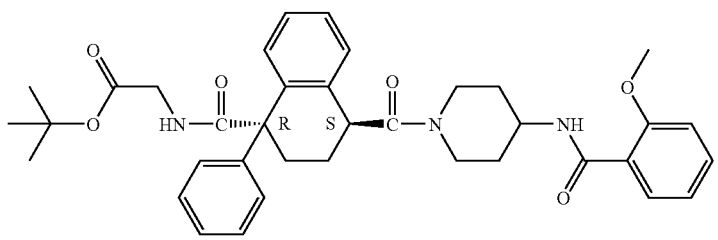
Co. No. 62; Ex. B.17; (1R, 4S)
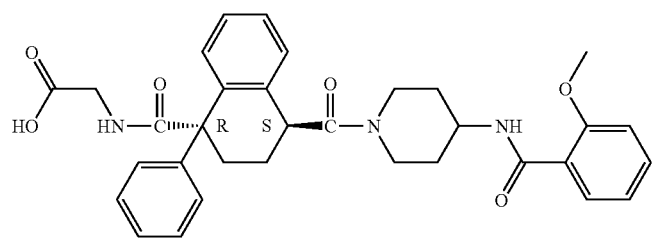
Co. No. 63; Ex. B.13; (1R, 4S)
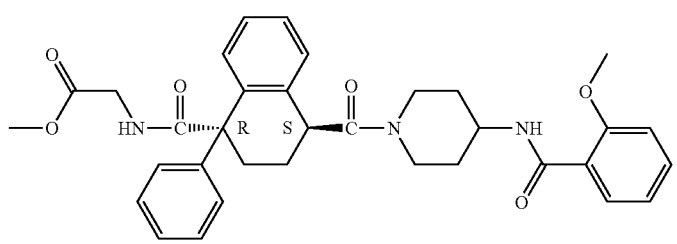
Co. No. 64; Ex. B.17; (1R, 4S)

TABLE F-1-continued
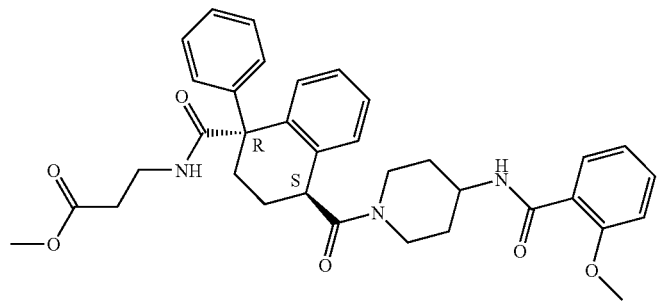
Co. No. 65; Ex. B.17; (1R, 4S); m.p.
188° C. (Büchi visual)
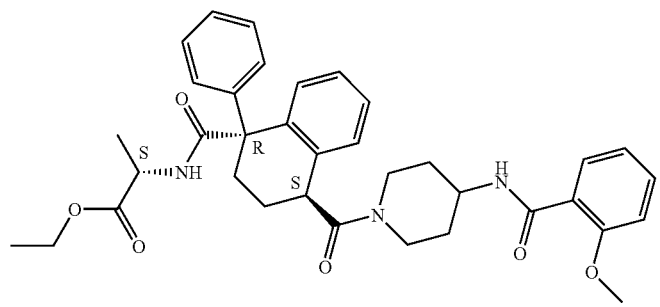
Co. No. 66; Ex. B.17; (1R(S), 4S)
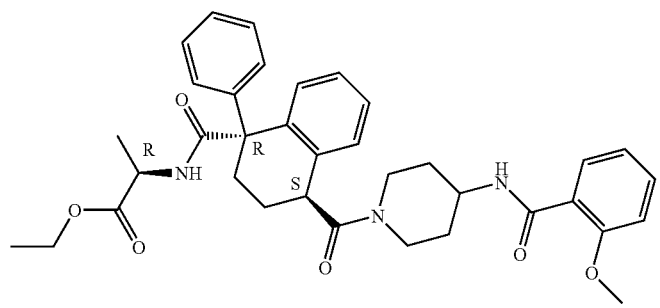
Co. No. 67; Ex. B.17; [1R(R), 4S]
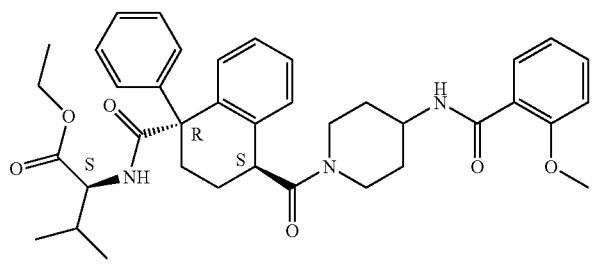
Co. No. 68; Ex. B.17; [1R(S), 4S]
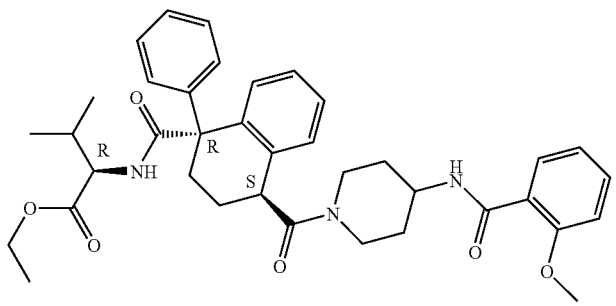
Co. No. 69; Ex. B.17; [1R(R), 4S]

TABLE F-1-continued
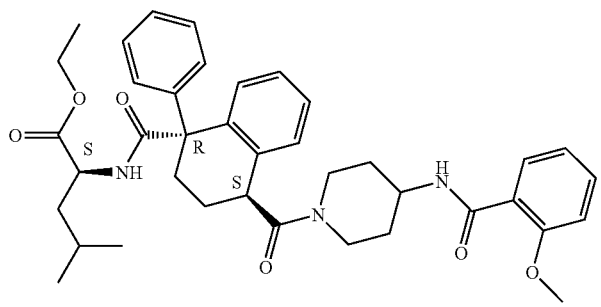
Co. No. 70; Ex. B.17; [1R(S), 4S]
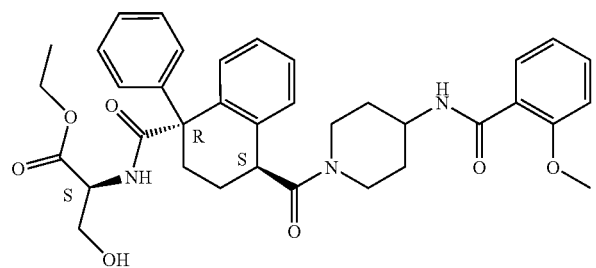
Co. No. 71; Ex. B.17; [1R(S), 4S]
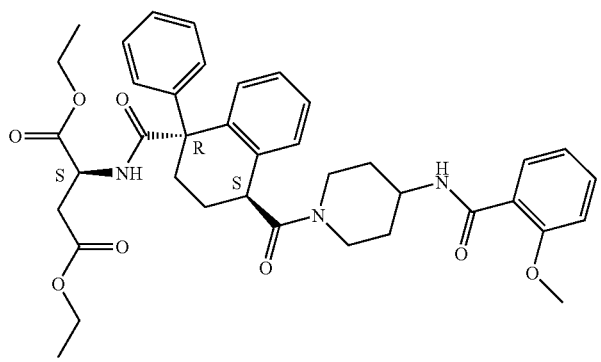
Co. No. 72; Ex. B.17; [1R(S), 4S]
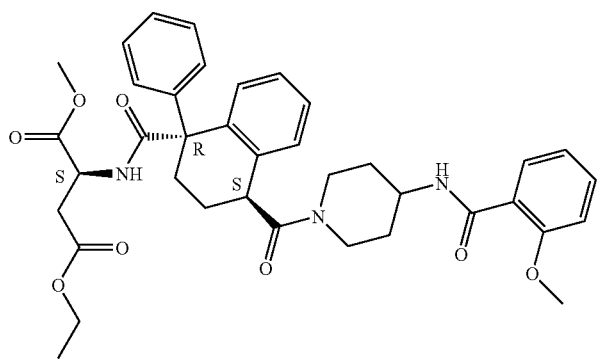
Co. No. 73; Ex. B.17; [1R(S), 4S]

TABLE F-1-continued
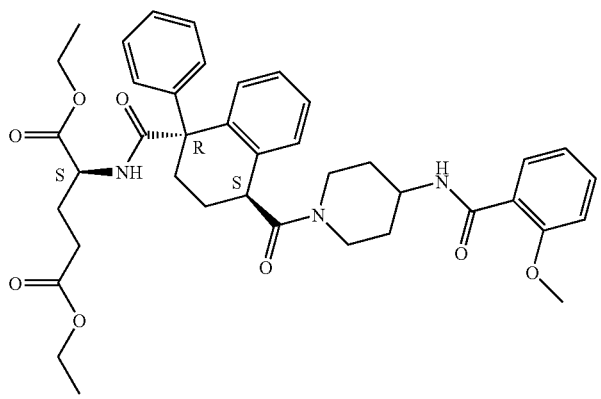
Co. No. 74; Ex. B.17; [1R(S), 4S]
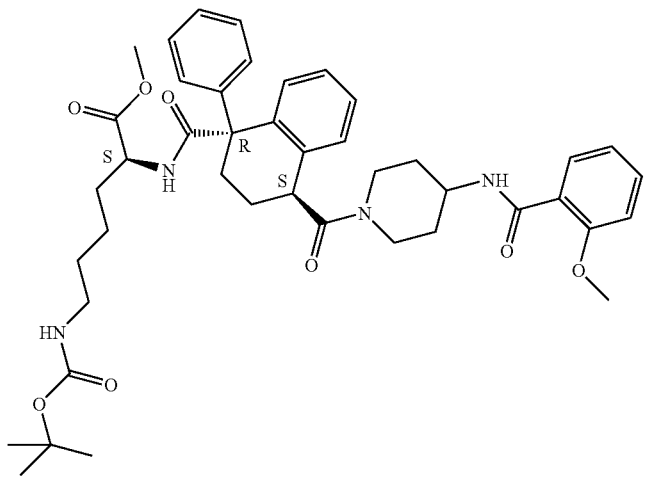
Co. No. 75; Ex. B.17; [1R(S), 4S]
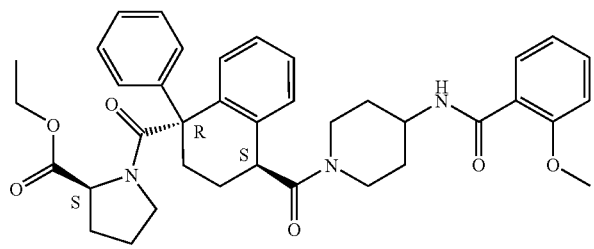
Co. No. 76; Ex. B.17; [1R(S), 4S]
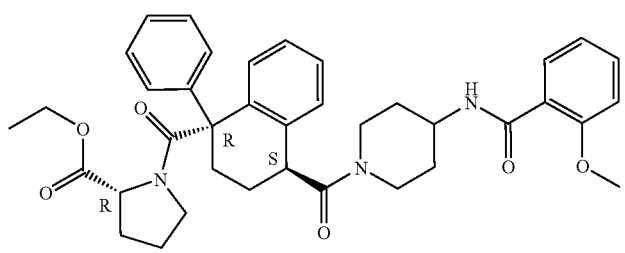
Co. No. 77; Ex. B.17; [1R(R), 4S]

TABLE F-1-continued
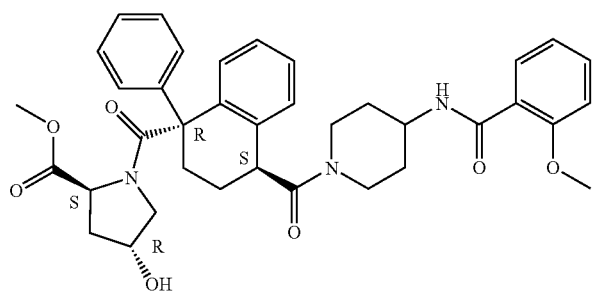
Co. No. 78; Ex. B.17; [1R(2S-trans), 4S]
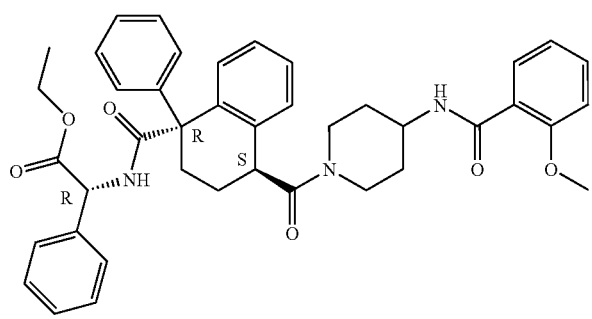
Co. No. 79; Ex. B.17; [1R(R), 4S]
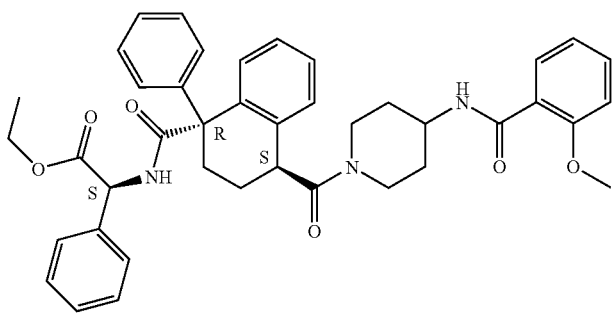
Co. No. 80; Ex. B.17; [1R(S), 4S]
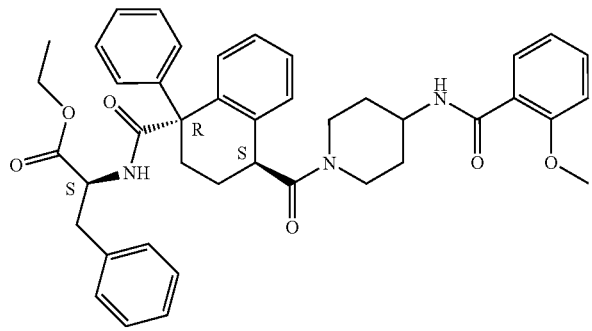
Co. No. 81; Ex. B.17; [1R(S), 4S]

TABLE F-1-continued
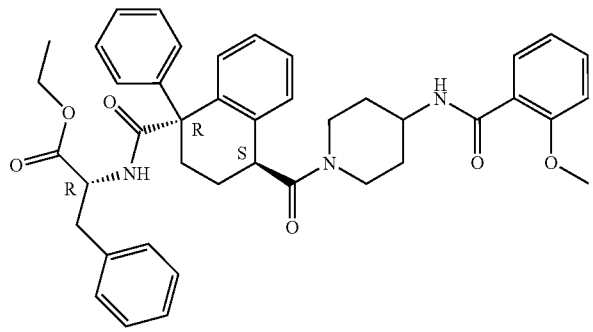
Co. No. 82; Ex. B.17; [1R(R), 4S]
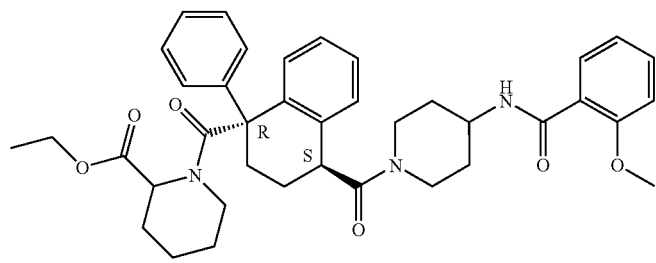
Co. No. 83; Ex. B.17; (1R, 4S)
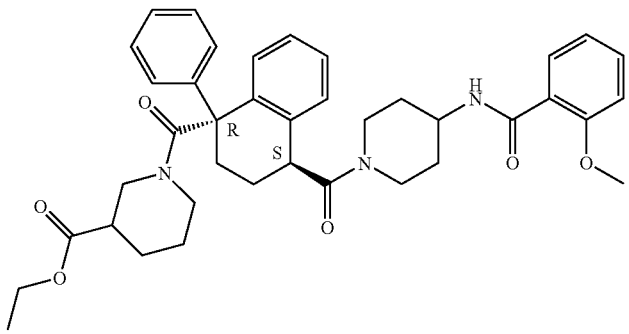
Co. No. 84; Ex. B.17; (1R, 4S)
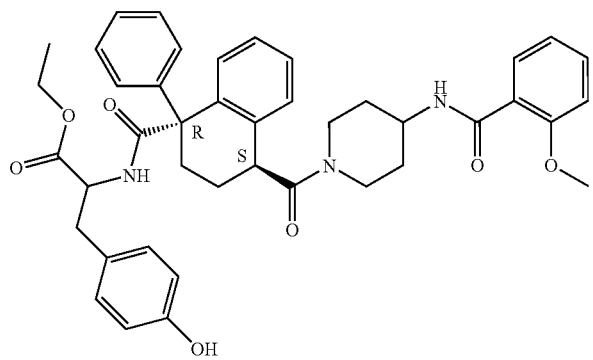
Co. No. 85; Ex. B.17; (1R, 4S)

TABLE F-1-continued
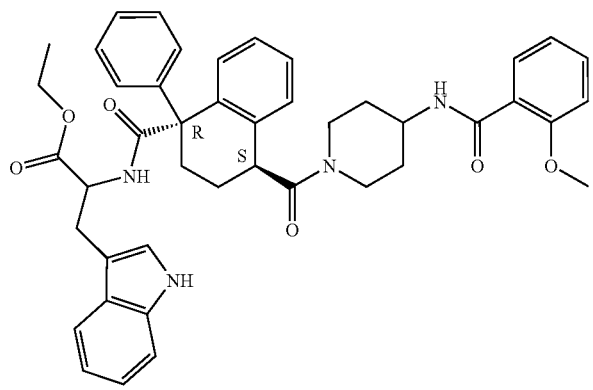
Co. No. 86; Ex. B.17; (1R, 4S)
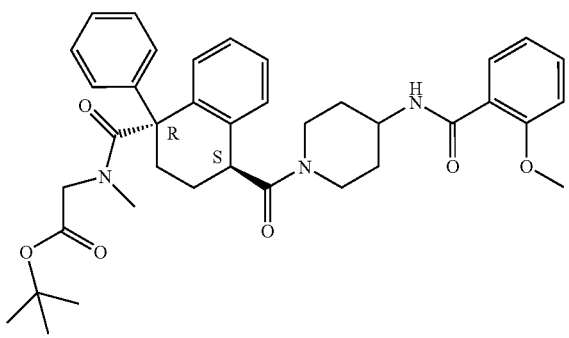
Co. No. 87; Ex. B.17; (1R, 4S)
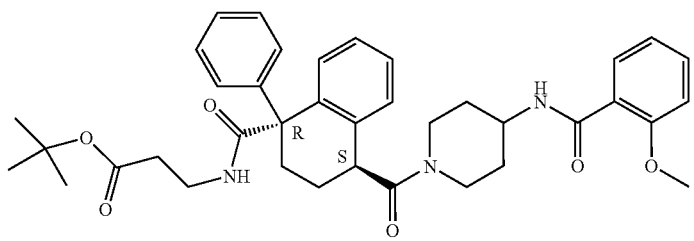
Co. No. 88; Ex. B.17; (1R, 4S)
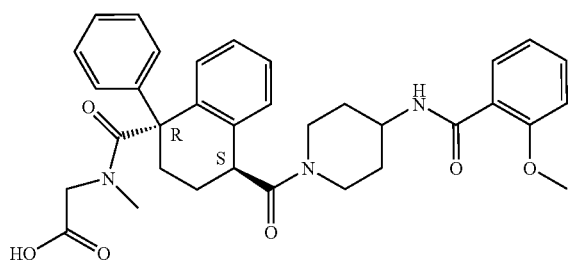
Co. No. 89; Ex. B.13; (1R, 4S)
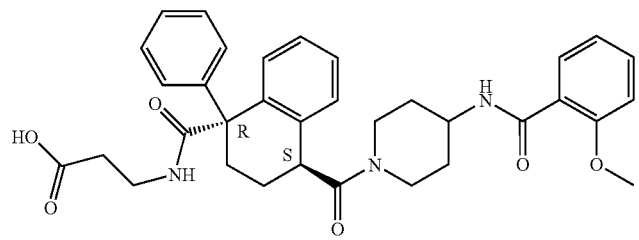
Co. No. 90; Ex. B.13; (1R, 4S)

TABLE F-1-continued
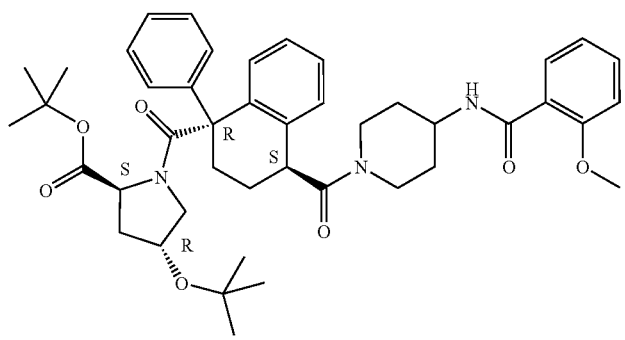
Co. No. 91; Ex. B.17; [1R(2S-trans), 4S]
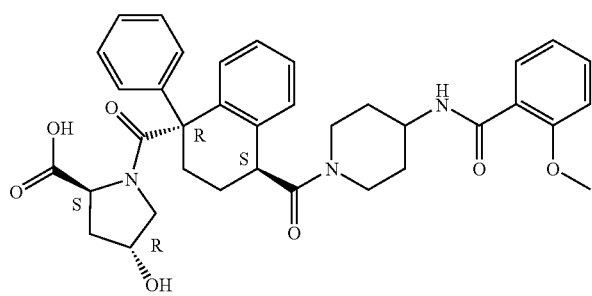
Co. No. 92; Ex. B.13; [1R(2S-trans), 4S]
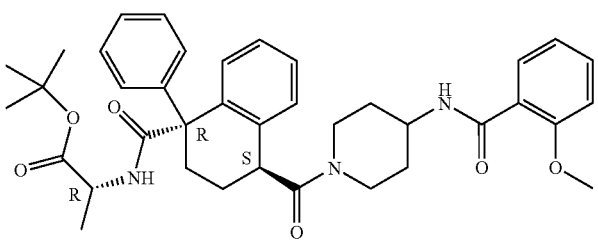
Co. No. 93; Ex. B.17; [1R(R), 4S]
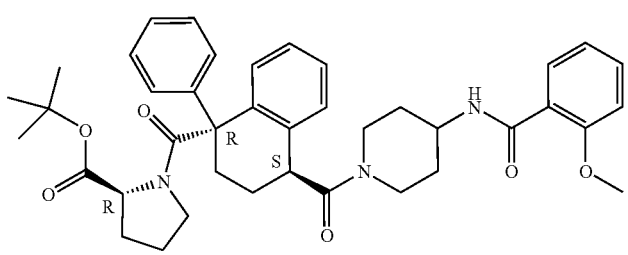
Co. No. 94; Ex. B.17; [1R(R), 4S]
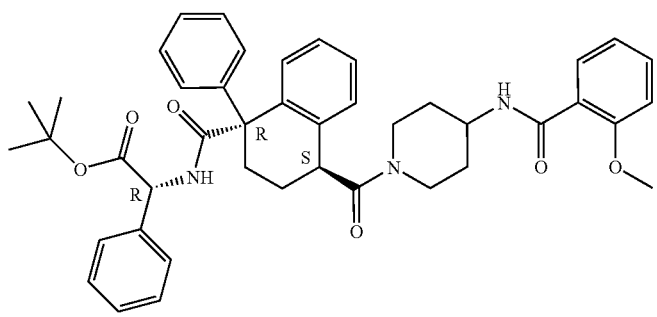
Co. No. 95; Ex. B.17; [1R(R), 4S]

TABLE F-1-continued
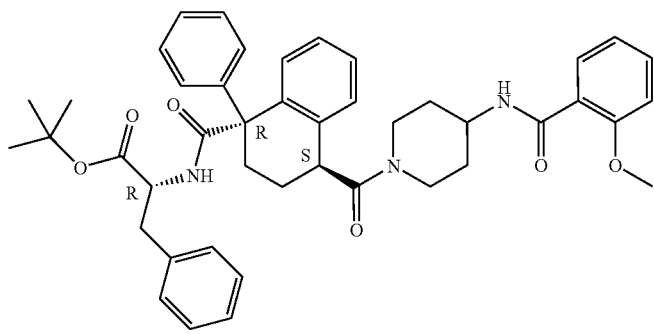
Co. No. 96; Ex. B.17; [1R(R), 4S]
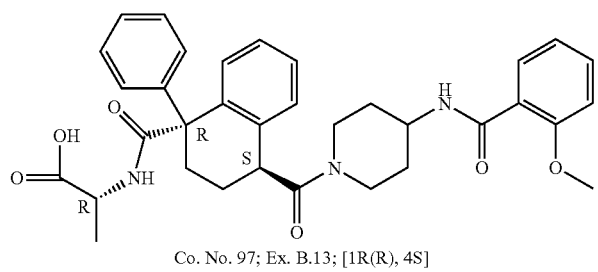
Co. No. 97; Ex. B.13; [1R(R), 4S]
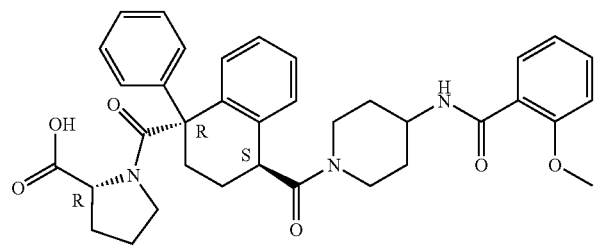
Co. No. 98; Ex. B.13; [1R(R), 4S]
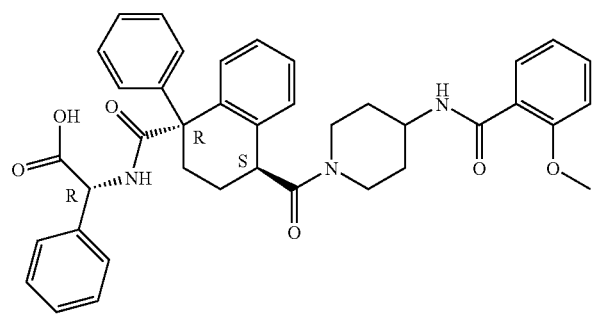
Co. No. 99; Ex. B.13, [1R(R), 4S]
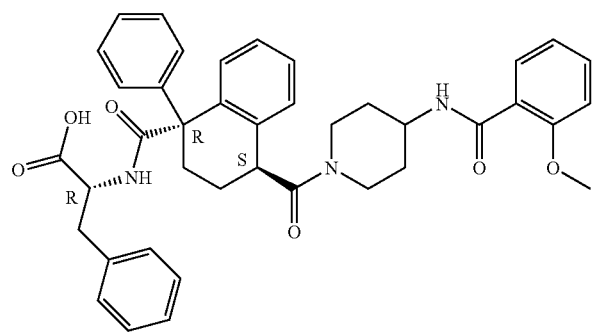
Co. No. 100; Ex. B.13; [1R(R), 4S]

TABLE F-1-continued
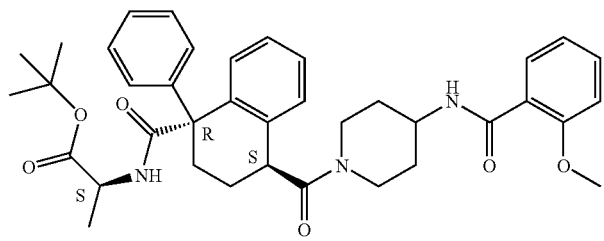
Co. No. 101; Ex. B.17; [1R(S), 4S]
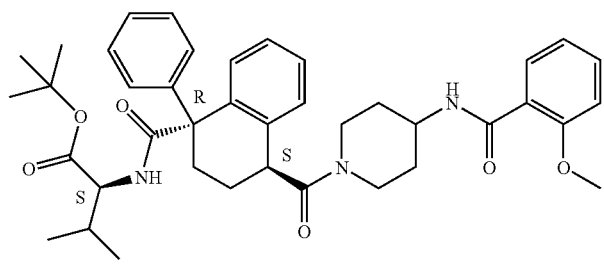
Co. No. 102; Ex. B.17; [1R(S), 4S]
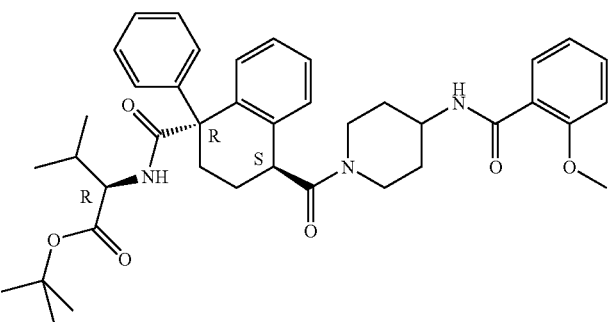
Co. No. 103; Ex. B.17; [1R(R), 4S]
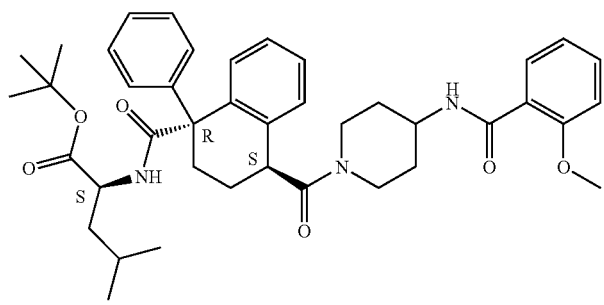
Co. No. 104; Ex. B.17; [1R(S), 4S]
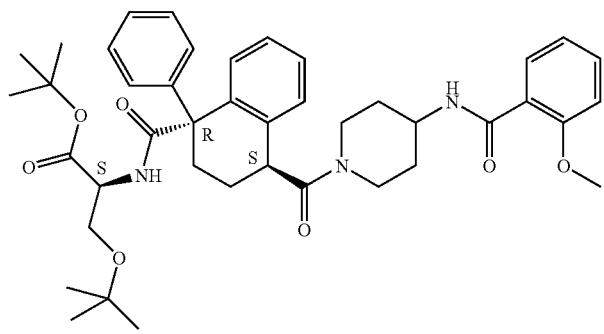
Co. No. 105; Ex. B.17; [1R(S), 4S]

TABLE F-1-continued
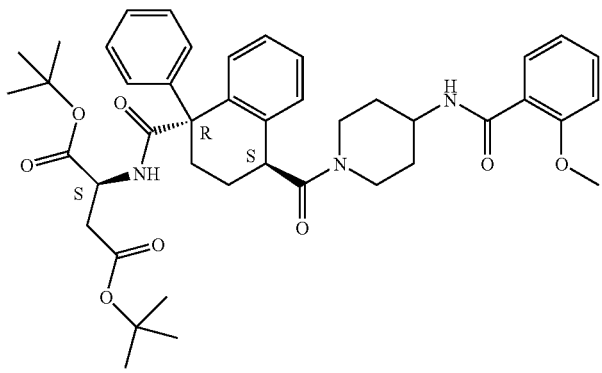
Co. No. 106; Ex. B.17; [1R(S), 4S]
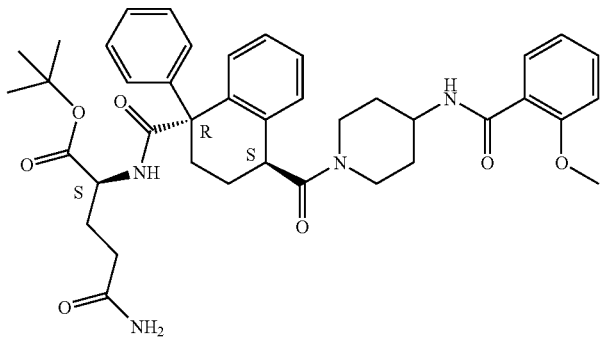
Co. No. 107; Ex. B.17; [1R(S), 4S]
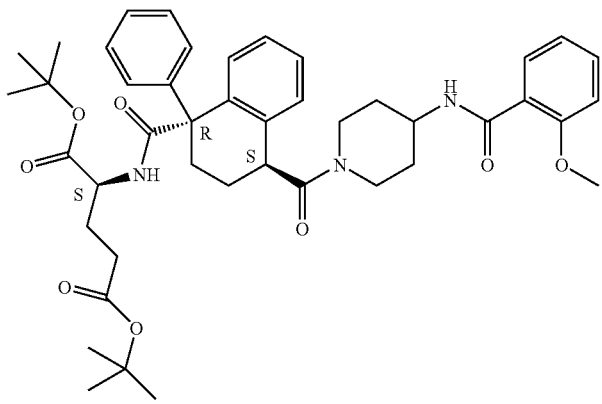
Co. No. 108; Ex. B.17; [1R(S), 4S]
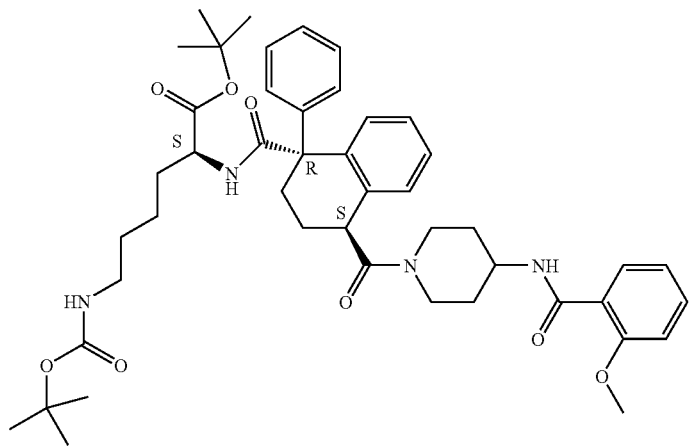
Co. No. 109; Ex. B.17; [1R(S), 4S]

TABLE F-1-continued
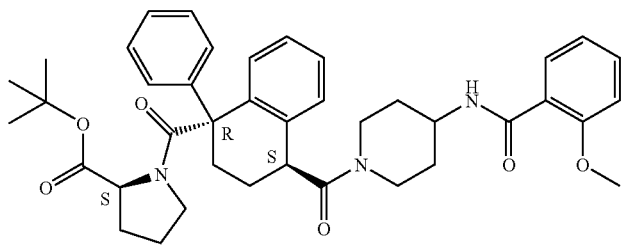
Co. No. 110; Ex. B.17; [1R(S), 4S]
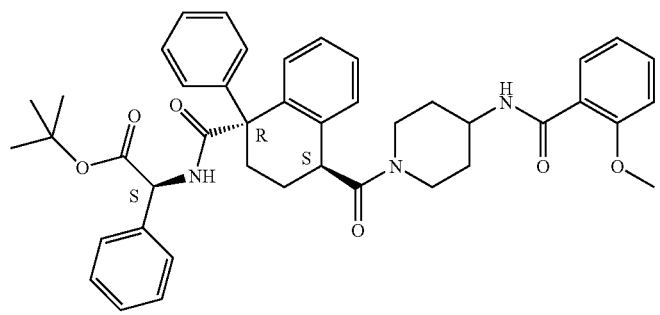
Co. No. 111; Ex. B.17; [1R(S), 4S]
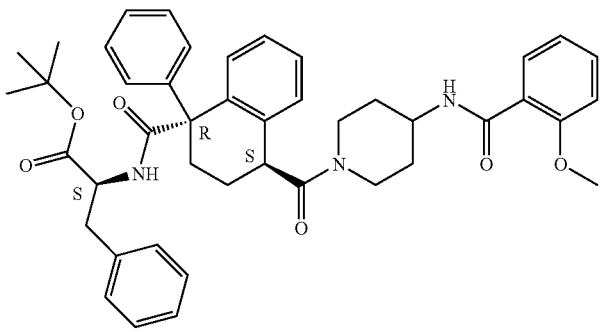
Co. No. 112; Ex. B.17; [1R(S), 4S]
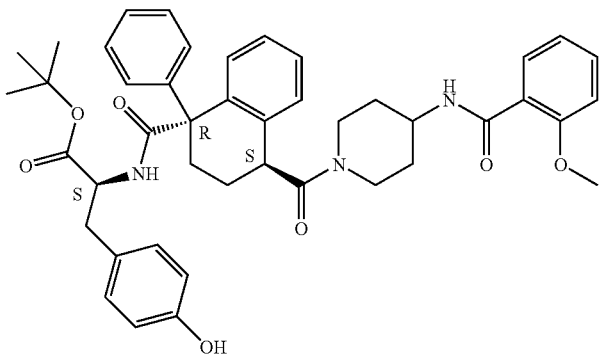
Co. No. 113; Ex. B.17; [1R(S), 4S]

TABLE F-1-continued
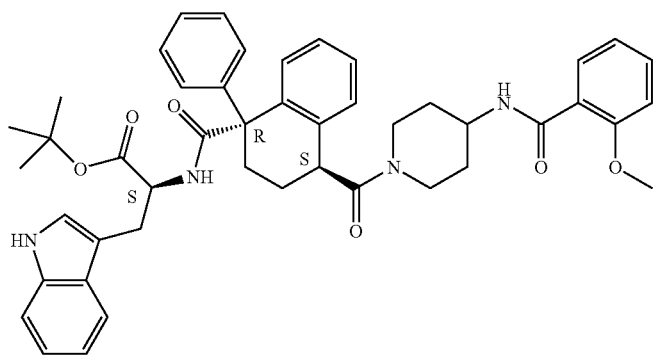
Co. No. 114; Ex. B.17; [1R(S), 4S]
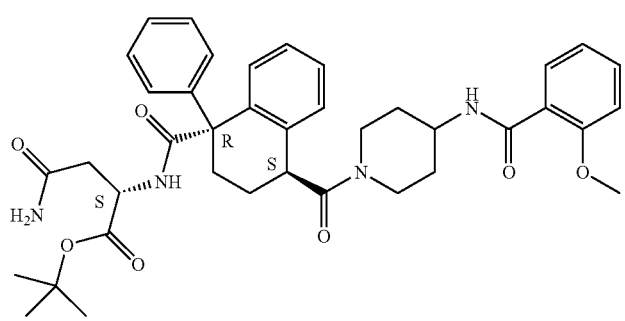
Co. No. 115; Ex. B.17; [1R(S), 4S]
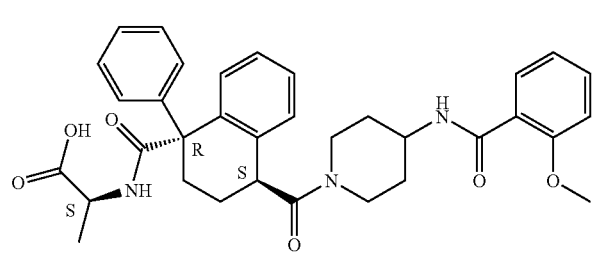
Co. No. 116; Ex. B.13; [1R(S), 4S]
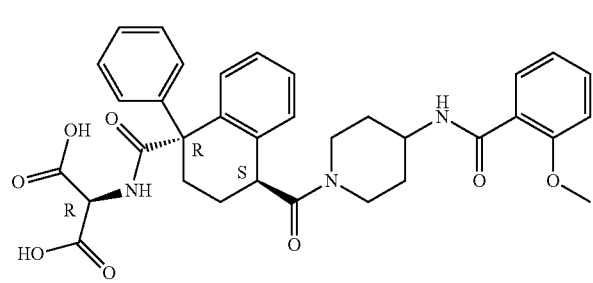
Co. No. 117; Ex. B.13; [1R(S), 4S]
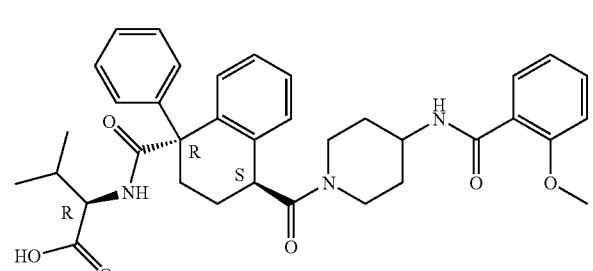
Co. No. 118; Ex. B.13; [1R(R), 4S]

TABLE F-1-continued
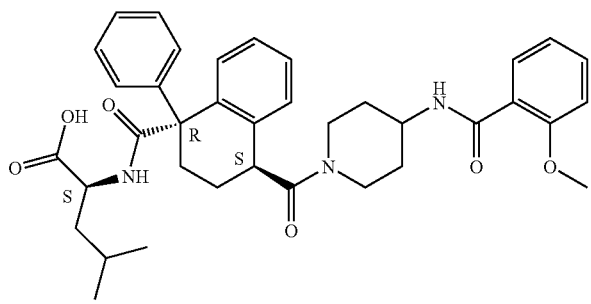
Co. No. 119; Ex. B.13; [1R(S), 4S]
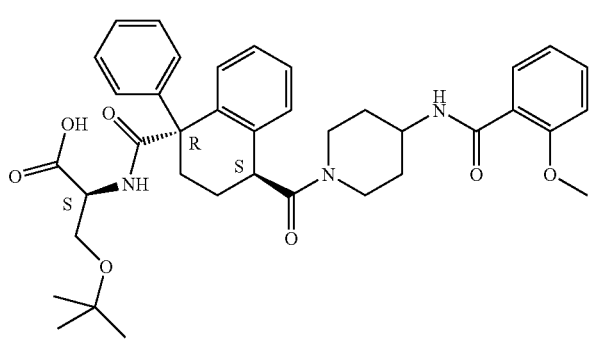
Co. No. 120; Ex. B.13; [1R(S), 4S]
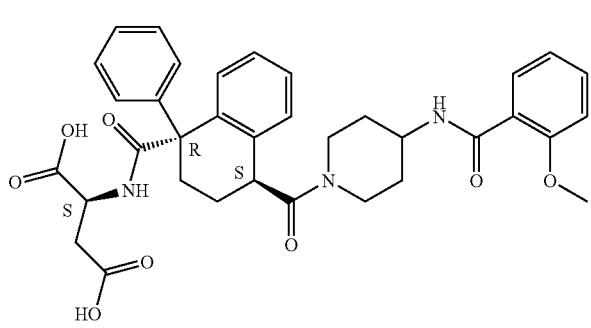
Co. No. 121; Ex. B.13; [1R(S), 4S]
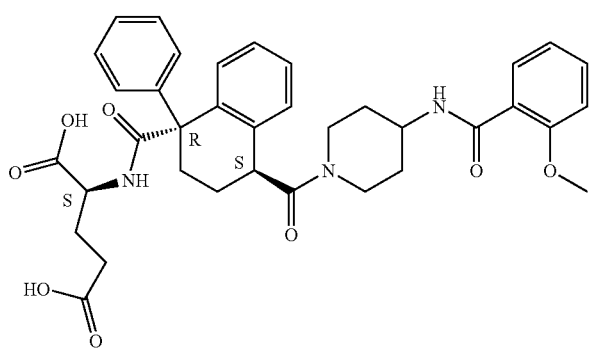
Co. No. 122; Ex. B.13; [1R(S), 4S]
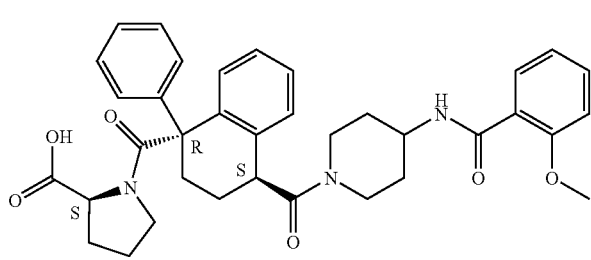
Co. No. 123; Ex. B.13; [1R(S), 4S]

TABLE F-1-continued
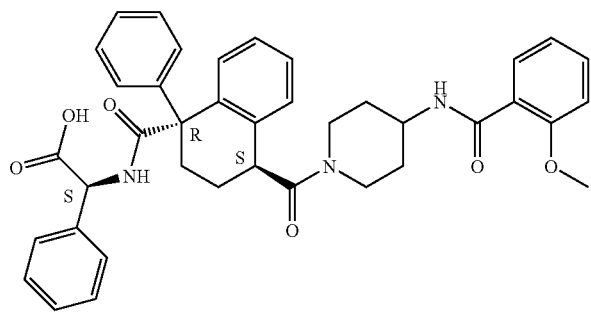
Co. No. 124; Ex. B.13; [1R(S), 4S]
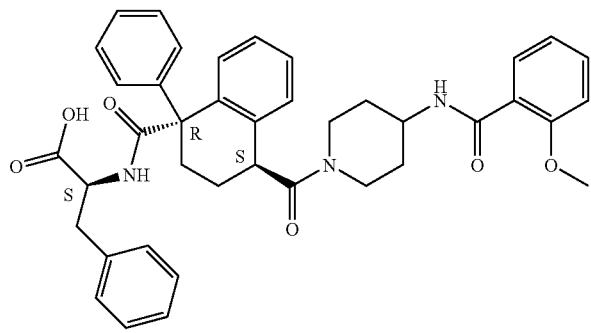
Co. No. 125; Ex. B.13; [1R(S), 4S]
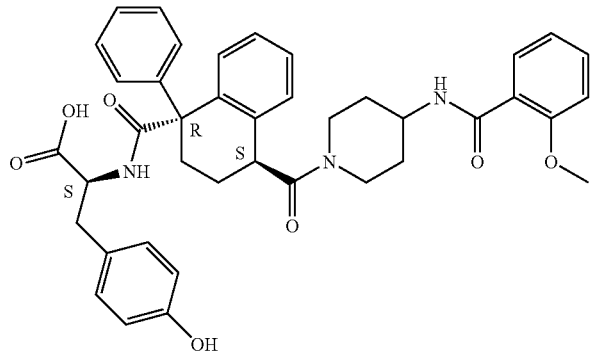
Co. No. 126; Ex. B.13; [1R(S), 4S]
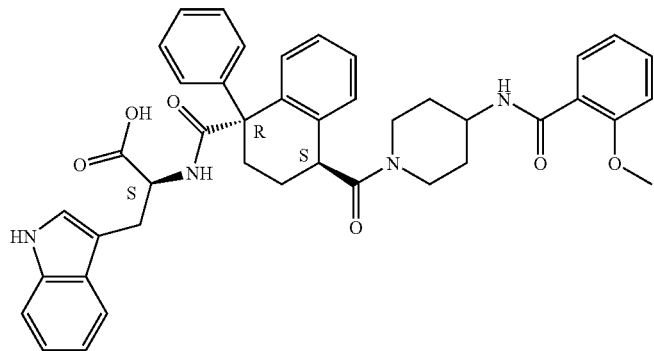
Co. No. 127; Ex. B.13; [1R((S), 4S]

TABLE F-1-continued
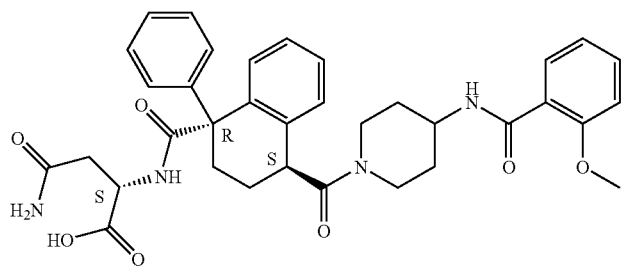
Co. No. 128; Ex. B.13; [1R(S), 4S]
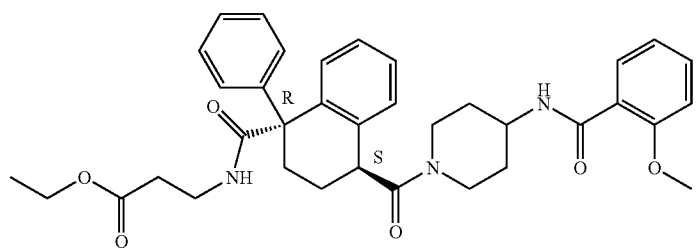
Co. No. 129; Ex. B.17; (1R, 4S)
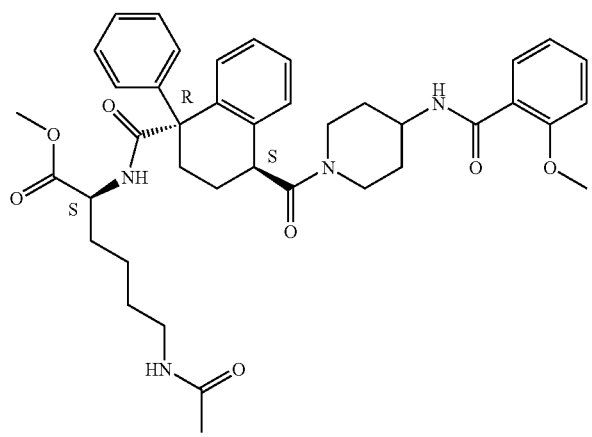
Co. No. 130; Ex. B.17; [1R(S), 4S]
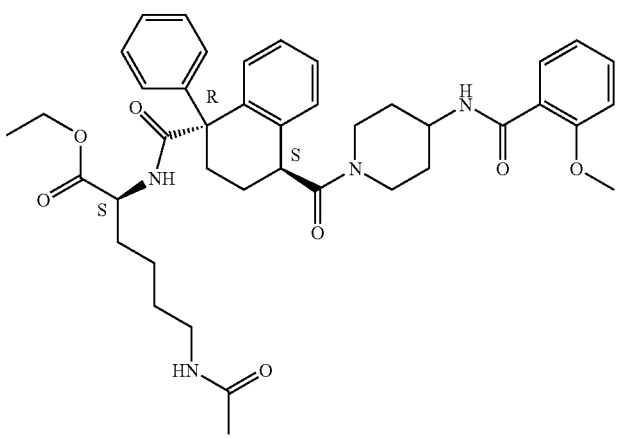
Co. No. 131; Ex. B.17; [1R(S), 4S]

TABLE F-1-continued
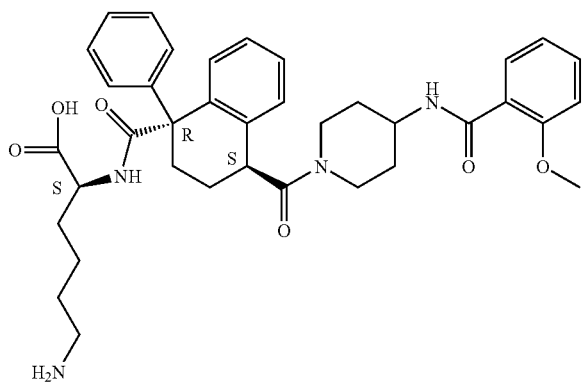
Co. No. 132; Ex. B.13; [1R(S), 4S]
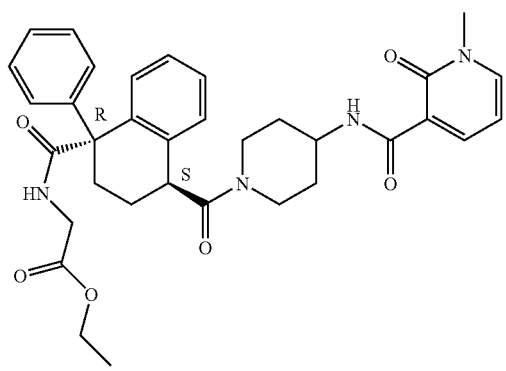
Co. No. 133; Ex. B.17; (1R, 4S)
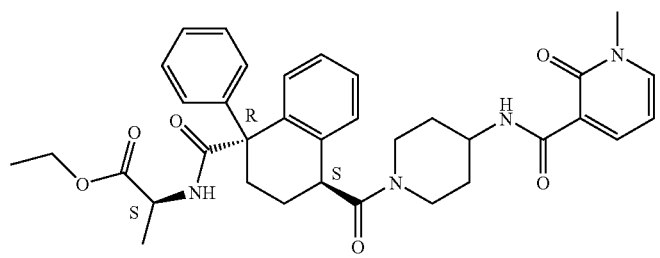
Co. No. 135; Ex. B.17; [1R(S), 4S]
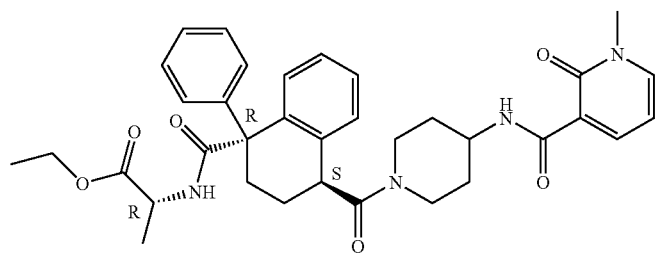
Co. No. 136; Ex. B.17; [1R(R), 4S]

TABLE F-1-continued
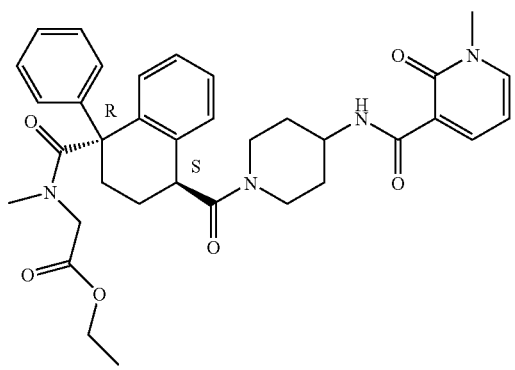
Co. No. 137; Ex. B.17; (1R, 4S)
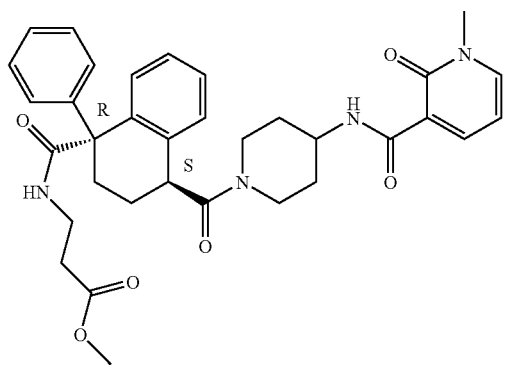
Co. No. 138; Ex. B.17; (1R, 4S)
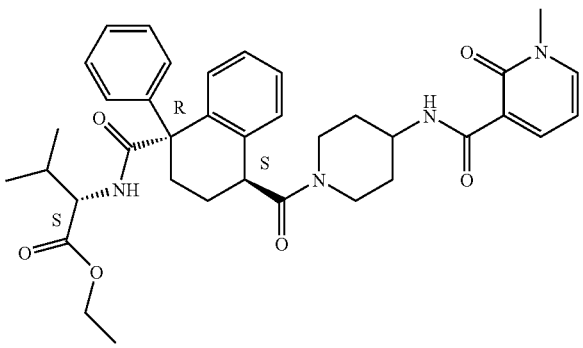
Co. No. 139; Ex. B.17; [1R(S), 4S]
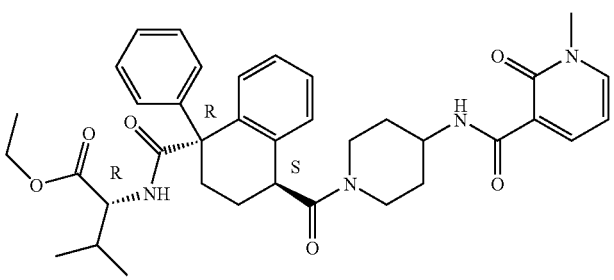
Co. No. 140; Ex. B.17; [1R(R), 4S]

TABLE F-1-continued
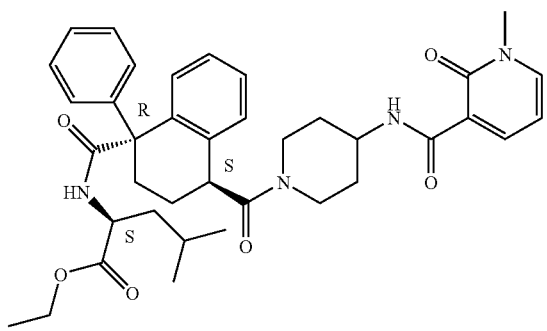
Co. No. 141; Ex. B.17; [1R(S), 4S]
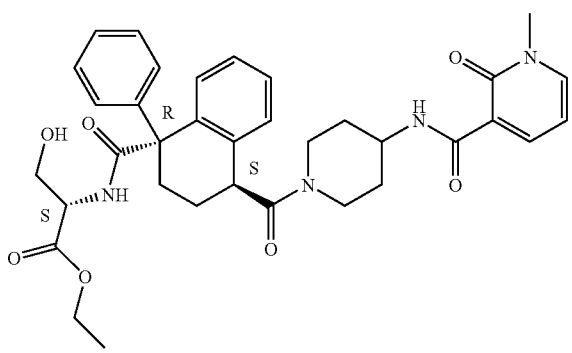
Co. No. 142; Ex. B.17; [1R(S), 4S]
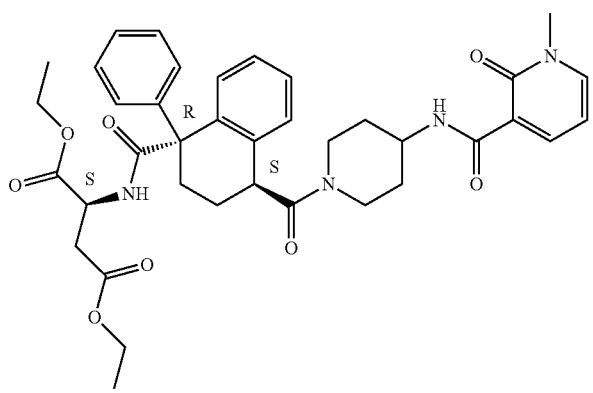
Co. No. 143; Ex. B.17; [1R(S), 4S]
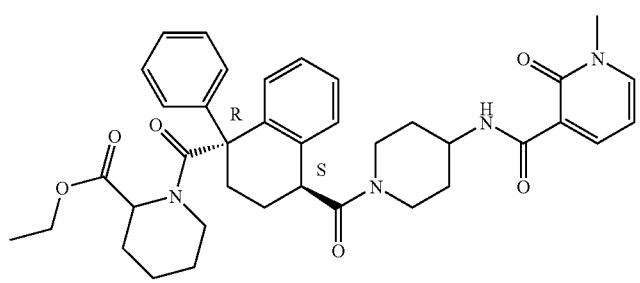
Co. No. 144; Ex. B.17; (1R, 4S)

TABLE F-1-continued
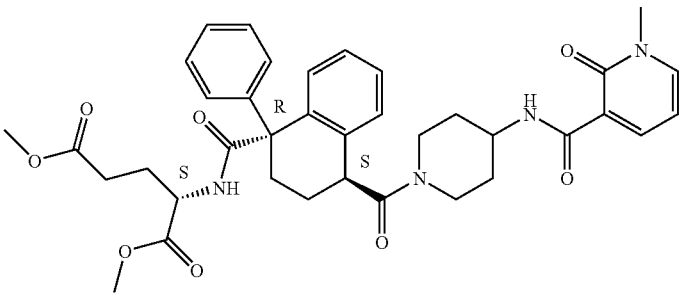
Co. No. 145; Ex. B.17; [1R(S), 4S]
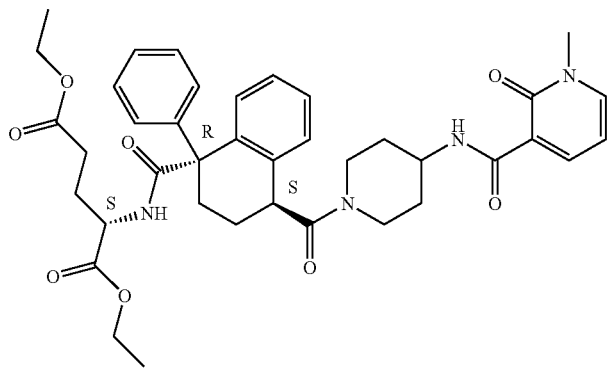
Co. No. 146; Ex. B.17; [1R(S), 4S]
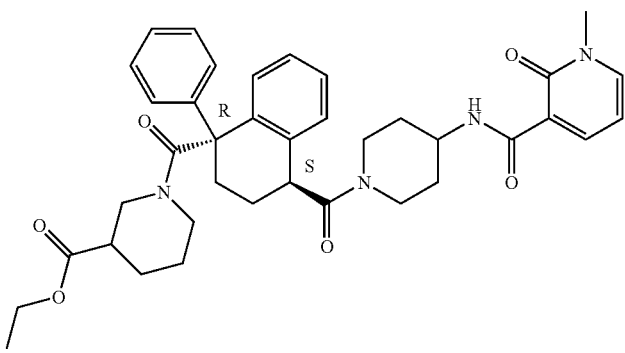
Co. No. 147; Ex. B.17; (1R, 4S)
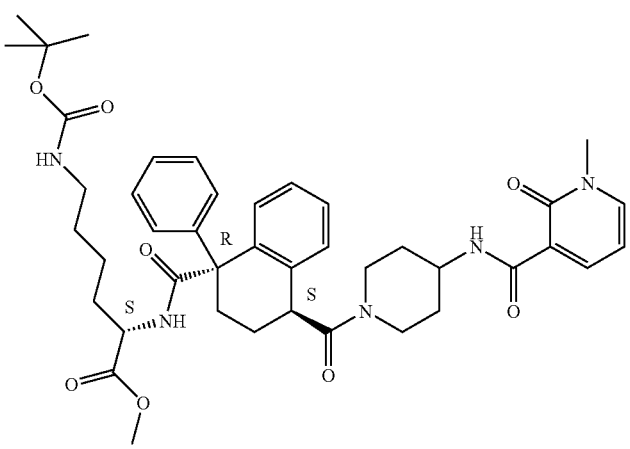
Co. No. 148; Ex. B.17; [1R(S), 4S]

TABLE F-1-continued
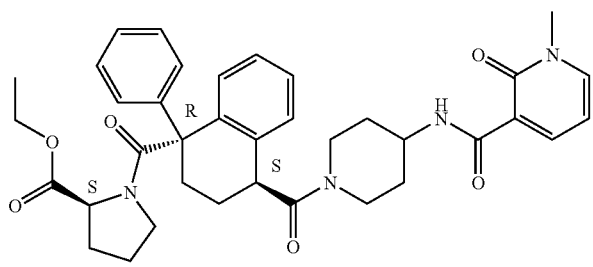
Co. No. 149; Ex. B.17; [1R(S), 4S]
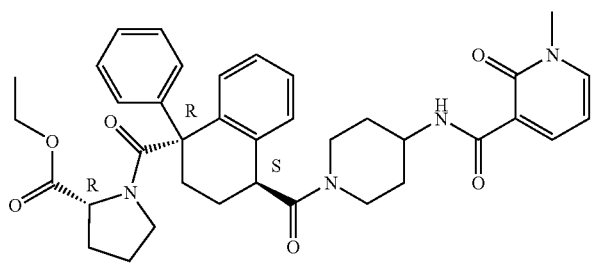
Co. No. 150; Ex. B.17; [1R(R), 4S]
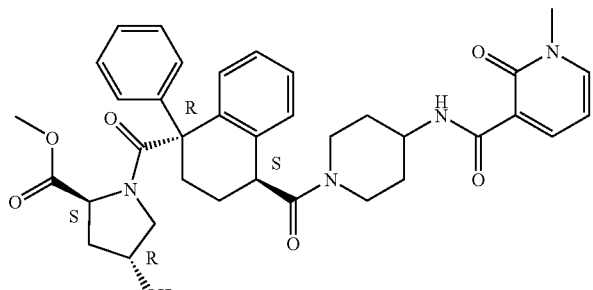
Co. No. 151; Ex. B.17; [1R(2S-trans), 4S]
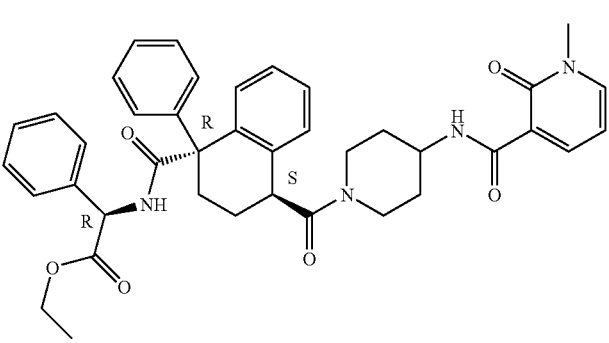
Co. No. 152; Ex. B.17; [1R(R), 4S]
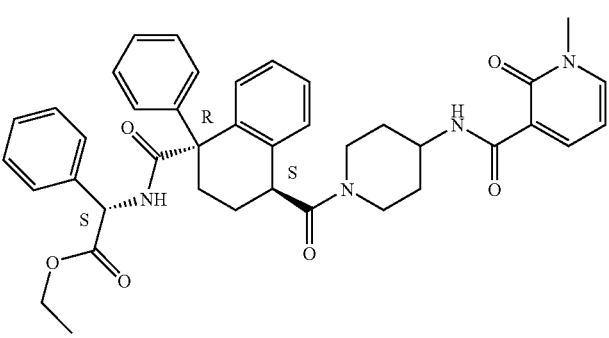
Co. No. 153; Ex. B.17; [1R(S), 4S]

TABLE F-1-continued
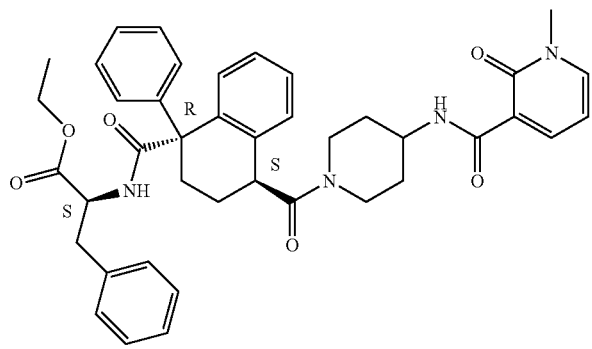
Co. No. 154; Ex. B.17; [1R(S), 4S]
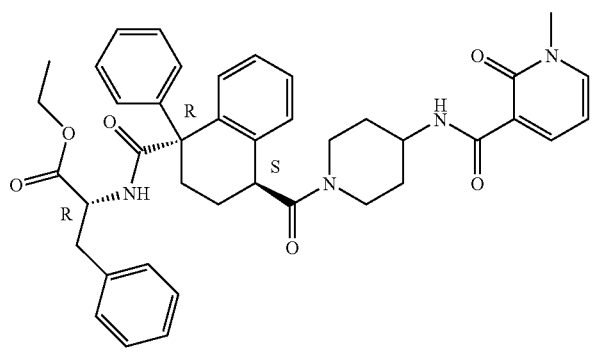
Co. No. 155; Ex. B.17; [1R(R), 4S]
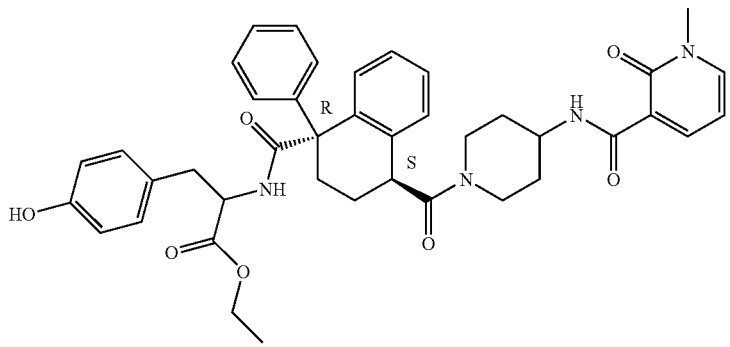
Co. No. 156; Ex. B.17; (1R, 4S)
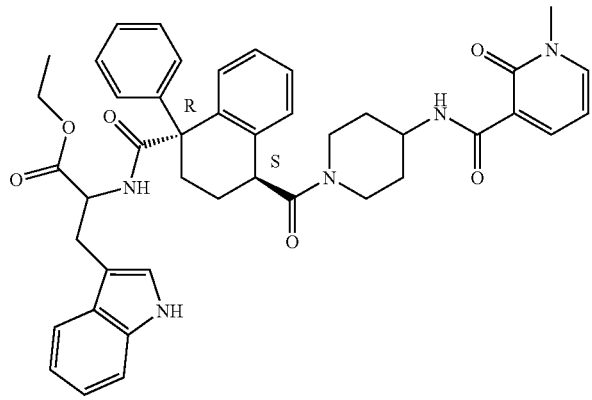
Co. No. 157; Ex. B.17; (1R, 4S)

TABLE F-1-continued
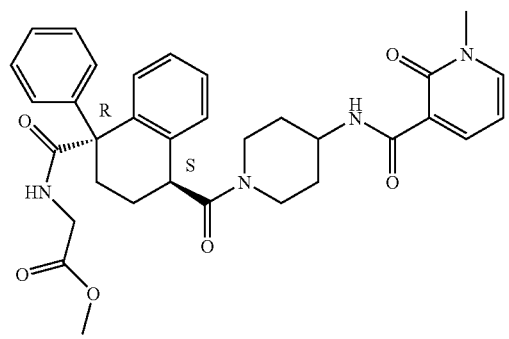
Co. No. 158; Ex. B.17; (1R, 4S)
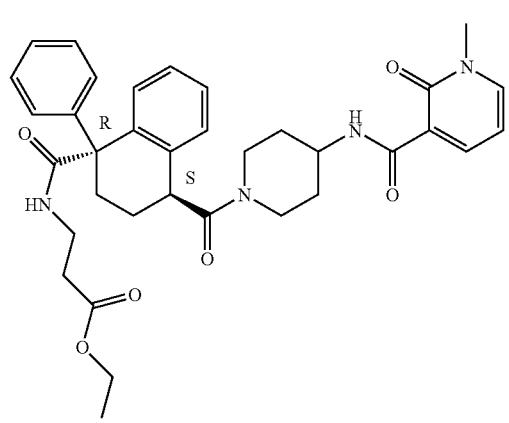
Co. No. 159; Ex. B.17; (1R, 4S)
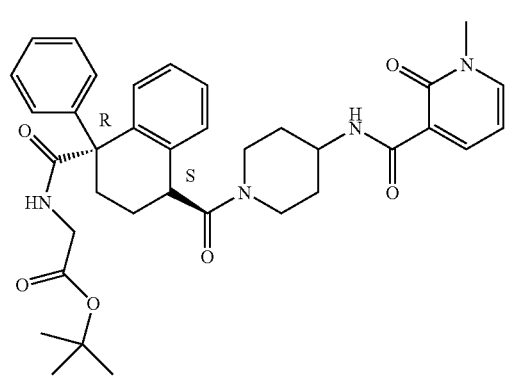
Co. No. 160; Ex. B.17; (1R, 4S)
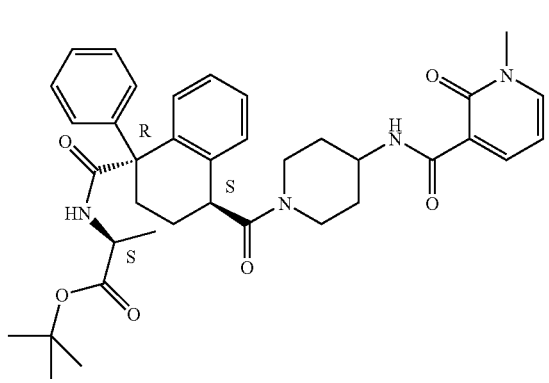
Co. No. 161; Ex. B.17; [1R(S), 4S]

TABLE F-1-continued
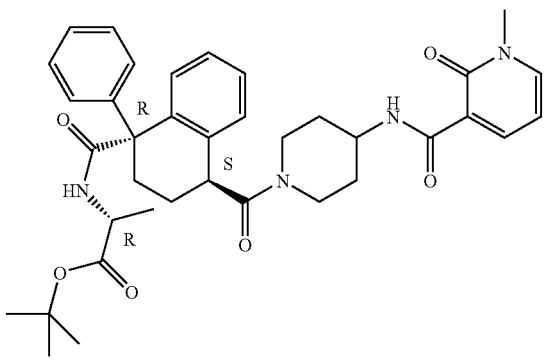
Co. No. 162; Ex. B.17; [1R(R), 4S]
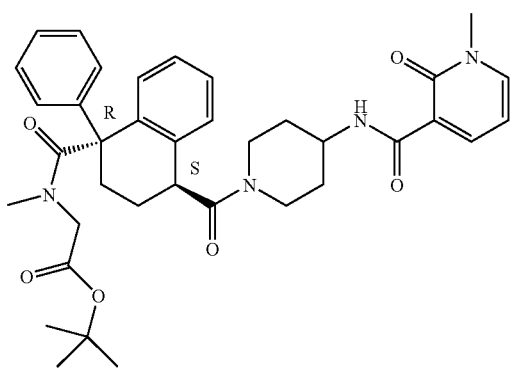
Co. No. 163; Ex. B.17; (1R, 4S)
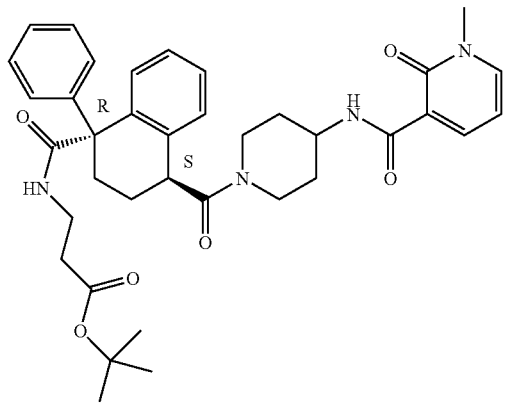
Co. No. 164; Ex. B.17; (1R, 4S)
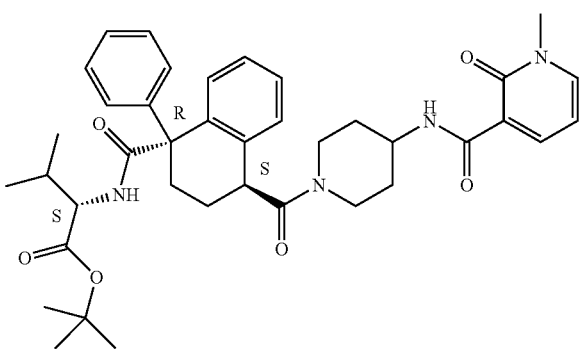
Co. No. 165; Ex. B.17; [1R(S), 4S]

TABLE F-1-continued
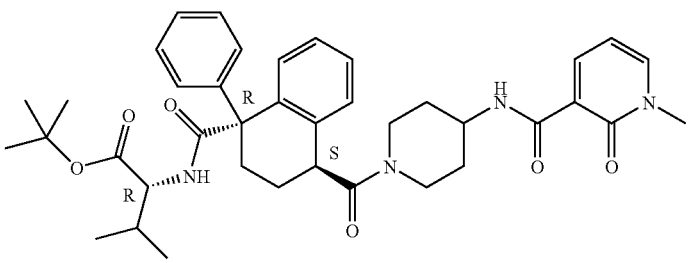
Co. No. 166; Ex. B.17; [1R(R), 4S]
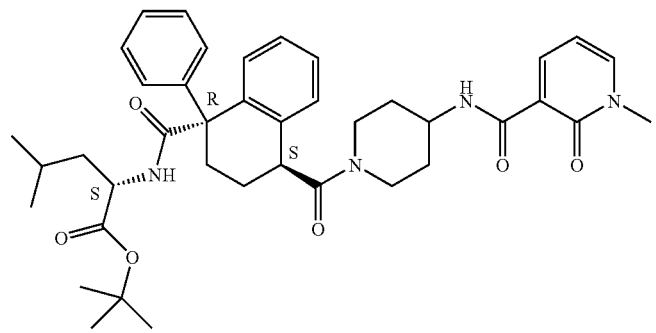
Co. No. 167; Ex. B.17; [1R(S), 4S]
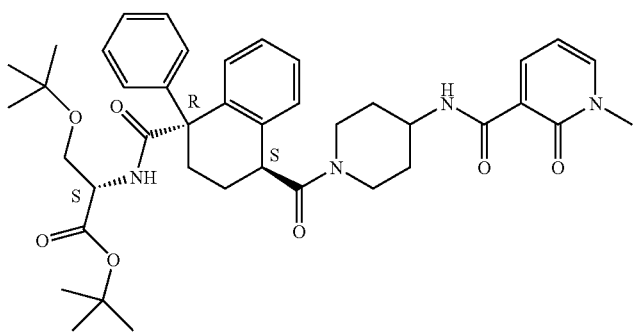
Co. No. 168; Ex. B.17; [1R(S), 4S]
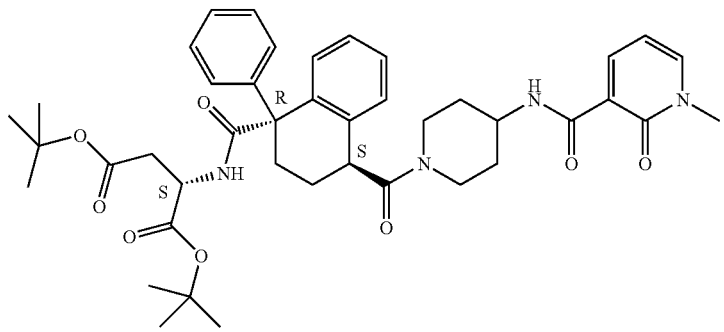
Co. No. 169; Ex. B.17; [1R(S), 4S]

TABLE F-1-continued
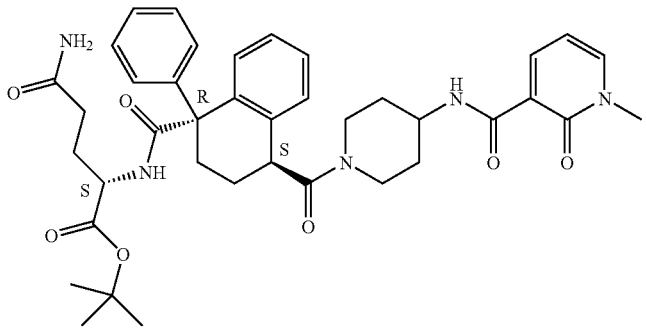
Co. No. 170; Ex. B.17; [1R(S), 4S]
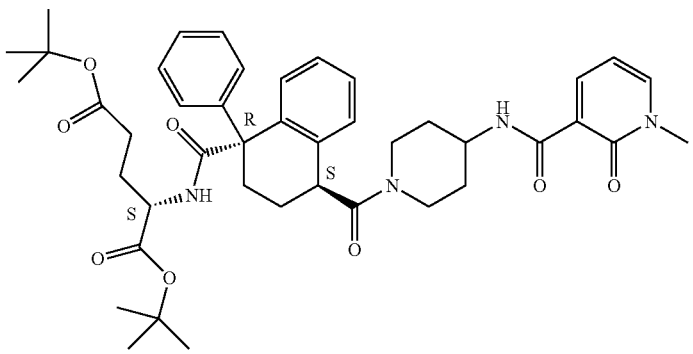
Co. No. 171; Ex. B.17; [1R(S), 4S]
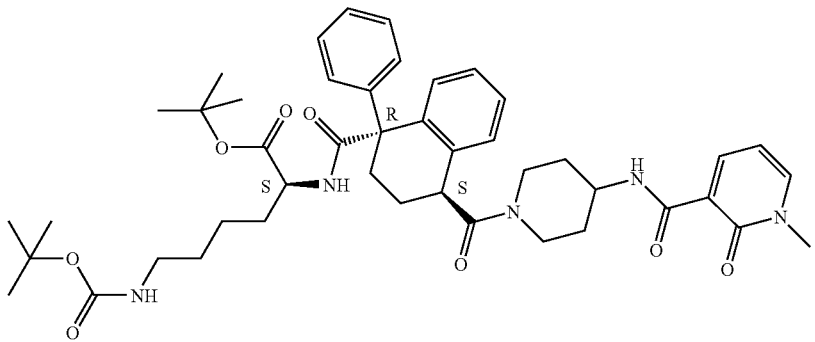
Co. No. 172; Ex. B.17; [1R(S), 4S]
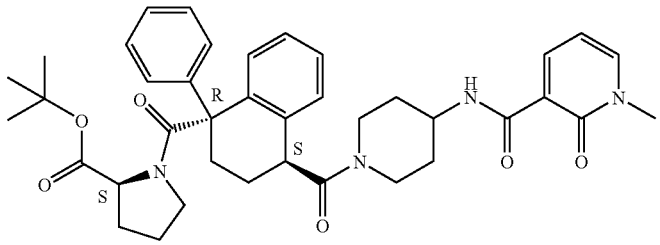
Co. No. 173; Ex. B.17; [1R(S), 4S]
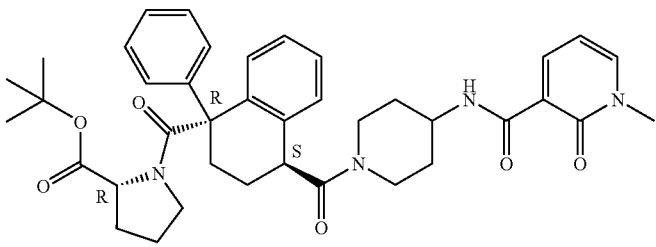
Co. No. 174; Ex. B.17; [1R(R), 4S]

TABLE F-1-continued
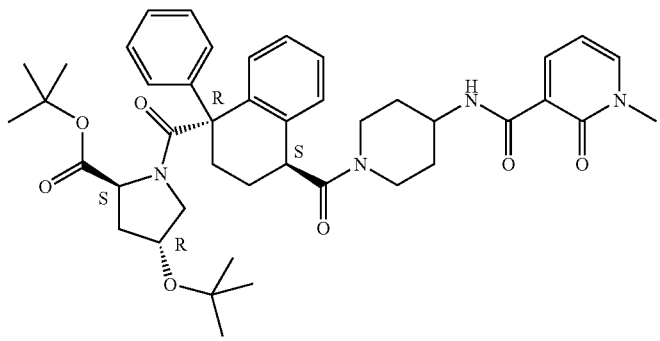
Co. No. 175; Ex. B.17; [1R(S-trans), 4S]
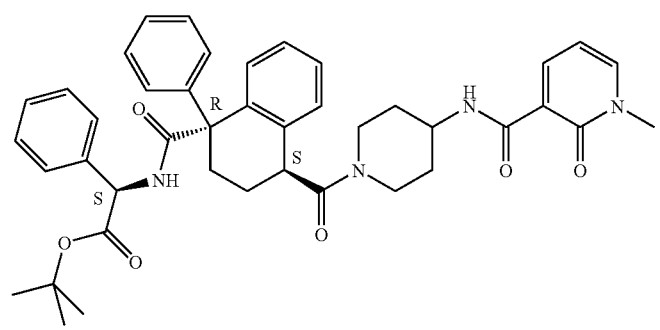
Co. No. 176; Ex. B.17; [1R(R), 4S]
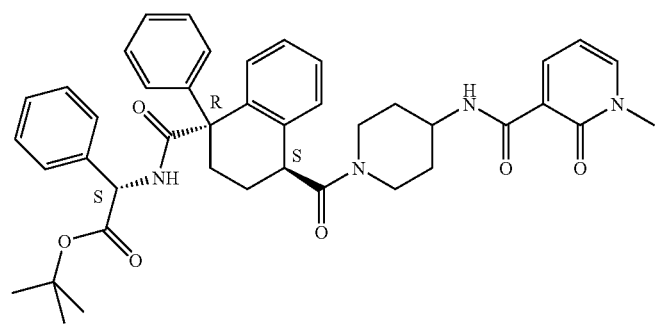
Co. No. 177; Ex. B.17; [1R(S), 4S]
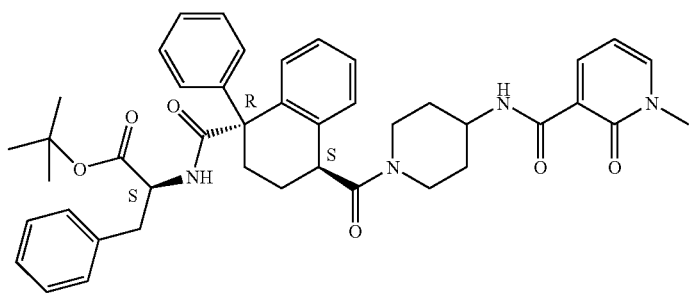
Co. No. 178; Ex. B.17; [1R(S), 4S]

TABLE F-1-continued
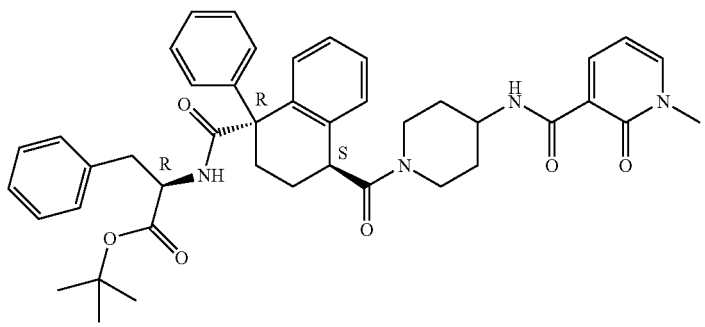
Co. No. 179; Ex. B.17; [1R(R), 4S]
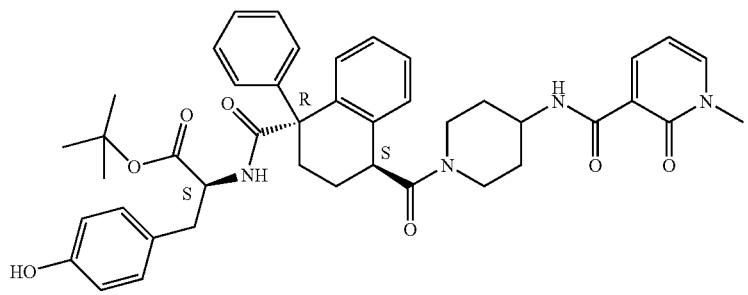
Co. No. 180; Ex. B.17; [1R(S), 4S]
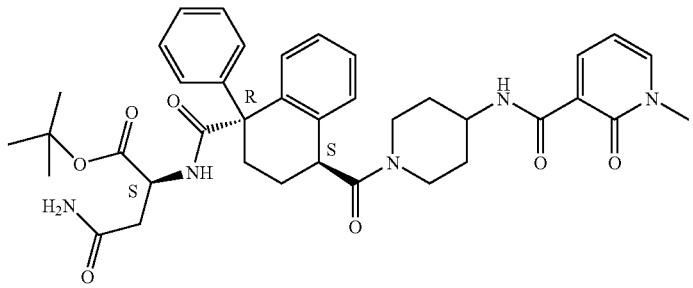
Co. No. 181; Ex. B.17; [1R(S), 4S]
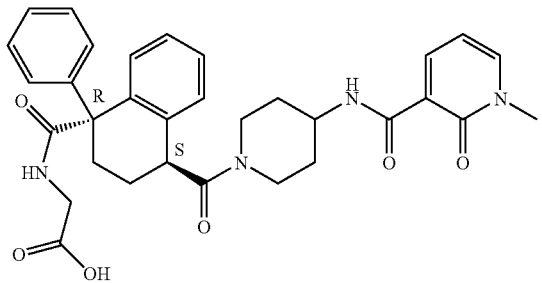
Co. No. 182; Ex. B.13; (1R, 4S)
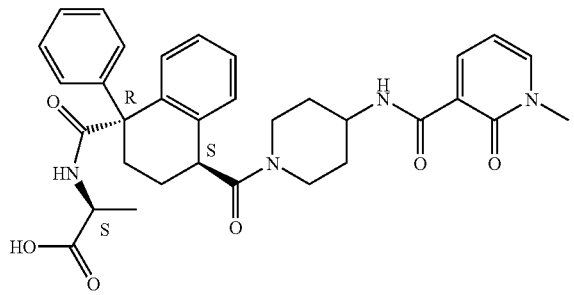
Co. No. 183; Ex. B.13; [1R(S), 4S]

TABLE F-1-continued
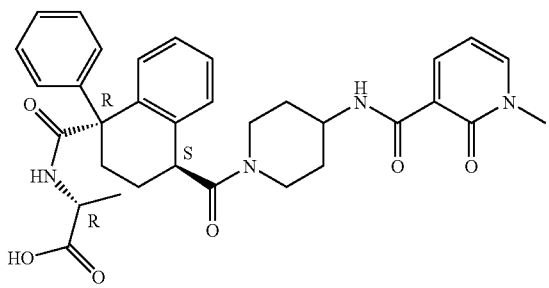
Co. No. 184; Ex. B.13; [1R(R), 4S]
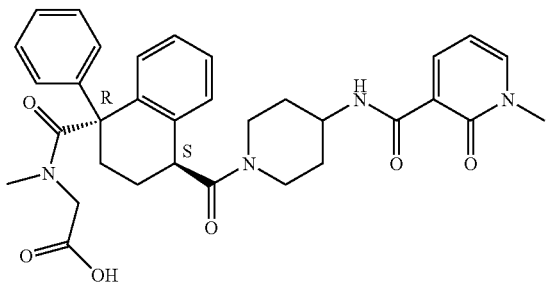
Co. No. 185; Ex. B.13; (1R, 4S)
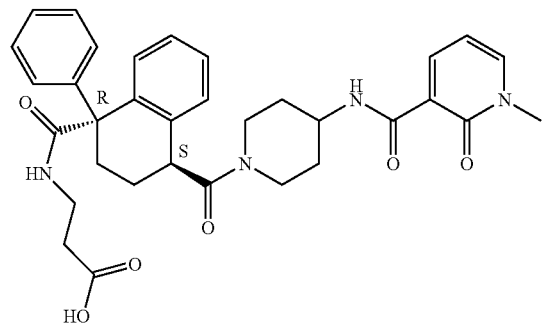
Co. No. 186; Ex. B.13; (1R, 4S)
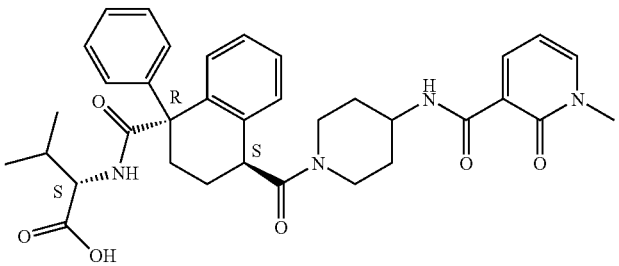
Co. No. 187; Ex. B.13; [1R(S), 4S]
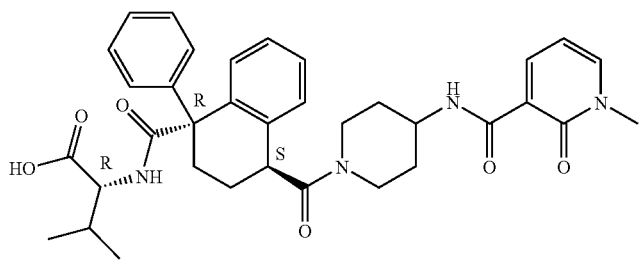
Co. No. 188; Ex. B.13; [1R(R), 4S]

TABLE F-1-continued
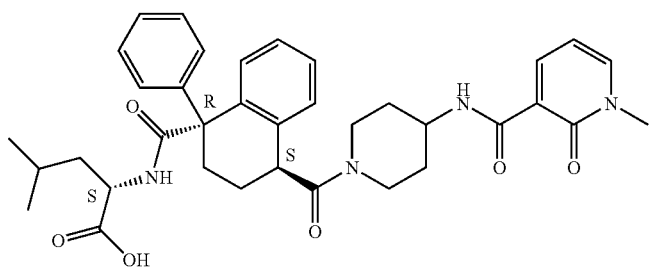
Co. No. 189; Ex. B.13; [1R(s), 4S]
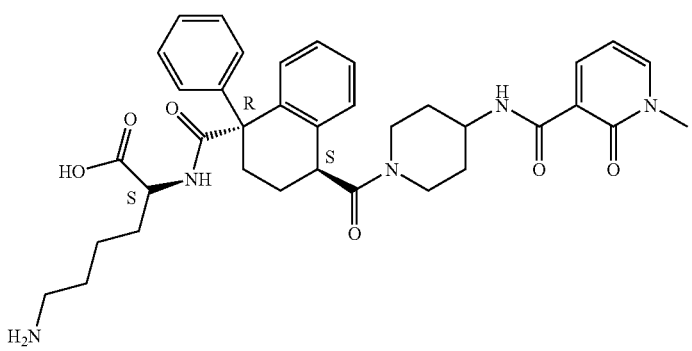
Co. No. 190; Ex. B.13; [1R(S), 4S]
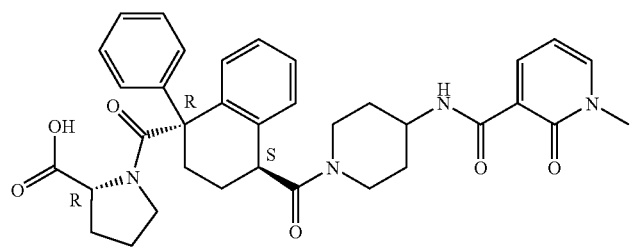
Co. No. 191; Ex. B.13; [1R(R), 4S]
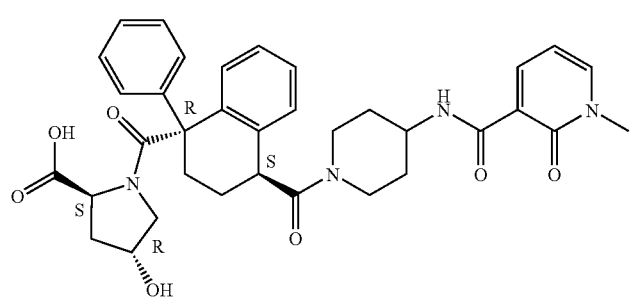
Co. No. 192; Ex. B.13; [1R(2S-trans), 4S]
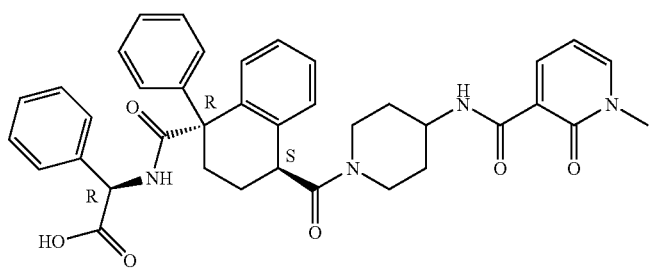
Co. No. 193; Ex. B.13; [1R(R), 4S]

TABLE F-1-continued
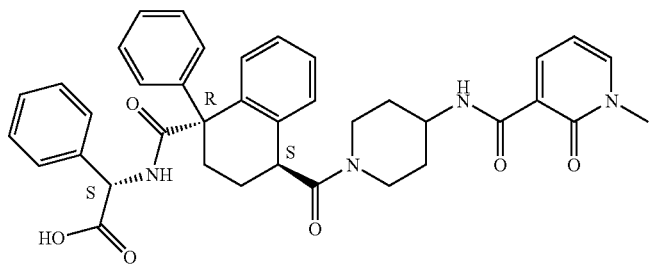
Co. No. 194; Ex. B.13; [1R(S), 4S]
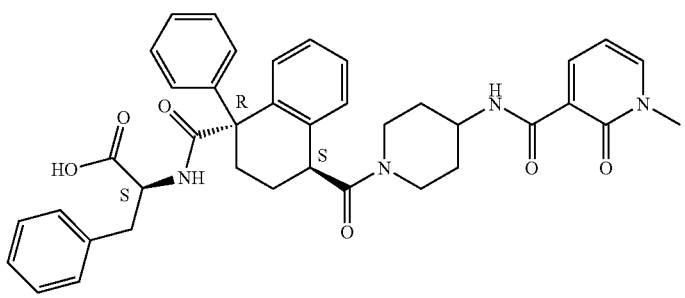
Co. No. 195; Ex. B.13; [1R(S), 4S]
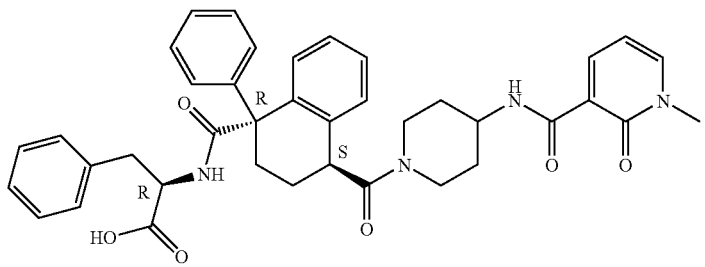
Co. No. 196; Ex. B.13; [1R(R), 4S]
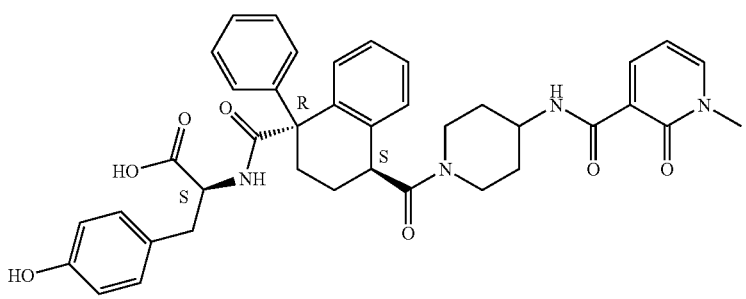
Co. No. 197; Ex. B.13; [1R(S), 4S]
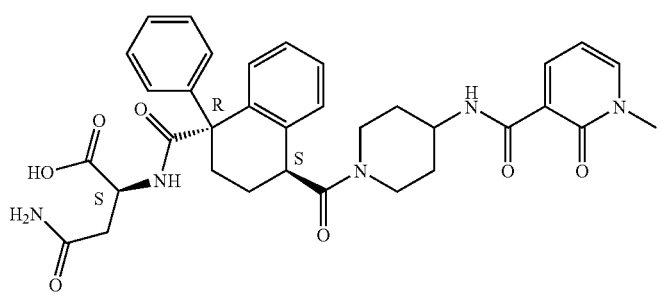
Co. No. 198; Ex. B.13; [1R(S), 4S]

TABLE F-1-continued
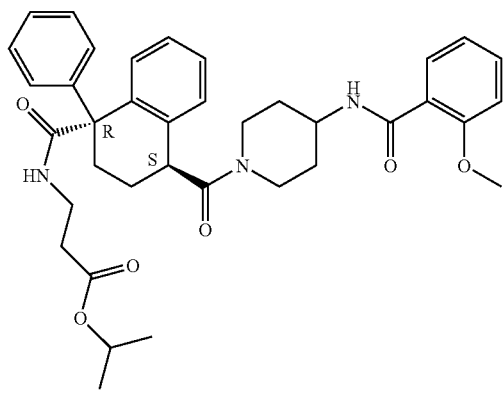
Co. No. 199; Ex. B.17; (1R, 4S);
m.p. 161° C. (Büchi visual)
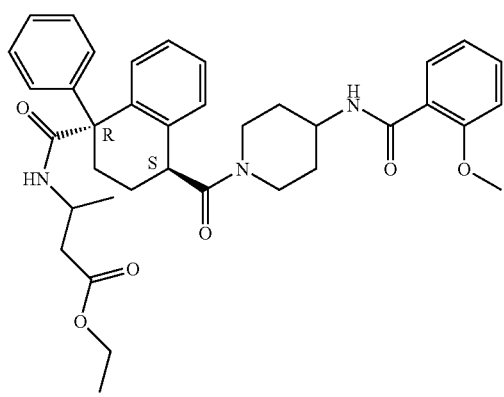
Co. No. 200; Ex. B.17; (1R, 4S)
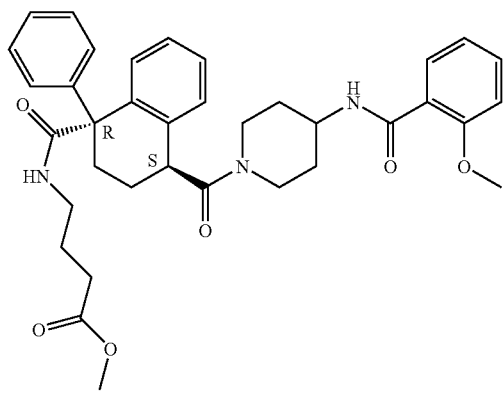
Co. No. 201; Ex. B.17; (1R, 4S)

TABLE F-1-continued
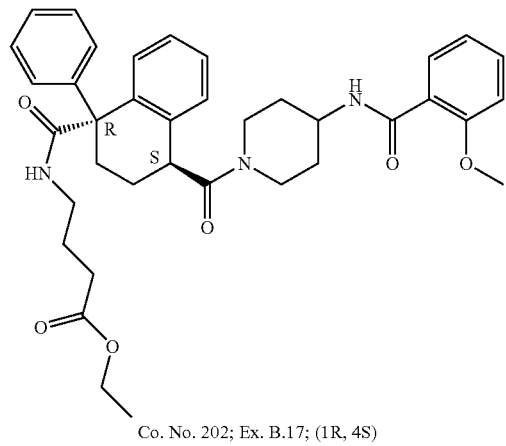
Co. No. 202; Ex. B.17; (1R, 4S)
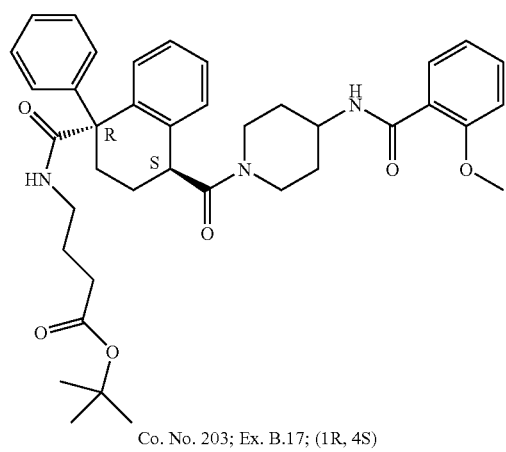
Co. No. 203; Ex. B.17; (1R, 4S)
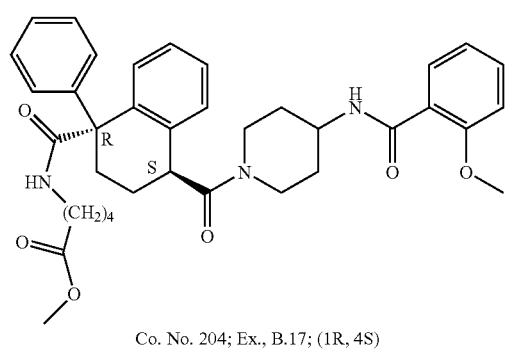
Co. No. 204; Ex., B.17; (1R, 4S)
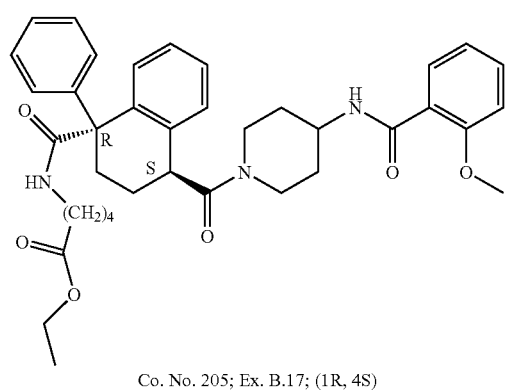
Co. No. 205; Ex. B.17; (1R, 4S)

TABLE F-1-continued
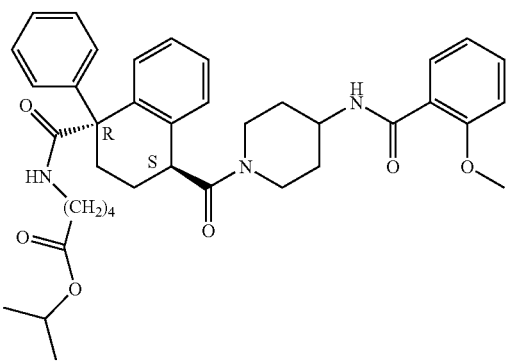
Co. No. 206; Ex. B.17; (1R, 4S)
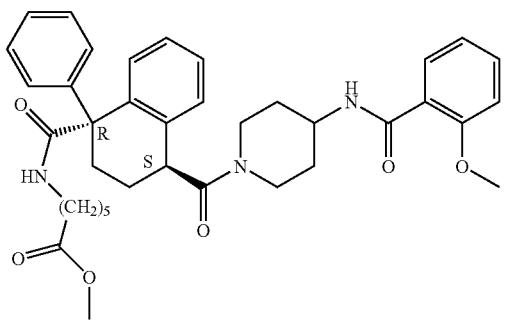
Co. No. 207; Ex. B.17; (1R, 4S)
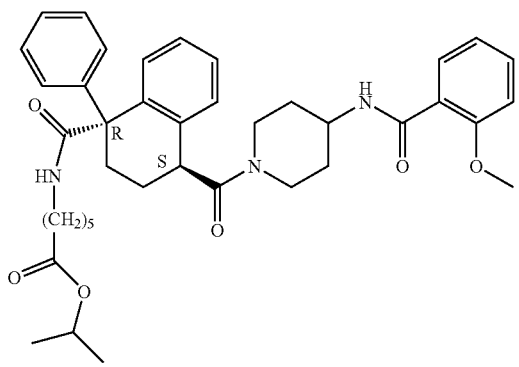
Co. No. 208; Ex. B.17; (1R, 4S)
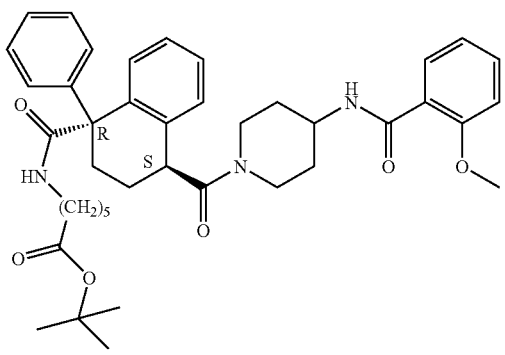
Co. No. 209; Ex. B.17; (1R, 4S)

TABLE F-1-continued
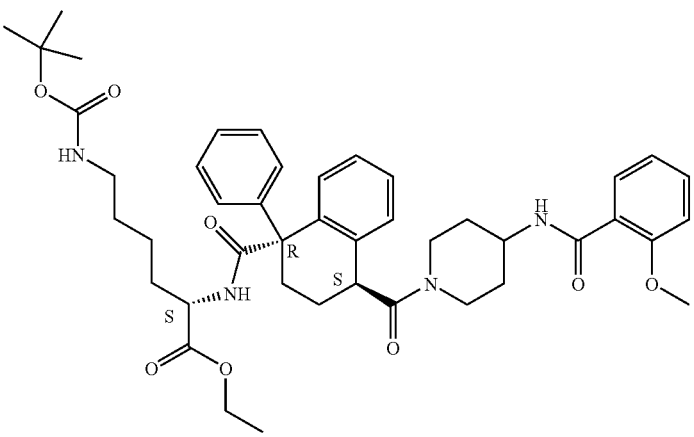
Co. No. 210; Ex. B.17; [1R(S); 4S]
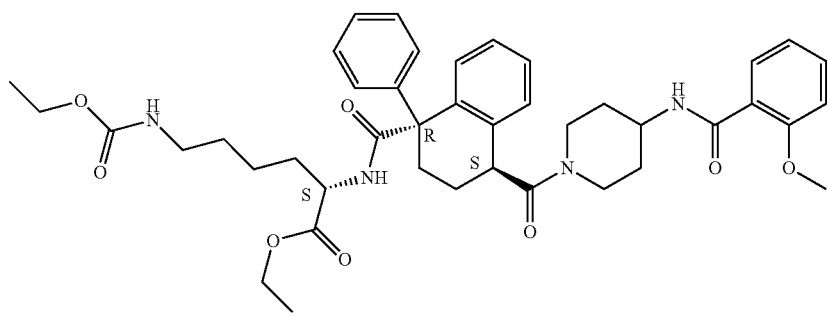
Co. No. 211; Ex. B.17; [1R(S), 4S]
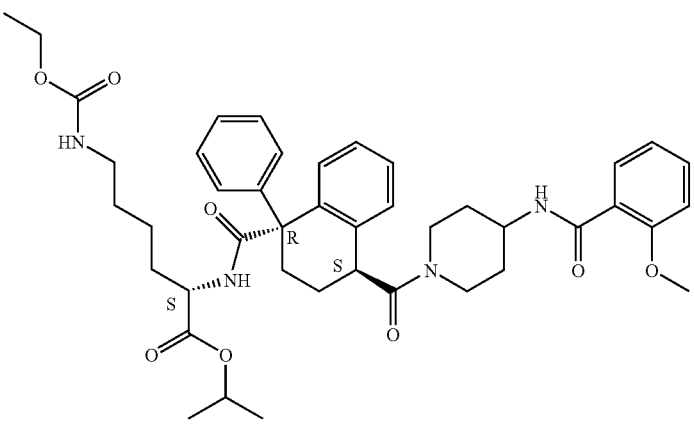
Co. No. 212; Ex. B.17; [1R(S), 4S]

TABLE F-1-continued
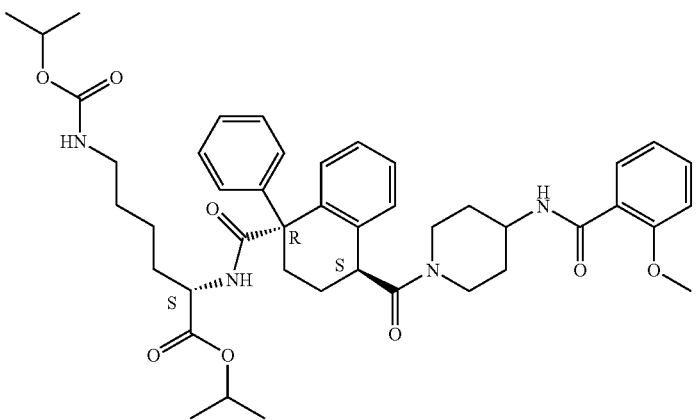
Co. No. 213; Ex. B.17; [1R(S), 4S]
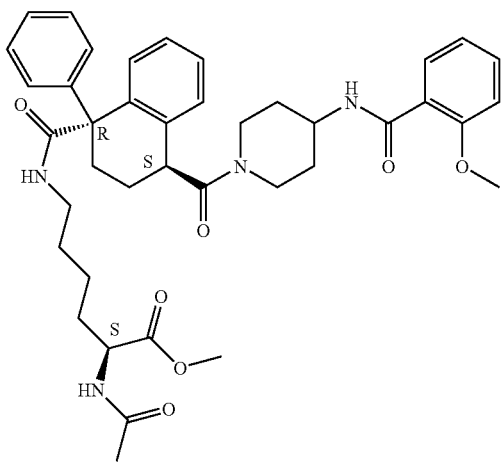
Co. No. 214; Ex. B.17; [1R(S), 4S]
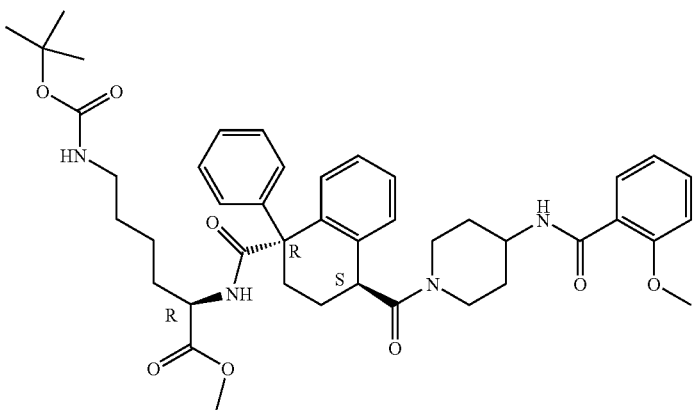
Co. No. 215; Ex. B.17; [1R(R), 4S]

TABLE F-1-continued
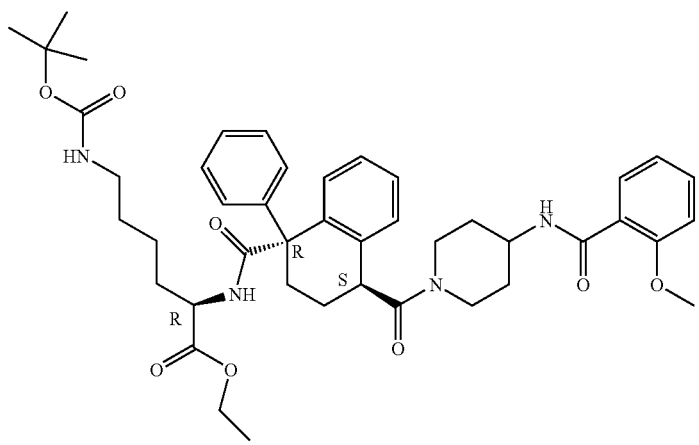
Co. No. 216; Ex. B.17; [1R(R), 4S]
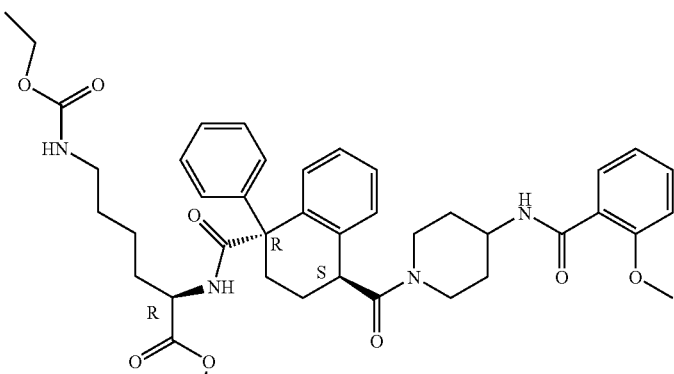
Co. No. 217; Ex. B.17; [1R(R), 4S]
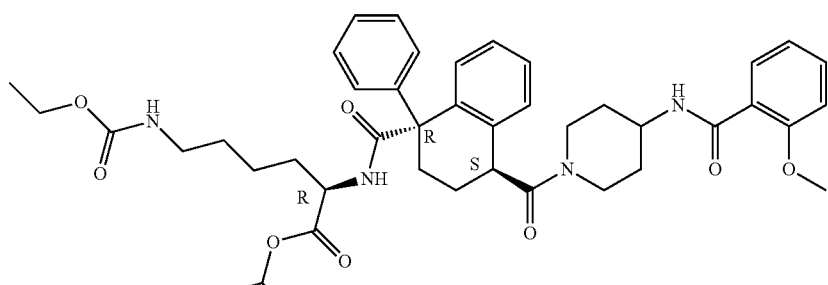
Co. No. 218; Ex. B.17; [1R(R), 4S]
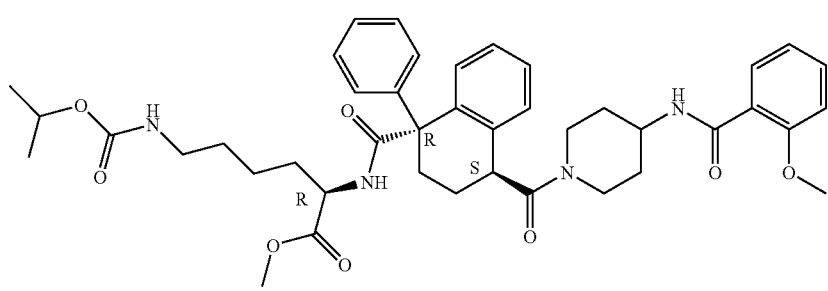
Co. No. 219; Ex. B.17; [1R(R), 4S]

TABLE F-1-continued
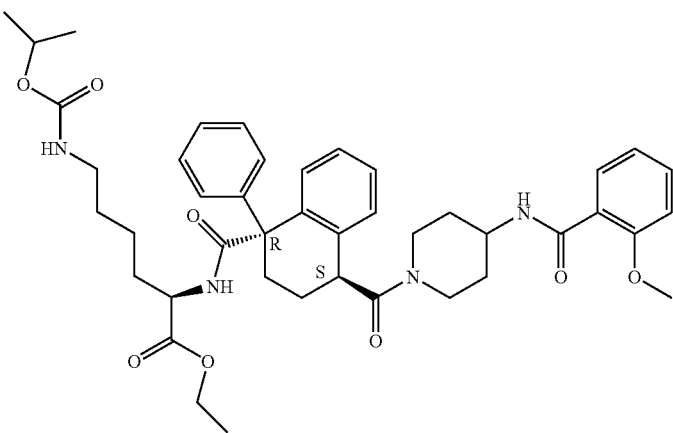
Co. No. 220; Ex. B.17; [1R(R), 4S]
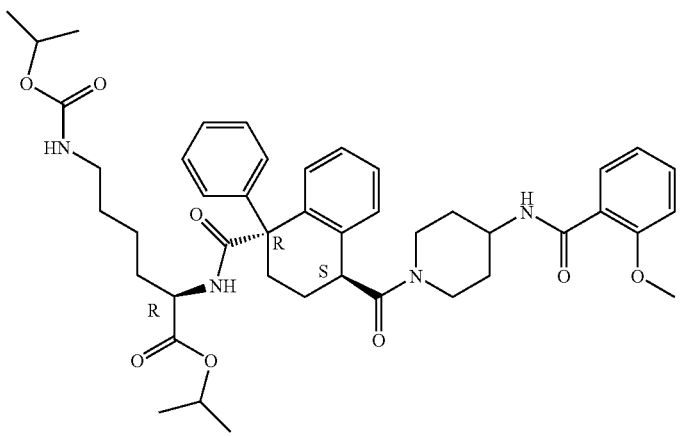
Co. No. 221; Ex. B.17; [1R(R), 4S]
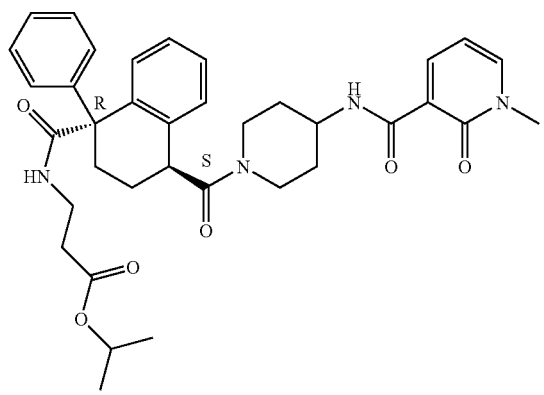
Co. No. 222; Ex. B.17; (1R, 4S)

TABLE F-1-continued
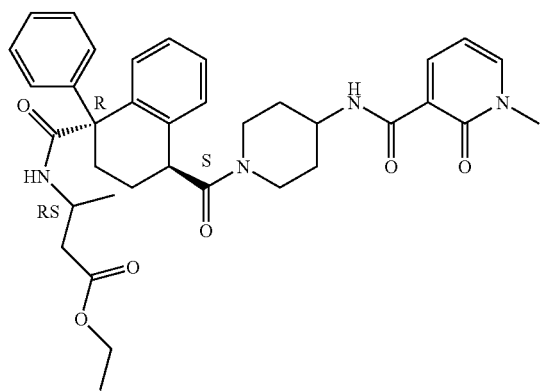
Co. No. 223; Ex. B.17; [1R(RS), 4S]
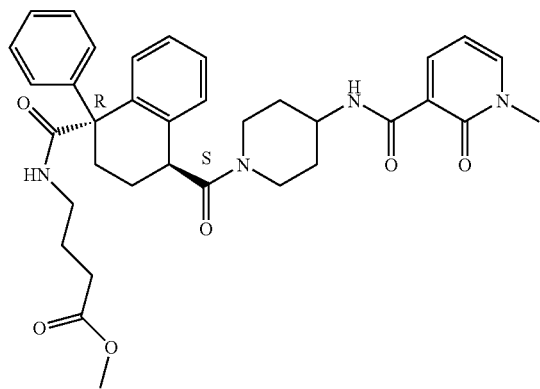
Co. No. 224; Ex. B.17; (1R, 4S)
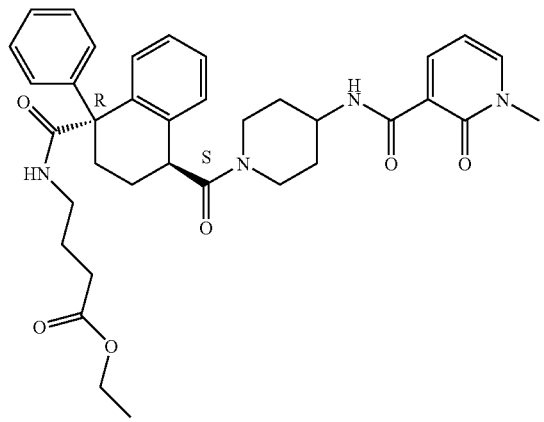
Co. No. 225; Ex. B.17; (1R, 4S)

TABLE F-1-continued
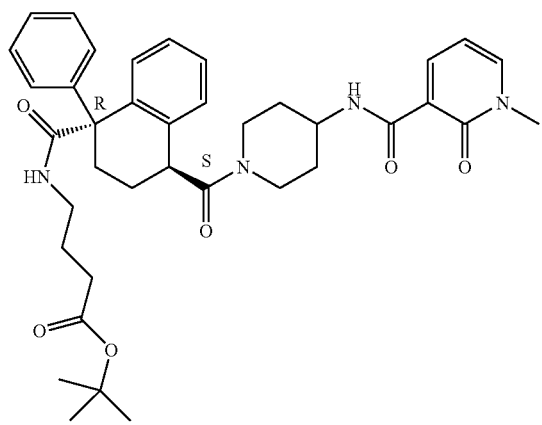
Co. No. 226; Ex. B.17; (1R, 4S)
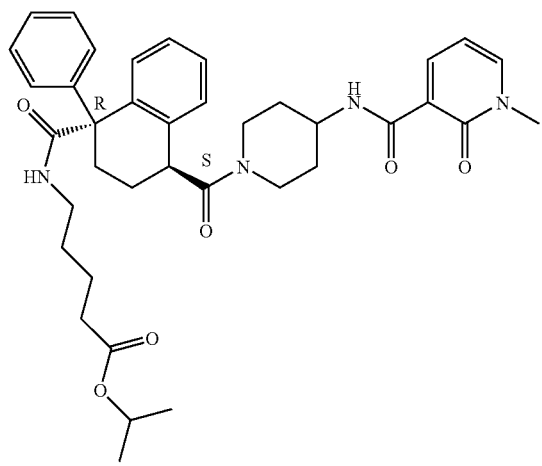
Co. No. 227; Ex. B.17; (1R, 4S)
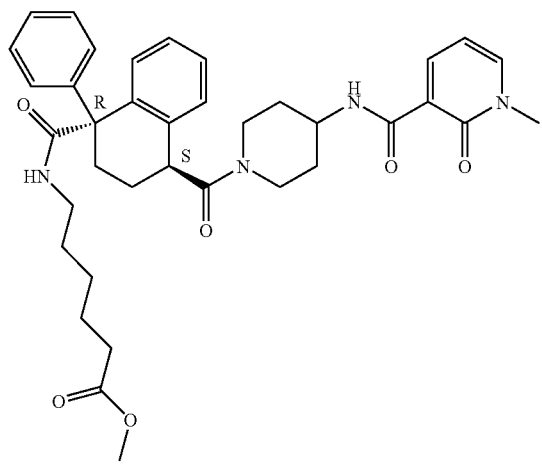
Co. No. 228; Ex. B.17; (1R, 4S)

TABLE F-1-continued
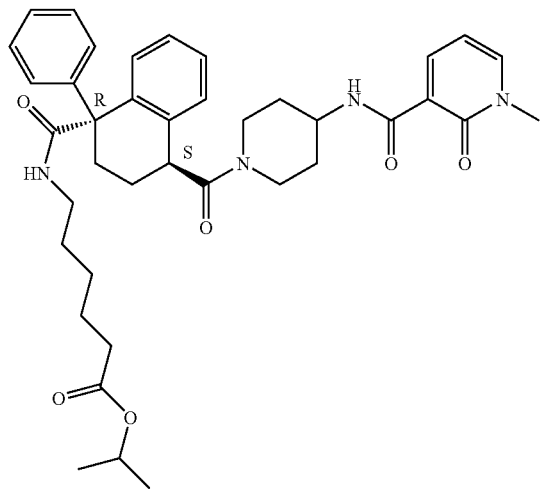
Co. No. 229; Ex. B.17; (1R, 4S)
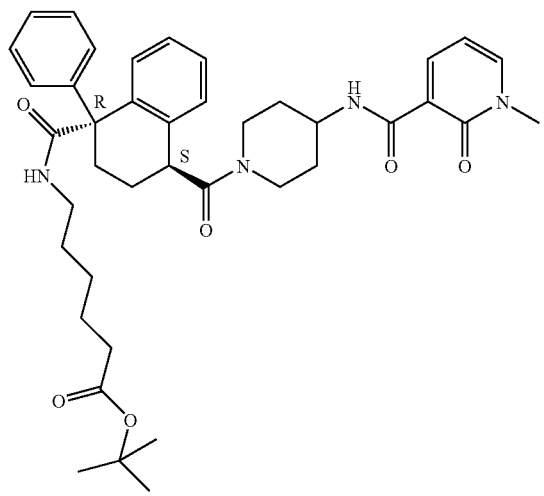
Co. No. 230; Ex. B.17; (1R, 4S)
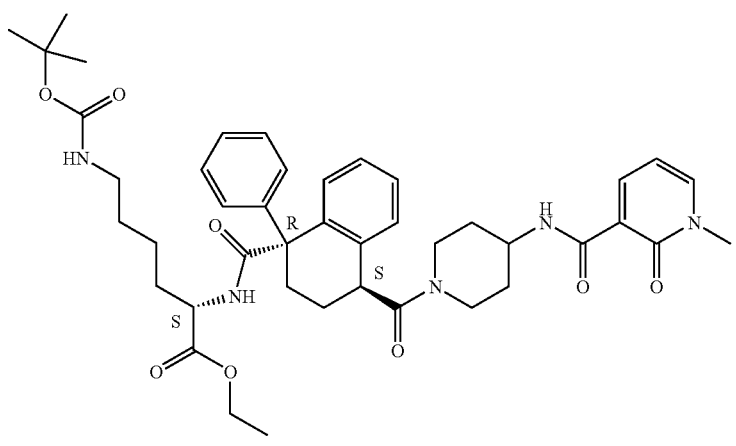
Co. No. 231; Ex. B.17; [1R(S), 4S]

TABLE F-1-continued
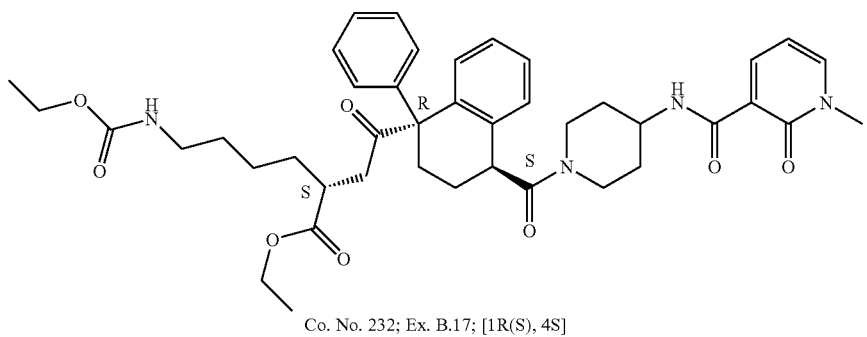
Co. No. 232; Ex. B.17; [1R(S), 4S]
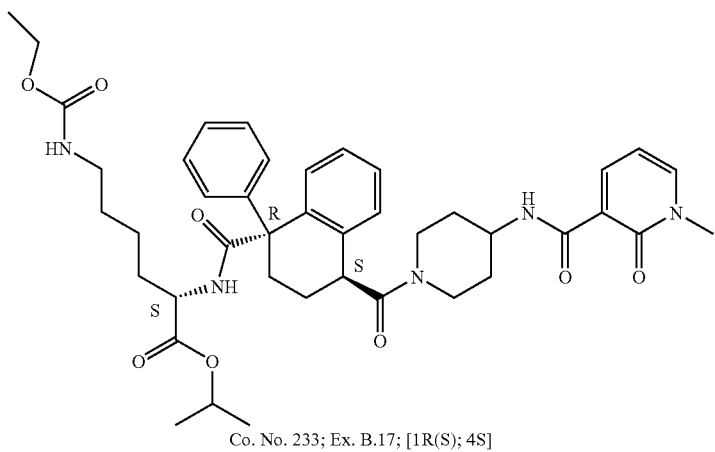
Co. No. 233; Ex. B.17; [1R(S); 4S]
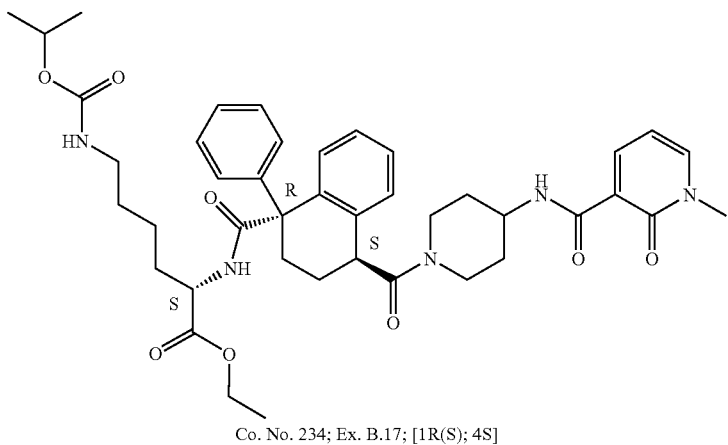
Co. No. 234; Ex. B.17; [1R(S); 4S]
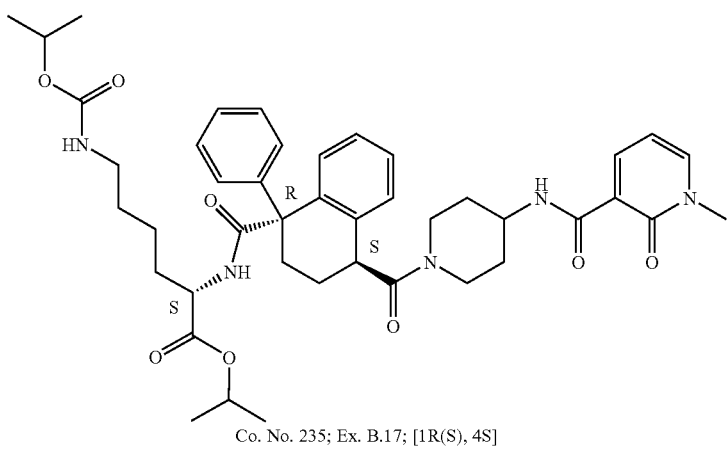
Co. No. 235; Ex. B.17; [1R(S), 4S]

TABLE F-1-continued
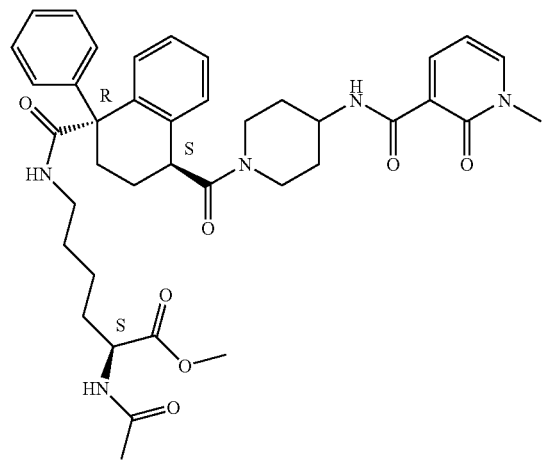
Co. No. 236; Ex. B.17; [1R(S), 4S]
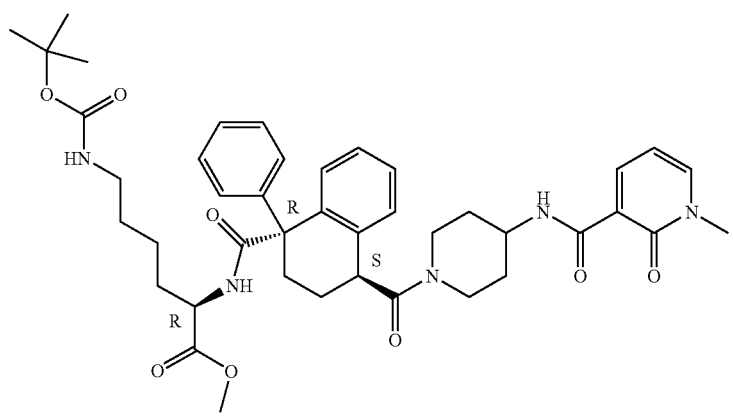
Co. No. 237; Ex. B.17; [1R(R), 4S]
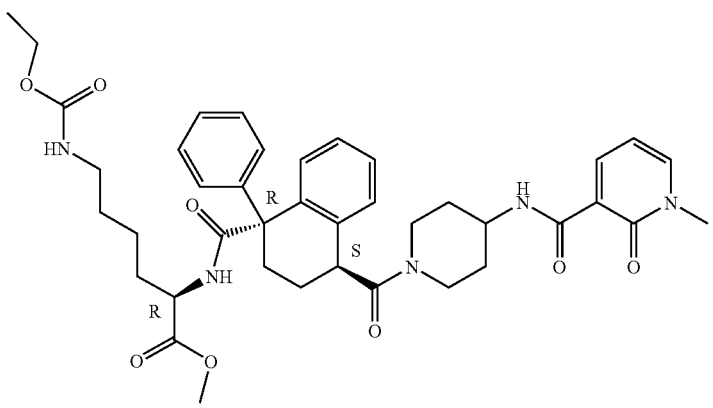
Co. No. 238; Ex. B.17; [1R(R), 4S]

TABLE F-1-continued
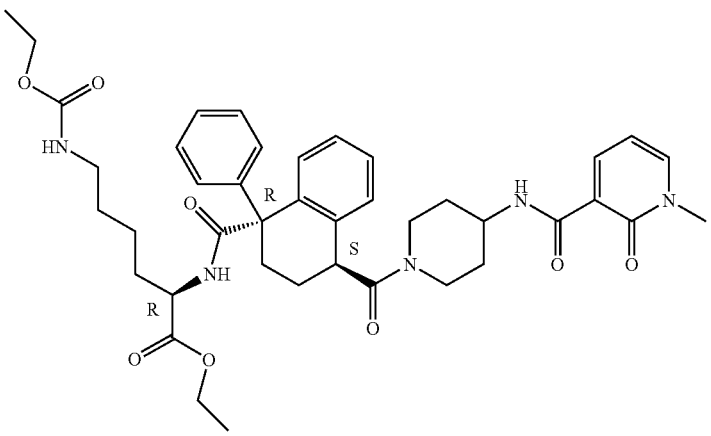
Co. No. 239; Ex. B.17; [1R(R), 4S]
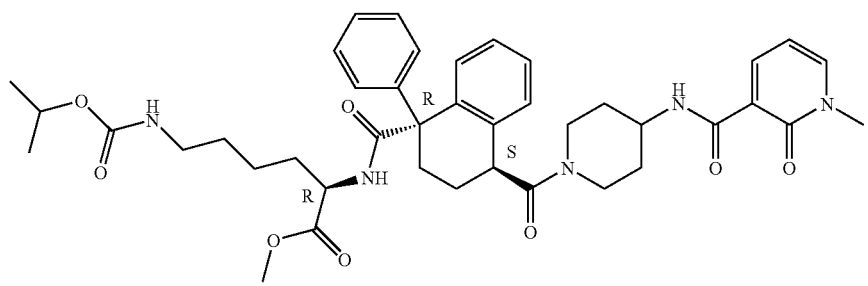
Co. No. 240; Ex. B.17; [1R(R), 4S]
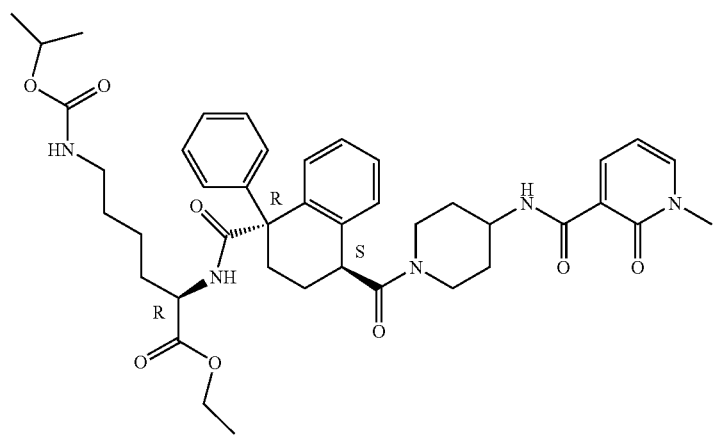
Co. No. 241; Ex. B.17; [1R(R), 4S]

TABLE F-1-continued
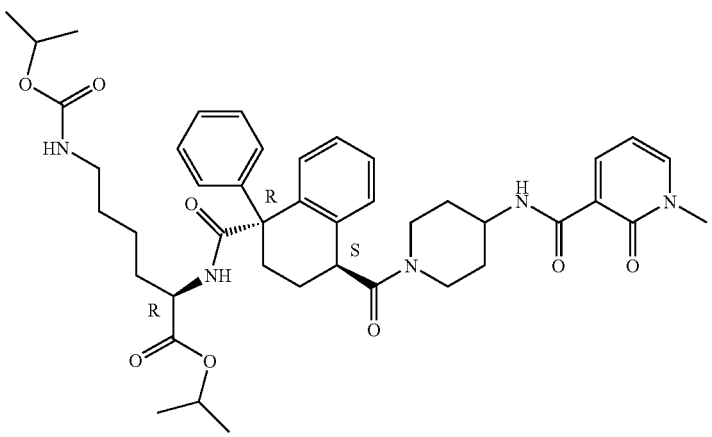
Co. No. 242; Ex. B.17; [1R(R), 4S]
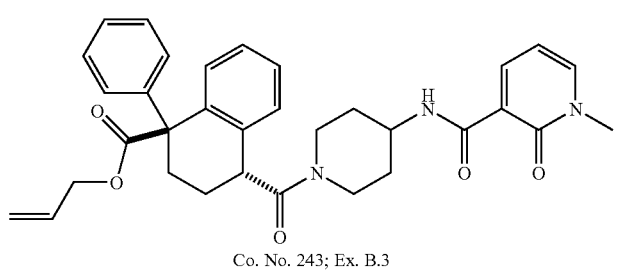
Co. No. 243; Ex. B.3
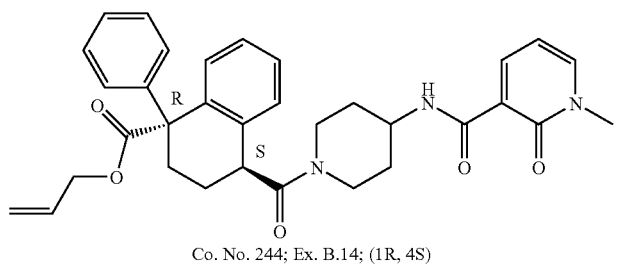
Co. No. 244; Ex. B.14; (1R, 4S)
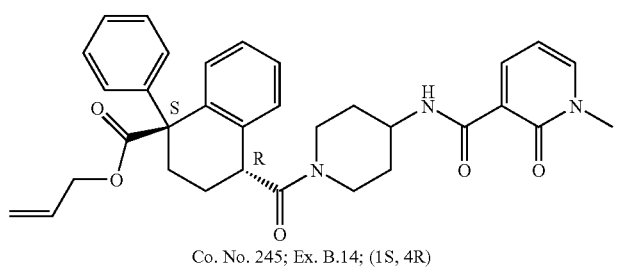
Co. No. 245; Ex. B.14; (1S, 4R)
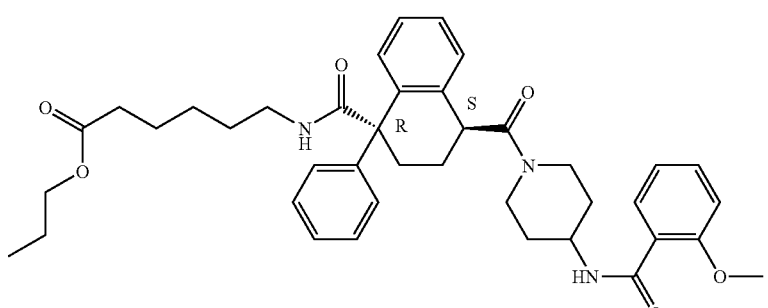
Co. No. 246; Ex. B.15; (1R, 4S)

TABLE F-1-continued
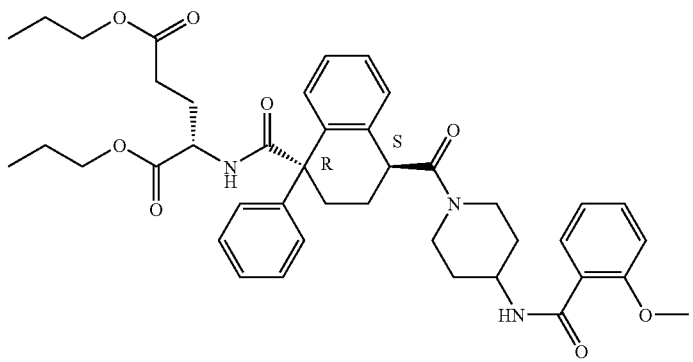
Co. No. 247; Ex. B.11b; (1R, 4S)
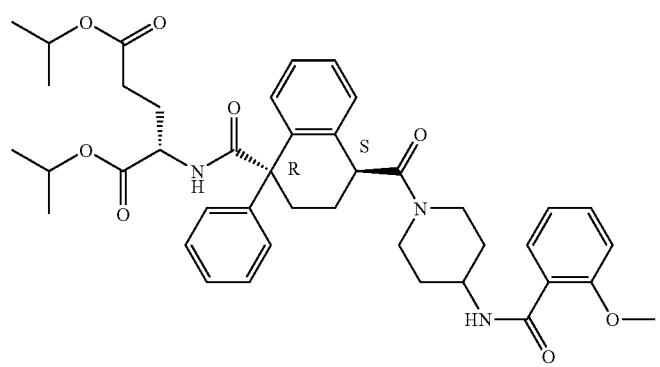
Co. No. 248; Ex. B.11b; (1R, 4S)
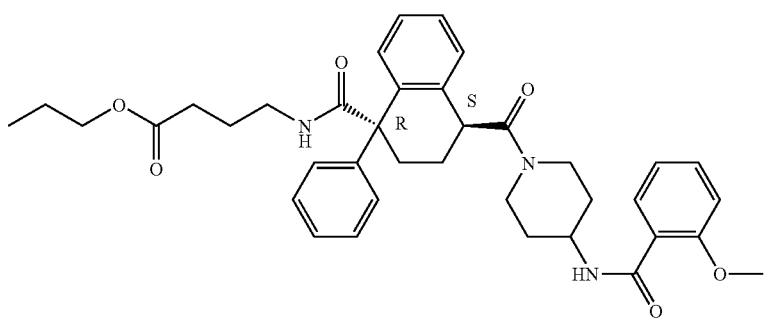
Co. No. 249; Ex. B.11b; (1R, 4S)
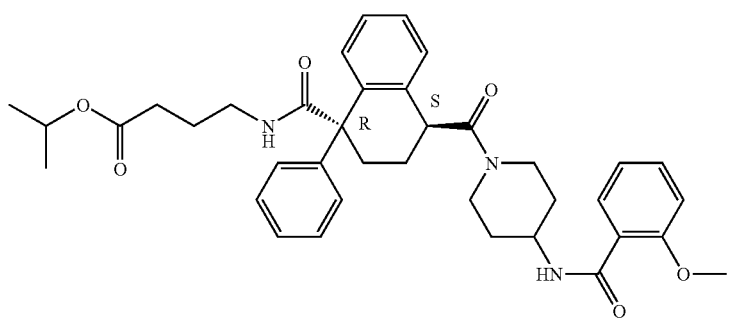
Co. No. 250; Ex. B.11b; (1R, 4S)

TABLE F-1-continued
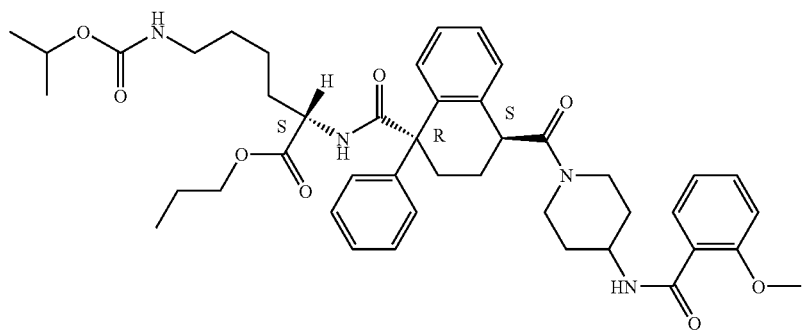
Co. No. 251; Ex. B.11b; [1R(S), 4S]
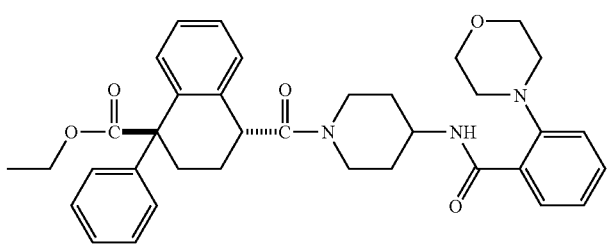
Co. No. 252; Ex. B.19
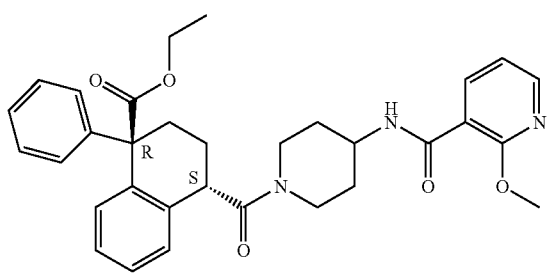
Co. No. 253; Ex. B.19; (1R, 4S)
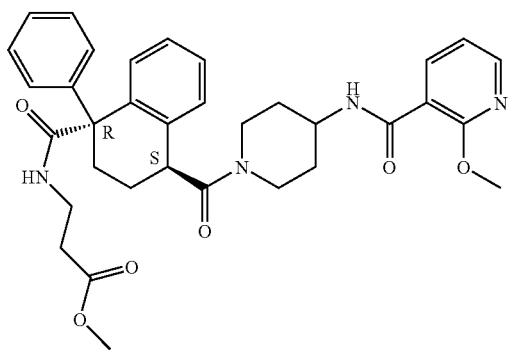
Co. No. 254; Ex. B.17; (1R, 4S)

TABLE F-1-continued
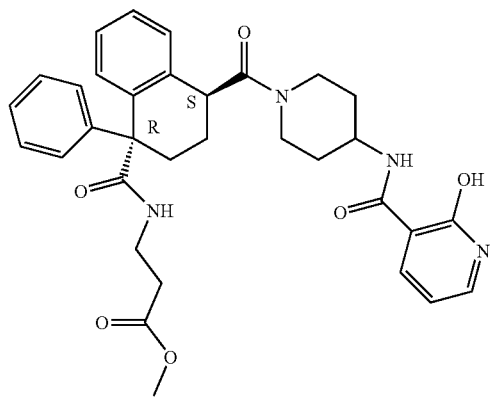
Co. No. 255; Ex. B.17; (1R, 4S); m.p. 133° C. (Büchi visual)
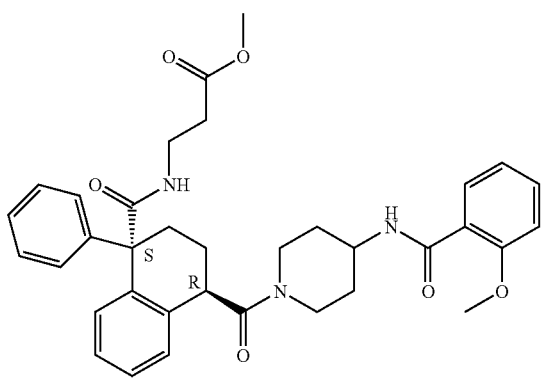
Co. No. 256; Ex. B.18; (1S, 4R)
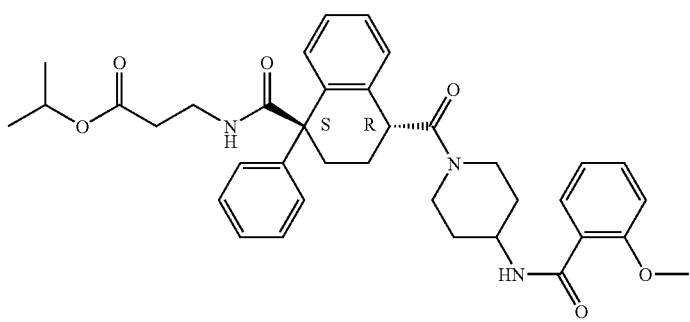
Co. No. 257; Ex. B.15.b
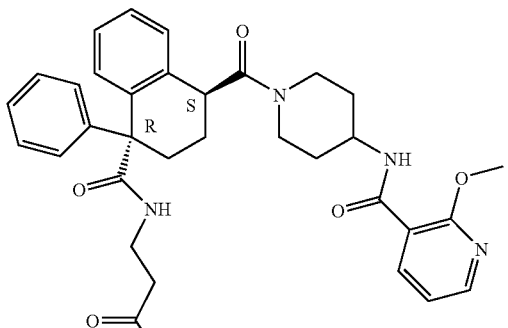
Co. No. 258; Ex. B.13; (1R, 4S)

TABLE F-1-continued
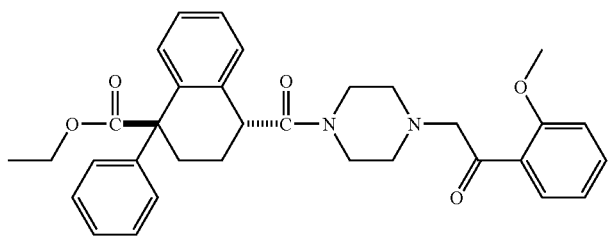
Co. No. 259; Ex. B.19
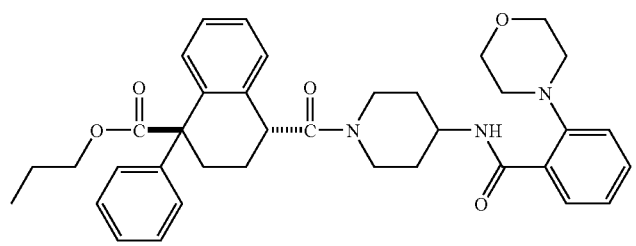
Co. No. 260; Ex. B20a; m.p. 179.36° C. (DSC)
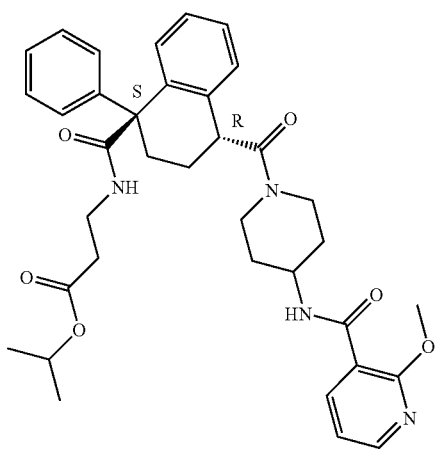
Co. No. 261; Ex. B.18.b; (1S, 4R)
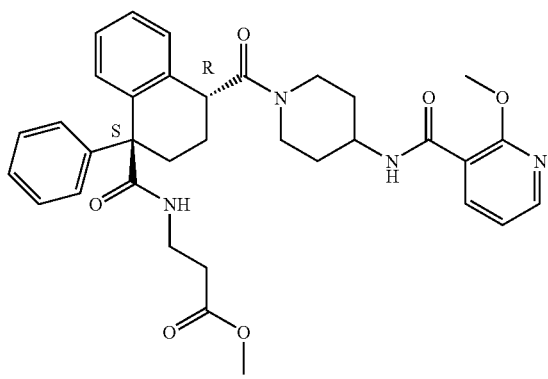
Co. No. 262; Ex. B.18.b; (1S, 4R)

TABLE F-1-continued
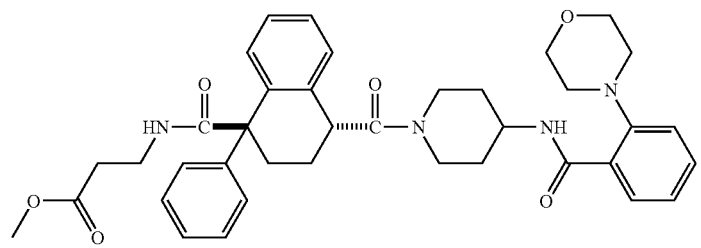
Co. No. 263; Ex. B.20b
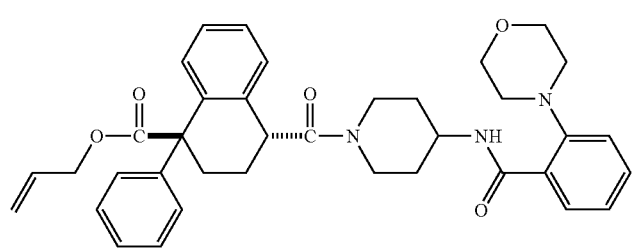
Co. No. 264; Ex. B.19
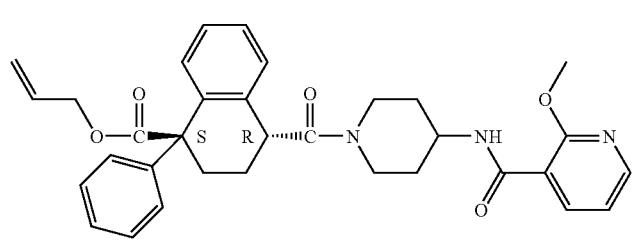
Co. No. 265; Ex. B.16; (1S, 4R)
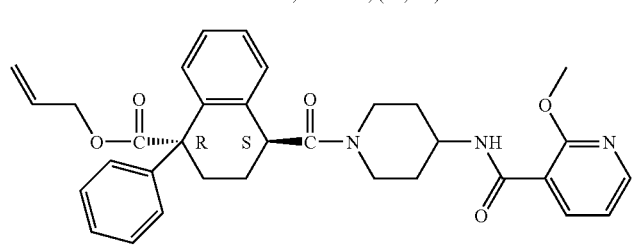
Co. No. 266; Ex. B.16; (1R, 4S)
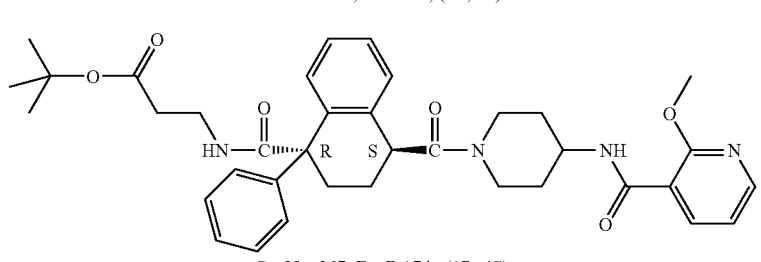
Co. No. 267; Ex. B.17.b; (1R, 4S)
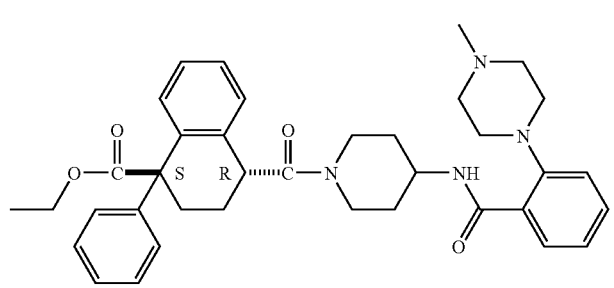
Co. No. 268; Ex. B.19

TABLE F-1-continued
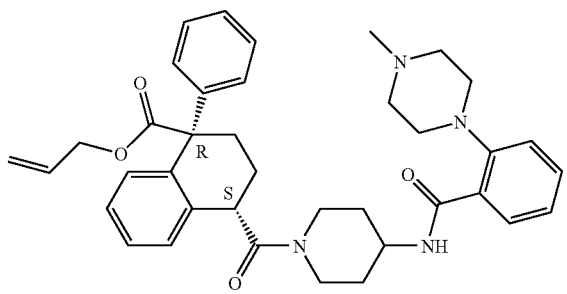
Co. No. 269; Ex. B.19; (1R, 4S);
m.p. 139.30° C. (DSC)
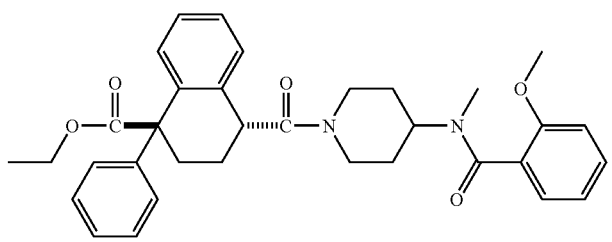
Co. No. 270; Ex. B.19; m.p.
176.49° C. (DSC)
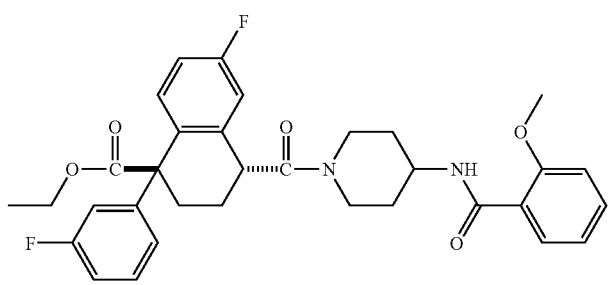
Co. No. 271; Ex. B.19; 200.36° C. (DSC)
TABLE F-1a
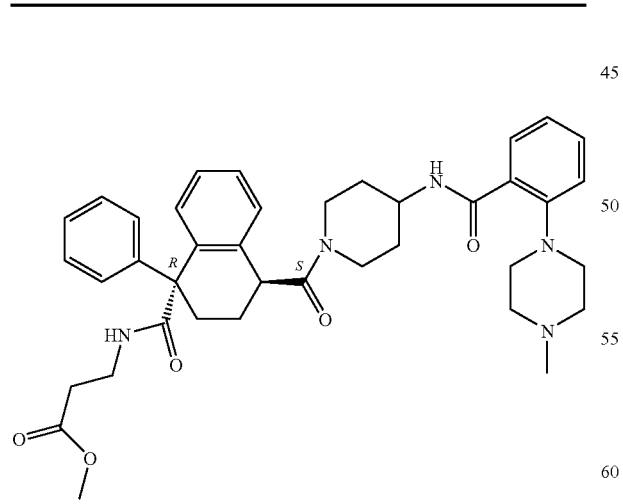
Co. No. 272; Ex. B.21
TABLE F-1a-continued
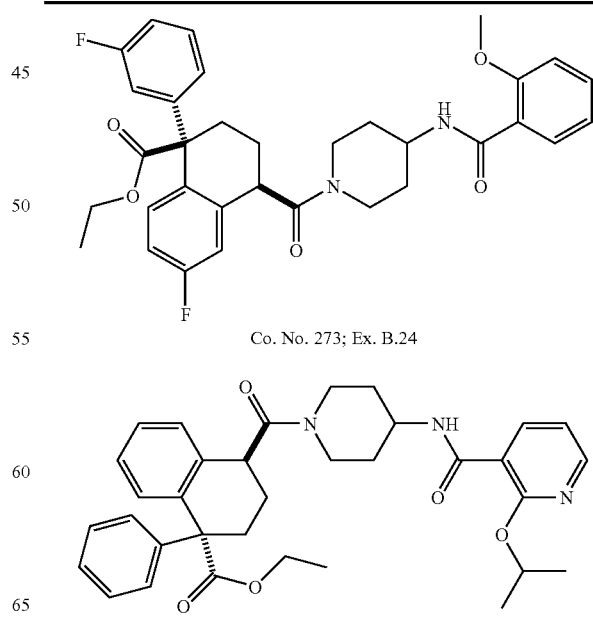
Co. No. 273; Ex. B.24
Co. No. 274; Ex. B.4

TABLE F-1a-continued
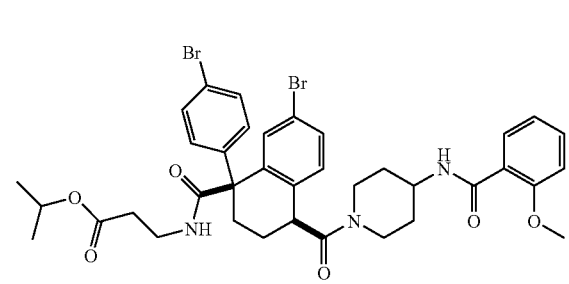
Co. No. 275; Ex. B.25
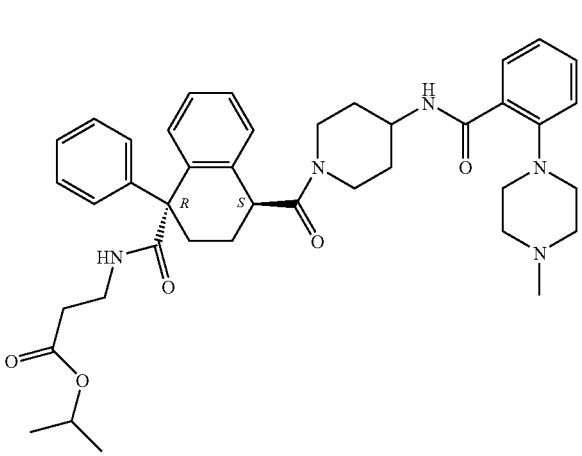
Co. No. 276; Ex. B.21; (1R, 4S)
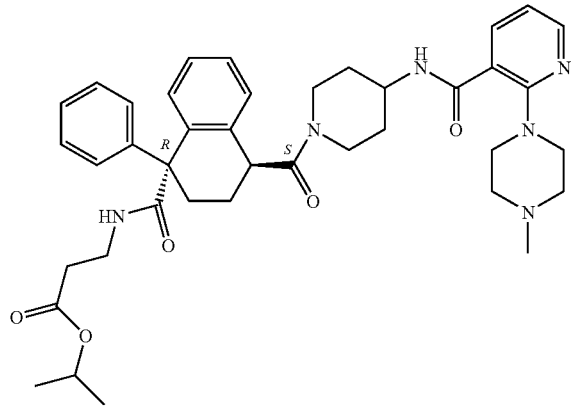
Co. No. 277; Ex. B.23; (1R, 4S)
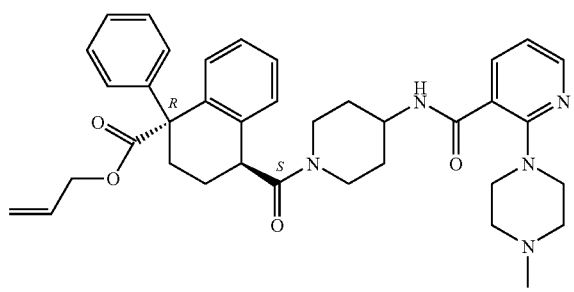
Co. No. 278; Ex. B.22; (1R, 4S)
TABLE F-1a-continued
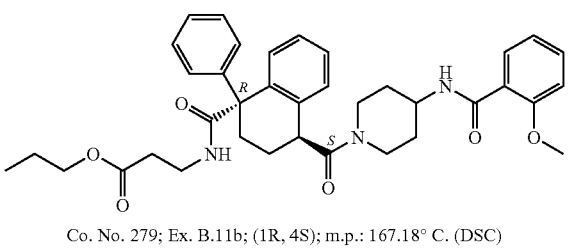
Co. No. 279; Ex. B.11b; (1R, 4S); m.p.: 167.18° C. (DSC)
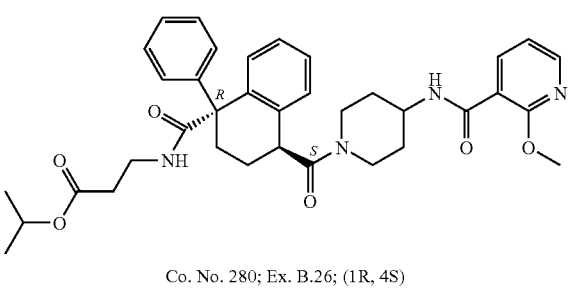
Co. No. 280; Ex. B.26; (1R, 4S)
TABLE 2
intermediates of formula (XVII) prepared in accordance with the procedures of the Experimental Part
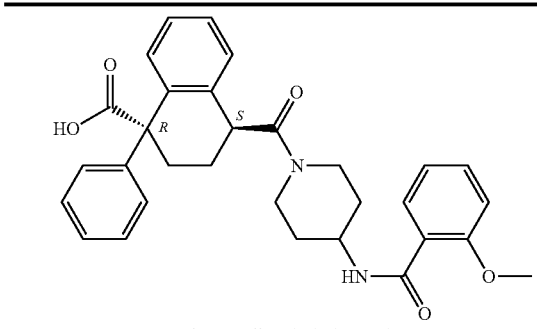
intermediate (79); (1R, 4S)
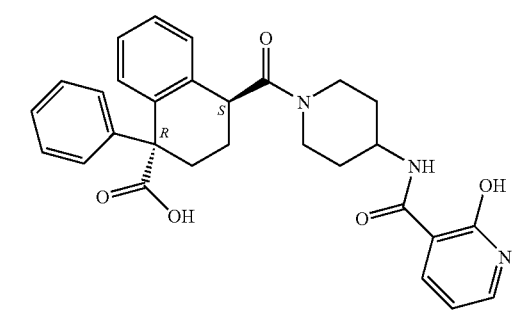
intermediate (80); (1R, 4S)
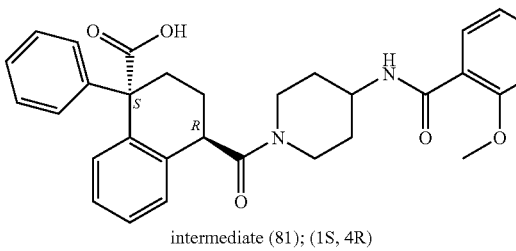
intermediate (81); (1S, 4R)

TABLE 2-continued intermediates of formula (XVII) prepared in accordance with the procedures of the Experimental Part

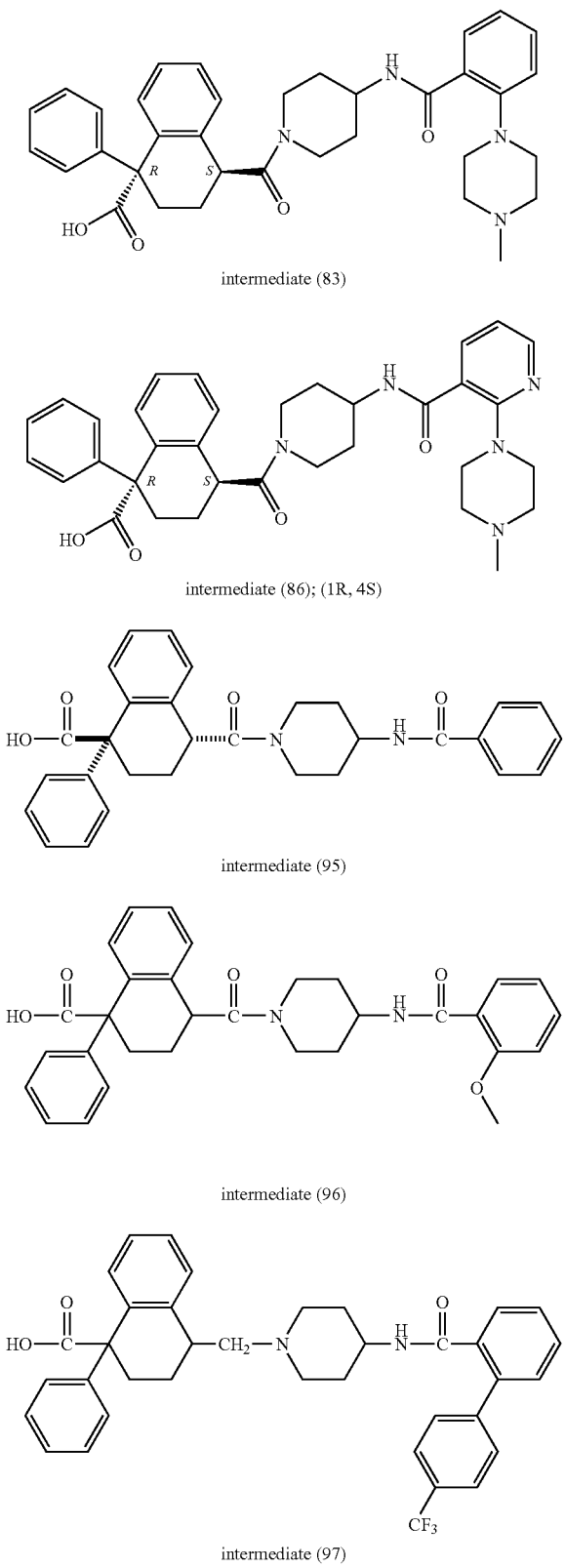

intermediate (83)

intermediate (86); (1R, 4S)

intermediate (95)

intermediate (96)

intermediate (97)

TABLE 2-continued intermediates of formula (XVII) prepared in accordance with the procedures of the Experimental Part

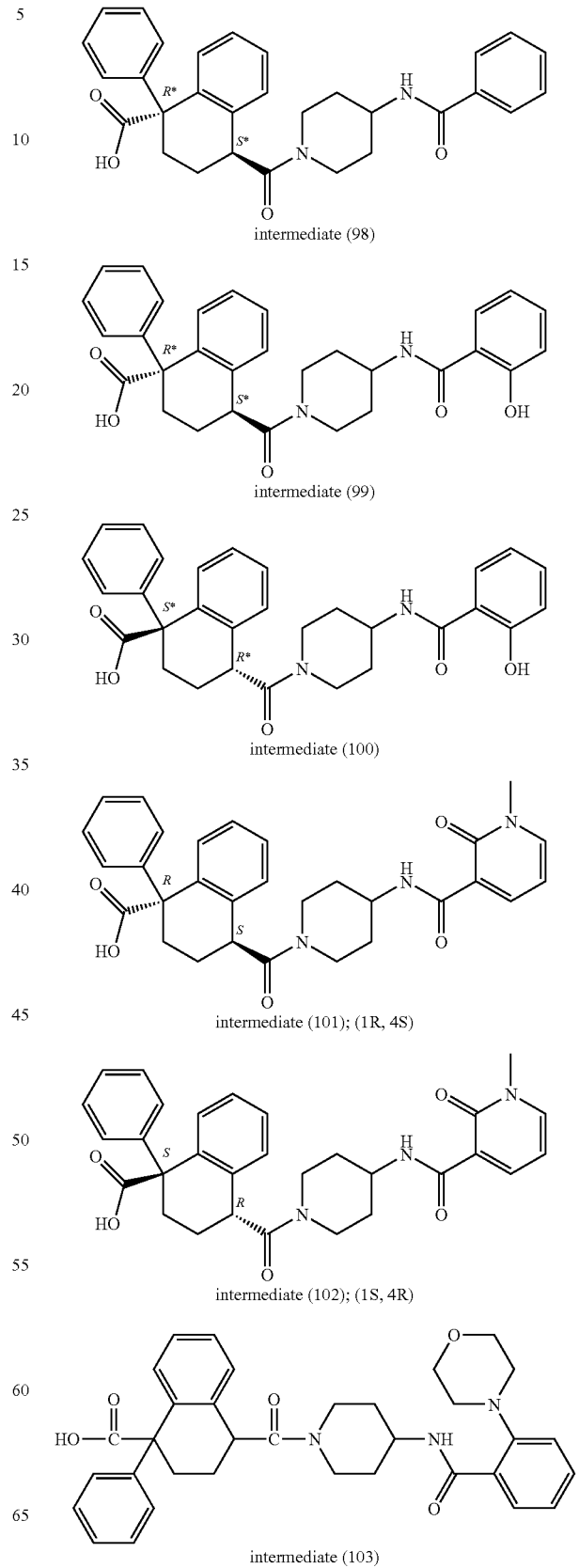

intermediate (98)

intermediate (99)

intermediate (100)

intermediate (101); (1R, 4S)

intermediate (102); (1S, 4R)

intermediate (103)

TABLE 2-continued intermediates of formula (XVII) prepared in accordance with the procedures of the Experimental Part

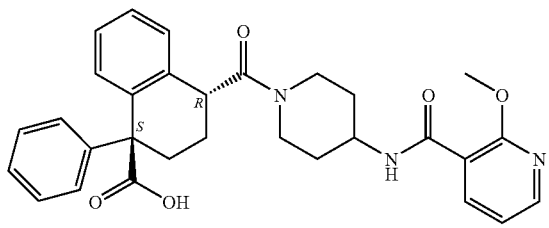

intermediate (104); (1S, 4R)

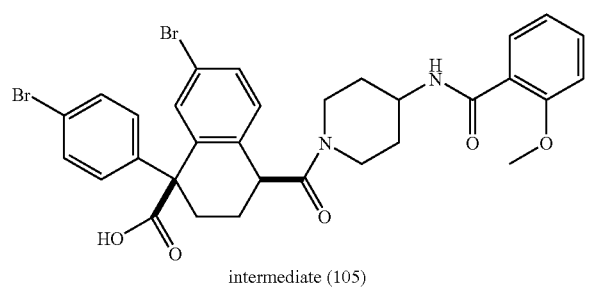

intermediate (105)

Compound Identification

General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source.

Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure C

The HPLC measurement was performed using a Shimadzu 2010 LCMS-system comprising a pump, diode array detector detector (DAD) (set at 200-300 nm) and a ELSD (evaporative light scattering detector), a column oven (set at 40° C.) and a column as specified in the respective methods below. Flow from the column was split to a MS spectrometer.

An APCI (atmospheric pressure chemical ionization) source was used as standard in positive and negative ionisation modes (two separate runs). Mass spectra were acquired by scanning from e.g. 150 to 500 in 0.7 seconds using a dwell time of 0.3 seconds (other ranges are possible). Typical parameter settings used a probe current of 6.80 µA for positive ionization and −13.50 µA for negative ionization. The probe bias was 4.5 kV for positive ionization and −4.00 kV for negative ionization. The APCI probe temperature was 400° C. The CDL (Curved Desolvation Line with heated capillary) temperature was 250° C. The CDL voltage was −5 V for positive ionization mode and +5 V for negative ionization mode. The heat block temperature was 200° C. Nitrogen was used as the nebulizer gas (2.50 l/min).

Occasionally (depending on type of compound), electrospray ionization was used in positive and negative ionization modes. The nebulizing gas flow was 4.5 l/min. Typical parameter settings for positive ionization used a probe current of 4.20 µA, a probe bias of 4.50 kV, a CDL voltage of 25 V and a CDL temperature of 250° C. The heat block temperature was 200° C. Typical parameter settings for negative ionization used a probe current of −3.50 µA, a probe bias of −3.50 kV, a CDL voltage of −25 V and a CDL temperature of 250° C.

Method 1

In addition to general procedure A: Reversed phase HPLC was carried out on an Xterra MS C18 column (3.5 µm, 4.6× 100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

Method 2

In addition to general procedure B: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (mobile phase A: 0.1% formic acid in H₂O/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

Method 3

In addition to general procedure A: Reversed phase HPLC was carried out on a Chromolith (4.6×25 mm) with a flow rate of 3 ml/min. Three mobile phases (mobile phase A: 95% 25 mM ammoniumacetate +5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 µl was used. Cone voltage was 10 V for positive ionization mode and 20 V for negative ionization mode.

Method 4

In addition to general procedure A: Reversed phase HPLC was carried out on a Chromolith (4.6×25 mm) with a flow rate of 3 ml/min. Three mobile phases (mobile phase A: 95% 25 mM ammoniumacetate +5% acetonitrile; mobile phase B: acetonitrile; mobile phase C: methanol) were employed to run a gradient condition from 100% A, to 50% B and 50% C in 0.9 minutes, to 100% B in 0.3 minutes and hold for 0.2 minutes. An injection volume of 2 µl was used. Cone voltage was 10 V for positive ionization mode and 20 V for negative ionization mode.

Method 5

In addition to general procedure A: Reversed phase HPLC was carried out on an Xterra MS C18 column (3.5 μm, 4.6×100 mm) with a flow rate of 1.2 ml/min. Three mobile phases (mobile phase A: 95% 25 mM ammoniumacetate +5% acetonitrile; mobile phase B: acetonitrile; mobile phase C: methanol) were employed to run a gradient condition from 100% A to 50% B and 50% C in 10 minutes, to 100% B in 1 minute, 100% B for 3 minutes and reequilibrate with 100% A for 1.5 minutes. An injection volume of 10 μl was used.

Method 6

In addition to general procedure A: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate +5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 μl was used. Cone voltage was 10 V for positive ionization mode and 20 V for negative ionization mode.

Method 7

In addition to general procedure A: Reversed phase HPLC was carried out on an Xterra MS C18 column (3.5 μm, 4.6×100 mm) with a flow rate of 1.2 ml/min. Three mobile phases (mobile phase A: 95% 25 mM ammoniumacetate +5% acetonitrile; mobile phase B: acetonitrile; mobile phase C: methanol) were employed to run a gradient condition from 100% A to 2% A, 49% B and 49% C in 10 minutes, to 1% A and 99% B in 1 minute and hold these conditions for 3 minutes and reequilibrate with 100% A for 2.5 minutes. An injection volume of 10 μl was used. Cone voltage was 10 V for positive ionization mode and 20 V for negative ionization mode. Column temperature was 45° C.

Method 8

In addition to general procedure C: Reversed phase HPLC was carried out on a Phenomenex column (Gemini 5u C18) (50 mm×4.6 mm) with a flow rate of 1 ml/min. Two mobile phases (mobile phase A: 10 mM ammonium acetate in $H_2O$; mobile phase B: acetonitrile) were used. First 80% A and 20% B was hold for 30 seconds. Then a linear gradient was applied to 10% A and 90% B over 3.5 minutes. 10% A and 90% B was hold for 1 minute and then 80% A and 20% B was hold for 2 minutes. Typical injection volumes of 1-5 μl were used.

Method 9

In addition to general procedure A: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate +5% acetonitrile; mobile phase B: acetonitrile; mobile phase C: methanol) were employed to run a gradient condition from 100% A to 30% A, 35% B; 35% C in 3 minutes to 50% B and 50% C in 3.5 minutes, to 100% B in 0.5 minutes. An injection volume of 10 μl was used. Cone voltage was 10 V for positive ionization mode.

TABLE 3

Analytical data
When a compound is a mixture of isomers which give different peaks in the LCMS method, only the retention time of the main component is given in the LCMS table (Rt: Retention time in minutes).

| Co. No. | $R_t$ | $(MH)^+$ | Meth. |
| --- | --- | --- | --- |
| 2 | 1.36 | 558 | 2 |
| 3 | 1.38 | 572 | 2 |
| 4 | 1.34 | 524 | 2 |
| 5 | 1.01 | 510 | 2 |
| 6 | 1.20 | 654 | 2 |
| 7 | 1.25 | 540 | 2 |
| 8 | 1.38 | 553 | 2 |
| 9 | 1.32 | 540 | 2 |
| 10 | 1.39 | 654 | 2 |
| 11 | 1.44 | 654 | 2 |
| 12 | 1.40 | 523 | 2 |
| 13 | 1.36 | 523 | 2 |
| 14 | 1.22 | 510 | 2 |
| 15 | 0.96 | 526 | 2 |
| 16 | 1.16 | 640 | 2 |
| 17 | 6.05 | 496 | 1 |
| 18 | 5.72 | 510 | 1 |
| 19 | 6.75 | 667 | 1 |
| 20 | 5.76 | 570 | 1 |
| 21 | 5.98 | 574 | 1 |
| 22 | 5.48 | 524 | 1 |
| 23 | 5.55 | 619 | 1 |
| 24 | 6.16 | 590 | 1 |
| 26 | 5.95 | 541 | 1 |
| 27 | 6.09 | 527 | 1 |
| 28 | 6.78 | 641 | 1 |
| 29 | 6.22 | 497 | 1 |
| 30 | 6.19 | 527 | 1 |
| 31 | 6.86 | 641 | 1 |
| 32 | 5.61 | 511 | 1 |
| 33 | 5.61 | 511 | 1 |
| 34 | 5.78 | 541 | 1 |
| 34 | 1.36 | 541 | 2 |
| 35 | 5.78 | 541 | 1 |
| 36 | 5.91 | 527 | 1 |
| 37 | 5.21 | 512 | 1 |
| 38 | 5.11 | 540 | 1 |
| 39 | 5.10 | 540 | 1 |
| 40 | 1.25 | 512 | 2 |
| 41 | 1.25 | 512 | 2 |
| 42 | 5.92 | 527 | 1 |
| 43 | 1.15 | 512 | 2 |
| 44 | 1.15 | 512 | 2 |
| 45 | 5.85 | 553 | 1 |
| 46 | 5.85 | 553 | 1 |
| 46 | 1.38 | 553 | 2 |
| 47 | 0.96 | 598 | 4 |
| 48 | 5.28 | 598 | 1 |
| 49 | 7.79 | 557 | 5 |
| 50 | 7.91 | 557 | 5 |
| 51 | 8.22 | 541 | 7 |
| 52 | 6.89 | 606 | 7 |
| 53 | 8.28 | 625 | 7 |
| 54 | 7.81 | 563 | 7 |
| 55 | 8.56 | 543 | 7 |
| 56 | 7.66 | 528 | 7 |
| 57 | 8.06 | 542 | 7 |
| 58 | 7.44 | 556 | 7 |
| 59 | 7.47 | 559 | 7 |
| 60 | 1.32 | 527 | 2 |
| 61 | 7.33 | 543 | 7 |
| 62 | 5.86 | 626 | 1 |
| 63 | 1.15 | 570 | 2 |
| 64 | 1.15 | 584 | 2 |
| 65 | 0.96 | 598 | 3 |
| 66 | 5.96 | 612 | 1 |
| 67 | 5.96 | 612 | 1 |
| 68 | 6.46 | 640 | 1 |
| 69 | 6.41 | 640 | 1 |
| 70 | 6.6 | 654 | 1 |
| 71 | 5.38 | 628 | 1 |
| 72 | 6.05 | 684 | 1 |
| 73 | 5.88 | 670 | 1 |
| 74 | 6.15 | 698 | 1 |
| 75 | 6.22 | 755 | 1 |

TABLE 3-continued

Analytical data
When a compound is a mixture of isomers which give different peaks in the LCMS method, only the retention time of the main component is given in the LCMS table (Rt: Retention time in minutes).

| Co. No. | $R_t$ | $(MH)^+$ | Meth. |
|---|---|---|---|
| 76 | 6.15 | 638 | 1 |
| 77 | 6.12 | 638 | 1 |
| 78 | 5.2 | 640 | 1 |
| 79 | 6.38 | 674 | 1 |
| 80 | 6.43 | 674 | 1 |
| 81 | 6.48 | 688 | 1 |
| 82 | 6.45 | 688 | 1 |
| 83 | 6.45 | 652 | 1 |
| 84 | 6.16 | 652 | 1 |
| 85 | 5.89 | 704 | 1 |
| 86 | 6.31 | 727 | 1 |
| 87 | 6.32 | 640 | 1 |
| 88 | 6.26 | 640 | 1 |
| 89 | 4.38 | 584 | 1 |
| 90 | 1.11 | 584 | 2 |
| 91 | 6.28 | 738 | 6 |
| 92 | 3.57 | 626 | 6 |
| 93 | 6.39 | 640 | 1 |
| 94 | 6.52 | 666 | 1 |
| 95 | 6.73 | 702 | 1 |
| 96 | 6.15 | 716 | 6 |
| 97 | 4.35 | 584 | 1 |
| 98 | 4.59 | 610 | 1 |
| 99 | 4.23 | 646 | 6 |
| 100 | 4.93 | 660 | 1 |
| 101 | 6.43 | 640 | 1 |
| 102 | 6.79 | 668 | 1 |
| 103 | 6.76 | 668 | 1 |
| 104 | 6.26 | 682 | 6 |
| 105 | 6.91 | 712 | 1 |
| 106 | 6.79 | 740 | 1 |
| 107 | 5.03 | 697 | 6 |
| 108 | 6.19 | 754 | 6 |
| 109 | 6.69 | 798 | 1 |
| 110 | 5.89 | 666 | 6 |
| 111 | 6.75 | 702 | 1 |
| 112 | 6.78 | 716 | 1 |
| 113 | 5.63 | 732 | 6 |
| 114 | 6.60 | 755 | 1 |
| 115 | 4.94 | 683 | 6 |
| 116 | 4.49 | 584 | 1 |
| 117 | 4.92 | 612 | 1 |
| 118 | 4.66 | 612 | 1 |
| 119 | 5.19 | 626 | 1 |
| 120 | 4.71 | 656 | 6 |
| 121 | 3.66 | 628 | 1 |
| 122 | 3.69 | 642 | 1 |
| 123 | 4.56 | 610 | 1 |
| 124 | 4.99 | 646 | 1 |
| 125 | 5.19 | 660 | 1 |
| 126 | 4.49 | 676 | 1 |
| 127 | 4.99 | 699 | 1 |
| 128 | 3.57 | 627 | 6 |
| 129 | 1.22 | 612 | 2 |
| 130 | 1.16 | 697 | 2 |
| 131 | 1.19 | 711 | 2 |
| 132 | 0.94 | 641 | 2 |
| 133 | 5.05 | 599 | 1 |
| 135 | 5.46 | 613 | 1 |
| 136 | 5.39 | 613 | 1 |
| 138 | 4.82 | 599 | 1 |
| 139 | 6.08 | 641 | 1 |
| 140 | 5.99 | 641 | 1 |
| 141 | 6.23 | 655 | 1 |
| 142 | 4.68 | 629 | 1 |
| 143 | 5.58 | 685 | 1 |
| 144 | 6.02 | 653 | 1 |
| 146 | 5.69 | 699 | 1 |
| 147 | 5.66 | 653 | 1 |
| 148 | 5.79 | 756 | 1 |
| 149 | 5.59 | 639 | 1 |
| 150 | 5.58 | 639 | 1 |
| 152 | 5.99 | 675 | 1 |
| 153 | 6.06 | 675 | 1 |
| 154 | 6.12 | 689 | 1 |
| 155 | 6.05 | 689 | 1 |
| 157 | 5.93 | 728 | 1 |
| 158 | 4.73 | 585 | 1 |
| 159 | 5.16 | 613 | 1 |
| 160 | 5.65 | 627 | 1 |
| 161 | 6.02 | 641 | 1 |
| 162 | 5.99 | 641 | 1 |
| 163 | 5.86 | 641 | 1 |
| 169 | 1.36 | 741 | 2 |
| 179 | 6.49 | 717 | 1 |
| 181 | 4.89 | 684 | 1 |
| 182 | 5.05 | 571 | 9 |
| 183 | 5.12 | 585 | 9 |
| 184 | 4.83 | 585 | 9 |
| 185 | 4.80 | 585 | 9 |
| 186 | 5.05 | 585 | 9 |
| 187 | 5.51 | 613 | 9 |
| 188 | 5.06 | 613 | 9 |
| 189 | 5.35 | 627 | 9 |
| 190 | 5.00 | 642 | 9 |
| 191 | 5.24 | 611 | 9 |
| 192 | 4.69 | 627 | 9 |
| 193 | 5.01 | 647 | 9 |
| 194 | 5.60 | 647 | 9 |
| 195 | 5.74 | 661 | 9 |
| 196 | 5.24 | 661 | 9 |
| 197 | 4.9 | 677 | 9 |
| 198 | 4.89 | 628 | 9 |
| 199 | 1.27 | 626 | 2 |
| 200 | 6.82 | 626 | 9 |
| 201 | 6.24 | 612 | 9 |
| 202 | 6.44 | 626 | 9 |
| 203 | 7.2 | 654 | 9 |
| 204 | 6.61 | 626 | 9 |
| 205 | 6.63 | 640 | 9 |
| 206 | 6.85 | 654 | 9 |
| 207 | 6.83 | 640 | 9 |
| 208 | 7.29 | 668 | 9 |
| 209 | 7.34 | 682 | 9 |
| 210 | 7.03 | 769 | 9 |
| 211 | 6.84 | 741 | 9 |
| 212 | 6.81 | 755 | 9 |
| 213 | 7.26 | 769 | 9 |
| 214 | 6.22 | 697 | 9 |
| 215 | 6.88 | 755 | 9 |
| 216 | 7.05 | 769 | 9 |
| 217 | 6.65 | 741 | 9 |
| 218 | 7.15 | 755 | 9 |
| 219 | 6.87 | 741 | 9 |
| 220 | 7.09 | 755 | 9 |
| 221 | 7.05 | 769 | 9 |
| 222 | 6.38 | 627 | 9 |
| 223 | 6.34 | 627 | 9 |
| 224 | 5.80 | 613 | 9 |
| 225 | 6.02 | 627 | 9 |
| 226 | 6.71 | 655 | 9 |
| 227 | 6.45 | 655 | 9 |
| 228 | 6.32 | 641 | 9 |
| 229 | 6.59 | 669 | 9 |
| 230 | 6.83 | 683 | 9 |
| 231 | 6.85 | 770 | 9 |
| 232 | 6.18 | 742 | 9 |
| 233 | 6.36 | 756 | 9 |
| 234 | 6.37 | 756 | 9 |
| 235 | 6.77 | 770 | 9 |
| 236 | 5.59 | 698 | 9 |
| 237 | 6.41 | 756 | 9 |
| 238 | 6.05 | 728 | 9 |
| 239 | 6.3 | 742 | 9 |

TABLE 3-continued

Analytical data
When a compound is a mixture of isomers which give different peaks in the LCMS method, only the retention time of the main component is given in the LCMS table (Rt: Retention time in minutes).

| Co. No. | $R_t$ | $(MH)^+$ | Meth. |
|---|---|---|---|
| 240 | 6.41 | 742 | 9 |
| 241 | 6.41 | 756 | 9 |
| 242 | 6.64 | 770 | 9 |
| 244 | 5.30 | 554 | 6 |
| 245 | 5.31 | 554 | 6 |
| 246 | 1.35 | 668 | 2 |
| 247 | 1.36 | 726 | 2 |
| 248 | 1.35 | 726 | 2 |
| 249 | 1.29 | 640 | 2 |
| 250 | 1.28 | 640 | 2 |
| 251 | 4.70 | 769 | 8 |
| 252 | 6.24 | 596 | 1 |
| 253 | 6.20 | 542 | 1 |
| 254 | 5.35 | 599 | 1 |
| 255 | 4.54 | 585 | 1 |
| 256 | 0.90 | 598 | 3 |
| 257 | 5.97 | 626 | 1 |
| 258 | 0.78 | 585 | 3 |
| 259 | 1.09 | 541 | 2 |
| 260 | 1.37 | 610 | 2 |
| 261 | 1.26 | 627 | 2 |
| 262 | 1.16 | 599 | 2 |
| 263 | 1.18 | 653 | 2 |
| 264 | 6.32 | 608 | 1 |
| 265 | 6.30 | 554 | 1 |
| 266 | 6.29 | 554 | 1 |
| 267 | 1.08 | 641 | 3 |
| 268 | 1.06 | 609 | 2 |
| 269 | 1.08 | 621 | 2 |
| 270 | 1.30 | 555 | 2 |
| 271 | 1.34 | 577 | 2 |
| 272 | 5.19 | 666 | 1 |
| 273 | 1.38 | 577 | 2 |
| 274 | 1.42 | 570 | 2 |
| 275 | 1.46 | 782 | 2 |
| 276 | 1.03 | 694 | 2 |
| 277 | 1.00 | 695 | 2 |
| 279 | 5.77 | 626 | 1 |
| 280 | 1.29 | 627 | 2 |

Optical Rotation:

The optical rotation was measured using a Perkin Elmer 341 polarimeter. $[\alpha]_D^{20}$ indicates the optical rotation measured with light at the wavelength of the D-line of sodium (589 nm) at a temperature of 20° C. The cell pathlength is 1 dm. Behind the actual value the concentration and solvent of the solution which was used to measure the optical rotation are mentioned.

| Co. No. | $[\alpha]_D^{20}$ | concentration | solvent |
|---|---|---|---|
| 32 | −30.79° | 25.17 mg/5 ml | EtOH |
| 33 | +29.84° | 24.46 mg/5 ml | EtOH |
| 34 | −28.21° | 25.35 mg/5 ml | EtOH |
| 35 | +27.70° | 25.27 mg/5 ml | EtOH |
| 36 | −26.91° | 24.90 mg/5 ml | DMF |
| 38 | +13.82° | 25.68 mg/5 ml | EtOH |
| 39 | −13.80° | 25.36 mg/5 ml | EtOH |
| 40 | +68.8° | 24.20 mg/5 ml | EtOH |
| 41 | −67.30° | 24.07 mg/5 ml | EtOH |
| 42 | +27.24° | 24.96 mg/5 ml | DMF |
| 45 | −31.12° | 14.62 mg/5 ml | MeOH |
| 46 | +31.63° | 9.80 mg/5 ml | EtOH |
| 47 | −12.85° | 22.96 mg/5 ml | DMF |
| 48 | +12.26° | 23.65 mg/5 ml | DMF |
| 62 | −14.13° | 20.52 mg/5 ml | DMF |
| 65 | −15.29° | 7.52 mg/5 ml | MeOH |
| 90 | −12.66° | 10.67 mg/5 ml | MeOH |
| 199 | −16.30° | 8.28 mg/5 ml | MeOH |
| 208 | −19.29° | 19.96 mg/5 ml | MeOH |
| 213 | −28.33° | 12.00 mg/5 ml | MeOH |
| 244 | −37.55° | 26.10 mg/5 ml | MeOH |
| 246 | −20.81° | 10.57 mg/5 ml | MeOH |
| 247 | −33.40° | 10.78 mg/5 ml | MeOH |
| 248 | −33.89° | 13.28 mg/5 ml | MeOH |
| 249 | −21.64° | 11.32 mg/5 ml | MeOH |
| 250 | −20.72° | 14.24 mg/5 ml | MeOH |
| 253 | −27.74° | 6.67 mg/5 ml | EtOH |
| 254 | −64.08° | 6.32 mg/5 ml | MeOH |
| 255 | −20.18° | 5.45 mg/5 ml | MeOH |
| 256 | +14.93° | 19.09 mg/5 ml | MeOH |
| 257 | +14.89° | 7.05 mg/5 ml | MeOH |
| 258 | −7.40° | 58.10 mg/5 ml | $CHCl_3$ |
| 261 | +15.60° | 14.74 mg/5 ml | MeOH |
| 262 | +12.55° | 10.76 mg/5 ml | MeOH |
| 265 | +31.68° | 12.94 mg/5 ml | MeOH |
| 266 | −34.09° | 8.80 mg/5 ml | MeOH |
| 269 | −25.49° | 46.10 mg/5 ml | MeOH |
| 276 | −11.82° | 12.27 mg/5 ml | MeOH |
| 277 | −13.12° | 10.67 mg/5 ml | MeOH |
| 279 | −15.70° | 23.25 mg/5 ml | DMF |
| 280 | −16.36° | 6.42 mg/5 ml | MeOH |

SFC-MS:

For some compounds SFC-MS (Supercritical fluid chromatography-mass spectrometry) was measured with an analytical SFC system from Berger Instruments (Newark, Del., USA) comprising a dual pump control module (FCM-1200) for delivery of carbon dioxide ($CO_2$) and modifier, a thermal control module for column heating (TCM2100) with temperature control in the range of 1-150° C. and column selection valves (Valco, VICI, Houston, Tex., USA) for six different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

For Co. No. (44) a very small amount (0.01%) of a second isomer was detected when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: 2-propanol containing 0.2% 2-propylamine) were employed to run a condition from 40% B (hold for 19.5 minutes) to 50% B in 1 minute and hold for 4.10 minutes. Column temperature was set at 50° C.

For Co. No. (279) a very small amount (0.1%) of a second isomer was detected when SFC-MS was carried out on a Chiralcel OJ-H column (500×4.6 mm) (Daicel Chemical Industries Ltd) with a flow rate of 3 ml/min. Two mobile phases (mobile phase A: $CO_2$; mobile phase B: methanol containing 0.2% 2-propylamine) were employed to run a condition from 10% B to 40% B in 18.75 minutes. Then a gradient was applied from 40% B to 50% B in 2 minutes and hold for 3.6 minutes.

For Co. No. (280) an enantiomeric excess was found of 100% when a screening was performed with 4 different columns (Chiralcel OJ-H, Chiralpak AD-H, Chiralcel OD-H, Chiralpak AS-H; 500×4.6 mm; Daicel Chemical Industries Ltd) and 3 different solvents (MeOH, EtOH, 2-propanol; the solvent is containing 0.2% 2-propylamine). SFC-MS was carried out with one of the columns mentioned above with a flow rate of 3 ml/min. Two mobile phases (mobile phase A: $CO_2$; mobile phase B: one of the solvents mentioned above containing 0.2% 2-propylamine) were employed to run a condition from 10% B to 40% B in 18.75 minutes. Then a gradient was applied from 40% B to 50% B in 2 minutes and hold for 3.6 minutes. Column temperature was set at 50° C.

C. Pharmacological Examples

C.1. Quantification of the Secretion of ApoB

HepG2 cells were cultured in 24-well plates in MEM Rega 3 containing 10% fetal calf serum. At 70% confluency, the medium was changed and the test compound or carrier (DMSO, 0.4% final concentration) was added. After 24 hours of incubation, the medium was transferred to Eppendorf tubes and cleared by centrifugation. A sheep antibody directed against either apoB was added to the supernatant and the mixture was kept at 8° C. for 24 hours. Then, rabbit anti-sheep antibody was added and the immune complex was allowed to precipitate for 24 hours at 8° C. The immunoprecipitate was pelleted by centrifugation for 25 minutes at 1320 g and washed twice with a buffer containing 40 mM Mops, 40 mM $NaH_2PO_4$, 100 mM NaF, 0.2 mM DTT, 5 mM EDTA, 5 mM EGTA, 1% Triton-X-100, 0.5% sodium deoxycholate (DOC), 0.1% SDS, 0.2 μM leupeptin and 0.2 μM PMSF. Radioactivity in the pellet was quantified by liquid scintillation counting. The $IC_{50}$ values are usually converted to pIC50 values (=–log $IC_{50}$ value) for ease of use.

TABLE 4

| Co. No. | pIC50 |
|---|---|
| 1 | 5.735 |
| 2 | 7.128 |
| 3 | 7.094 |
| 4 | 6.643 |
| 5 | 5.718 |
| 6 | 7.691 |
| 7 | 8.642 |
| 8 | 8.188 |
| 10 | 8.732 |
| 11 | <7 |
| 13 | 7.541 |
| 14 | 6.194 |
| 15 | 6.731 |
| 16 | 7.824 |
| 19 | 8.121 |
| 20 | 7.641 |
| 21 | 7.559 |
| 22 | 6.811 |
| 23 | 6.635 |
| 24 | 6.695 |
| 25 | 7.824 |
| 26 | 8.196 |
| 27 | 6.109 |
| 28 | 6.483 |
| 32 | 8.124 |
| 33 | <6 |
| 34 | 8.421 |
| 35 | 5.27 |
| 36 | 7.932 |
| 39 | 8.504 |
| 40 | 7.151 |
| 41 | 7.446 |
| 42 | 6 |
| 43 | 6.574 |
| 44 | 6.975 |
| 45 | 8.58 |

TABLE 4-continued

| Co. No. | pIC50 |
|---|---|
| 46 | 6.649 |
| 47 | 7.565 |
| 48 | 5.01 |
| 49 | 6.195 |
| 50 | 7.793 |
| 51 | 8.022 |
| 53 | 7.209 |
| 54 | 7.182 |
| 55 | <6 |
| 56 | 8.65 |
| 57 | 7.157 |
| 58 | 8.691 |
| 59 | 6.648 |
| 61 | 6.544 |
| 62 | 7.376 |
| 63 | <5 |
| 64 | 7.75 |
| 65 | 8.098 |
| 66 | <6 |
| 67 | 6.059 |
| 68 | <6 |
| 69 | 6.813 |
| 70 | <6 |
| 72 | <6 |
| 73 | <6 |
| 74 | <6 |
| 75 | 7.695 |
| 79 | 6.894 |
| 80 | 6.261 |
| 81 | <6 |
| 82 | 6.539 |
| 83 | 6.174 |
| 84 | <6 |
| 85 | <6 |
| 86 | 6.185 |
| 88 | 7.687 |
| 90 | <6 |
| 96 | 6.291 |
| 102 | 6.775 |
| 103 | 6.418 |
| 104 | 6.767 |
| 105 | 6.567 |
| 106 | 6.733 |
| 107 | <6 |
| 108 | 7.126 |
| 109 | 8.558 |
| 110 | 6.61 |
| 112 | 6.866 |
| 121 | <6 |
| 129 | 8.361 |
| 138 | <6 |
| 148 | <6 |
| 159 | <6 |
| 164 | <6 |
| 172 | <6 |
| 199 | 8.133 |
| 200 | 6.594 |
| 201 | <6 |
| 202 | 6.101 |
| 203 | 7.523 |
| 204 | <6 |
| 205 | 7.122 |
| 206 | 7.373 |
| 207 | <6 |
| 208 | 7.239 |
| 209 | <6 |
| 210 | 8.062 |
| 211 | 7.019 |
| 212 | 7.652 |
| 213 | 8.229 |
| 214 | <6 |
| 215 | 7.736 |
| 216 | 7.507 |
| 217 | 6.591 |
| 218 | 7.187 |
| 219 | 6.523 |

TABLE 4-continued pIC50 values

| Co. No. | pIC50 |
|---|---|
| 220 | 7.676 |
| 221 | 6.87 |
| 222 | <6 |
| 225 | <6 |
| 226 | <6 |
| 229 | <6 |
| 231 | <6 |
| 233 | <6 |
| 235 | <6 |
| 246 | 6.631 |
| 247 | 6.418 |
| 248 | 6.736 |
| 249 | 6.232 |
| 250 | 6.465 |
| 252 | 8.454 |
| 253 | 8.49 |
| 254 | 7.768 |
| 255 | <6 |
| 256 | <6 |
| 257 | <6 |
| 258 | <6 |
| 260 | 8.198 |
| 261 | <6 |
| 262 | <6 |
| 263 | 7.191 |
| 266 | 8.691 |
| 272 | 6.174 |
| 273 | 6 |
| 274 | 7.761 |
| 275 | <6 |
| 276 | 7.124 |
| 277 | 6.966 |
| 279 | 7.851 |
| 280 | 8.418 |

C.2. MTP Assay

MTP activity was measured using an assay similar to one described by J. R. Wetterau and D. B. Zilversmit in *Chemistry and Physics of Lipids*, 38, 205-222 (1985). To prepare the donor and acceptor vesicles, the appropriate lipids in chloroform were put into a glass test tube and dried under a stream of nitrogen. A buffer containing 15 mM Tris-HCl pH 7.5, 1 mM EDTA, 40 mM NaCl, 0.02% $NaN_3$ (assay buffer) was added to the dried lipid. The mixture was vortexed briefly and the lipids were then allowed to hydrate for 20 minutes on ice. Vesicles were then prepared by bath sonication (Branson 2200) at room temperature for maximum 15 minutes. Butylated hydroxytoluene was included in all vesicle preparations at a concentration of 0.1%. The lipid transfer assay mixture contained donor vesicles (40 nmol phosphatidylcholine, 7.5 mol % of cardiolipin and 0.25 mol % glycerol tri [1-$^{14}$C]-oleate), acceptor vesicles (240 nmol phosphatidylcholine) and 5 mg BSA in a total volume of 675 μl in a 1.5 ml microcentrifuge tube. Test compounds were added dissolved in DMSO (0.13% final concentration). After 5 minutes of pre-incubation at 37° C., the reaction was started by the addition of MTP in 100 μl dialysis buffer. The reaction was stopped by the addition of 400 μl DEAE-52 cellulose pre-equilibrated in 15 mM Tris-HCl pH 7.5, 1 mM EDTA, 0.02% $NaN_3$ (1:1, vol/vol). The mixture was agitated for 4 minutes and centrifuged for 2 minutes at maximum speed in an Eppendorf centrifuge (4° C.) to pellet the DEAE-52-bound donor vesicles. An aliquot of the supernatant containing the acceptor liposomes was counted and the [$^{14}$C]-counts were used to calculate the percent triglyceride transfer from donor to acceptor vesicles.

TABLE 5 pIC50 values

| Co. No. | pIC50 |
|---|---|
| 3 | 7.751 |
| 4 | 7.373 |
| 6 | 7.796 |
| 7 | 8.189 |
| 8 | 8.549 |
| 9 | 6.162 |
| 10 | 8.708 |
| 11 | 6.664 |
| 12 | 6.109 |
| 13 | 8.218 |
| 14 | 7.708 |
| 15 | 7.299 |
| 16 | 8.495 |
| 17 | 6.558 |
| 18 | 5.568 |
| 19 | 8.334 |
| 20 | 7.9 |
| 21 | 8.007 |
| 22 | 7.539 |
| 23 | 7.22 |
| 24 | 7.261 |
| 25 | 8.415 |
| 26 | 8.716 |
| 27 | 7.186 |
| 28 | <7 |
| 29 | 5.476 |
| 30 | 6.221 |
| 31 | 6.459 |
| 32 | 8.721 |
| 33 | <6 |
| 34 | 8.934 |
| 35 | 5.767 |
| 36 | 8.46 |
| 37 | 5.106 |
| 38 | 5.418 |
| 39 | 8.523 |
| 40 | <5 |
| 41 | <5 |
| 42 | <5 |
| 43 | 7.044 |
| 44 | <6 |
| 47 | 8.625 |
| 48 | 7.875 |
| 49 | 7.743 |
| 50 | 7.934 |
| 51 | 7.892 |
| 52 | 6.203 |
| 53 | 8.016 |
| 54 | 7.985 |
| 55 | 7.217 |
| 56 | 8.773 |
| 57 | 8.246 |
| 58 | 6.826 |
| 59 | <7 |
| 60 | 8.601 |
| 61 | <5 |
| 62 | 9.147 |
| 63 | <6 |
| 64 | 8.412 |
| 65 | 8.543 |
| 66 | 7.694 |
| 67 | 7.694 |
| 68 | 7.747 |
| 69 | 7.612 |
| 70 | 7.452 |
| 71 | 6.307 |
| 72 | 7.972 |
| 73 | <7 |
| 74 | 8.294 |
| 75 | 8.649 |
| 76 | 6.487 |
| 77 | 6.664 |
| 78 | 5.418 |
| 79 | 7.477 |
| 80 | 7.154 |
| 81 | 7.901 |

TABLE 5-continued pIC50 values

| Co. No. | pIC50 |
|---|---|
| 82 | 7.89 |
| 83 | 7.146 |
| 84 | 6.643 |
| 85 | <7 |
| 86 | 7.177 |
| 87 | 7.931 |
| 88 | 8.667 |
| 89 | 6 |
| 90 | 5.671 |
| 91 | <7 |
| 92 | <5 |
| 93 | 8.03 |
| 94 | 6.678 |
| 95 | 6.855 |
| 96 | 7.418 |
| 97 | 5.385 |
| 98 | 5.323 |
| 99 | <5 |
| 100 | 5.218 |
| 101 | 8.377 |
| 102 | 7.868 |
| 103 | 7.215 |
| 104 | 7.665 |
| 105 | 7.312 |
| 106 | 7.793 |
| 107 | <7 |
| 108 | 8.037 |
| 109 | 8.614 |
| 110 | <7 |
| 111 | 6.659 |
| 112 | 7.745 |
| 113 | 6.789 |
| 114 | 6.692 |
| 115 | 6.521 |
| 116 | 5.075 |
| 117 | 5.323 |
| 118 | 6.052 |
| 119 | <5 |
| 120 | <5 |
| 121 | <5 |
| 122 | 5.323 |
| 123 | 5.418 |
| 124 | <5 |
| 125 | 5.065 |
| 126 | 5.208 |
| 127 | <5 |
| 128 | <5 |
| 129 | 8.752 |
| 130 | 6.582 |
| 131 | 7.341 |
| 132 | 6.45 |
| 133 | 6.099 |
| 135 | 5.872 |
| 136 | 5.963 |
| 137 | 6.324 |
| 138 | 6.225 |
| 139 | 6.083 |
| 140 | 5.962 |
| 141 | 5.731 |
| 142 | <5 |
| 143 | 5.716 |
| 144 | 5.417 |
| 145 | 5.269 |
| 146 | 6.11 |
| 147 | 5 |
| 148 | 6.883 |
| 149 | <5 |
| 150 | <5 |
| 151 | <5 |
| 152 | 5.787 |
| 153 | 5.954 |
| 154 | 5.733 |
| 155 | 6.136 |
| 156 | 5.814 |
| 157 | 5.782 |
| 158 | 6.072 |
| 159 | 6.89 |
| 160 | 6.437 |
| 161 | 6.339 |
| 162 | 5.748 |
| 163 | 5.84 |
| 164 | 7.186 |
| 165 | 6.296 |
| 166 | 6.122 |
| 167 | 6.101 |
| 168 | 6.157 |
| 169 | 5.757 |
| 170 | <5 |
| 171 | 6.379 |
| 172 | 7.474 |
| 173 | 5.482 |
| 174 | 5.564 |
| 175 | 5.429 |
| 176 | 5.726 |
| 177 | 5.79 |
| 178 | 5.827 |
| 179 | 5.878 |
| 180 | 5.573 |
| 181 | <5 |
| 182 | <5 |
| 183 | <5 |
| 184 | <5 |
| 185 | <5 |
| 186 | <5 |
| 187 | <5 |
| 188 | <5 |
| 189 | <5 |
| 190 | <5 |
| 191 | <5 |
| 192 | <5 |
| 193 | <5 |
| 194 | <5 |
| 195 | <5 |
| 196 | <5 |
| 197 | <5 |
| 198 | <5 |
| 199 | 8.879 |
| 200 | 8.168 |
| 201 | 8.11 |
| 202 | 8.501 |
| 203 | 8.689 |
| 204 | 7.231 |
| 205 | 8.264 |
| 206 | 8.528 |
| 207 | 8.586 |
| 208 | 8.731 |
| 209 | 7.441 |
| 210 | 8.53 |
| 211 | 8.215 |
| 212 | 8.363 |
| 213 | 8.509 |
| 214 | 7.572 |
| 215 | 8.534 |
| 216 | 8.174 |
| 217 | 8.085 |
| 218 | 8.618 |
| 219 | 8.373 |
| 220 | 8.731 |
| 221 | 8.75 |
| 222 | 7.339 |
| 223 | 5.748 |
| 224 | 5.943 |
| 225 | <7 |
| 226 | 6.955 |
| 227 | 6.643 |
| 228 | 6.513 |
| 229 | 8.121 |
| 230 | 6.77 |
| 231 | <7 |
| 232 | 5.477 |
| 233 | 6.931 |
| 234 | <5 |

TABLE 5-continued

| Co. No. | pIC50 |
|---|---|
| 235 | 6.963 |
| 236 | 5.574 |
| 237 | 6.631 |
| 238 | 5.633 |
| 239 | 6.192 |
| 240 | 6.543 |
| 241 | 6.614 |
| 242 | 5.627 |
| 246 | 8.412 |
| 247 | 8.225 |
| 248 | 8.18 |
| 249 | 8.579 |
| 250 | 8.747 |
| 252 | 8.604 |
| 253 | 9.007 |
| 254 | 8.523 |
| 255 | 6.233 |
| 256 | <6 |
| 257 | <6 |
| 258 | 5.745 |
| 259 | 7.2 |
| 260 | 8.439 |
| 261 | 6.121 |
| 262 | <6 |
| 263 | 7.805 |
| 266 | 9.015 |
| 268 | 7.838 |
| 269 | 8.073 |
| 270 | 7.851 |
| 271 | 8.532 |
| 272 | 7.293 |
| 273 | 6.782 |
| 274 | 8.329 |
| 275 | <6 |
| 276 | 8.457 |
| 277 | 7.944 |
| 279 | 8.824 |
| 280 | 9.086 |

The invention claimed is:

1. Compound of formula (I)

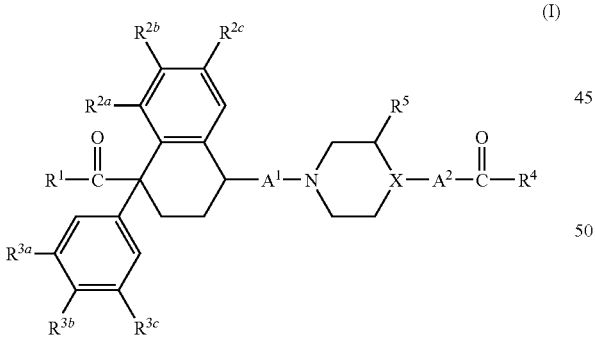

the pharmaceutically acceptable acid addition salts thereof, the N-oxides thereof, and the stereochemically isomeric forms thereof, wherein X is N, or CH;
$A^1$ is —$CH_2$—, or —(C=O)—;
$A^2$ is absent or represents —$CH_2$—, when X represents N, or
$A^2$ is —$NR^6$—, when X represents CH, wherein $R^6$ is hydrogen or $C_{1-4}$alkyl;
$R^1$ is —$NR^7R^8$ or —$OR^9$;
  wherein each $R^7$ and O are independently selected from hydrogen,
  $C_{1-8}$alkyl,
  $C_{1-8}$alkyl substituted with one, two or three substituents each independently from one another selected from halo, cyano, $C_{3-8}$cycloalkyl, $C_{1-4}$alkylcarbonyl, $C_{1-4}$alkyloxycarbonyl, polyhalo$C_{1-4}$-alkyl, hydroxycarbonyl, —$OR^{10}$, —$NR^{10}R^{11}$, —$CONR^{12}R^{13}$, aryl, polycyclic aryl, or heteroaryl;
  $C_{3-8}$cycloalkyl;
  $C_{3-8}$cycloalkenyl;
  $C_{3-8}$alkenyl;
  $C_{3-8}$alkynyl;
  aryl;
  polycyclic aryl;
  heteroaryl;
  or $R^7$ and $R^8$ combined with the nitrogen atom bearing $R^7$ and $R^8$ may form an azetidinyl, pyrrolidinyl, piperidinyl, morpholinyl, azepanyl, or azocanyl ring wherein each of these rings is optionally substituted with one or two substituents each independently selected from $C_{1-4}$alkyl, $C_{1-4}$alkyloxy, hydroxy, hydroxycarbonyl, $C_{1-4}$alkyloxycarbonyl or $C_{1-4}$alkyloxycarbonyl$C_{1-4}$alkyl;
wherein $R^{10}$ is hydrogen, $C_{1-4}$alkyl, $C_{1-4}$alkylcarbonyl, $C_{1-4}$alkyloxycarbonyl, $R^{12}$—NH-carbonyl, aryl, aryl$C_{1-4}$-alkyl, polycyclic aryl, heteroaryl;
  $R^{11}$ is hydrogen or $C_{1-4}$alkyl;
  $R^{12}$ is hydrogen, $C_{1-4}$alkyl, phenyl or phenyl$C_{1-4}$alkyl;
  $R^{13}$ is hydrogen, $C_{1-4}$alkyl, phenyl or phenyl$C_{1-4}$alkyl;
$R^9$ is $C_{1-8}$alkyl,
  $C_{1-8}$alkyl substituted with one, two or three substituents each independently from one another selected from halo, cyano, $C_{3-8}$cycloalkyl, $C_{1-4}$alkylcarbonyl, $C_{1-4}$alkyloxycarbonyl, polyhalo$C_{1-4}$-alkyl, hydroxycarbonyl, —$OR^{10}$, —$NR^{10}R^{11}$, —$CONR^{12}R^{13}$, aryl, polycyclic aryl, or heteroaryl;
  $C_{3-8}$cycloalkyl;
  $C_{3-8}$cycloalkenyl;
  $C_{3-8}$alkenyl;
  $C_{3-8}$alkynyl;
  aryl;
  polycyclic aryl;
  heteroaryl;
wherein
aryl is phenyl; phenyl substituted with one to five substituents each independently selected from $C_{1-4}$alkyl, $C_{1-4}$alkyloxy, halo, hydroxy, trifluoromethyl, cyano, $C_{1-4}$alkyloxycarbonyl, $C_{1-4}$alkyloxycarbonyl$C_{1-4}$-alkyl, methylsulfonylamino, methylsulfonyl, $NR^{10}R^{11}$, $C_{1-4}$alkyl$NR^{10}R^{11}$, $CONR^{12}R^{13}$ or $C_{1-4}$alkyl$CONR^{12}R^{13}$;
polycyclic aryl is naphthalenyl, indanyl, fluorenyl, or 1,2,3,4-tetrahydronaphtalenyl, and said polycyclic aryl is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^{10}R^{11}$, $C_{1-4}$alkyl$NR^{10}R^{11}$, $CONR^{12}R^{13}$, $C_{1-4}$alkyl$CONR^{12}R^{13}$ or $C_{1-4}$alkyloxycarbonylamino and
heteroaryl is pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, thienyl; quinolinyl; isoquinolinyl; 1,2,3,4- tetrahydro-isoquinolinyl; benzothiazolyl; benzo[1,3]dioxolyl; 2,3-dihydro-benzo[1,4]dioxinyl; indolyl; 2,3-dihydro-1H-indolyl; 1H-benzoimidazolyl; and said heteroaryl is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^{10}R^{11}$, $C_{1-4}$alkyl$NR^{10}R^{11}$, $CONR^{12}R^{13}$ or $C_{1-4}$alkyl$CONR^{12}R^{13}$;

$R^{2a}$, $R^{2b}$, and $R^{2c}$ are independently from one another selected from hydrogen, $C_{1-4}$alkyl, $C_{1-4}$alkyloxy, halo, hydroxy, cyano, nitro, polyhalo$C_{1-4}$alkyl, polyhalo$C_{1-4}$alkyloxy or $C_{1-4}$alkyloxycarbonyl;

$R^{3a}$, $R^{3b}$, and $R^{3c}$ are independently from one another selected from hydrogen, $C_{1-4}$alkyl, $C_{1-4}$alkyloxy, halo, hydroxy, cyano, nitro, polyhalo$C_{1-4}$alkyl, polyhalo$C_{1-4}$alkyloxy or $C_{1-4}$alkyloxycarbonyl;

$R^4$ is phenyl; phenyl substituted with one to five substituents each independently selected from $C_{1-4}$alkyl, halo, hydroxy, $C_{1-4}$alkyloxy, amino, cyano, nitro, polyhalo$C_{1-4}$alkyl, polyhalo$C_{1-4}$alkyloxy, $C_{1-4}$alkylcarbonyl, $C_{1-4}$alkyloxycarbonyl, sulfamoyl, a heterocyclic group, or phenyl optionally substituted with 1, 2 or 3 substituents each independently selected from $C_{1-4}$alkyl, halo, $C_{1-4}$alkyloxy, or trifluoromethyl; or heteroaryl selected from the group consisting of pyridinyl, pyrazinyl, pyrimidinyl, pyridazinyl, triazinyl, furanyl, and thienyl, wherein each of these heteroaryls is optionally substituted with one or two substituents each independently selected from $C_{1-4}$alkyl, halo, hydroxy, $C_{1-4}$alkyloxy, oxo, cyano, polyhalo$C_{1-4}$ alkyl, $C_{1-4}$alkylcarbonyl, $C_{1-4}$alkyloxycarbonyl or a heterocyclic group;

wherein heterocyclic group is selected from azetidinyl, pyrrolidinyl, piperidinyl, piperazinyl, morpholinyl, azepanyl, and azocanyl which is optionally substituted with one or two substituents each independently selected from $C_{1-4}$alkyl or halo; and $R^5$ is hydrogen, $C_{1-4}$alkyl, $C_{1-4}$alkyloxy, hydroxy or halo.

2. Compound as claimed in claim 1 wherein $A^1$ is —(C=O)—.

3. Compound as claimed in claim 1 wherein $A^1$ is —$CH_2$—.

4. Compound as claimed in claim 1 wherein $R^1$ is $NR^7R^8$.

5. Compound as claimed in claim 1 wherein $R^1$ is $OR^9$.

6. Compound as claimed in claim 1 wherein $R^{2a}$=$R^{3a}$, $R^{2b}$=$R^{3b}$ and $R^{2c}$=$R^{3c}$.

7. A pharmaceutical composition comprising a pharmaceutically acceptable carrier and an amount of a compound as claimed in claim 1.

8. A process for preparing a pharmaceutical composition as claimed in claim 7 wherein the amount of the compound is intimately mixed with a pharmaceutically acceptable carrier.

9. An intermediate compound of formula (XVII) wherein the substituents $R^{2a}$, $R^{2b}$, $R^{2c}$, $R^{3a}$, $R^{3b}$, $R^{3c}$, $R^4$, $R^5$, $A^1$, $A^2$, and X are as defined as in claim 1

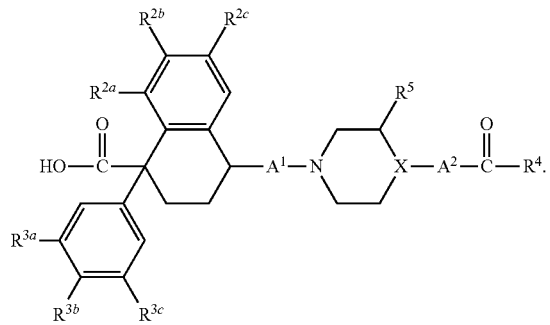

(XVII)

10. A process for preparing a compound of claim 1 wherein a) an intermediate of formula (II) wherein W is an appropriate leaving group is reacted with an intermediate of formula (III) in a reaction-inert solvent and optionally in the presence of a suitable base thereby yielding a compound of formula (I-a) defined as a compound of formula (I) wherein $A^1$ represents —$CH_2$—;

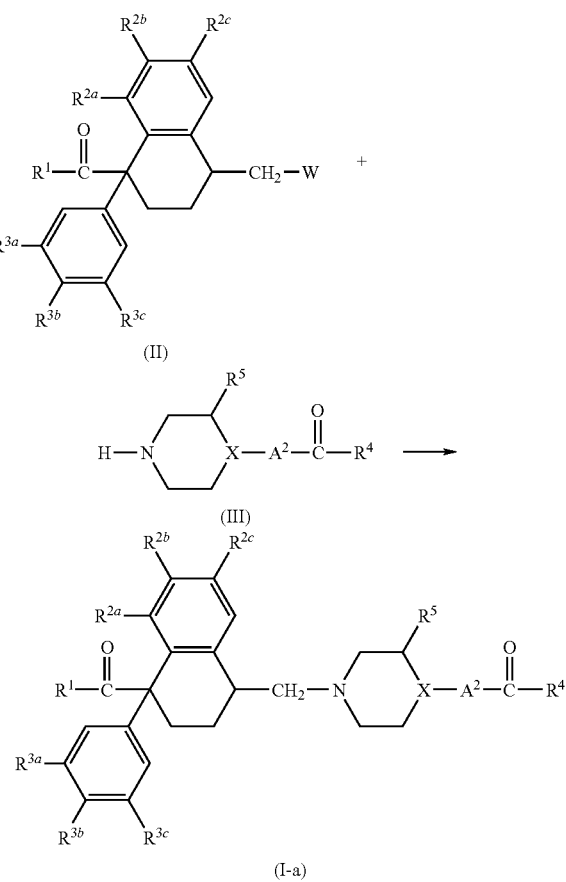

b) or; an intermediate of formula (IV) is reacted with an intermediate of formula (V) in a reaction-inert solvent and optionally in the presence of a suitable coupling reagent and/or a suitable base thereby yielding a compound of formula (I-b) defined as a compound of formula (I) wherein $A^1$ represents —(C=O)—;

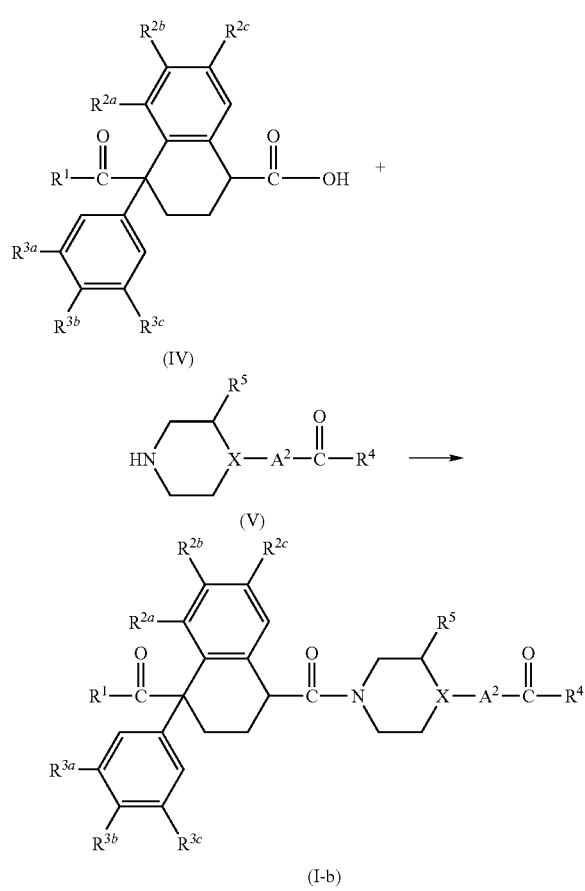

(IV)

(V)

(I-b)

c) or; converting compounds of formula (I-c), defined as compounds of formula (I) wherein $R^1$ represents $OR^9$ and $R^9$ is hydrogen, into compounds of formula (I-d), defined as compounds of formula (I) wherein $R^1$ represents $NR^7R^8$, by an N-alkylation methods using $H-NR^7R^8$ as the reagent;

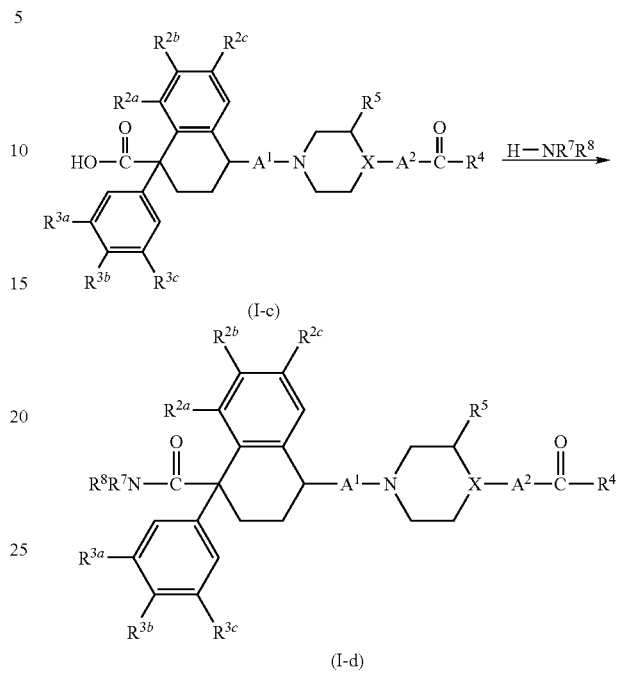

(I-c)

(I-d)

d) or, a compound of formula (I) is converted into a pharmaceutically acceptable acid addition salt, or conversely, an acid addition salt of a compound of formula (I) is converted into a free base form with alkali; and, optionally, preparing stereochemically isomeric forms thereof.

\* \* \* \* \*